United States Patent
LaBarbera et al.

(10) Patent No.: US 12,291,502 B2
(45) Date of Patent: May 6, 2025

(54) TOPOISOMERASE II-ALPHA INHIBITORS AND METHODS OF TREATING CANCER USING THE SAME

(71) Applicant: The Regents of the University of Colorado, Denver, CO (US)

(72) Inventors: Daniel V. LaBarbera, Aurora, CO (US); Qiong Zhou, Aurora, CO (US); Adedoyin D. Abraham, Aurora, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 827 days.

(21) Appl. No.: 17/599,193

(22) PCT Filed: Apr. 1, 2020

(86) PCT No.: PCT/US2020/026206
§ 371 (c)(1),
(2) Date: Sep. 28, 2021

(87) PCT Pub. No.: WO2020/205991
PCT Pub. Date: Oct. 8, 2020

(65) Prior Publication Data
US 2023/0105776 A1    Apr. 6, 2023

Related U.S. Application Data

(60) Provisional application No. 62/827,818, filed on Apr. 1, 2019.

(51) Int. Cl.
*C07D 215/14* (2006.01)
*C07D 401/12* (2006.01)
*C07D 405/04* (2006.01)

(52) U.S. Cl.
CPC ......... *C07D 215/14* (2013.01); *C07D 401/12* (2013.01); *C07D 405/04* (2013.01)

(58) Field of Classification Search
None
See application file for complete search history.

(56) References Cited

U.S. PATENT DOCUMENTS

| | | | |
|---|---|---|---|
| 9,616,047 B2 | 4/2017 | Bode et al. | |
| 2001/0051620 A1 | 12/2001 | Berger et al. | |
| 2008/0175814 A1 | 7/2008 | Phiasivongsa et al. | |
| 2014/0309257 A1 | 10/2014 | LaBarbera | |

FOREIGN PATENT DOCUMENTS

WO    WO2013/071306 A1  *  5/2013  ............. A01N 55/02

OTHER PUBLICATIONS

Abraham (Dec. 2011) "Design and Synthesis of Novel Topoisomerase IIα Inhibitors," Master's degree thesis, University of Colorado Denver, 79 pp.
Abraham et al. (Nov. 2019) "Drug Design Targeting T-Cell Factor-Driven Epithelial—Mesenchymal Transition as a Therapeutic Strategy for Colorectal Cancer," J. Med. Chem. 62, 22, 10182-10203.
Bailly (2012) "Contemporary Challenges in the Design of Topoisomerase II Inhibitors for Cancer Chemotherapy," Chem. Rev. 112:3611-3640.
Bates et al. (2011) "The ancestral role of ATP hydrolysis in type II topoisomerases: prevention of DNA double-strand breaks," Nucleic Acids Res. 39:6327-6339.
Chène et al. (2009) "Catalytic inhibition of topoisomerase II by a novel rationally designed ATP-competitive purine analogue," BMC Chem. Biol. 9:1, doi: 10.1186/1472-6769-9-1.
Daumar et al. (2014) "Synthesis and evaluation of $^{18}$F-labeled ATP competitive inhibitors of topoisomerase II as probes for imaging topoisomerase II expression," Eur. J. Med. Chem. 86:769-781.
International Search Report and Written Opinion dated Jul. 28, 2020 in PCT/US2020/026206, from which the present application claims priority, 15 pp.
Jain, et al. (2015) "Selective killing of G2 decatenation checkpoint defective colon cancer cells by catalytic topoisomerase II inhibitor," Biochimica et Biophysica Ata 1853:1195-1204.
Kagaya et al. (2006) "NK314, a novel antitumor agent, induces rapid double strand DNA breaks by specific inhibition of topoisomerase IIα," [Abstract 5525] Proc Am Assoc Cancer Res 2006; 47:1299-a.
LaBabera et al. (2007) "The Total Synthesis of Neoamphimedine," J. Org. Chem. 72:8501-8505.
Li et al. (2014) "An Improved High Yield Total Synthesis and Cytotoxicity Study of the Marine Alkaloid Neoamphimedine: An ATP-Competitive Inhibitor of Topoisomerase IIα and Potent Anticancer Agent," Mar. 12 Drugs, 4833-4850.
Nakahara, et al. "Synthesis of pantherinine, a cytotoxic fused tetracyclic aromatic alkaloid," Tetrahedron Letters 39(31) :5521-5522 (Abstract Only), (1998).
Nitiss (2009) "DNA topoisomerase II and its growing repertoire of biological functions," Nature Rev. Cancer, 9:327-337.
Nitiss (2009) "Targeting DNA topoisomerase II in cancer chemotherapy," Nature Rev. Cancer, 9:338-350.
Ponder et al. (2011) "Neoamphimedine Circumvents Metnase-Enhanced DNA Topoisomerase IIα Activity Through ATP-Competitive Inhibition," Mar. 9 Drugs, 2397-2408.
Rogojina et al. (Jan. 2012) Chapter 11 Topoisomerase II Inhibitors: Chemical Biology, p. 211-243.
Suresh et al. (2003) "A facile approach to dibenzo [b,f][1,6]naphthyridines using Vilsmeier conditions," Heterocyclic Communications 9(1), 83-88.
Toyoda (2008) "NK314, a Topoisomerase II Inhibitor That Specifically Targets the α Isoform," Journal of Biological Chemistry, 283, 35, 23711-23720.

(Continued)

*Primary Examiner* — Brian J Davis
(74) *Attorney, Agent, or Firm* — Leydig, Voit & Mayer, Ltd.

(57) ABSTRACT

A compound, or a pharmaceutically acceptable salt, solvate or prodrug thereof, having the chemical structure of formula I as defined in the text and methods of using these compounds to inhibit topoisomerase IIα and treat or prevent metastasis of cancer in a subject.

19 Claims, 7 Drawing Sheets

(56) References Cited

OTHER PUBLICATIONS

Wei et al. (2005) "Nucleotide-dependent Domain Movement in the ATPase Domain of a Human Type IIA DNA Topoisomerase," J. Biol. Chem. 280, 37041-37047.

Zhou et al. (2016) "Topoisomerase IIα mediates TCF-dependent epithelial—mesenchymal transition in colon cancer," Oncogene 35:4990-4999.

* cited by examiner

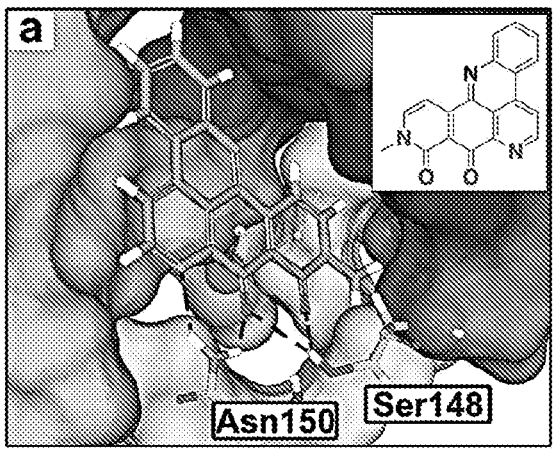
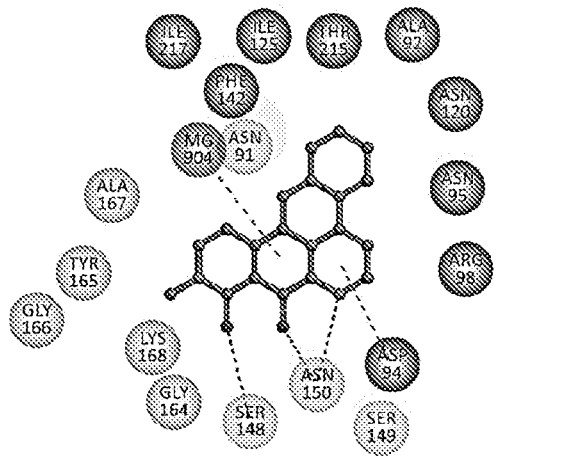
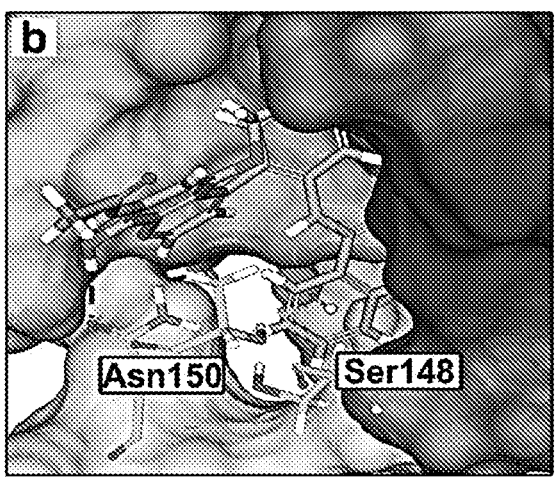
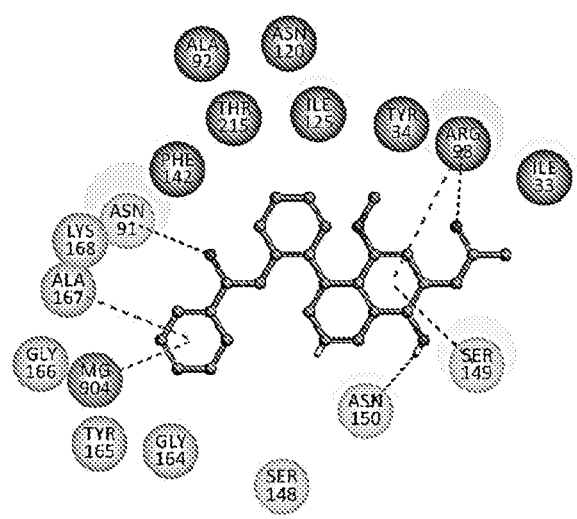
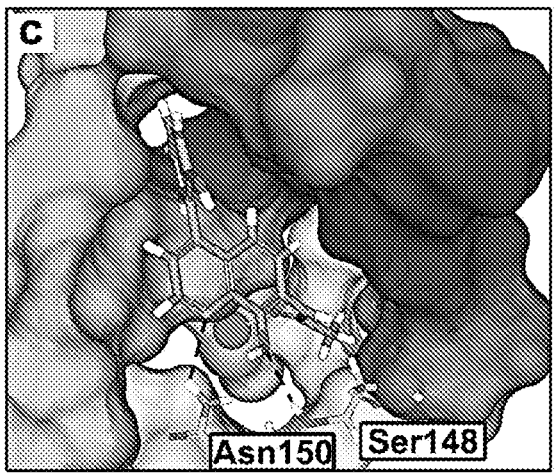
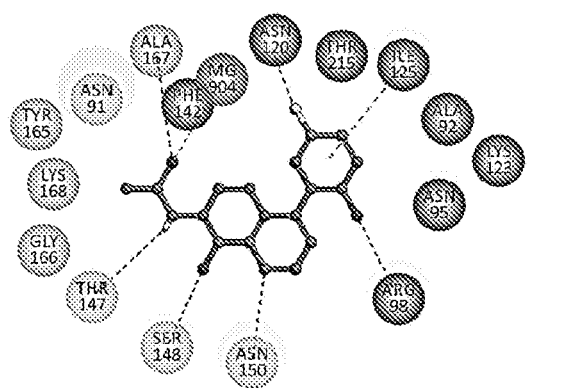
FIGs. 1A-C

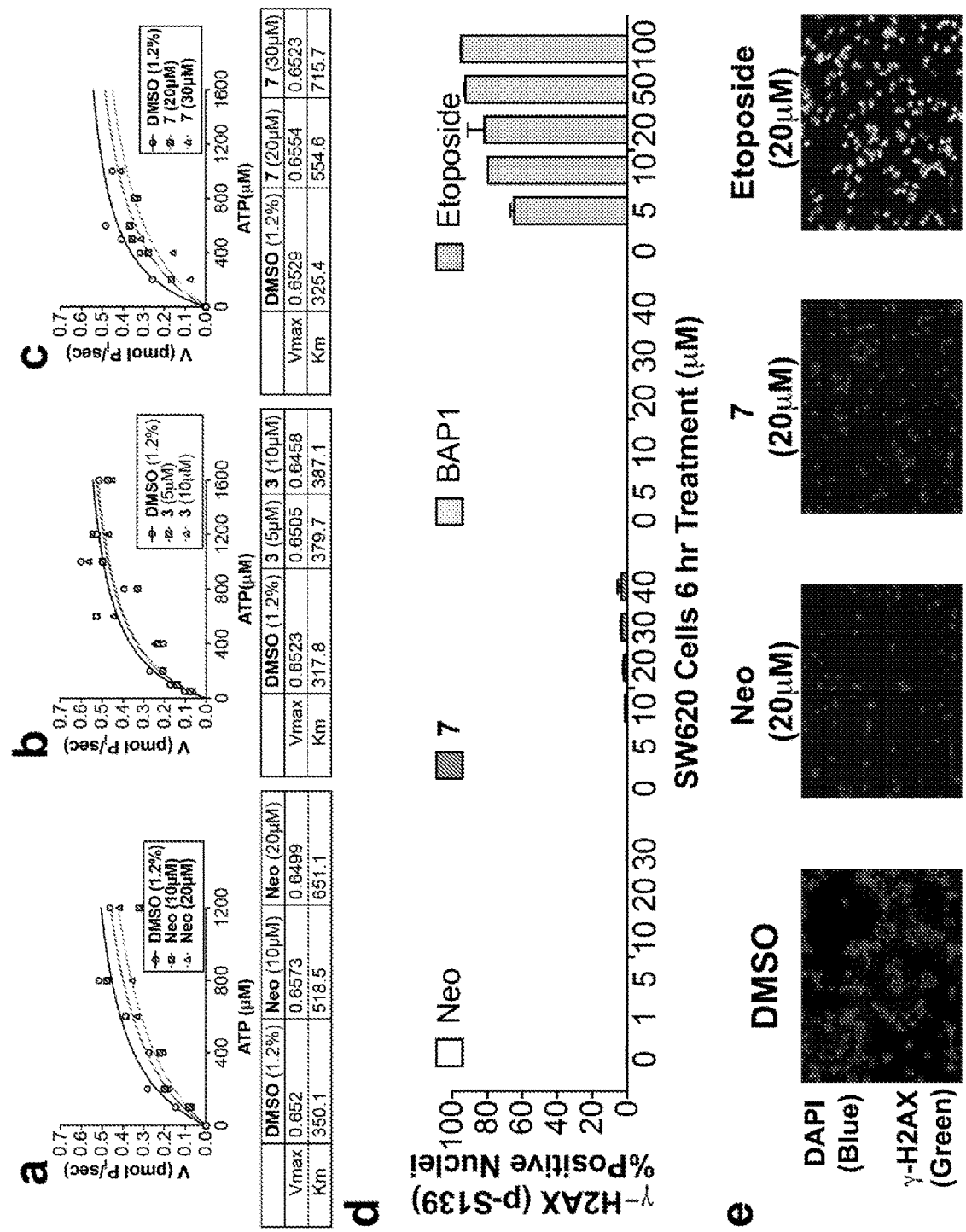
FIGs. 2A-E

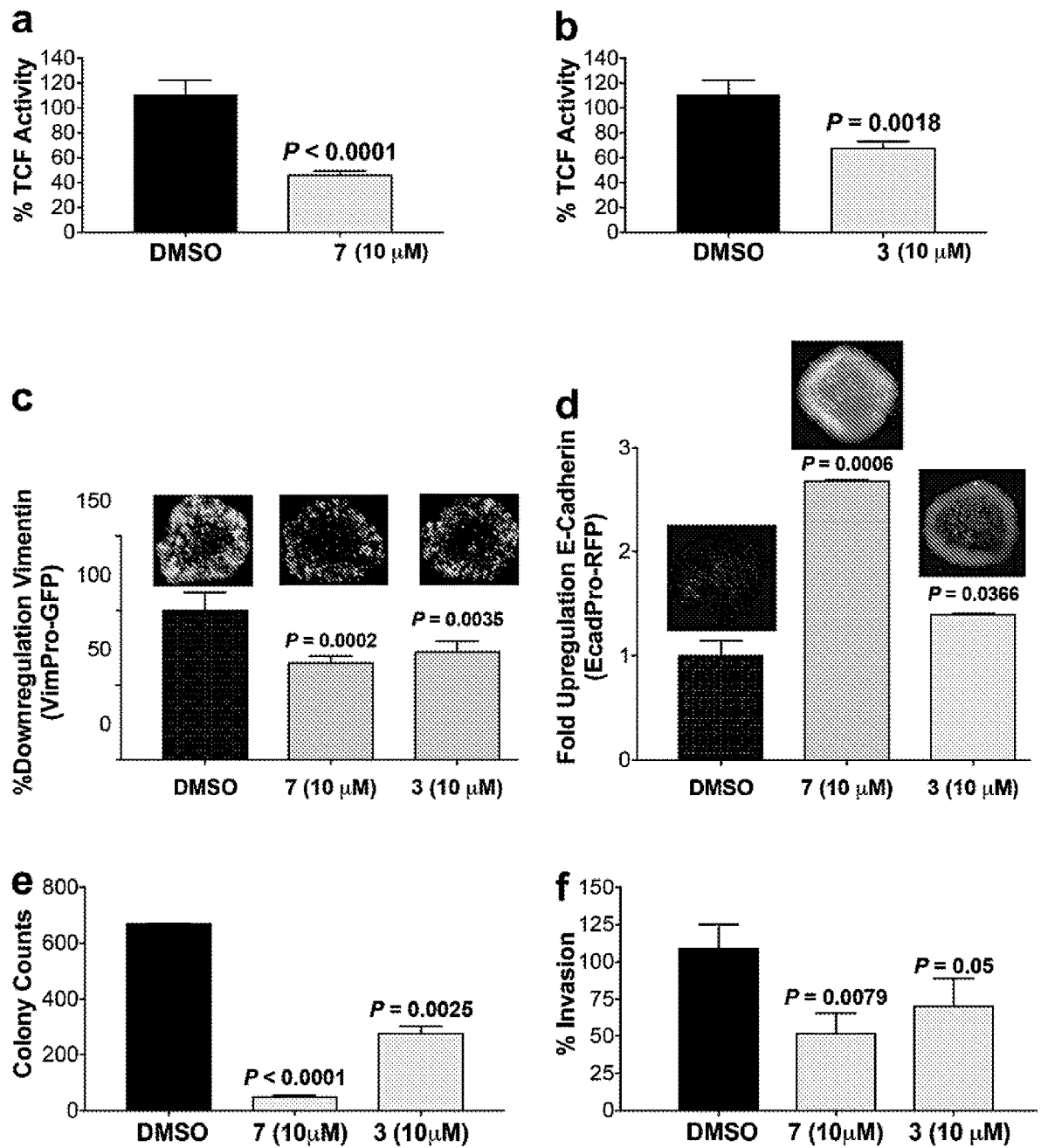
FIG. 3A-F

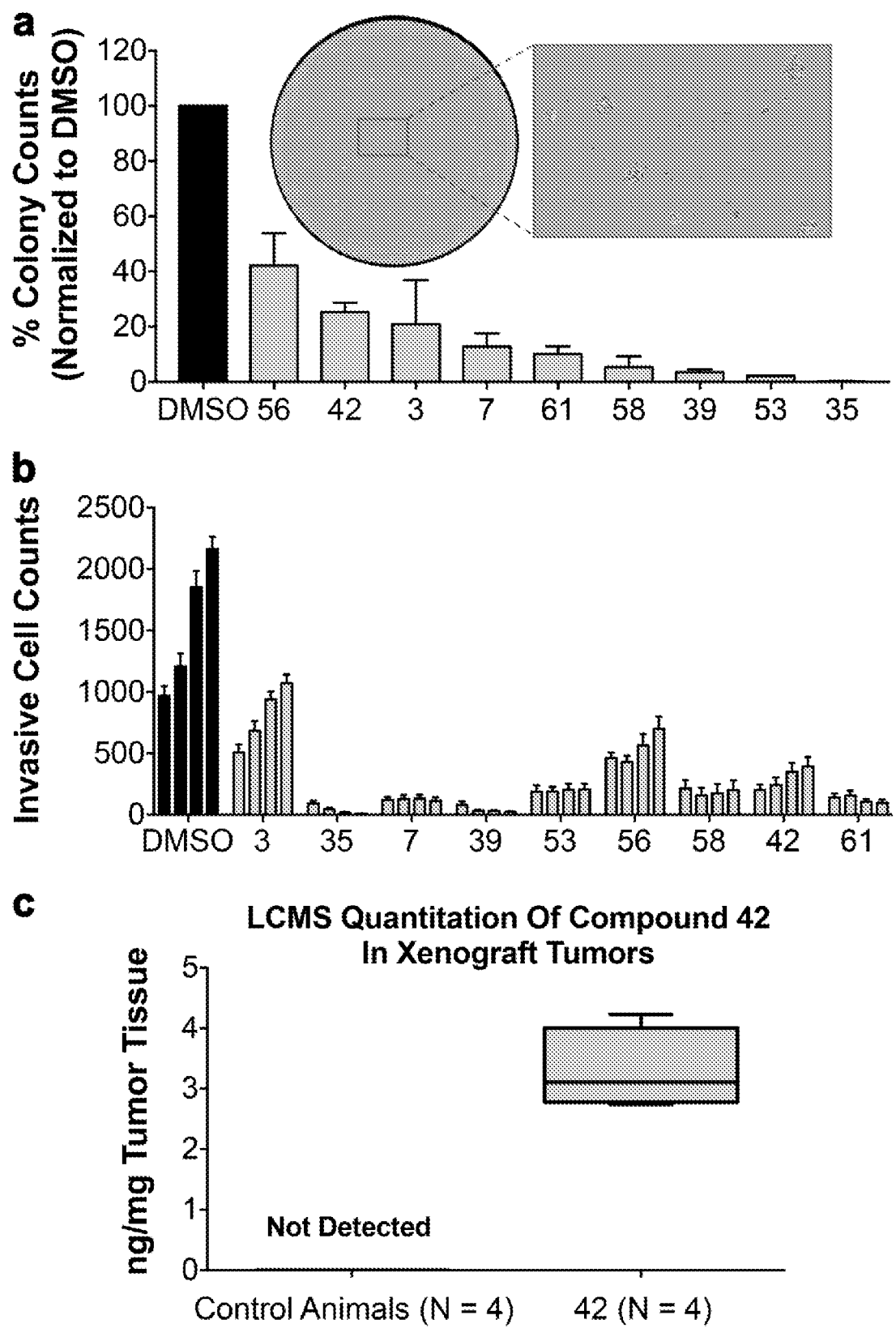
FIGs. 5A-C

TOPOISOMERASE II-ALPHA INHIBITORS AND METHODS OF TREATING CANCER USING THE SAME

CROSS-REFERENCE TO RELATED APPLICATIONS

This application is a U.S. National Stage Application under 35 U.S.C. § 371 of International Application No. PCT/US2020/026206, filed Apr. 1, 2020, which claims the benefit of U.S. provisional application 62/827,818, filed Apr. 1, 2019, each of which is incorporated by reference herein in its entirety.

STATEMENT REGARDING GOVERNMENT INTEREST

This invention was made with Government support under grant number W81XWH-13-1-0344 and W81XWH-18-1-0142 awarded by the Department of Defense (DoD). The U.S. Government has certain rights in this invention.

TECHNICAL FIELD

The invention relates to improvements in cancer chemotherapy.

BACKGROUND OF THE INVENTION

Many types of cancer initiate through mutations in the Wnt signaling pathway, leading to constitutive activation of T-Cell Factor/Lymphoid Enhancer Factor transcription, denoted as TCF-transcription or TCF-complex. For example, aberrant TCF-transcription is a driving force promoting metastatic colorectal cancer (mCRC) by stimulating epithelial-mesenchymal transition (EMT), a mechanism that increases invasive potential, multi-drug resistance (MOR), and cancer stem cells (CSC) in solid tumors. Drug development targeting the Wnt/TCF pathway has been hindered by significant challenges in identifying effective drug targets. Some of the approaches include targeting CK1 and CDK8 kinases, the acetyltransferase porcupine, and tankyrases (TNKS). A major strategy has been to target protein-protein interactions between β-catenin and other TCF-complex proteins. See, for example, U.S. Pat. No. 9,616,047. Directly targeting TCF-transcription has proven a successful and clinically relevant approach, as exemplified by the investigational new drug, PRI-724, which inhibits protein interactions between β-catenin-CBP (CREB Binding Protein). Hence, directly targeting TCF-transcription may be the most effective strategy for the treatment of late stage and metastatic cancer.

A variety of small molecule topoisomerase II (TOP2) inhibitors have been reported. [Bailly C (2012) "Contemporary Challenges in the Design of Topoisomerase II Inhibitors for Cancer Chemotherapy," Chem. Rev. 112:3611-3640] These include the topoisomerase poisons, such as etoposide, which are reported to accumulate DNA double stranded breaks in cells and result in cell death. Additional small molecule TOP2 inhibitors have been described which are reported to inhibit by a mechanism distinct from that of topoisomerase poisons. Various mechanisms of TOP2 inhibition have been described and illustrated. [Nitiss J (2009) "Targeting DNA topoisomerase II in cancer chemotherapy," Nature Rev. Cancer, 9:338-350, see FIG. 1 therein] Among catalytic inhibitors of TOP2, purine derivatives, such as QAP1, are reported to be TOP2 ATP-competitive inhibitors:

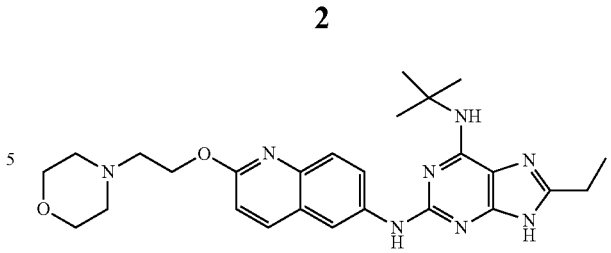

[Chène P et al. (2009) "Catalytic inhibition of topoisomerase II by a novel rationally designed ATP-competitive purine analogue," BMC Chem. Biol. 9:1. doi: 10.1186/1472-6769; Dauman P et al. (2014) "Synthesis and evaluation of $^{18}$-F-labeled ATP competitive inhibitors of topoisomerase II as probes for imaging topoisomerase II expression," Eur. J. Med. Chem. 86:769-781] The marine alkaloid neoamphimedine is also reported to inhibit TOP2A as an ATP-competitive inhibitor:

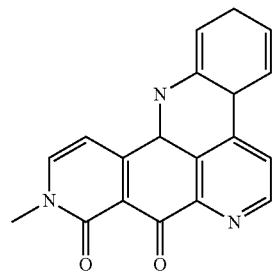 [SMILES: Cn1ccc2c(c1=O)C(=O)c1nccc3c1C2NC1=CCC=CC13]

[LaBabera D V at al. (2007) "The Total Synthesis of Neoamphimedine," J. Org. Chem. 72:8501-8505; Ponder J et al. (2011) "Neoamphimedine Circumvents Metnase-Enhanced DNA Topoisomerase IIα Activity Through ATP-Competitive Inhibition," Mar. Drugs 9:2397-2408; Li L et al. (2014) "An Improved High Yield Total Synthesis and Cytotoxicity Study of the Marine Alkaloid Neoamphinedine: An ATP-Competitive Inhibitor of Topoisomerase IIα and Potent Anticancer Agent," Mar. Drugs 12:4833-4850] U.S. published application 2014/0309257 reports TOP2A inhibitors of formula:

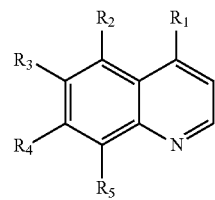

wherein variables $R_1$-$R_5$ are as defined therein. This published application is incorporated by reference herein in its entirety for definitions of these variables.

Thus, there is a desire for chemotherapeutic treatments that can inhibit TCF-transcription and EMT, to treat cancer and prevent or reduce cancer metastasis.

SUMMARY OF THE INVENTION

The inventors have identified a new therapeutic strategy to directly inhibit aberrant TCF-transcription by discovering that topoisomerase IIα (TOP2A) is a DNA binding factor required for TCF-transcription. TOP2A forms protein-protein interactions with TCF4 and Q-catenin, and protein-DNA interactions with Wnt response elements (WRE) and with promoter sites of genes directly regulated by TCF-transcription. TOP2A is an important drug target for the treatment of many types of cancer, especially those that overexpress or amplify the enzyme. For example, TOP2A is overexpressed in colorectal cancer (CRC), particularly mCRC or recurring CRC. The inventors have now validated TOP2A as a druggable target preventing TCF-transcription by using short hairpin RNA knockdown and small molecule N-terminal ATP-competitive inhibitors, notably, the marine alkaloid neoamphimedine (neo). Neo's mode of action inhibits TOP2A and the TCF-complex from binding to WRE/promoter sites. This in turn prevents TCF-transcription, leading to the reversion of EMT and its associated malignant properties. Unlike neo, conventional TOP2A inhibitors that bind to the C-terminal domain such as etoposide and merbarone do not inhibit TOP2A mediated TCF-transcription. This lack of inhibition was primarily attributed to alterations in TOP2A C-terminal drug binding sites that arise from TOP2A participation in the TCF-complex, but also potentially from other TOP2A associated MDR mechanisms.

Without intending to be bound by theory, it is believed TOP2A is recruited by the TCF-complex to help dynamically regulate EMT genes and other metastatic genes (e.g. c-Myc) promoting mCRC. TOP2A-DNA interactions essential to this process are facilitated by ATP binding and hydrolysis. Thus, N-terminal ATP sites are conserved during TOP2A-mediated TCF-transcription, providing an Achilles' heel to MDR and optimal sites for drug design. Although neo displays promising antitumor activity in several models of cancer, it also displays a suboptimal in vivo pharmacokinetics (PK) profile. The inventors have therefore designed, synthesized, and evaluated the biological activity of novel TOP2A ATP-competitive inhibitors with improved drug-like physicochemical properties that are effective at preventing TOP2A mediated TCF-transcription and reverse EMT.

Thus, one aspect of this invention provides a compound, or a pharmaceutically acceptable salt, solvate, or prodrug thereof, having the chemical structure:

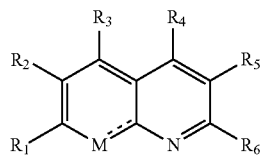

or salts or solvates thereof,
wherein:
M is >CO or —OH, where the dotted bond is absent when N is >CO;
$R_1$ is —$NR^7CO$—$R^8$ or —CO—NR—$R^8$, wherein $R^7$ is H or C1-C3 alkyl optionally substituted with one or more halogen, hydroxy, or C1-C3 alkoxy and $R^8$ is H, alkyl, or cycloalkyl optionally substituted with one or more halogen, hydroxyl, C1-C3 alkyl, C1-C3 alkoxy, or heterocyclic optionally substituted with one or more oxo (═O), halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic;
$R^2$, $R^3$ and $R^5$ are independently H, halogen, C1-C3 alkyl or ORG, wherein $R^6$ is H or C1-C3 alkyl where the C1-C3 alkyls are optionally substituted with one or more halogen, hydroxyl, C1-C3 alkoxy or C1-C3 hydroxyalkyl;
$R^4$ is $NHR^{10}$, wherein $R^{10}$ is aryl, arylalkyl, heteroaryl or heteroarylalkyl each of which is optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic; or
$R^4$ is aryl or heteroaryl which are optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic; and
$R^6$ is H, $COOR^{11}$, —$CONR^{12}R^{13}$ or derivatives thereof, or a detectable label, wherein $R^{10}$, $R^{11}$, and $R^{12}$ are independently alkyl or cycloalkyl optionally substituted with one or more halogen, hydroxyl, C1-C3 alkyl, C1-C3 alkoxy, or heterocyclic in turn optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic, or aryl or heterocyclic optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.

In embodiments, M is OH.
In embodiments, M is >C═O.
In embodiments, $R_1$ is —$NR^7CO$—$R^8$.
In embodiments, $R_1$ is or —CO—$NR^7$—$R^8$.
In embodiments, $R^1$ is —$NR^7CO$—$R^6$, where $R^3$ is alkyl, or cycloalkyl optionally substituted with a heterocyclic group which is optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.
In embodiments, $R^1$ is —NHCO—$CH_3$.
In embodiments, $R^8$ is unsubstituted C1-C4 alkyl.
In embodiments, $R^8$ is alkyl, or cycloalkyl optionally substituted with a heterocyclic group which is in turn optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.
In embodiments, $R^8$ is C1-C6 alkyl optionally substituted with an unsubstituted heterocyclic group. In embodiments, $R^8$ is C1-C6 alkyl optionally substituted with a morpholino group.
In embodiments, $R^2$, $R^3$ and $R^5$ are independently, H, halogen, or C1-C3 alkyl.
In embodiments, $R^2$, $R^3$ and $R^5$ are each H.
In embodiments, $R^6$ is H.
In embodiments, $R^4$ is $NHR^{10}$, wherein $R^{10}$ is aryl, arylalkyl, heteroaryl or heteroarylalkyl each of which is optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.
In embodiments, $R^4$ is aryl or heteroaryl which are optionally substituted with one or more halogen, hydroxyl, C1-C6 alkyl, C3-C6 cycloalkyl, C1-C6 acyl, C1-C3 haloalkyl, C1-C3 alkoxy, 01-03 hydroxyalkyl, or heterocyclic.
In embodiments, $R^4$ is a phenyl group substituted with at least one fluorine.
In embodiments, $R^4$ is an optionally-substituted heteroaryl group.
In embodiments, $R^4$ is a furyl, thienyl or benzofuranyl group each of which is optionally substituted.
In embodiments, fluorine is the preferred halogen.

Another aspect of this invention provides pharmaceutical compositions comprising at least one topoisomerase IIα (TOP2A) inhibitor compound of this invention and at least one pharmaceutically acceptable additive.

Another aspect of this invention provides pharmaceutical kits containing a pharmaceutical composition of this invention, prescribing information for the composition, and a container.

Another aspect of this invention provides methods for inhibiting TOP2A activity in a subject, including administering to the subject a therapeutically effective amount of a TOP2A inhibitor compound of this invention, or a pharmaceutically acceptable salt thereof.

This invention also provides methods of preventing, treating, or ameliorating cancer, or preventing metastasis of a cancer in a subject, including administering a therapeutically-effective amount of a compound of this invention that inhibits TOP2A to a subject in need thereof.

In embodiments of these methods, the cancer is any form or type of cancer where cancerous tissue or tumors contain detectable levels of topoisomerase II. In embodiments of these methods, the cancer may be colorectal cancer, breast cancer, sarcomas, testicular cancer, lung cancer, lymphoma, leukemia, neuroblastoma, or ovarian cancer. In specific embodiments of these methods, the cancer is colorectal cancer.

In these methods, the TOP2A inhibitor compound may be administered to the subject within a pharmaceutical composition. The pharmaceutical composition may be a monophasic pharmaceutical composition suitable for parenteral or oral administration comprising a therapeutically-effective amount of the TOP2A inhibitor compound, and a pharmaceutically acceptable additive.

In these methods, the pharmaceutical composition may be administered in combination with one or more of conventional chemotherapy, CAR-T cell therapy, immune therapy, radiation, or combinations thereof. Combined administration may be administration at the same time, and by the same route of administration or at selected different times and by selected different routes of administration. Administration at the same time is within minutes up to an hour. Administration at different times is from greater than one hour up to one week and more specifically from greater than one hour up to 72 hours.

In related aspects, this invention also provides the use of a TOP2A inhibitor compound of this invention, or a pharmaceutically acceptable salt or solvate thereof, in the manufacture of a medicament for the treatment of cancer. Similarly, this invention provides a TOP2A inhibitor compound or a pharmaceutically acceptable salt or solvate thereof, for use in the treatment of cancer. In specific embodiments, medicaments and TOP2A inhibitors are for use in the treatment of colorectal cancer and metastatic colorectal cancer.

This Summary is neither intended nor should it be construed as being representative of the full extent and scope of the present invention. Moreover, references made herein to "the present invention," or aspects thereof, should be understood to mean certain embodiments of the present invention and should not necessarily be construed as limiting all embodiments to a particular description. The present invention is set forth in various levels of detail in this Summary as well as in the attached drawings and the Detailed Description and no limitation as to the scope of the present invention is intended by either the inclusion or non-inclusion of elements, components, etc. in this Summary.

Additional aspects of the present invention will become readily apparent from the Detailed Description, particularly when taken together with the figures.

BRIEF DESCRIPTION OF FIGURES

FIGS. 1A-1D depict computer aided drug design (CADD) also referred to as structure-based drug design and synthesis of novel TOP2A ATP-competitive inhibitors. FIG. 1A is a 3D rendering of the molecular model of neo docked into the ATP-binding site of the N-terminal domain of TOP2A (PDB:1ZXM, 1.87 Å). The colored regions represent hydrophobic (blue), hydrophilic (green). Walker A motif residues (orange), and $Mg^{2+}$ (pink sphere). This figure in color is available from Abrahm, A D, et al. (2019) J. Med. Chem. 62(22):10182-10203, which is incorporated by reference herein in its entirety. Based on CADD, the pharmacophore of neo was deduced to be a substituted quinoline shown as red bonds in the chemical structure. Novel TOP2A ATP-competitive inhibitor prototypes 3 (FIG. 1B) and 7 (FIG. 1C) were designed using CADD and the pharmacophore of neo. TOP2A ATP-binding site interactions are shown with a 2D rendering as dashed lines: H-bonds (black), $Mg^{2+}$ π-cation or chelation (orange), π-sigma (pink), π-loan pair (blue), and halogen hydrogen bond (red). FIGS. 1D and 1E depict schemes for syntheses of quinolines 3 and 7 prototype TOP2A ATP-competitive inhibitors, respectively.

FIGS. 2A-2E show the results of TOP2A enzyme Michaelis-Menten inhibition studies measuring ATP hydrolysis with (a) neo (FIG. 2A), 3 (FIG. 2B), and 7 (FIG. 2C). Like neo, the quinoline based pharmacophores of 3 and 7 display an ATP-competitive mode of inhibition against TOP2A, evidenced by clear shifts in $K_M$ with no changes in $V_{max}$. FIG. 2D shows TOP2A ATP-competitive inhibitors Neo, 7, and BAP1 do not cause DNA DSBs, over a concentration range from 0-40 μM, measured by H2AX S139 phosphorylation immunofluorescence (known as γ-HA2X), while the TOP2A poison, etoposide, caused significant DNA damage over a concentration range from 5-100 μM. FIG. 2E shows representative fluorescence images showing that Neo and 7 do not cause induction of γ-HA2X, while etoposide caused significant induction of γ-HA2X.

FIGS. 3A-3F demonstrate the antitumor activity of prototypes 3 and 7. Compounds 7 (FIG. 3A) and 3 (FIG. 31B) demonstrate the ability to significantly inhibit TOP2A-dependent TCF-transcription using SW620 tumor organoids transduced with the TOPflash luminescent reporter. Compounds 7 (FIG. 3C) and 3 (FIG. 3D) also demonstrated the ability to reverse EMT using SW620 tumor organoids transduced with EcadPro-RFP or VimPro-GFP EMT biomarker reporters over a 72 h treatment time course. Reversion of EMT is characterized by downregulation of vimentin and upregulation of E-cadherin promoter activity. FIG. 3E demonstrates that compounds 7 and 3 also significantly inhibit clonogenic colony formation over seven days, which is a measure of the loss of cancer stem cell sternness. FIG. 3F shows SW620 tumor organoids treated with 7 and 3 for 72 h, tumor organoids were dissociated, and viable cell invasive potential was measured for an additional 72 h incubation.

FIGS. 5A-5C show TOP2A inhibitor effects on malignant properties of SW620 tumor organoids, and in vivo disposition. FIG. 5A shows the clonogenic assay results with TOP2A inhibitors demonstrate significant inhibition of CSC colony formation. The inset is a representative image of a DMSO control well of a 6-well plate. The expansion view shows detail of colonies formed, which are identified using area (μm²) min: 1×10⁴ max: 4×10⁹, and masked in orange color for contrast. FIG. 5B shows the results of the invasion assay with TOP2A inhibitors demonstrating significant loss of invasive potential. The results in panels A and B were determined to be statistically significant using one-way ANOVA analysis, where P≤0.0008 for each analog tested. FIG. 5C shows LCMS quantitation of compound 42 in tumors after i.p. administration, 5×/week over 28 days.

DETAILED DESCRIPTION

Figure 1D:
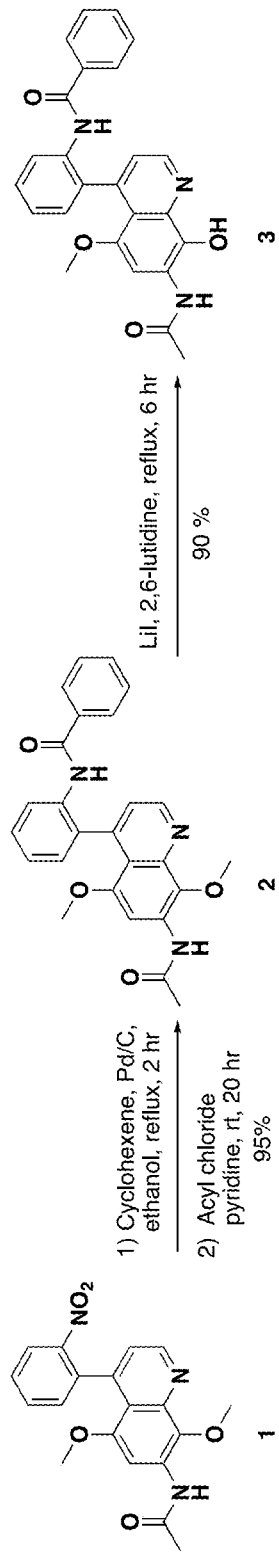

The present invention is drawn to topoisomerase IIα (TOP2A) inhibitors that prevent T-cell factor (TCF)-transcription and reverse epithelial-mesenchymal transition (EMT) and have significantly improved pharmacokinetic characteristics.

The present invention provides compounds, or a pharmaceutically acceptable salt, solvate, or prodrug thereof, having the chemical structure formula I:
the chemical structure:

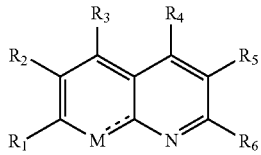

or salts or solvates thereof,
wherein:
M is >CO or —OH, where the dotted bond is absent when M is >CO;
$R_1$ is —NR⁷CO—R⁸ or —CO—NR⁷—R⁸, wherein R⁷ is H or C1-C3 alkyl optionally substituted with one or more halogen, hydroxy, or C1-C3 alkoxy and R⁸ is H, alkyl, or cycloalkyl optionally substituted with one or more halogen, hydroxyl, C1-C3 alkyl, C1-C3 alkoxy, or heterocyclic optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic;
$R^2$, $R^3$ and $R^5$ are independently H, halogen, C1-C3 alkyl or ORG, wherein $R^6$ is H or C1-C3 alkyl where the C1-C3 alkyls are optionally substituted with one or more halogen, hydroxyl, C1-C3 alkoxy or C1-C3 hydroxyalkyl;
$R^4$ is NHR¹⁰, wherein R¹⁰ is aryl, arylalkyl, heteroaryl or heteroarylalkyl each of which is optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic; or $R^4$ is aryl or heteroaryl which are optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic; and
$R^6$ is H, COOR¹¹, —CONR¹²R¹³ or derivatives thereof, or a detectable label, wherein R¹⁰, R¹¹, and R¹² are independently alkyl or cycloalkyl optionally substituted with one or more halogen, hydroxyl, C1-C3 alkyl, C1-C3 alkoxy, or heterocyclic in turn optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic, or aryl or heterocyclic optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.

In embodiments, M is OH.

In embodiments, $R_1$ is —NR⁷CO—R⁸.

In embodiments, $R_1$ is or —CO—NR⁷—R⁸.

In embodiments, $R^1$ is —NR⁷CO—R⁶, where R⁸ is alkyl, or cycloalkyl optionally substituted with a heterocyclic group which is optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.

In embodiments, $R^1$ is —NHCO—CH₃.

In embodiments, $R^8$ is unsubstituted C1-C4 alkyl.

In embodiments, $R^6$ is alkyl, or cycloalkyl optionally substituted with a heterocyclic group which is in turn optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.

In embodiments, $R^u$ is C1-C6 alkyl optionally substituted with an unsubstituted heterocyclic group. In embodiments, $R^8$ is C1-C6 alkyl optionally substituted with a morpholino group.

In embodiments, $R^2$, $R^3$ and $R^5$ are independently, H, halogen, or C1-C3 alkyl.

In embodiments, $R^2$, $R^3$ and $R^5$ are each H.

In embodiments, $R^6$ is H.

In embodiments, $R^4$ is NHR¹⁰, wherein R¹⁰ is aryl, arylalkyl, heteroaryl or heteroarylalkyl each of which is optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.

In embodiments, $R^4$ is aryl or heteroaryl which are optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.

In embodiments, $R^4$ is a phenyl group substituted with at least one fluorine.

In embodiments, $R^4$ is an optionally-substituted heteroaryl group.

In embodiments, $R^4$ is a furyl, thienyl or benzofuranyl group each of which is optionally substituted.

In embodiments, the invention provides compounds of formula:

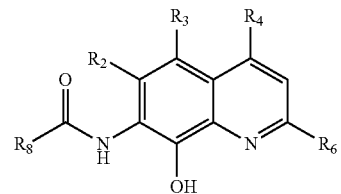

or salts or solvates thereof, where variables are as defined in formula I above. IN specific embodiment In embodiments, the invention provides a compound other than a compound described in U.S. patent application 2014/0309257. In embodiments, the invention provides a compound other than a compound of formula:

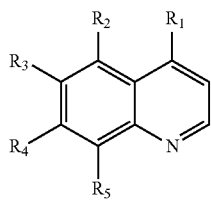

wherein variables $R_1$-$R_5$ are as defined In U.S. patent application 2014/0309257.

In embodiments, the invention provides each compound listed in Table 1 herein.

In embodiments, the invention provides compounds 7, 29, -34, 36-38, 40-43, and 53-61 of Table 1. In embodiments, the invention provides compounds 29, 31, 32, 37, 42, 56, 57, 58, 60 and 61 of Table 1. In embodiments, the invention provides compounds 3, 7, 35, 39, 42, 53 and 56 or salts or solvates thereof of Table 1. In embodiments, the invention provides compounds 7, 42, 53 and 56 or salts or solvates thereof of Table 1. In embodiments, the invention provides compounds 7, 42 and 56 or salts or solvates thereof of Table 1.

In embodiments, the invention provides each one of the compounds or salts or solvates thereof listed in Table 3. In embodiments, the invention provides compound AA-29-147 of Table 3 or a salt or solvate thereof.

In embodiments, the invention provides one or more compound illustrated in Scheme 1. In embodiment, the invention provides compounds 7 and 42 or 29, 29A and 29B, or 31, 31A and 31B, or 32, 32A and 32B or 37, 37A, and 37B, or 56, 56A, and 56B, or 57, 57A and 57B, or 58, 58A and 58B or 53, 60 and 61. In embodiments, the invention provides, compounds 29A, 298, 31A, 31B, 32, A, 328, 37A, 37B, 56A, 56B, 57A, 57B, 58A and/or 58B.

To facilitate an understanding of the embodiments presented, the following definitions are provided.

The singular terms "a," "an," and "the" include plural referents unless context clearly indicates otherwise. Similarly, the word "or" is intended to include "and" unless the context clearly indicates otherwise. The term "comprises" means "includes." Also, "comprising A or B" means including A or B, or A and B, unless the context clearly indicates otherwise. It is to be further understood that all molecular weight or molecular mass values given for compounds are approximate and are provided for description.

Although methods and materials similar or equivalent to those described herein can be used in the practice or testing of this invention, suitable methods and materials are described below. In addition, the materials, methods, and examples are illustrative only and not intended to be limiting.

"Administration of" and "administering a" compound or agent should be understood to mean providing a compound or agent, a prodrug of a compound or agent, or a pharmaceutical composition as described herein. The compound, agent or composition can be administered by another person to the subject (e.g., intravenously) or it can be self-administered by the subject (e.g., tablets or capsules).

The term "subject" refers to mammals (for example, humans and veterinary animals such as dogs, cats, pigs, horses, sheep, and cattle).

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include alkyl groups, hydroxyl groups, alkoxy groups, acyloxy groups, mercapto groups, and aryl groups.

"Substituted" or "substitution" refer to replacement of a hydrogen atom of a molecule or an R-group with one or more additional R-groups such as halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, nitro, sulfato, or other R-groups. Alkyl groups in substituents preferably have 1-3 carbon atoms.

As to any of the chemical groups herein that are substituted, i.e., contain one or more non-hydrogen substituents, it is understood, that such groups do not contain any substitution or substitution patterns which are sterically impractical and/or synthetically non-feasible. In addition, the compounds of this invention include all stereochemical isomers arising from the substitution of these compounds.

"Acyl" refers to a group having the structure RCO—, where R may be alkyl, or substituted alkyl. "Lower acyl" groups are those that contain one to six carbon atoms.

Acyl groups also include those which have 1 to 3 carbon atoms and particularly includes acetyl.

"Acyloxy" refers to a group having the structure RCOO—, where R may be alkyl or substituted alkyl. "Lower acyloxy" groups contain one to six carbon atoms.

"Alkenyl" refers to a cyclic, branched or straight chain group containing only carbon and hydrogen, and unless otherwise mentioned typically contains two to twelve carbon atoms and contains one or more double bonds that may or may not be conjugated. Alkenyl groups may be unsubstituted or substituted. "Lower alkenyl" groups contain one to six carbon atoms. Alkenyl groups also include those having 2 or 3 carbon atoms. Alkenyl groups include cycloalkenyl groups having a carbocyclic ring of 3 to 12 or more specifically 3 to 7 and yet more specifically 5 or 6 carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms or 1-3 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogen, halogenated alkyl, alkoxy, heterocyclyl or heterocyclylalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms and those having 1-3 carbon atoms. Alkyl groups include cycloalkyl groups having a carbocyclic ring of 3 to 12 or more specifically 3 to 7 and yet more specifically 5 or 6 carbon atoms. Alkyl groups may be "substituted alkyls" wherein one or more hydrogen atoms are substituted with a substituent such as halogen, cycloalkyl, alkoxy, amino, hydroxyl, aryl, alkenyl, heterocyclyl, heteroaryl or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$) cycloalkyl can be cyclopropyl, cyclobutyl, cyclopentyl, or cyclohexyl; (Cr $C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, I-hydroxybutyl, 4-hydroxybutyl, 1-hydroxypentyl, 5-hydroxypentyl, 1-hydroxyhexyl, or 6-hydroxyhexyl; ($C_1$-$C_6$) alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy. A specifically preferred alkyl group is a methyl groups.

"Alkynyl" refers to a cyclic, branched or straight chain group containing only carbon and hydrogen, and unless otherwise mentioned typically contains one to twelve carbon atoms and contains one or more triple bonds. Alkynyl groups may be unsubstituted or substituted. "Lower alkynyl" groups are those that contain two to six carbon atoms. Alkynyl groups include cycloalkynyl groups.

The term "halogen" refers to fluoro, bromo, chloro, and iodo substituents. Preferred halogens are fluorine and chlorine.

"Aryl" refers to a monovalent unsaturated aromatic carbocyclic group having a single ring (e.g., phenyl) or multiple condensed rings (e.g., naphthyl or anthryl), which can optionally be unsubstituted or substituted. An aryl group can contain multiple aromatic rings joined by a single bond, e.g., biphenyl. Aryl groups include those with 6-14 carbon atoms and those with 6 to 10 carbon atoms. A preferred aryl group is a phenyl group which is optionally substituted.

Arylalkyl groups are alkyl groups substituted with an aryl group. Preferred arylalkyl groups are those with a methyl or ethyl group. Arylalkyl groups include among others benzyl groups and phenethyl groups, which are optionally substituted.

The term "amino" refers to an R-group having the structure —$NH_2$, which can be optionally substituted with, for example, lower alkyl groups, to yield an amino group having the general structure —NHR (monoalkylamino) or —$NR_2$ (dialkylamino).

"Nitro" refers to an R-group having the structure —$NO_2$.

The term "aliphatic" as applied to cyclic groups refers to ring structures in which any double bonds that are present in the ring are not conjugated around the entire ring structure.

The term "aromatic" as applied to cyclic groups refers to ring structures which contain double bonds that are conjugated around the entire ring structure, possibly through a heteroatom such as an oxygen atom or a nitrogen atom. Aromatic groups include aryl groups and heteroaryl groups. Aryl groups, pyridyl groups and furan groups (exemplary heteroaryl groups) are examples of aromatic groups. The conjugated system of an aromatic group contains a characteristic number of electrons, for example, 6 or 10 electrons that occupy the electronic orbitals making up the conjugated system, which are typically un-hybridized p-orbitals.

A heterocyclic group is a group having one or more saturated or unsaturated carbon rings and which contains one to three heteroatoms (e.g., N, O or S) per ring. These groups optionally contain one, two or three double bonds. To satisfy valence requirement, a ring atom may be substituted as described herein. One or more carbons in the heterocyclic ring can be —CO— groups. Heterocyclic groups include those having 3-12 carbon atoms, and 1-6, heteroatoms, wherein 1 or 2 carbon atoms are replaced with a —CO— group. Heterocyclic groups include those having 3-12 or 3-10 ring atoms of which up to three can be heteroatoms other than carbon. Heterocyclic groups can contain one or more rings each of which is saturated or unsaturated. Heterocyclic groups include bicyclic and tricyclic groups. Preferred heterocyclic groups have 5- or 6-member rings. Heterocyclic groups are optionally substituted as described herein. Specifically, heterocyclic groups can be substituted with one or more alkyl groups. Heterocyclic groups include those having 5- and 6-member rings with one or two nitrogens and one or two double bonds. Heterocyclic groups include those having 5- and 6-member rings with an oxygen or a sulfur and one or two double bonds. Heterocyclic group include those having 5- or 6-member rings and two different heteroatoms, e.g., N and 0, 0 and S or N and S. Specific heterocyclic groups include among others among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups.

Heterocycylalky groups are alkyl groups substituted with one or more heterocycyl groups wherein the alkyl groups optionally carry additional substituents and the heterocycyl groups are optionally substituted. Specific groups are heterocycyl-substituted methyl or ethyl groups.

Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, pyridinyl, pyrazinyl, pyrimidinyl, quinolinyl, purinyl, benzofuranyl, benzothiophenyl, or indolyl groups. In a specific embodiment, the heteroaryl group is an indolyl group and more specifically is an indol-3-yl group.

Heteroatoms include O, N, S, P or B. More specifically heteroatoms are N, O or S. In specific embodiments, one or more heteroatoms are substituted for carbons in aromatic or carbocyclic rings. To satisfy valence any heteroatoms in such aromatic or carbocyclic rings may be bonded to H or a substituent group, e.g., an alkyl group or other substituent.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid, and the like.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned above are meant to comprise the therapeutically active non-toxic acid and base addition salt forms which the compounds can form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic, and like acids. Conversely, these salt forms can be converted into the free base form by treatment with an appropriate base.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine, and the like.

Some of the compounds described herein may also exist in their tautomeric form.

A "therapeutically effective amount" of the disclosed compounds is a dosage of the compound that is sufficient to achieve a desired therapeutic effect, such as an anti-tumor or anti-metastatic effect. In some examples, a therapeutically effective amount is an amount sufficient to achieve tissue concentrations at the site of action that are similar to those that are shown to modulate TCF-transcription and/or epithelial-mesenchymal transition (EMT) in tissue culture, in vitro, or in vivo. For example, a therapeutically effective amount of a compound may be such that the subject receives a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day.

The term "stereoisomer" refers to a molecule that is an enantiomer, diastereomer or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

The term "modulate" refers to the ability of a disclosed compound to alter the amount, degree, or rate of a biological function, the progression of a disease, or amelioration of a condition. For example, modulating can refer to the ability of a compound to elicit an increase or decrease in angiogenesis, to inhibit TCF-transcription and/or EMT, or to inhibit tumor metastasis or tumorigenesis.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer or a disease associated with a compromised immune system. "Preventing" a disease or condition refers to prophylactically administering a composition to a subject who does not exhibit signs of a disease or exhibits only early signs of the disease, for the purpose of decreasing the risk of developing a pathology or condition, or diminishing the severity of a pathology or condition.

As used herein, a "prodrug" is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability, and are readily metabolized into the active TOP2A inhibitors in vivo. Prodrugs of compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999. In general, protecting groups are removed under conditions which will not affect the remaining portion of the molecule. These methods are well known in the art and include acid hydrolysis, hydrogenolysis, and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known, and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds may include one or more asymmetric centers. Thus, these compounds can exist in different stereoisomeric forms. Accordingly, compounds and compositions may be provided as individual pure enantiomers or as stereoisomeric mixtures, including racemic mixtures. The compounds disclosed herein may be synthesized in, or are purified to be in, substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is itself substituted (e.g. substituted aryl). In some embodiments, the number of substituted groups linked together is limited to two (e.g. substituted alkyl is substituted with substituted aryl, wherein the substituent present on the aryl is not further substituted). In exemplary embodiments, a substituted group is not substituted with another substituted group (e.g. substituted alkyl is substituted with unsubstituted aryl).

The present invention provides novel therapeutic strategies for targeting TCF-driven EMT, a process that promotes tumor cell heterogeneity, MDR, and metastasis. The inventors' structure-based drug design has produced novel potent ATP-competitive inhibitors of TOP2A, which functions as a DNA binding factor for the TCF-transcription complex. However, unlike conventional TOP2A poisons (e.g. Etoposide), the TOP2A inhibitors of this invention do not damage DNA and thus are expected to have limited adverse effects associated with DNA damaging agents, rather, they effectively inhibit TOP2A dependent TCF-transcription leading to the reversion of EMT and associated malignant properties. Reversion of EMT by this class of compounds may be an effective treatment when used in combination with cytotoxic chemotherapy and targeted antitumor drugs as well as radiation therapy. These EMT-targeting agents may also sensitize both primary tumors and metastatic lesions to clinically relevant therapies, and potentially inhibit tumor cell metastasis.

Thus, one aspect of this invention are compounds that inhibit TOP2A enzymes with significantly improved specificity for TOP2A and can therefore be used to treat or prevent metastasis of a wide variety of advanced solid tumors and blood cancers. Pharmaceutically acceptable salts, prodrugs, stereoisomers, and metabolites of all the TOP2A compounds of this invention also are contemplated.

An aspect of this invention provides compounds, or pharmaceutically acceptable salts thereof, having the following chemical structure (formula II):

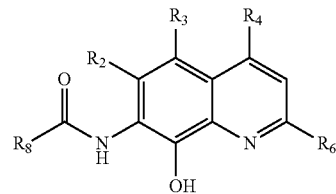

wherein:

$R^2$ is H or $OCH_3$;

$R^3$ is H or $OCH_3$;

$R^4$ is $NHR^{10}$, wherein $R^{10}$ is phenyl, benzoic acid, benzofuranyl, furyl or thienyl, or indole each optionally substituted with halogen or $C_{1-3}$ alkyl; or $R^{10}$ is phenyl optionally substituted with one or more of halogen, hydroxyl, or halomethyl; or $R^4$ is phenyl optionally substituted with one or more of halogen, hydroxyl, C1-C6 acyl, or optionally-substituted heterocyclylalkyl; or $R^4$ is benzofuranyl, furyl or thienyl each of which is optionally substituted with one or more of halogen, hydroxyl, C1-C3 alkyl or halomethyl;

$R^6$ is H, COOH or derivatives thereof, or a detectable label; and $R^6$ is H, optionally-substituted C1-C6 alkyl, or optionally-substituted heterocyclylalkyl.

In embodiments, $R^2$ is H. In embodiments, $R^3$ is hydrogen. In embodiments, $R^6$ is hydrogen. In embodiments, each of $R^2$ and $R^3$ are hydrogen. In embodiments, each of $R^2$, $R^3$ and $R^6$ are hydrogen.

In embodiments, $R^8$ is morpholino-C1-C4 alkyl.

In embodiments, $R^4$ is phenyl substituted with one or more of halogen, hydroxyl, C1-C6 acyl, or optionally-substituted heterocyclylalkyl.

In embodiments, $R^4$ is phenyl substituted with one or more of halogen or hydroxyl.

In embodiments, $R^4$ is unsubstituted furyl, thienyl or benzofuranyl.

In embodiments of formula II, each of $R^2$, $R^3$ and $R^6$ are hydrogen, $R^8$ is methyl, ethyl or n-propyl or a methyl, ethyl or propyl group substituted with an optionally-substituted heterocyclic group as illustrated in Scheme 2, and $R^4$ is a phenyl group substituted with one or more fluorine, trifluoromethyl, or hydroxyl or $R^4$ is a furyl, thienyl or benzofuranyl group.

In embodiments, $R^4$ is —$NHR^{13}$, where $R^{10}$ is an optionally-substituted heteroaryl group. In embodiments, $R^4$ is —$NHR^{10}$, where $R^{10}$ is an unsubstituted heteroaryl group. In embodiments, $R_{10}$ is indoyl. In embodiments, $R^{10}$ is indo-4-yl. In embodiments, the invention provides compound AA-29-147.

In embodiments of formula II, each of $R^2$, $R^3$ and $R^6$ are hydrogen, $R^8$ is methyl, a morpholino-substituted methyl, or a morpholino-substituted ethyl and $R^4$ is a 3-F-phenyl, 4-F-phenyl, 3-CF-phenyl, a 4-$CF_3$-phenyl, a 3-F, 6-OH-phenyl, a 1-OH, 5-trifluoromethyl-phenyl, a benzofuran-2-yl, a thien-2-yl, a thien-3-yl, a fur-2-yl, or a fury-3-yl group.

Illustrative compounds of this invention include those of Scheme 1.

Scheme 2 illustrates exemplary optionally substituted heterocyclic groups, where R represents optionally substitution with one or more oxo (=O), halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic, Y is —CH— or —N($R_N$)—, and $R_N$ is hydrogen, C1-C6 alkyl, C3-C3 cycloalkyl or a heterocyclic group. These exemplary optionally-substituted heterocyclic groups can in embodiments be substituted on C1-C6 alkyl groups as $R^8$ in the formulas herein.

Scheme 1

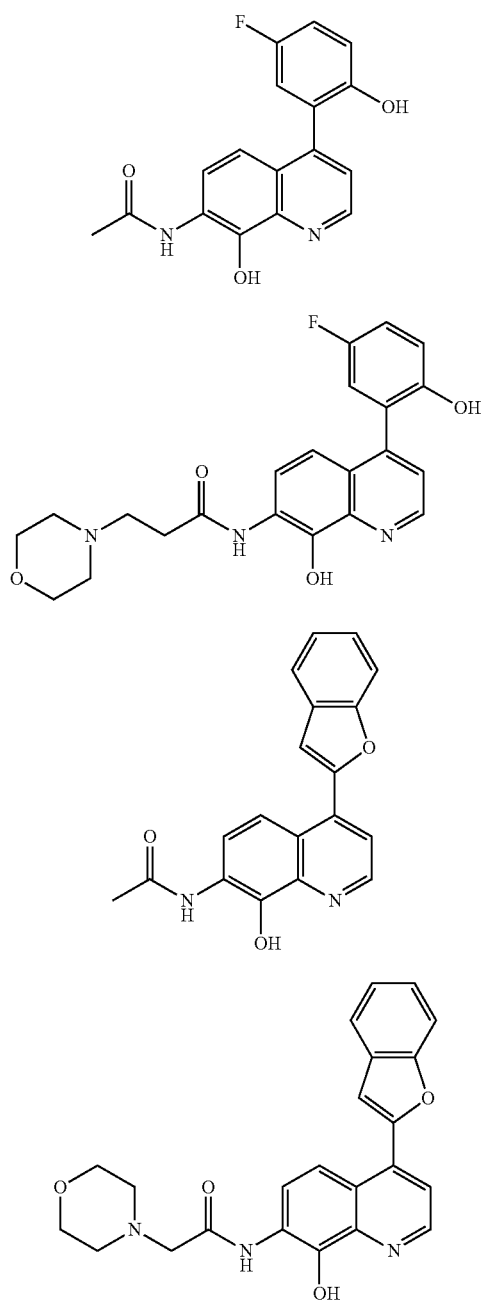

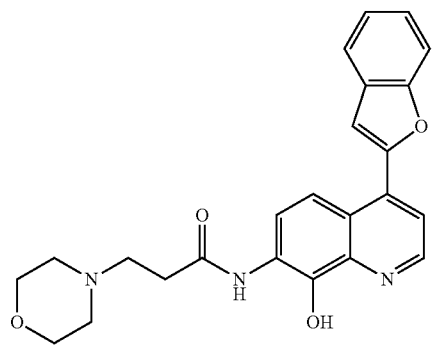

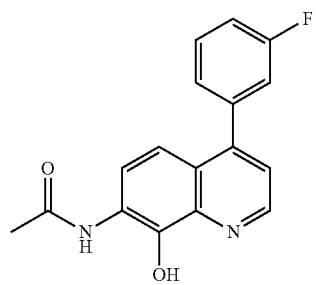

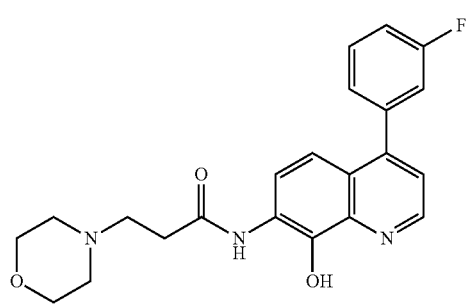

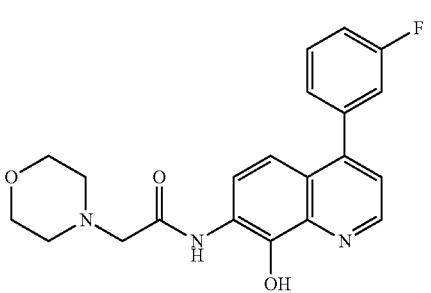

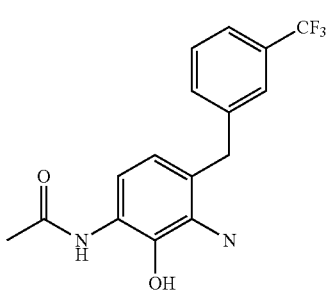

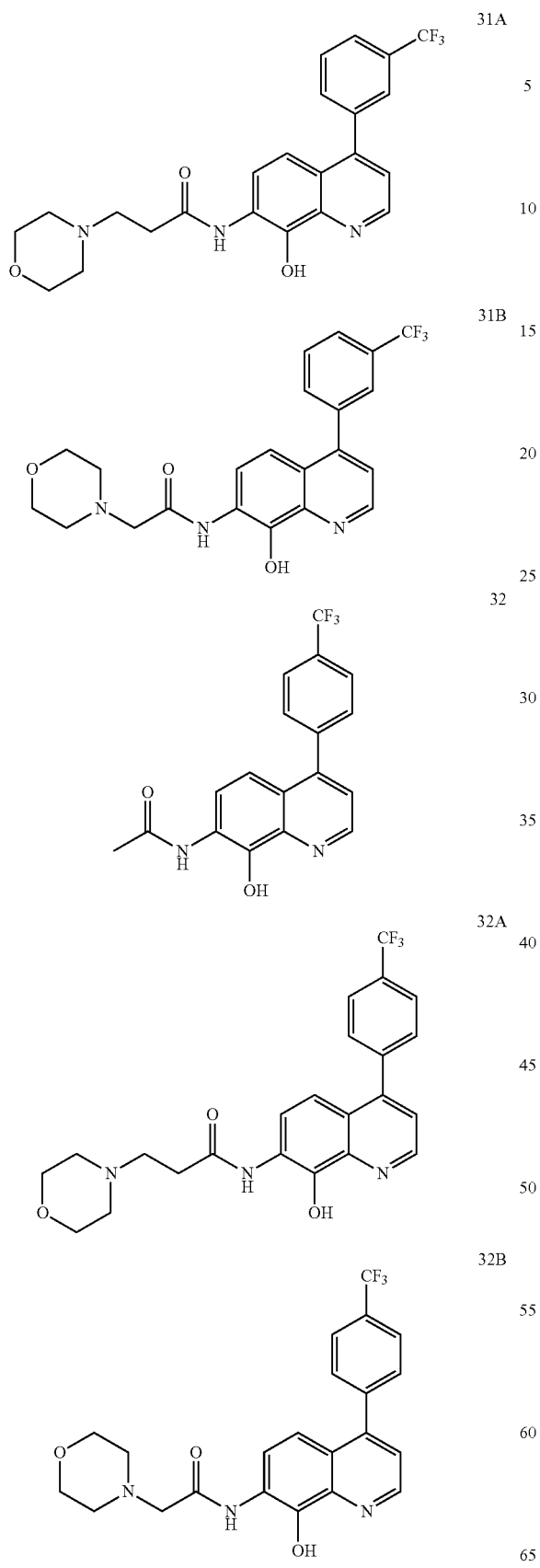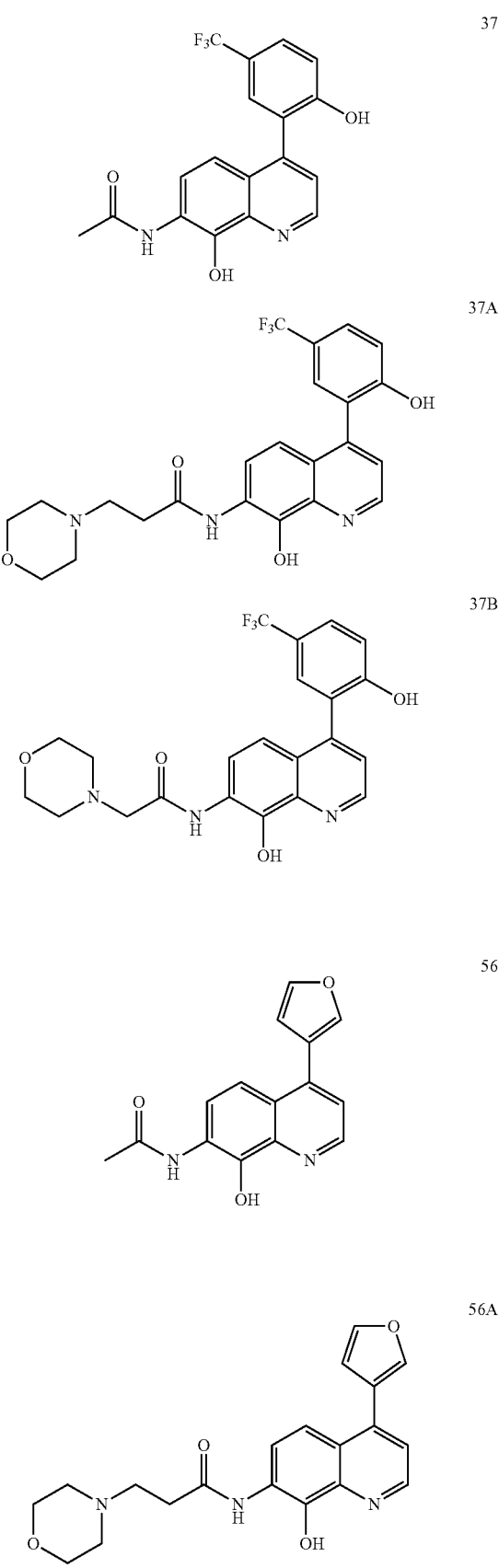

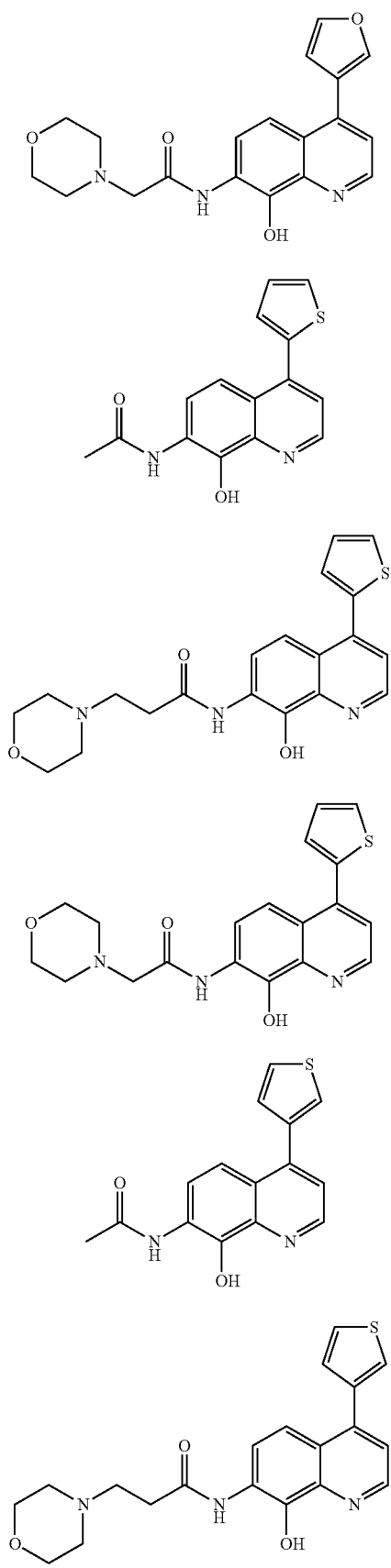
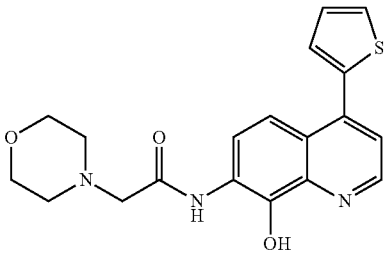
Scheme 2
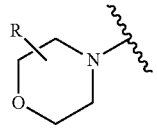 A1
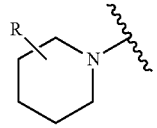 A2
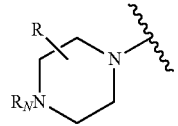 A3
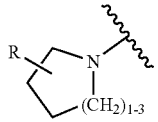 A4
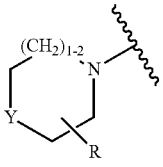 A5
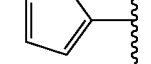 A6
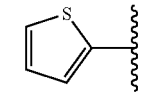 A7
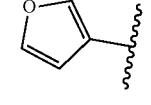 A8
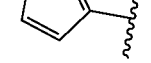 A9
The term "prodrug" includes any covalently bonded carriers that release an active TOP2A inhibitor compound of this invention in vivo when the prodrug is administered to a subject. Because prodrugs often have enhanced properties relative to the active TOP2A inhibitor, such as solubility and bioavailability, the TOP2A inhibitor compounds disclosed herein can be delivered in prodrug form. Thus, also contemplated are prodrugs of the presently disclosed TOP2A inhibitor compounds, methods of delivering prodrugs, and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs may include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. For example, a prodrug of the TOP2A inhibitor compounds of this invention may include a lower alkyl phosphonate ester, such as an isopropyl phosphonate ester.

The TOP2A inhibitor compounds, and prodrugs thereof, disclosed herein may be used to prevent, treat, or ameliorate cancer, or prevent metastasis of cancer, in a subject by administering a therapeutically-effective amount of a compound of this invention that inhibits TOP2A. For example, the disclosed compounds may be used to treat colorectal cancer, breast cancer, sarcomas, testicular cancer, lung cancer, lymphoma, leukemia, neuroblastoma, or ovarian cancer. These compounds may be particularly useful in treating colorectal cancer.

Therapeutically effective amounts of the disclosed compounds can be administered to a subject with a tumor to achieve an anti-tumor effect, such as inhibition of tumorigenesis or tumor metastasis, inhibiting TCF-transcription and epithelial-mesenchymal transition (EMT).

Further, a method for inhibiting the activity of the TOP2A in a subject using the disclosed compounds is provided. The method includes administering a therapeutically effective amount of a disclosed compound to a subject to achieve a TOP2A inhibitory effect. The compounds of this invention having TOP2A-inhibitory effects are useful for treating many malignant diseases. These include, but are not limited to, cancer, tumor growth, and cancer metastasis.

The disclosed compounds can be used in combination with other compositions and procedures for the treatment of diseases. For example, a cancer may be treated conventionally with surgery, radiation or chemotherapy in combination with one or more of the TOP2A inhibitor compounds disclosed herein. Additionally, a cancer may be treated conventionally with a chemotherapeutic and one or more of the TOP2A inhibitor compounds disclosed herein may be administered to reduce chemotherapeutic drug resistance of the cancer cells to the conventional chemotherapeutic.

Examples of other chemotherapeutic agents that can be used in combination with the disclosed compounds include 5FU, oxaliplatin, irinotecan, and biologics (e.g. bevacizumab), or combinations thereof.

The disclosed compounds also may be combined with radiotherapy employing radioisotopes (such as $^{32}P$, $^{90}Y$, $^{125}I$, $^{131}I$, and $^{177}Lu$), particle beams (such as proton, neutron and electron beams) and electromagnetic radiation (such as gamma rays, x-rays and photodynamic therapy using photosensitizers and visible or ultraviolet rays).

The disclosed compounds may be combined with pharmaceutically acceptable excipients, and optionally sustained-release matrices, such as biodegradable polymers, to form therapeutic compositions. Therefore, also disclosed are pharmaceutical compositions including one or more of any of the compounds disclosed above and a pharmaceutically acceptable carrier. The composition may comprise a unit dosage form of the composition, and may further comprise instructions for administering the composition to a subject to inhibit cancer progression or metastasis, for example, instructions for administering the composition to achieve an anti-tumor effects or to inhibit a pathological cellular proliferation. Such pharmaceutical compositions may be used in methods for treating or preventing cancer growth in a subject by administering to the subject a therapeutically effective amount of the composition.

These pharmaceutical compositions can be in the form of tablets, capsules, powders, granules, lozenges, liquid or gel preparations, such as oral, topical, or sterile parenteral solutions or suspensions (e.g., eye or ear drops, throat or nasal sprays, etc.), transdermal patches, and other forms known in the art.

Pharmaceutical compositions can be administered systemically or locally in any manner appropriate to the treatment of a given condition, including orally, parenterally, intrathecally, rectally, nasally, buccally, vaginally, topically, optically, by inhalation spray, or via an implanted reservoir. The term "parenterally" as used herein includes, but is not limited to subcutaneous, intravenous, intramuscular, intrasternal, intrasynovial, intrathecal, intrahepatic, intralesional, and intracranial administration, for example, by injection or infusion. For treatment of the central nervous system, the pharmaceutical compositions may readily penetrate the blood-brain barrier when peripherally or intraventricularly administered.

Pharmaceutically acceptable carriers include, but are not limited to, ion exchangers, alumina, aluminum stearate, lecithin, serum proteins (such as human serum albumin), buffers (such as phosphates), glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Tablets and capsules for oral administration can be in a form suitable for unit dose presentation and can contain conventional pharmaceutically acceptable excipients. Examples of these include binding agents such as syrup, acacia, gelatin, sorbitol, tragacanth, and polyvinylpyrrolidone; fillers such as lactose, sugar, corn starch, calcium phosphate, sorbitol, or glycine; tableting lubricants, such as magnesium stearate, talc, polyethylene glycol, or silica; disintegrants, such as potato starch; and dispersing or wetting agents, such as sodium lauryl sulfate. Oral liquid preparations can be in the form of, for example, aqueous or oily suspensions, solutions, emulsions, syrups or elixirs, or can be presented as a dry product for reconstitution with water or other suitable vehicle before use.

The pharmaceutical compositions can also be administered parenterally in a sterile aqueous or oleaginous medium. The composition can be dissolved or suspended in a non-toxic, parenterally-acceptable diluent or solvent, e.g., as a solution in 1,3-butanediol. Commonly used vehicles and solvents include water, physiological saline, Hank's solution, Ringer's solution, and sterile, fixed oils, including synthetic mono- or di-glycerides, etc. For topical application, the drug may be made up into a solution, suspension, cream, lotion, or ointment in a suitable aqueous or non-aqueous vehicle. Additives may also be included, for example buffers such as sodium metabisulphite or disodium edeate; preservatives such as bactericidal and fungicidal agents, including phenyl mercuric acetate or nitrate, benzalkonium chloride or chlorhexidine, and thickening agents, such as hypromellose.

The dosage unit involved depends, for example, on the condition treated, nature of the formulation, nature of the condition, embodiment of the claimed pharmaceutical compositions, mode of administration, and condition and weight of the patient. Dosage levels are typically sufficient to achieve a tissue concentration at the site of action that is at least the same as a concentration that has been shown to be active in vitro, in vivo, or in tissue culture. For example, a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day can be useful for treatment of a particular condition.

The compounds can be used in the form of pharmaceutically acceptable salts derived from inorganic or organic acids and bases, including, but not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include, but are not limited to, ammonium salts, alkali metal salts (such as sodium and potassium salts), alkaline earth metal salts (such as calcium and magnesium salts), salts with organic bases (such as dicyclohexylamine salts), N-methyl-D-glucamine, and salts with amino acids (such as arginine, lysine, etc.). Basic nitrogen-containing groups can be quaternized, for example, with such agents as C1-8 alkyl halides (such as methyl, ethyl, propyl, and butyl chlorides, bromides, and iodides), dialkyl sulfates (such as dimethyl, diethyl, dibutyl, an diamyl sulfates), long-chain halides (such as decyl, lauryl, myristyl, and stearyl chlorides, bromides, and iodides), aralkyl halides (such as benzyl and phenethyl bromides), etc. Water or oil-soluble or dispersible products are produced thereby.

Pharmaceutically acceptable salts of the presently disclosed TOP2A inhibitor compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function, such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

Each publication or patent cited herein is incorporated herein by reference in its entirety. The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

The invention expressly includes pharmaceutically usable solvates of compounds according to formulas herein. Specifically useful solvates are hydrates. The compounds of formulas herein and salts thereof can be solvated (e.g., hydrated). The solvation can occur in the course of the manufacturing process or can take place (e.g., as a consequence of hygroscopic properties of an initially anhydrous compound of formulas herein (hydration)).

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. A prodrug is an active or inactive compound that is modified chemically through in vivo physiological action, such as hydrolysis, metabolism and the like, into an active compound following administration of the prodrug to a subject. The term prodrug as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability, and are readily metabolized into the active TOP2A inhibitors in vivo. Prodrugs of compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

All references throughout this application, for example patent documents including issued or granted patents or equivalents; patent application publications; and non-patent literature documents or other source material; are hereby incorporated by reference herein in their entireties, as though individually incorporated by reference. All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (e.g., to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of the group and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the invention.

When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Additionally, unless otherwise specified, all isotopic variants of compounds disclosed herein are intended to be encompassed by the invention. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the invention herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

CHD1 L inhibitors of this invention are commercially available or can be prepared without undue experimentation by the methods disclosed herein or by routine adaptation of such methods using starting materials and reagents which are commercially available or which can be made by known methods. It will be appreciated that it may be necessary, dependent upon the compound to be synthesized, to protect potentially reactive groups in starting materials from undesired conjugation. Useful protective groups, for various reactive groups are known in the art, for example as described in Wutts, P. G. and Greene, T. (2007) Green's Protecting Groups in Organic Synthesis (Fourth Edition) John Wiley & Sons, N.Y.

Compounds herein be in the form of salts, for example ammonium salts, with a selected anion or quaternized ammonium salts. The salts can be formed as is known in the art by addition of an acid to the free base. Salts can be formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In specific embodiments, compounds of the invention can contain one or more negatively charged groups (free acids) which may be in the form of salts. Exemplary salts of free acids are formed with inorganic base include, but are not limited to, alkali metal salts (e.g., Li+, Na+, K+), alkaline earth metal salts (e.g., Ca2+, Mg2+), non-toxic heavy metal salts and ammonium (NH4+) and substituted ammonium (N(R')4+ salts, where R' is hydrogen, alkyl, or substituted alkyl, i.e., including, methyl, ethyl, or hydroxyethyl, specifically, trimethyl ammonium, triethyl ammonium, and triethanol ammonium salts), salts of cationic forms of lysine, arginine, N-ethylpiperidine, piperidine, and the like. Compounds of the invention can also be present in the form of zwitterions. Compound herein can be in the form of pharmaceutically acceptable salts, which refers to those salts which retain the biological effectiveness and properties of the free bases or free acids, and which are not biologically or otherwise undesirable.

The scope of the invention as described and claimed encompasses the racemic forms of the compounds as well as the individual enantiomers and non-racemic mixtures thereof. The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis. In a preferred embodiment of the invention, enantiomers of the invention exhibit specific rotation that is +(positive). Preferably, the (+) enantiomers are substantially free of the corresponding (−) enantiomer. Thus, an enantiomer substantially free of the corresponding enantiomer refers to a compound which is isolated or separated via separation techniques or prepared free of the corresponding enantiomer. "Substantially free," means that the compound is made up of a significantly greater proportion of one enantiomer. In preferred embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N.Y., 1962); Wilen, S. H. Tables of Resolving Agents and Optical Resolutions p. 268 (E. L. Eliel, Ed, Univ. of Notre Dame Press, Notre Dame, Ind. 1972).

Compounds of the invention, and salts thereof, may exist in their tautomeric form, in which hydrogen atoms are transposed to other parts of the molecules and the chemical bonds between the atoms of the molecules are consequently rearranged. It should be understood that all tautomeric forms, that may exist, are included within the invention.

Every formulation, compound or combination of components described or exemplified herein can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, alternative therapies, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the invention.

The singular terms "a," "an," and "the" include plural referents unless context clearly indicates otherwise. Similarly, the word "or" is intended to include "and" unless the context clearly indicates otherwise. The term "comprises" means "includes." Also, "comprising A or B" means including A or B, or A and B, unless the context clearly indicates otherwise. It is to be further understood that all molecular weight or molecular mass values given for compounds are approximate and are provided for description. Although methods and materials similar or equivalent to those described herein can be used in the practice or testing of this invention, suitable methods and materials are described below. In addition, the materials, methods, and examples are illustrative only and not intended to be limiting.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions that have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

The following experimental methods were used in the following 8 Examples. General Experimental Section. All commercial chemicals were used as supplied unless otherwise stated. All solvents used were dried and distilled using standard procedures. All reactions were performed under an inert atmosphere of ultrapure nitrogen with oven-dried glassware unless otherwise noted. All organic extracts were dried over sodium sulfate. Thin layer chromatography (TLC) was performed using Aluminum backed plates coated with 60 Å Silica gel F254 (Sorbent Technologies, Norcross, Ga., USA). Plates were visualized using a UV lamp (λmax=254 nm). Column chromatography was carried out using 230-400 mesh 60 Å silica gel. Proton (δH) and carbon (δC) nuclear magnetic resonances were recorded on a Bruker Avance III 400 ($^1$H 400 MHz, $^{13}$C 100 MHz). Varian 500 MHz spectrometer (500 MHz proton, 125.7 MHz carbon). All chemical shifts are recorded in parts per million (ppm), referenced to residual solvent frequencies ($^1$H NMR: Me4Si=0, CDCL$_3$=7.26, D$_2$O=4.79, CD$_3$OD=4.37 or 3.31, DMSO-d6=2.50, Acetone-d6=2.05 and $^{13}$C NMR: CDCl$_3$=77.16; CD$_3$OD=49.0, DMSO-d6=39.5, Acetone-d6=29.9 Coupling constants (J) values are expressed in hertz (Hz). The following splitting abbreviations were used: s=singlet, d=doublet, t=triplet, q=quartet, p=pentet, m=multiplet, br=broad, dd=doublet of doublets, dt=doublet of triplets, td=triplet of doublets. High-resolution mass spectra (HRMS) were recorded on a Bruker Q-TOF-2 Micromass spectrometer equipped with lock spray, using ESI with methanol as the carrier solvent. Accurate mass measurements were performed using leucine enkephalin as a lock mass and the data were processed using MassLynx 4.1. Exact m/z values are reported in Daltons. HRMS were also recorded using Q Exactive mass spectrometer (Thermo Fisher Scientific, San Jose, CA, USA) operated independently in positive or negative ion mode, scanning in full MS mode (2 ρscans) from 150 to 1500 m/z at 140,000 resolution, with 4 kV spray voltage, 45 sheath gas, 15 auxiliary gas. Acquired data were then converted from raw to mzXML file format using Mass Matrix (Cleveland, OH, USA). Metabolites assignments, isotopologue distributions, and correction for expected natural abundances of deuterium, $^{13}$C, and $^{15}$N isotopes were performed using MAVEN (Princeton, NJ, USA). Melting points (m.p.) were determined using a Stuart melting point apparatus (SMP20 and SMP40) and the values are uncorrected. Infrared (IR) spectra were recorded on a Thermo Nicolet vatar 360 FT-IR fitted with a Smart Orbit diamond ATR sampler (oils and solids were examined neat), and Bruker ALPHA platinum ATR. Absorption maxima (#max) are recorded in wavenumbers (cm−1).

Compounds with relevant biological activity were assessed by NMR and HPLC with purity≥95% as determined by Shimadzu prominence HPLC system equipped with a photodiode array detector (PDA) and a Phenomenex Kinetex C18 reverse phase column (5 μm, 100 Å, 250 mm×4.6 mm) with a flow rate of 1.0 mL/min. Compounds were eluted with a gradient of methanol to water over 25-40 minutes.

General Methods for Suzuki Coupling. To 1 molar equivalent of intermediates 5, 8-10, were added 2 molar equivalents of boronic acids, 3 molar equivalents of $K_2CO_3$ or $Cs_2CO_3$, 0.1 molar equivalents of Pd(II) acetate, 0.1 molar equivalent of DPPE (ligand) and dioxane/$H_2O$ (10:1). The mixture was heated at 80-85° C. under $N_2$ for 1-5 hr. The reaction was cooled to room temperature and filtered over a pad of celite and washed with ethyl acetate. The filtrate was concentrated in vacuo to remove the solvent to give a crude coupling product. The crude product was chromatographed using silica gel as the adsorbent medium, while the mobile phase consists of hexanes (0-30%) in ethyl acetate to afford pure product from 80-90% yield.

Inhibition of TOP2A activity. Human TOP2A, kDNA, and assay buffers were obtained from TopoGEN (Buena Vista, CO). The synthesized compounds were screened for their TOP2A inhibitory activity by the intensity of DNA decatenation bands on a DNA gel when compared to the vehicle. Compounds were initially incubated with TOP2A (3 U/reaction) for 20 min at a 30 μM and 1.2% DMSO concentration in a 37° C. incubator without $CO_2$.

The decatenation reaction was initiated immediately after by adding 2 mM ATP and 35 ng/reaction of kDNA, then incubated for 1 hour in a 37° C. water bath. The samples were loaded into a 0.8% agarose gel in 1× Tris-Borate-EDTA (TBE) at a 0.2 μg/mL ethidium bromide concentration and allowed to run in an electrophoretic chamber for 1 hour at 100V. Compounds with the highest inhibitory activity were selected for 2-fold serial dilution dose-response assays (58.6 nM-30 μM). The dose-response assays followed the same protocol with the exception of 4 U/reaction of TOP2A.

TOP2A inhibition (Michaelis-Menten). TOP2A Mode of Inhibition was tested with a relaxation assay and the inorganic phosphate (pi) generated was measured with phosphate reagent (Abcam) in black polystyrene 384-well assay plates (Thermo Fisher Scientific). ATP-dependent DNA relaxation assays in 15 μl contained 2 U hTopoIIa (Topogen), 85 μg/mil (10 nM) supercoiled plasmid (a gift from AstraZeneca), and various concentrations of ATP (between 0 and 1800 nM) and analog 3 and 7 (between 0 and 20 μM) in 50 mM Tris-HCl (pH 7.5), 150 mM KCl, 5% (v/v) glycerol, 10 mM $MgCl_2$, 1 mM dithiothreitol, 0.002% (w/v) Brij-35, and 200 nM bovine serum albumin (BSA). A duplicate plate was prepared in the same way except for the omission of the enzyme. Reactions were conducted at 37° C. for 1 hour. An addition of 70 μL of dd$H_2O$ and 15 μL of phosphate reagent were added to each well and the plates were incubated in dark at room temp for 30 min before $OD_{600}$ was read with a BioTek plate reader.

3D cell culture. Cell lines were cultured as tumor organoid using phenol red free RPMI-1640 containing 5% FBS. Tumor organoid were generated by seeding 20,000 cells/well into un-coated 96-well U-bottom Ultra Low Attachment Microplates (Corning Inc.) and centrifuging for 15 min at 1000 rpm for cells to aggregate. A final concentration of 2% Matrigel™ was then added and tumor organoid were formed for 3 days before treatment.

VimPro-GFP and EcadPro-mCherry reporter assays. VimPiro-GFP: SW620 cells were first transduced with NucLight Red virus (Essen BioSciences) and selected with Zeocin at 200 μg/mL, and then transduced with pCDH-VimPro-GFP-EF1-puro virus and selected with puromycin at 4 μg/mL. The dual fluorescently labeled cells were plated and treated in 3D tumor organoid as described. Tumor organoid images were recorded every 2 hours over a 72 hours period using an incucyte ZOOM content imaging system (Essen BioSciences) or PerkinElmer Phenix imager (PerkinElmer).

EcadPro-mCherry: SVW620 cells were transduced with pCDH-EcadPro-mCherry-EF1-puro virus and selected with puromycin at 4 μg/mL. Cells were plated and treated in 3D tumor organoid as described. Tumor organoid were stained with 16 μM of Hoechst 33342 for 1 hour before images were recorded using a PerkinElmer Phenix imager (PerkinElmer).

Tumor organoid cytotoxicity. Fluorescence image-based method: The CellTox™ Green assay (Promega, Madison, WI, USA) was used with 3D tumor organoid to measure spheroid death. 0.1% CellTox™ Green was included in each well at the time of analogs dosing. 10% lysis solution was used as a cell death control. Fluorescence was measured at various time points with 465-510 nm excitation and 520-530 nm emission. Luminescence plate reader method: A 1:1 ratio of CellTiter-Glo™ 3D reagent (Promega) was added to 3D tumor organoid and the plate was shaken at 400 rpm for 30 min before luminescence was read with a PerkinElmer Envision plate reader.

TCF reporter assay in 3D Tumor organoid. Stable engineered cells containing pCDH-TOPflash-luc-EF1-puro were used to generate tumor organoid arrayed in 96-well plates and treated for 72 hours. One-Glo™ luciferase reagent and CellTiter-Glo™ 3D cell viability reagent (Promega) were used to determine the TCF reporter activity in viable cells.

Clonogenic assay. SW620 cells were plated to allow for 70% confluency within 24 hours. Analogs 3, 7, and vehicle (DMSO) were then added to cells for 24 hours as pretreatment. A total of 1000 viable cells per well were plated into a six-well plate and medium was changed 2× per week. After 10 days in culture, the medium was removed and cells colonies were washed with PBS and fixed with acetic acid:methanol (1:7 v-v) at room temperature for 5 min. The fixed colonies were stained with 0.5% (w/v) crystal violet in 25% (v/v) methanol solution for 2 hours at room temperature. The stain was rinsed off with water and the plate was air dried at room temperature. Digital pictures were taken, and the images were saved in greyscale (8-bit). Images were adjusted for threshold with imaged software (Bethesda, MD, USA), the area of analysis was circled, and particles were analyzed by size (100-2000) and circularity (0.5-1).

3D clonogenic assay. SW620 cells were grown in monolayer in RPMI-1640 media supplemented with 5% FBS, then seeded at 20,000 cells/well in an ultra-low attachment 96-well plate (PerkinElmer, MA) supplemented with Matrigel (Corning, NY). The SW620 organoids were cultured for 72 hours, then treated with 10 μM of analogs in 0.19% DMSO for an additional 72 hours. Afterwards, the organoids were collected and dissociated using 0.25% Trypsin-EDTA for 5-10 min, then neutralized in FBS containing media, spun down at 500 g, and resuspended in media. Suspended cells were then counted, and only live cells were plated at 1,000 cells/well in a 6-well plate in 2 mL of growth medium. After 7 days of culture, a whole well image was obtained using the Incucyte S3 (Sartorius, Germany). Colonies were counted using the Incucyte S3 2018 Å software with the following parameters: "Segmentation Adjustment 0"; "Hole Fill (μm$^2$)=0"; "Area (μm$^2$) min: 1×10$^4$ max: 4×10$^5$"; No filter restrictions for "Eccentricity".

γ-H2AXDNA damage assay. Colon cancer cell lines HT29 and SW620 were plated to black clear bottom 96 well plates at 20,000 cells/well in 100 μL of phenol red free medium. After cells attached, various concentrations of neo, 7 and etoposide were added for 6 or 24 hours. Cells were fixed with 4% paraformaldehyde at room temp for 20 min, washed 3 times with 400 μL/well of PBS, permeabilized and blocked with 100 μL of 3% BSA and 0.1% IGEPAL in PBS for 20 min. Cells were then incubated in γ-H2AX primary antibody (Cell Signaling, 1:400 dilution) at 4° C. overnight, washed 4 times with PBS, and incubated with FITC conjugated anti-rabbit secondary antibody (Cell Signaling, 1:200 dilution) at room temp for 1 hour, and washed 4 times with PBS. Cells were stained with 10 μM of Hoechst 33342 at room temp for 10 min, washed 4 times with PBS before imaged with a 20× objective using PerkinElmer Operetta imager.

3D Invasion Assay. SW620 cells were transduced with NucLight®-Red virus (Essen BioSciences, MI) and selected with Zeocin (200 μg/mL). Transduced cells were cultured in RPMI-1640 media supplemented with 5% FBS and allowed to grow in a 10 cm$^2$ dish until ~80% confluent. Afterwards, cells were plated in a CellCarrier Spheroid Ultra-Low Attachment 96-well plate (PerkinElmer, MA) at 5,000 cells/well in 2% Matrigel (Corning, NY) and allowed to grow for 72 hours. Cells were then treated with 10 μM of analogs at 01% DMSO and cultured for an additional 72 hours. Organoids were then collected, half a 96-well plate per treatment condition, spun down at 500 g, washed with PBS, and dissociated with 500 μL of Cultrex® Organoid Harvesting Solution (Trevigen, MD) for 30 min in ice with moderate mixing. Single cells were then spun down at 500 g, the supernatant was discarded, cells were washed with PBS, re-centrifuged, and resuspended in RPMI-1640 media supplemented with 0.5% FBS. Live cells were counted and then plated in an Incucyte® ClearView 96-well cell migration plate (Essen BioSciences, MI) in a 1:1 ratio of Matrigel (Corning, NY) and RPMI-1640 media supplemented with 0.5% FBS and 1% penicillin/streptomycin at 5,000 cells/well. The plate was spun down at 50 g for 3 min at 4° C. Afterwards, the migration plate was placed on a 37° C. pre-warmed CoolSink 96F plate (Essen BioSciences) for polymerization of Matrigel and was incubated for 1 hour at 37° C. in a tissue culture incubator. Finally, 200 μL of RPMI-1640 media supplemented with 20% FBS and 1% penicillin/streptomycin was added to the bottom wells and 40 μL of media in 0.5% FBS was added to the top chamber wells. The Incucyte® ClearView 96-well cell migration plate was prepared as per manufacturer's protocol. Briefly, the plate was maintained in a CoolBox™ 96F system with a frozen gel pack for uniform cooling and the membrane was hydrated in ice cold PBS for 20 min prior to the addition of cells. All cell handling was performed in ice or at 4° C. to avoid polymerization of Matrigel until its corresponding protocol step. Cell invasion was monitored using the Incucyte® ZOOM imaging system (Essen BioSciences, MI) for bottom fluorescence of invading cells per manufacturer's recommendations.

CADD Molecular Modeling Method. Computer aided drug design were performed using the Discovery Studio (Dassault Systemes Biovia). The crystal structure of Topolla (PDB:1ZXM, 1.87 Å) was obtained from the protein data bank and prepared using the CHARM force field in the Discovery Studio. Water molecules were removed, and the residues were corrected for physiological pH. Binding sites were identified as stated in the discovery studio protocol and were defined as whole residues within a 10 Å. Neo and other analogs were prepared using discovery studio and preferred to not generate isomers of the analogs prepared. The receptor and the rest analogs were minimized based on Discovery Studio algorithm using a root-mean-square gradient tolerance of 3. The CDOCKER and Libdock protocol were used for the docking studies of neo and its analogs in the ATP binding site. The CDOKER approach was set to generate 10 poses of each analogs, while the Libdock was set to generate 100 poses of each analog. Top ranked poses were analyzed for binding interactions.

Mass spectrometry analysis and Sample preparation. Tumor tissue was isolated, flash frozen in liquid nitrogen, and stored at −80° C. until analysis. Prior to LC-MS analysis, samples were milled in liquid nitrogen and weighed. Tissue was then placed in tubes containing ~50-75 μL of glass beads (NextAdvance SKU GB10), resuspended to 15 mg/ml in methanol:acetonitrile:water (5:3:2, v:v:v) and processed using a Bullet Blender® (Next Advance, Troy, NY, USA) for 5 minutes at level 4 at 4° C. Suspensions were then vortexed continuously for 30 min at 4° C. Insoluble material was removed by centrifugation at 10,000 g for 10 min at 4° C. and supernatants were isolated for metabolomics analysis by UHPLC-MS. Standard curves were prepared by serial dilution of the purified AA-29-141 compound into a pool of vehicle-treated tumor extract.

UHPLC-MS analysis for quantification of 42 in tumor tissue. Analyses were performed as previously published. Briefly, the analytical platform employs a Vanquish UHPLC system (Thermo Fisher Scientific, San Jose, CA, USA) coupled online to a Q Exactive mass spectrometer (Thermo Fisher Scientific, San Jose, CA, USA). Samples were resolved over a Kinetex C18 column, 2.1×150 mm, 1.7 μm particle size (Phenomenex, Torrance, CA, USA) equipped with a guard column (SecurityGuard™ Ultracartridge—UHPLC C18 for 2.1 mm ID Columns—AJO-8782—Phenomenex, Torrance, CA, USA) using an aqueous phase (A) of water and 0.1% formic acid and a mobile phase (B) of acetonitrile and 0.1% formic acid. Samples were eluted from the column using either an isocratic elution of 5% B flowed at 250 μl/min and 25° C. or a gradient from 0-5% B over 0.5 min; 5-95% B over 0.6 min, hold at 95% B for 1.65 min; 95-5% B over 0.25 min; hold at 5% B for 2 min, flowed at 450 μl/min and 35° C. The Q Exactive mass spectrometer (Thermo Fisher Scientific, San Jose, CA, USA) was operated independently in positive or negative ion mode, scanning in Full MS mode (2 μscans) from 60 to 900 m/z at 70,000 resolution, with 4 kV spray voltage, 45 shealth gas, auxiliary gas. Calibration was performed prior to analysis using the Pierce™ positive and Negative Ion Calibration Solutions (Thermo Fisher Scientific). Acquired data was then converted from raw to mzXML file format using Mass Matrix (Cleveland, OH, USA). Metabolite assignments, isotopologue distributions, and correction for expected natural abundances of deuterium, $^1$C, and $^{15}$N isotopes were performed using MAVEN (Princeton, NJ, USA).

Graphs were plotted through GraphPad Prism 5.0 (GraphPad Software Inc., La Jolla, CA, USA) and Excel (Microsoft, Redmond, WA, USA).

Example 1

Structure Based Drug Design

An in silico molecular model was developed using neo and the crystal structure of the N-terminal ATPase domain of TOP2A (PDB:1ZXM, 1.87 Å) (Ponder, et al., *Mar. Drugs* 2011, 9, 2397-408; Wei, et al., J. Biol. Chem. 2005, 280, 37041-7; Li, et al., *Mar. Drugs* 2014, 12, 4833-50). Molecular docking studies using this model showed neo preferentially binds to the TOP2A N-terminal ATP-binding sites compared to other sites in the TOP2A structure. Neo is anchored in the ATP-binding site through a network of hydrogen bonds with Ser148 and Asn150, and through a charge transfer π-cation interaction within the active site magnesium ion (FIG. 1A). Neo's binding interactions mimic those of the non-hydrolysable form of ATP, 5-adenylyl-imidodiphosphate (AMPPNP), including hydrophobic interactions with adenine and H-bonds between the ribose ring and Ser148 and Asn150. Based on these docking studies, it was concluded that the flat 5-membered pyrido acridine ring system of neo is dispensable and that neo's interactions with Ser148, Asn150, and magnesium are key to its biological activity. Therefore, the pharmacophore of neo was characterized as the substituted quinoline shown as red bonds in the 2D structure of FIG. 1A. In addition, the flat pyrido acridine ring was postulated to be the primary cause of neo's unfavorable PK disposition by hindering diffusion through lipophilic barriers. Using computer-aided drug design (CADD) and the pharmacophore of neo, novel TOP2A ATP-competitive inhibitors were designed. The design goals were to increase interactions between the hydrophobic region (blue), hydrophilic region (green), magnesium ion (pink), and the Walker A motif (orange), while maintaining the key H-bonding observed with neo (FIG. 1A), and to optimize these inhibitors for in vivo efficacy, overcoming the poor PK disposition observed with neo.

Deconstructing neo's pyridoacridine ring using retro synthetic analysis provided known intermediate 1, which was used in conjunction with CADD to design and prepare compounds 2 and 3 (FIG. 1D). CADD revealed that the 8-methoxy group of 2 lost key H-bonding with Ser148 and Asn150, which appears to be due to steric effects. However, the 8-hydroxy functionality of compound 3 anchors in the ATP site similar to neo and maintains H-bonding interactions with Asn150 (FIG. 1B). In addition, 3 forms a 2n-lone pair interaction with Ser149 and the amide group in the 7-position forms favorable chelation interactions with the active site magnesium ion. CADD also revealed that the 4-phenyl ring system of 3 could be functionalized to increase van der Waals and other interactions in the ATP binding site. Furthermore, the 5-methoxy group of 3 appears to be dispensable with no observed interactions in the ATP-binding site. As a result, compounds 3 was further optimized to generate 4-aryl analogs exemplified by compound 7 that is prepared from intermediate 4 in three steps (FIG. 4E). Compound 7 also anchors in the ATP-binding site similar to neo, maintaining H-bonding with Ser148 and Asn150, but also forms more interactions compared to 3 and neo (FIG. 1C). Interestingly, 7 forms a fluoro-halogen hydrogen bond with Asn120, and this type of bonding interaction is favorable in drug design strategies.

Figure 1E:
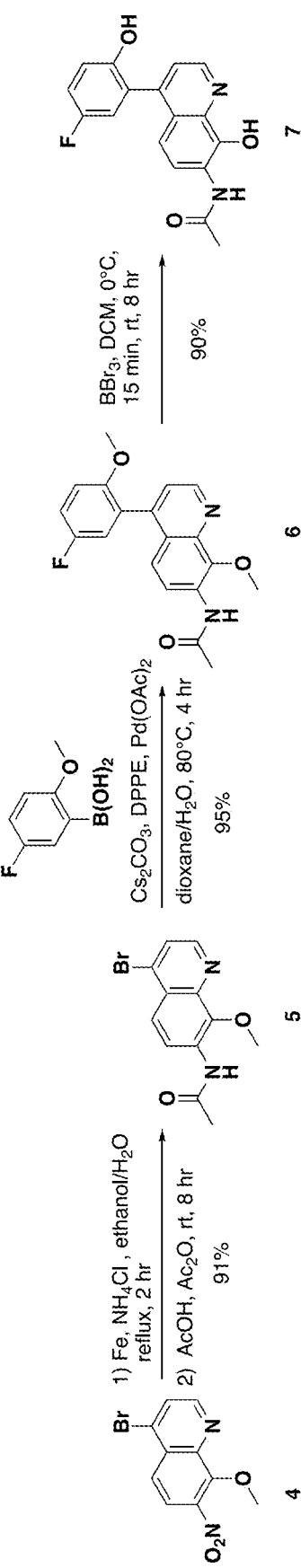

The synthesis of 3 starts with catalytic reduction of the nitro group of 1, followed by acylation using acetic anhydride and benzoyl chloride to provide 2 in good yield (FIG. 1D). Selective demethylation of 2 using lithium iodide and 2,6-lutidine gave 3 in 90% yield. Compound 7 was synthesized from 4 by catalytic reduction of the nitro group, followed by acetylation using acetic acid and acetic anhydride, providing 5 (FIG. 1E). Next, Suzuki cross coupling using phenyl boronic acids in the presence of 1,2-bis(diphenylphosphino)ethane (DPPE), cesium carbonate, palladium (II)acetate and intermediate 5 was used to obtain coupled products 6 in 95% yield. The final product was obtained by demethylation of the methoxy groups using borontribromide (BBr$_3$), which afforded 7 in 90% yield.

Example 2

Biological Evaluation of Compounds 3 and 7

To validate the drug design, biological evaluation of compounds 3 and 7 was conducted using TOP2A recombinant enzyme inhibition studies, 2D cell models, and 3D tumor organoid models to measure TOP2A-dependent TCF-transcription (TOPflash assay) and the reversion of EMT using biomarker reporters of E-cadherin promoter mCherry red fluorescent protein (EcadPro-RFP) and Vimentin promoter green fluorescent protein (VimPro-GFP). Like neo, and consistent with the drug design, both compounds 3 and 7 maintain a competitive mode of TOP2A inhibition, measured by Michaelis-Menten kinetics of ATP hydrolysis using our established malachite green assay (FIG. 2A). For enzyme reactions treated with neo, 3 and 7, the $V_{max}$ does not change but the $K_M$ significantly changes, indicating a competitive mode of inhibition. Despite being TOP2A inhibitors, neo and the novel quinoline pharmacophore do not damage DNA compared to the TOP2A poison etoposide, which generates DNA double stranded breaks (DSB) (FIG. 2B). This was demonstrated using three different TOP2A ATP-competitive inhibitors neo, compound 7, and benzo-amino purine (BAP-1, developed by Novartis) measuring DSB by γ-H2AX staining. γ-H2AX is a clinical pharmacodynamics (PD) biomarker used to assess DNA damaging chemotherapy in patients. Bates et al. proposed that the energy of ATP hydrolysis by TOP2A is used to strengthen both TOP2A homodimer interactions and TOP2A-DNA interactions by inducing favorable binding conformations, which increases binding affinity for DNA (Bates, et al., Nucleic Acids Res. 2011, 39:6327-39). This theory agrees with the findings presented here.

Example 3

Testing TOP2A-Dependent TCF-Transcription

After characterizing 3 and 7 as TOP2A ATP-competitive inhibitors, these compounds were next tested for their ability to inhibit TOP2A-dependent TCF-transcription using the well characterized TOPflash (TOP) luminescent reporter, which was used to generate a stably transduced SW620-TOP reporter cells as described previously (Zhou, et al., Oncogene 2016, 35:4990-9). These cells were used to generate single 3D tumor organoids (700 μm in diameter) uniformly arrayed in 96-well plates, which mimic aspects of tumor function observed in vivo. Both compounds 3 and 7 significantly inhibit TOP-activity (FIGS. 3A and 3B), which correlates with a dose-dependent downregulation of vimentin and upregulation of E-cadherin measured by VimPro-GFP and EcadPro-RFP biomarker reporter activity in SW620 tumor organoids, providing effective concentration 50% ($EC_{50}$) values for the reversion of EMT (FIGS. 3C and 3D). Like neo, the mode of action of compounds 3 and 7 also results in significant antitumor activity (FIGS. 3E-3H). Pretreating SW620 cells with 3 or 7 for 24 hours, followed by washing and plating viable cells for the clonogenic assay, is sufficient to inhibit colony formation over 7 days compared to the DMSO control. In other words, the activity of 3 and 7 is long lasting, suppressing CSC stemness and related tumorigenicity. EMT is a major driving force promoting tumor cell invasion and metastasis. To assess if the reversion of EMT by 3 or 7 also inhibits the invasive potential, SV620 tumor organoids were treated as indicated over 72 hours. Tumor organoids were dissociated, and viable cells were washed and plated into the top chamber of 96-well invasion plate coated with Matrigel and incubated for an additional 72 hours without adding any additional compound. The results demonstrate that both 3 and 7 inhibit the invasive potential of SW620 tumor organoids cells. Taken together, the biological activity of 3 and 7 is consistent with the activity of neo, inhibiting TOP2A-dependent TCF-transcription that in turn reverses EMT while inhibiting the associated tumorigenic properties of mCRC.

Example 4

Further Drug Design and Synthesis of Prototype 7 Analogs

Figure 4A:
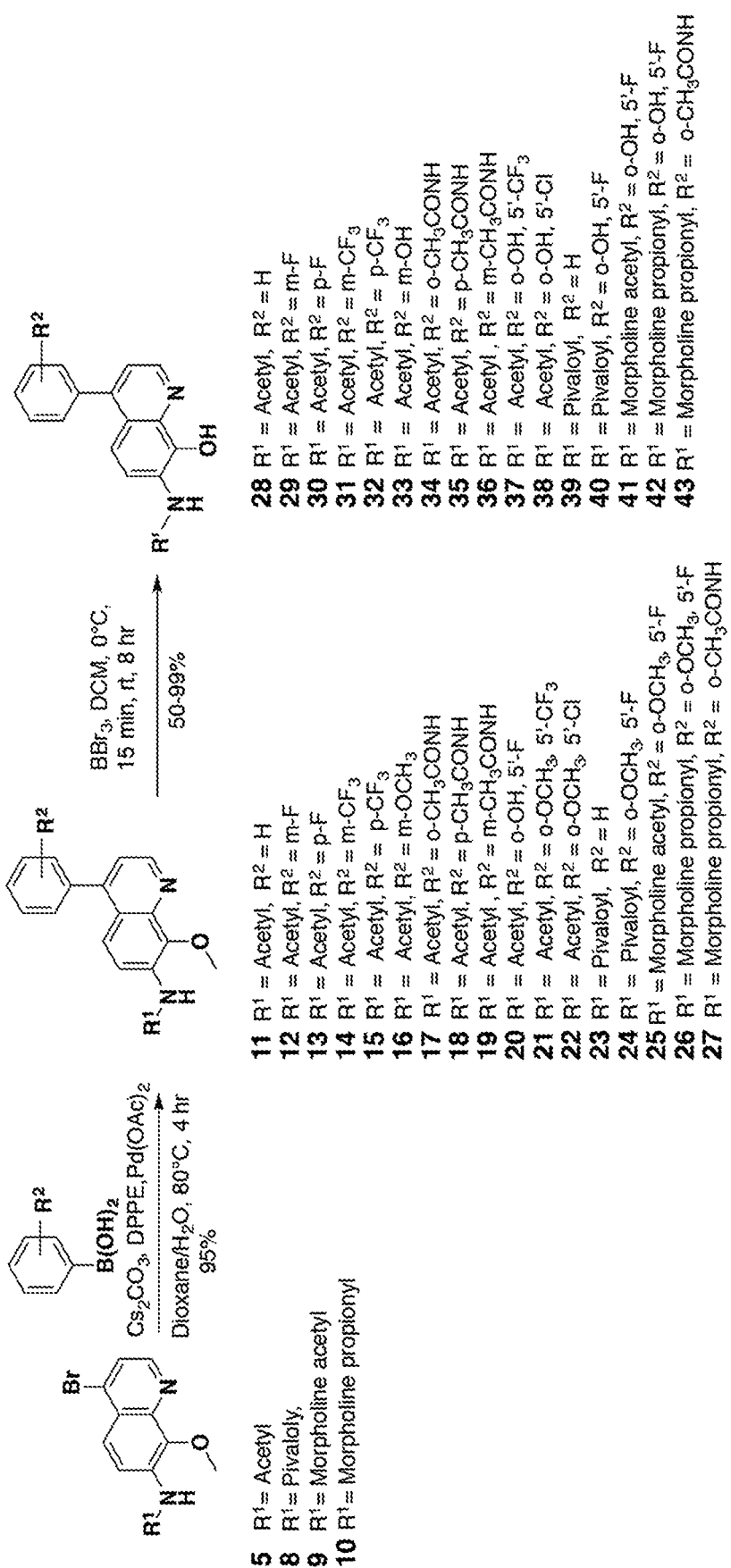
FIG. 4A depicts the syntheses of prototype 7 designed analogs.

Given the promising biological activity of 7, further drug design optimization was conducted using the CADD approach with the goal to improve the physicochemical properties (e.g. water solubility) while improving potency against TOP2A and efficacy in cell-based tumor models. These CADD studies led to the design and synthesis of novel intermediates and final analogs 28-43 (FIG. 4A). CADD indicated that introducing a pivalamide or morpholine propionamide functionality into $R^1$ increased favorable hydrophobic and hydrophilic properties, respectively. In addition, these functional groups improved interactions with the Walker A motif in the TOP2A ATP-binding pocket. In particular, the morpholine oxygen forms a chelation interaction with the active site magnesium, with a bond length of 2.2 Å. Thus, a brominated quinoline 4 was utilized to generate intermediates 5, 8, 9, and 10. Catalytic reduction of 4 followed by acylation with pivaloyl chloride gave intermediate 8, while peptide coupling using morpholine acetic acid or morpholine propionic acid in the presence of propyl phosphonic anhydride (T3P) provided 9 and 10, respectively.

Figure 4B:
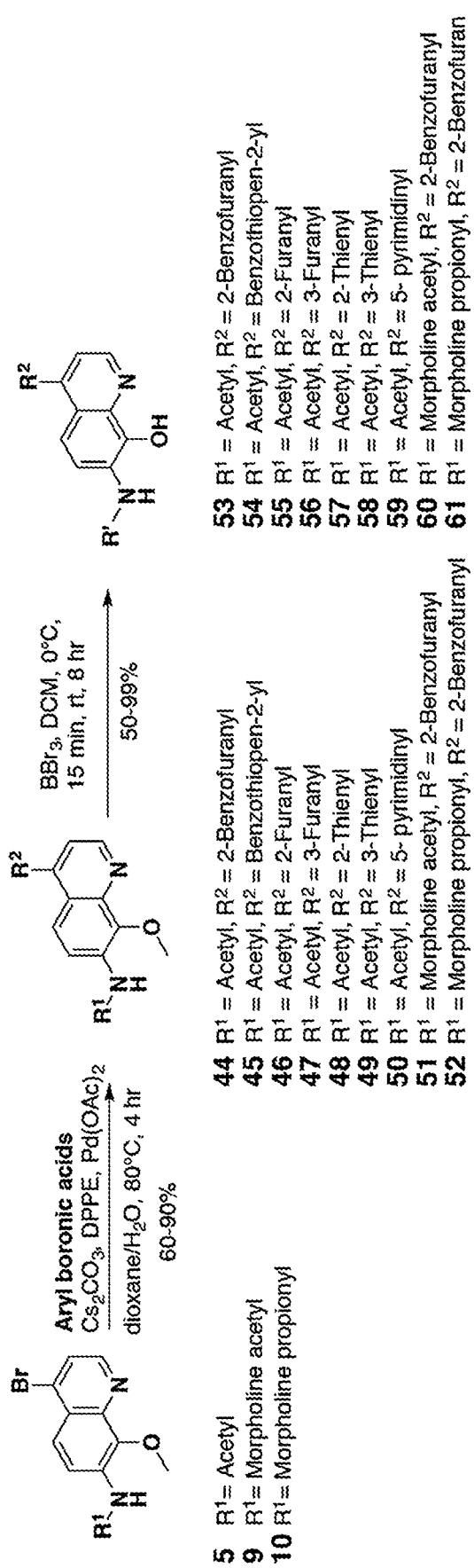
FIG. 4B depicts the syntheses of prototype 7 analogs with position 4 aromatic ring variations.

Next, to enhance interactions in the lipophilic pocket of the ATP-binding site, a facile Suzuki cross coupling methodology using phenyl boronic acids with various substituent groups was used, as directed by CADD, in the presence of 1,2-bis(diphenylphosphino)ethane (DPPE), cesium carbonate, palladium(II)acetate and key intermediate 5, 8-10 to obtain coupled products 11-27. The final products were obtained by demethylation of the methoxy functionality of the coupled products using boron tribromide ($BBr_3$), which afforded the syntheses of 28-43 in excellent yields (FIG. 4A). Similarly, Suzuki coupling with 5, 9 and 10 was utilized to introduce a diversity of aromatic ring systems to generate compounds 44-52. As in the scheme of FIG. 4A, demethylation using $BBr_3$ afforded compounds 53-61 as the final products (FIG. 4B).

Example 5

Biological Evaluation of Prototype 7 Analogs

Inhibition studies of TOP2A and observed structure activity relationships (SAR). DNA catenation/decatenation or linking/unlinking of DNA is one of the main TOP2A functions essential for regulating DNA topology, and this is ATP dependent. The TOP2A DNA decatenation assay is robust and neo significantly inhibits TOP2A mediated DNA decatenation. Thus, as a starting point, the synthesized analogs were screened against TOP2A-dependent decatenation using 30 μM fixed concentrations, and the DNA from reactions were resolved on 0.8% agarose gels containing ethidium bromide. The analogs displayed potent inhibition of TOP2A decatenation, ranging from 80-100% inhibition (Table 1 and 2).

Subsequently, dose response studies were conducted using select analogs that displayed at least 80% inhibition of TOP2A decatenation to determine the inhibition concentration 50% ($IC_{50}$) values (Table 1). These studies demonstrate potent inhibition of TOP2A ranging from nanomolar to low micromolar activity. Notably, compounds 53 and 42 proved to be the most potent TOP2A inhibitors with $IC_{50}$ values of 0.24 μM and 0.6 μM, respectively, compared to prototype 7 ($IC_{50}$=5.81). Moreover, these studies provided interesting SAR, which shed light on the potential lead drug target binding interactions and affinity, biological activity, and future drug design optimization with this unique class of TOP2A inhibitors.

TABLE 1

TOP2A decatenation inhibition studies with prototype 7 analogs (ND = not determined)

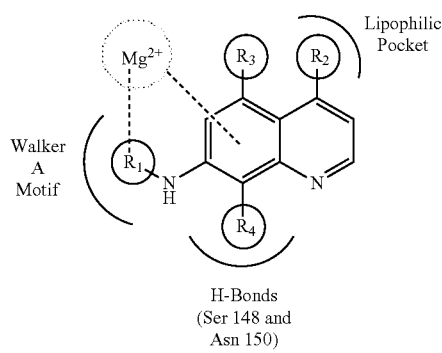

| Analog | R1 | R2 | R3 | R4 | % Inhibition TOP2A (30 μM) | % Inhibition TOP2A ($IC_{50}$ Values) |
|---|---|---|---|---|---|---|
| 2 | ![pivaloyl] | ![phenacyl-phenyl] | $OCH_3$ | $OCH_3$ | 0.0 | ND |

TABLE 1-continued
TOP2A decatenation inhibition studies with prototype 7 analogs (ND = not determined)
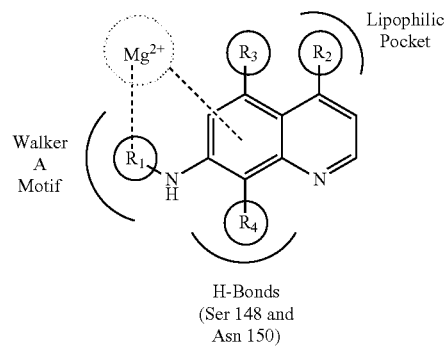
| Analog | R1 | R2 | R3 | R4 | % Inhibition TOP2A (30 μM) | % Inhibition TOP2A (IC$_{50}$ Values) |
|---|---|---|---|---|---|---|
| 3 | acetyl | 2-(phenacyl)phenyl | OCH$_3$ | OH | 100.0 | 1.2 |
| 6 | acetyl | 4-fluoro-2-methoxyphenyl | H | OCH$_3$ | 0.0 | ND |
| 7 | acetyl | 4-fluoro-2-hydroxyphenyl | H | OH | 99.0 | 5.8 |
| 20 | acetyl | 4-fluoro-2-hydroxyphenyl | H | OCH$_3$ | 0.0 | ND |
| 28 | acetyl | phenyl | H | OH | 25.0 | ND |
| 29 | acetyl | 3-fluorophenyl | H | OH | 100.0 | 7.8 |

TABLE 1-continued
TOP2A decatenation inhibition studies with prototype 7 analogs (ND = not determined)
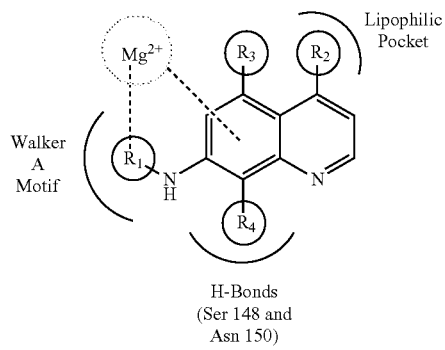
H-Bonds
(Ser 148 and
Asn 150)
| Analog | R1 | R2 | R3 | R4 | % Inhibition TOP2A (30 µM) | % Inhibition TOP2A (IC$_{50}$ Values |
|---|---|---|---|---|---|---|
| 30 | acetyl | 4-F-phenyl | H | OH | 1.0 | ND |
| 31 | acetyl | 3-CF$_3$-phenyl | H | OH | 97.0 | 3.4 |
| 32 | acetyl | 4-CF$_3$-phenyl | H | OH | 97.0 | 0.7 |
| 33 | acetyl | 3-OH-phenyl | H | OH | 0.0 | ND |
| 34 | acetyl | 2-NHAc-phenyl | H | OH | 1.0 | ND |
| 35 | acetyl | 4-NHAc-phenyl | H | OH | 97.0 | 1.9 |

TABLE 1-continued

TOP2A decatenation inhibition studies with prototype 7 analogs (ND = not determined)

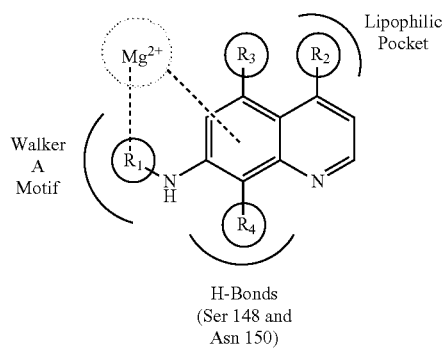

| Analog | R1 | R2 | R3 | R4 | % Inhibition TOP2A (30 μM) | % Inhibition TOP2A (IC$_{50}$ Values) |
|---|---|---|---|---|---|---|
| 36 | acetyl | 3-acetamidophenyl | H | OH | 3.0 | ND |
| 37 | acetyl | 5-CF$_3$-2-hydroxyphenyl | H | OH | 100.0 | 9.0 |
| 38 | acetyl | 5-Cl-2-hydroxyphenyl | H | OH | 0.0 | ND |
| 39 | pivaloyl | phenyl | H | OH | 97.0 | 1.3 |
| 40 | pivaloyl | 5-F-2-hydroxyphenyl | H | OH | 0.0 | ND |
| 41 | morpholinoacetyl | 5-F-2-hydroxyphenyl | H | OH | 4.0 | ND |
| 42 | 3-morpholinopropanoyl | 5-F-2-hydroxyphenyl | H | OH | 90.0 | 0.6 |

TABLE 1-continued
TOP2A decatenation inhibition studies with prototype 7 analogs (ND = not determined)
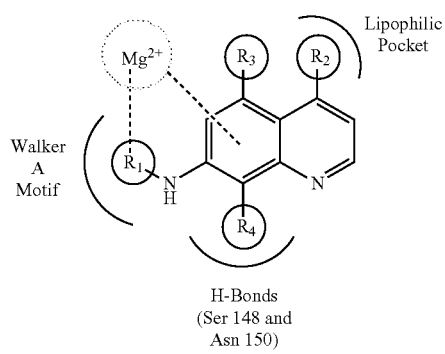
| Analog | R1 | R2 | R3 | R4 | % Inhibition TOP2A (30 μM) | % Inhibition TOP2A (IC$_{50}$ Values) |
|---|---|---|---|---|---|---|
| 43 | morpholine-CH$_2$CH$_2$-C(O)- | 2-acetamidophenyl | H | OH | 1.0 | ND |
| 53 | CH$_3$-C(O)- | benzofuran-2-yl | H | OH | 100.0 | 0.2 |
| 54 | CH$_3$-C(O)- | benzothiophen-2-yl | H | OH | 0.0 | ND |
| 55 | CH$_3$-C(O)- | furan-2-yl | H | OH | 0.0 | ND |
| 56 | CH$_3$-C(O)- | furan-3-yl | H | OH | 86.0 | 6.4 |
| 57 | CH$_3$-C(O)- | thiophen-2-yl | H | OH | 100.0 | 2.3 |
| 58 | CH$_3$-C(O)- | thiophen-3-yl | H | OH | 92.0 | 5.0 |

TABLE 1-continued

TOP2A decatenation inhibition studies with prototype 7 analogs (ND = not determined)

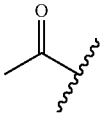 [SMILES: *C(C)=O]

| Analog | R1 | R2 | R3 | R4 | % Inhibition TOP2A (30 µM) | % Inhibition TOP2A (IC$_{50}$ Values) |
|---|---|---|---|---|---|---|
| 59 | 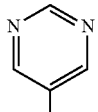 | 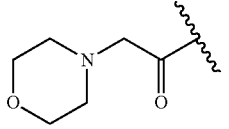 [SMILES: *C(=O)CN1CCOCC1] | H | OH | 0.0 | ND |
| 60 | 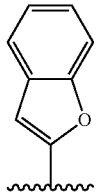 [SMILES: *c1cc2ccccc2o1] | 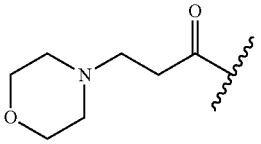 [SMILES: *C(=O)CCN1CCOCC1] | H | OH | 100.0 | 5.0 |
| 61 | 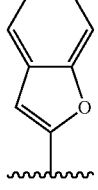 | | H | OH | 83.0 | 4.1 |

Compound 7, which contains a 5-fluoro-2-hydroxy phenyl ring showed complete enzyme inhibition of TOP2A at 30 µM with an IC$_{50}$ of 5.8 µM. A unique interaction observed with compound 7 is a halogen hydrogen bond between fluorine and the carbonyl oxygen of ASN120. This phenomenon may be explained by the r-hole model of halogen bonding, where a positive electrostatic potential crown exists directly opposite the carbon-halogen bond. Conversely, the electronegative potential exists as a shell around the halogen atom. Thus, one would expect the fluorine to be a halogen hydrogen bond donor when in direct orientation to an electronegative group such as a carbonyl oxygen. When the fluorine is perpendicular to the orientation of the halogen hydrogen bond (i.e. facing the electronegative shell) then fluorine becomes a halogen hydrogen bond acceptor with a proton hydrogen. Indeed, this was observed using the CADD model. This is further supported with analog 29, which has a meta fluoro functionality and this analog displays potent inhibition of TOP2A activity. However, when the fluorine is moved to the para position of the ring, as in analog 30, the activity is lost and may be attributed, in part, due to the loss of halogen hydrogen bonding. Interestingly, having trifluoro methyl groups meta (compounds 31 and 37) or para (compound 32) positions, resulted in excellent inhibitory activity. With the trifluoromethyl analogs both direct (halogen bond donor) and perpendicular (halogen bond acceptor) interactions were observed. But no activity was observed when the fluoro group was replaced with a chloro group as with analog 38. This loss of activity was attributed to a lack of fluoro-hydrogen bonding, due to steric effects resulting from the significant atom size of chloro compared to fluoro or the 2-phenolic group. As a result, compound 38 is oriented opposite of the fluorinated derivatives. Taken together, the fluoro-halogen bond interactions observed may be essential for potent TOP2A inhibition. Having an acetamide in the ortho and meta position of the 4-phenyl ring, as with analogs 34 and 36, caused significant loss of activity. However, moving the acetamide to the para position in 35 restored inhibitory activity against TOP2A, which was attributed to a H-bond resulting from the para position.

Substituting the 4-phenyl ring with various aromatic ring systems provides further SAR. Compound 53, containing a benzofuran ring, displayed complete inhibitory activity against TOP2A. Interestingly, inhibition was lost in 54 (benzothiophene ring) due to the minor substitution of oxygen with sulfur. In addition, analogs containing the smaller 5-membered furan rings, 55 and 56, displayed differential inhibitory activity due to the position of the oxygen. When the oxygen is in the $2^{nd}$ position, as in 55, significant loss of activity was observed compared to when the oxygen is in the $3^{rd}$ position as with analog 56. Unlike the benzoythiophene 54, the 3-thienyl ring of 58 improves activity compared to the 3-furanyl analog 56 (Table 2). Taken together, the stereo-electronic effects of the aromatic heteroatoms appear to play an important role in TOP2A inhibition.

Finally, the SAR resulting from $R^1$ substitutions (Table 1) was investigated. By CADD, the morpholino functionality of 42 allows for favorable binding with TOP2A through hydrogen bonding with Thr215 and the Walker A motif portion of the binding pocket, and through potential chelation interactions with $Mg^{2+}$. In addition, the mopholino group makes 42 water soluble while maintaining favorable calculated Log P of 2. Similarly, 3 and 39 display reasonably good $IC_{50}$ values (~1 µM) due to apparent increased lipophilic interactions with the TOP2A binding pocket. Compound 61, a morpholino derivative of 53, displayed a reasonable $IC_{50}$ of 4 µM, however, it is 20-fold less potent compared to 53 ($IC_{50}$=0.2 µM) but maintains water solubility, which is an important drug physicochemical property to consider.

Example 6

Prototype 7 Analogs Inhibit TOP2A-Dependent TCF Transcription in CRC

Similar to compound 7, these analogs were expected to significantly downregulate TOF-transcription. Thus, the most potent TOP2A inhibitor analogs were tested using SW620-TOP tumor organoids treated for 72 hours at various doses to determine dose responses (Table 2). A similar trend in $IC_{50}$ values was observed compared to TOP2A enzyme studies, further supporting our proposed mechanism of action as inhibition of TOP2A-dependent TCF-transcription. Notably, the benzofuranyl 53 was the most potent inhibitor of TCF-transcription with an $IC_{50}$ of 1.0 µM, followed by 35 ($IC_{50}$=2.0 µM), 42 ($IC_{50}$=3.2 µM), 41 ($IC_{50}$=4.7 µM), 57 ($IC_{50}$=7.0 µM), and 45 ($IC_{50}$=10.7 µM).

Analogs were also assessed for their ability to modulate or reverse EMT using VimPro-GFP and EcadPro-RFP SW620 reporter cells cultured as tumor organoids, determining $EC_{50}$ dose responses over 72 hours (Table 2). As observed with compound 7, analogs that inhibited TCF transcription also displayed excellent activity at downregulating vimentin (mesenchymal biomarker) expression and upregulating E-cadherin (epithelial biomarker) promoter activity, indicating the reversion of EMT.

Finally, SW620 tumor organoid cytotoxicity experiments were conducted using the CellTox Green assay, a fluorescence image-based method, to determine whether the inhibition of TCF transcription and effects on EMT are not the result of cytotoxicity. Unlike TOP2A poisons, ATP-competitive TOP2A inhibitors did not cause potent cytotoxicity to tumor organoids over 72-hour treatments (Table 2). All of the analogs tested display $IC_{50}$ dose response >30 µM and were higher compared to the $IC_{50}$ values obtained during the downregulation of TCF transcription activity, and the $EC_{50}$ values obtained for EMT modulation. Thus, the biological effects on TCF-transcription and EMT are not a result of tumor organoid cell death.

TABLE 2

The biological activity of TOP2A inhibitors using SW620 tumor organoid models of TCF-transcription, 3D cell viability, and EMT reporters of vimentin and E-cadherin.

| Analog | % TCP inhibition $IC_{50}$ (µM) | % Viability $IC_{50}$ (µM) | % Vimentin downregulation $EC_{50}$ (µM) | % E-cadherin upregulation $EC_{50}$ (µM) |
|---|---|---|---|---|
| 3 | 2.4 | >30 | 6.7 | 6.7 |
| 7 | 6.0 | >30 | 10.8 | 5.3 |
| 35 | 2.0 | >30 | 9.5 | 5.5 |
| 39 | 4.7 | >30 | 4.7 | 3.1 |
| 42 | 3.2 | >30 | 13.2 | 5.9 |
| 53 | 1.0 | >30 | 3.5 | 5.4 |
| 56 | 7.0 | >30 | 25.7 | 10.6 |

Example 7

Clonogenic and Invasion Assay

Common features of EMT-positive cell phenotypes are increased invasive potential, a tumor cell capability promoting metastatic dissemination and CSC stemness using the clonogenic colony formation assay, where SW620 tumor organoids are pretreated with analogs at 10 µM over 72 hours, followed by harvesting viable cells and plating in invasion or clonogenic assays. Significant potent inhibition was observed for all analogs tested (FIG. 5A). Interestingly, a trend that analogs with more potent $EC_{50}$ for reversion of EMT displayed better activity against colony formation by SW620 cells was observed, indicating that as the SW620 cells had become more epithelial the CSC stemness features associated with the mesenchymal phenotype were lost. Likewise, the analogs tested also significantly inhibited the invasive potential of viable cells harvested from SW620 tumor organoids (FIG. 5B).

Finally, a major goal of this drug design approach was to improve the in vivo physicochemical properties of TOP2A inhibitors compared to the natural product neo. Therefore, an in vivo study was conducted using the athymic nude mouse tumor xenograft model to determine if one of these drug leads could accumulate in tumors when administered via intraperitoneal injection (i.p.). For this experiment, compound 42 was used because of its relatively potent biological activity and significantly improved water solubility. Thus, compound 42 was administered i.p. at 50 mg/kg, 5× per week over 28 days. As expected, no loss of any tumor growth was observed, however, harvested tumors were homogenized and assessed by LCMS analysis, which identified significant HRMS quantity of 42 in tumors (FIG. 5C).

Example 8

Synthesis of Inhibitors

7-Acetamido-4-(2'-nitrophenyl)-5,8-dimethoxyquinoline (1). To a solution consisting of 7-Acetamido-5,8-dimethoxy-4-(2-nitrophenyl)-2-(trifluoromethane sulfonoxy) quinoline (6.5 g, 12.6 mmol), triethylamine (11.1 mL, 80 mmol), palladium (II) acetate (600 mg, 27 mmol), and 1,1-bis (diphosphino)ferrocene (3 g, 5.4 mmol) in 130 mL of dry dimethylformamide (DMF) at 0° C. was added formic acid (99%) drop manner, under nitrogen over 10 minutes. The reaction mixture was slowly warmed to 60° C., over 2 hours, poured into 1.5 L of water, and made basic with saturated aqueous NaHCO$_3$. The product was extracted with 3× (400 mL) with dichloromethane. The dichloromethane extracts were combined, washed with 200 mL of saturated aqueous sodium chloride (NaCl), dried with sodium sulfate (Na$_2$SO$_4$), and concentrated in vacuo to a give a crude product. The crude product was purified by silica chromatography eluting with 1:1 dichloromethane/ethyl acetate to afford 1 as a yellow crystal, which was further recrystallized in ethyl acetate to obtain (3.47 g, 75% yield). TLC (ethylacetate) R$_f$=0.20. $^1$H NMR (400 MHz, CDCl$_3$) δ 8.90 (d, J=4.4 Hz, 1H), 8.17 (d, J=9.2 Hz, 1H), 8.13 (s. 1H), 8.09 (s, 1H), 7.65 (t, J=7.6 Hz, 1H), 7.55 (t, J=8.6 Hz, 1H), 7.29 (d, J=8.8, 1H), 7.06 (d, J=4.4 Hz, 1H), 3.14 (a, 3H), 3.44 (s, 3H), 2.28 (s, 3H).

7-Acetamido-4-(2-benzamidophenyl)-5,8-dimethoxyquinoline (2), 120 mg (0.3266 mmol) of 1 was dissolved in 13.2 mL of ethanol, to which were added 260 mg of palladium on carbon, and 6.6 mL of cyclohexene. The mixture was refluxed for 2 hours to generate the amine product, which was filtered through a pad of celite to recover the amine product. The yellow solution was concentrated in vacuo and without purification was dissolved in 3 mL of pyridine under nitrogen, to this solution was added 46 μL (1.2 equivalent) of benzoyl chloride. Upon the addition of benzoyl chloride, the solution turned orange. The reaction was stirred at room temperature for 8 hours. The orange solution was concentrated in vacuo to give a crude product. The crude product was purified by column chromatography using ethyl acetate/dichloromethane (1:1) as the eluent and silica gel as the adsorbent material to give a tan color solid 126.5 mg (88% yield); TLC (ethyl acetate/dichloromethane (1:1)), R$_f$=0.41; Melting Point 204-206° C.; $^1$H NMR (400 MHz, CDCl$_3$) δ 8.93 (d, J=4.0 Hz, 1H), 8.34 (d, J=8.0 Hz, 1H), 8.17 (d, J=4.4 Hz, 2H), 7.45 (t, J=7.6 1H), 7.39 (s, 1H), 7.36 (t, J=4.2 Hz, 1H), 7.13 (s, 2H), 7.21-7.17 (m, 7H), 4.14 (s, 3H), 3.52 (s, 3H), 2.29 (s, 3H); $^{13}$C NMR (125.7 MHz, DMSO-d6) δ 169.2, 165.4, 152.6, 150.5, 144.1, 143.3, 136.6, 135.1, 135.0, 134.0, 133.6, 132.4, 131.9, 129.0, 128.7, 128.5, 126.9, 124.3, 122.9, 121.4, 116.3, 100.8, 62.6, 56.4, 25.6; IR (neat) v$_{max}$ 3406.5, 3301.8, 2971.2, 1652.0, 1520.7, 1498.5, 1446.3, 1385.1, 1257.4; ESI-HRMS [M+H]$^+$ calculated for C$_{26}$H$_{24}$N$_3$O$_4$, 442.1761, found. 442.1754.

7-Acetamido-4-(2'-benzamidophenyl)-8-hydroxyquinoline (3). To 160 mg (0.3624 mmol) of 2 were added 4 mL of 2,6-lutidine under N$_2$, and lithium iodide (67.8 mg, 0.507 mmol, 1.4 equivalent). The mixture was refluxed for 4 hours, and quenched by the addition of ice-cold water. The pH of the solution was adjusted with HCl to pH=7. The product was extracted with chloroform (50 mL×3) and dried over sodium sulfate. The product was concentrated and dried in vacuo to give a crude product, which was recrystallized using ethanol to give 92.3 ng, the filtrate was recover and purified by flash chromatography using ethyl acetate and silica gel to give a bright yellow solid 47.7 mg, with the total yield of 140 mg (90% yield) of the product. TLC (ethyl acetate/acetone (1:1)), R$_f$=0.34; Melting Point 218-219° C.; $^1$H NMR (400 MHz, DMSO) δ 9.54 (s, 1H), 9.43 (broad s, 1H), 9.33 (s, 1H), 8.79 (d, J=4.4 Hz, 1H), 7.63 (t, J=5.8 Hz, 2H), 7.45-7.38 (m, 2H), 7.303-7.26 (m, 6H), 7.21 (d, J=4.4 Hz, 1H), 3.35 (s, 3H). 2.14 (s, 3H); $^{13}$C NMR (100 MHz, CDCl$_3$) δ 168.2, 165.3, 148.7, 148.3, 144.1, 138.3, 135.1 134.7, 133.7, 133.5, 131.7, 128.8, 128.6, 126.7, 124.3, 123.3, 123.1, 121.6, 115.3, 102.4, 56.5, 25.1; IR (neat) v$_{max}$ 3305.8, 2948.6, 2832.3, 2361.8, 2325.2, 1670.6, 1622.7, 1582.6, 1525.8, 1448.6: ESI-HRMS [M+Na]$^+$ calculated for C$_{25}$H$_{21}$N$_3$NaO$_4$, 450.1424, found 450.1420.

4-Bromo-8-methoxy-7-nitroquinoline (4). To a solution of the nitroquinolone (164 mg, 0.745 mmol) in 2 mL of dimethylformamide was added 78 μL of phosphorus tribromide drop wise at 0° C. under N$_2$. The reaction solution was warmed to room temperature and stirred at that temperature for 1 hour. The reaction was quenched by the addition of ice-cold water. The pH of the solution was adjusted by the addition of saturated NaHCO$_3$ to pH=8. The product was extracted with ethyl acetate (20 mL×3). The organic extracts were combined and dried over sodium sulfate. The solvent was concentrated in vacuo to give a crude product, which was chromatographed on silica gel, using ethyl acetate as the eluent to afford a light yellow solid 188 mg (89% yield). TLC (ethyl acetate) R$_f$=0.61: Melting Point 142-144° C.; $^1$H NMR (400 MHz, CdCl$_3$) δ 8.80 (d, J=4.0 Hz, 1H), 8.02 (d, J=8.8 Hz, 1H), 7.93 (d, J=9.2 Hz, 1H), 7.86 (d, J=4.0 Hz, 1H) 4.35 (s, 3H); $^{13}$C NMR (125.7 MHz, CDCl$_3$) δ 150.5, 150.3, 150.2, 144.0, 142.9, 134.3, 130.9, 127.3, 127.3, 122.3, 122.1, 64.4; IR (neat) v$_{max}$ 3080.9, 3024.7, 2956.7, 2922.6, 2852.0, 1603.4, 1571.8, 1523.9; ESI-HRMS [M+Na]$^+$ calculated for C$_{10}$H$_7$N$_2$O$_3$Na 306.9517 found 306.9519.

7-Acetamido-4-bromo-8-methoxyquinoline (5). To 178 mg (0.629 mmol) of nitroquinoline were added 210.7 mg (6 equivalents) of iron powder, 2 mL (water/ethanol (2:8)), 67 mg (2 equivalents) ammonium chloride. The mixture was refluxed for 1.5 hours and allowed to cool to room temperature. The mixture was filtered over a pad of celite and washed with ethylacetate. The filtrate was diluted with water, and the pH was adjusted with NaHCO$_3$ to pH=8. The product was extracted with ethyl acetate, dried over sodium sulfate and concentrated in vacuo to generate the amine intermediate. Without purification, the amine was dissolved in 2 mL acetic acid and 2 mL acetic anhydride under drying tube for 8 hours. The solvents were removed by concentrating the product in vacuo to generate the crude product, which was purified by flash chromatography using silica gel as the solid phase, 35% ethyl acetate in hexane to afford 168 mg (91% yield). TLC (ethylacetate) R$_f$=0.21; Melting Point 132-133° C.; 1H NMR (500 MHz, CdCl$_3$) δ 8.80 (d, J=9.0 Hz, 1H), 8.64 (d, J=4.5 Hz, 1H), 8.14 (broad s, 1H), 7.95 (d, J=9.5 Hz, 1H), 7.63 (d, J=4.5, 1H), 4.21 (s, 3H), 2.32 (s, 3H), $^{13}$C NMR (125.7 MHz, CDCl$_3$) δ 171.3, 151.8, 145.2, 136.9, 134.9, 127.9, 126.6, 125.2, 123.8, 105.0, 65.1, 27.7; IR (neat) v$_m$ax 3217.9, 3074.8, 2973.2, 2931.9, 2896.1, 1650.1, 1606.0, 1573.2; ESI-HRMS [M+Na]$^+$ calculated for C$_{12}$H$_{11}$BrN$_2$NaO$_2$ 318.9876 found 318.9886.

7-Acetamido-4-(5'-fluorophenyl-2'-methoxy-5)-8-methoxyquinoline (6). The compound was prepared from 7-acetamido-4-bromo-8-methoxyquinoline and 5-fluoro-2-methoxyphenyl boronic acid using the general coupling procedure to give the title compound as an off white solid (50.6 mg, 68% yield). TLC (Ethylacetate) R$_f$=0.21; Melting Point 180-182° C.; $^1$H NMR (500 MHz, CDCl$_3$) δ 8.91 (d, J=4.0 Hz, 1H), 8.56 (d, J=9.5 Hz, 1H), 8.14 (s, 1H), 7.32 (d, J=9.5 Hz, 1H), 7.21 (d, J=4.5 Hz, 1H), 7.13 (td, J=3.5, 9.0 Hz, 1H), 6.98-6.95 (m, 2H), 4.21 (s, 3H), 3.66 (s, 3H), 2.27 (s, 3H); $^{13}$C NMR (125.7 MHz, CDCl$_3$) δ 168.7, 157.8, 155.9, 153.0, 149.6, 144.9, 142.5, 142.2, 131.2, 128.0 (d, $^3J_{C-F}$=7.8 Hz), 124.8, 122.0 (d, $^3J_{C-F}$=7.7 Hz), 121.0 (d, $^1J_{C-F}$=242.3 Hz), 118.0 (d, $^2J_{C-F}$=23.6 Hz), 116.0 (d, $^2J_{C-F}$=23.3 Hz), 112.2, 62.4, 56.2, 25.41; IR (neat) v$_{max}$ 3361.4, 3069.8, 3051.0, 3021.8, 2963.2, 2926.62849.4, 1685.7, 1611.8, 1586.4, 1501.8; ESI-HRMS [M+Na]$^+$ calculated for C$_{19}$H$_{17}$FN$_2$O$_3$Na 363.1115 found 363.1105.

7-Acetamido-4-(5'-fluoro-2'-hydroxyphenyl))-8-hydroxyquinoline (7). To a solution containing 33.0 mg (0.075 mmol) of the 7-acetamido-4-(5-fluoro-2-methoxyphenyl)-8-methoxyquinoline starting material in 1.0 mL dry dichloromethane was added 1.94 mL (10 equivalents) of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 26 mg (86% yield) of the product. TLC (Ethyl acetate) R$_f$=0.21; Melting Point 215-217° C.; $^1$H NMR (400 MHz, DMSO-d6) δ 958 (broad s, 1H), 9.56 (broad s, 1H), 8.85 (d, J=4.4 Hz, 1H), 7.99 (d, J=9.2 Hz, 1H), 7.36 (d, J=4.4 Hz, 1H), 7.17 (dt, J=3.2, 8.8 Hz, 1H), 7.07 (dd, J=3.2, 8.8 Hz, 1H), 7.01-6.98 (m, 2H), 2.26 (s, 3H); $^{13}$C NMR (125.7 MHz, DMSO-d6) δ 168.5, 155.1 (d, $^1J_{C-F}$=234.5 Hz), 151.1, 147.4, 144.4, 143.8, 138.9, 125.6 (d, $^3J_{C-F}$=7.54 Hz), 123.9, 123.1, 123.0, 121.4, 116.8, (d, $^2J_{C-F}$=24.5 Hz) 116.7 (d, $^1J_{C-F}$=8.54 Hz), 115.9 (d, $^2J_{C-F}$=22.6 Hz), 114.0, 113.9, 23.7: IR (neat) v$_{max}$ 3294.3, 3082.1, 2709.8, 2359.4, 1610.5, 1505.4, 1432.8, 1306.5: ESI-HRMS [M+Na]$^+$ calculated for C$_{17}$H$_{13}$FN$_2$NaO$_3$ 335.0802 found 335.0797.

4-Bromo-8-methoxy-7-pivalamidoquinoline (8). To 160 mg (0.5652 mmol) of 4-bromo-8-methoxy-7-nitroquinoline were added 220.6 mg (7 equivalents) of iron powder, 60.33 mg (2 equivalents) of ammonium chloride, 8.3 mL water/ethanol (2:8). The mixture was refluxed for 2 hours and allowed to cool to room temperature. The mixture was filtered over a pad of celite and washed with ethylacetate. The filtrate was diluted with water, and the pH was adjusted with NaHCO$_3$ to pH=8. The product was extracted with ethyl acetate, dried over sodium sulfate and concentrated in vacuo to generate the aniline intermediate (141.2 mg). Without purification, to the aniline were added (0.1 equivalent, 0.0557 mmol, 6.81 mg) dimethyl amino pyridine (DMAP), triethylamine (2 equivalents, 1.115 mmol, 155.7 μL pivaloyl chloride (0.669 mmol, 82 μL, 1.2 equivalents) and 5 mL of dry dichloromethane at 0° C. and stirred at that temperature for 40 minutes. The resulting dark orange solution became yellow after 5 minutes of stirring and was allowed to warm to room temperature and stirred at room temperature for 18 hours under nitrogen. The reaction was quenched by the addition of water, and the organic layer separated using dichloromethane 30 mL×3. The organic layers were combined and dried over sodium sulfate, concentrated in vacuo to give crude product, which was chromatographed using silica gel and 15% ethyl acetate in dichloromethane to give 189 ng as a syrupy product. TLC (20% ethylacetate in dichloromethane) R$_f$=0.21; $^1$H NMR (400 MHz, CDCl$_3$) δ 8.80 (d, J=9.2 Hz, 1H), 8.75 (d, J=4.8 Hz, 1H), 8.48 (s. 1H), 7.99 (d, J=9.2 Hz, 1H), 7.41 (d. J=4.8 Hz, 1H), 4.19 (s, 3H), 1.39 (s, 9H); $^{13}$C NMR (100 MHz, CDCl$_3$) δ 177.1, 149.4, 142.6, 142.5, 134.4, 132.7, 125.3, 124.0, 122.8, 121.3, 62.3, 40.3, 27.7: IR (neat) v$_{max}$ 3426.6, 2961.7, 2870.2, 1683.9, 1608.9, 1497.5, 1454.0, 1407.7; ESI-HRMS [M+H]$^+$ calculated for C$_{15}$H$_{17}$BrN$_2$O$_2$ 336.0473 found 337.0546.

4-Bromo-8-methoxy-7-morpholineacetamidoquinoline (9). To 250 mg (0.883 mmol) of 4-bromo-8-methoxy-7-nitroquinoline were added 346 mg (7 equivalents) of iron powder, 12.5 mL water/ethanol (2:8), 94.3 mg (2 equivalents) ammonium chloride. The mixture was refluxed for 2 hours and allowed to cool to room temperature. The mixture was filtered over a pad of celite and washed with Methanol. The filtrate was diluted with water, and the pH was adjusted with NaHCO$_3$ to pH=8. The product was extracted with ethyl acetate, dried over sodium sulfate and concentrated in vacuo to generate the aniline intermediate. Without purification, the aniline was dissolved in 5 mL of dry dichloromethane, to which were added 2 molar equivalents of morpholine acetic acid (286.76 mg), 344 μL triethlamine (2.5 equivalents, 249.68 mg), 1.047 mL (628.58 mg, 2.0 equivalents) of T3P. The resulting solution was stirred for 24 hours under nitrogen. The reaction was quenched by the addition of water, and the pH was adjusted with saturated NaHCO$_3$ until pH=8. The product was isolated using of dichloromethane (50 mL×3) and dried over sodium sulfate. The solvents were removed by concentrating the product in vacuo to generate the crude product, which was purified by flash chromatography using silica gel as the solid phase, and 50% hexane in acetone to afford 282 mg (75% yield) of syrupy product. TLC (50% hexane in acetone) R$_F$=0.21; $^1$H NMR (400 MHz, CDCl$_3$) δ 10.18 (s, 1H), 8.82 (d, J=9.2 Hz, 1H), 8.62 (d, J=4.4 Hz, 1H), 7.93 (d, J=9.2 Hz, 1H), 7.61 (d, J=4.4 Hz, 1H), 4.20 (s. 3H), 3.83 (t, J=4.4 Hz, 4H), 3.23 (s, 2H), 2.68 (t, J=4.2 Hz, 4H); $^{13}$C NMR (125 MHz, CDCl$_3$) δ 168.6, 149.4, 142.9, 142.5, 134.4, 131.9, 125.5, 124.1, 122.7, 122.8, 120.9, 67.4, 62.7, 62.5, 53.9; IR (neat) v$_{max}$ 3303.5, 2924.3, 2854.14, 1696.01, 1606.4, 1567.7, 1495.1, 1449.3, 1409.2; ESI-HRMS [M+H]$^t$ calculated for C$_{16}$H$_{18}$BrN$_3$O$_3$ 379.0532 found 380.0609.

4-Bromo-8-methoxy-7-morpholinepropionamidoquinoline (10). To 400 mg (1.413 mmol) of 4-bromo-8-methoxy-7-nitroquinoline were added 551.7 mg (7 equivalents) of iron powder, 20.5 mL water/ethanol (2:8), 150.9 mg (2 equivalents) ammonium chloride. The mixture was refluxed for 2 hours and allowed to cool to room temperature. The mixture was filtered over a pad of celite and washed with methanol. The filtrate was diluted with water, and the pH was adjusted with NaHCO$_3$ to pH=8. The product was extracted with ethyl acetate, dried over sodium sulfate and concentrated in vacuo to generate the amine intermediate. Without purification, the amine was dissolved in 5 mL of dry dichloromethane, to which were added 2 molar equivalents of morpholine propionic acid hydrochloride (553.01 mg), 490.6 μL triethylamine (2.5 equivalents, 357.33 mg), 1.096 mL (1.079 g, 1.2 equivalents) of T3P. The resulting solution was stirred for 24 hours under nitrogen. The reaction was quenched by the addition of water and basified with saturated NaHCO$_3$ until pH=8. The product was isolated using of dichloromethane (50 mL×3) and dried over sodium sulfate. The solvents were removed by concentrating the product in vacuo to generate the crude product, which was purified by flash chromatography using silica gel as the solid phase, and 50% hexane in acetone to afford 496 mg (89% yield) of syrupy product. TLC (50% hexane in acetone) R$_F$=0.21; $^1$H NMR (500 MHz, CDCl$_3$) δ 10.96 (s, 1H), 8.79 (d, J=11.5 Hz, 1H), 8.63 (d, J=5.5 Hz, 1H), 7.92 (d, J=12.0 Hz, 1H), 7.60 (d, J=5.5 Hz, 1H), 4.12 (s, 3H), 3.87 (s, 4H), 2.77 (t, J=6.8 Hz, 2H), 2.65 (t, J=7.5 Hz, 6H); $^{13}$C NMR (125 MHz, CDCl$_3$) δ 171.37, 149.3, 143.0, 143.0, 134.3, 132.9, 125.5, 122.7, 122.4, 66.7, 62.3, 54.5, 53.4, 33.2; IR (neat) v$_{max}$ 3508.6, 3313.3, 2966.0, 2932.4, 2854.0, 28200, 1676.8, 1608.5, 1517.8, 1494.5; ESI-HRMS [M+H]$^+$ calculated for C$_{17}$H$_{21}$BrN$_3$O$_3$ 394.0761 found 394.0759.

7-Acetamido-4-(phenyl)-8-methoxyquinoline (11). The compound was prepared from 7-acetamido-4-bromo-8-methoxyquinoline and phenyl boronic acid using the general coupling procedure to give the title compound as an off white solid (30.0 mg, 74% yield) as an off white solid. TLC (ethyl acetate) $R_f$=0.22; Melting Point 175-177° C., $^1$H NMR (500 MHz, CDCl$_3$) δ 8.9 (broad s, 1H), 8.59 (d, J=9.0 Hz, 1H), 8.13 (broad s, 1H), 7.67 (d, J=9.0 Hz, 1H), 7.60 (d, J=9.2 Hz, 1H), 7.51-7.47 (m, 5H), 7.26 (d, J=4.5 Hz, 1H), 4.23 (s, 3H), 2.29 (s, 3H); $^{13}$C NMR (125.7 MHz, CDCl$_3$) δ 169.0, 149.9, 149.1, 142.8, 131.6, 129.9, 124.8, 122.2, 120.8, 120.5, 62.7, 25.4; IR (neat) $v_{max}$ 3378.5, 2924.0, 2851.9, 1696.0, 1610.9, 1499.3, 1453.1; ESI-HRMS [M+Na]$^+$ calculated for C$_{18}$H$_{16}$N$_2$O$_2$Na 315.1104 found 315.0993.

7-Acetamido-4-(3'-fluorophenyl)-8-methoxyquinoline (12). The compound was prepared from 7-acetamido-4-bromo-8-methoxyquinoline and 3-fluorophenyl boronic acid using the general coupling procedure to give the title compound as an off white solid (256.4 mg, 95% yield). TLC (ethyl acetate) $R_f$=0.22; $^1$H NMR (500 MHz, CDCl$_3$) δ 8.83 (d, J=4.0 Hz, 1H), 8.54 (d, J=9.5 Hz, 1H), 8.27 (broad s, 1H), 7.54 (d, J=9.5 Hz, 1H), 7.38 (q, J=7.5 Hz, 1H), 7.16-7.07 (m, 4H), 4.14 (s, 3H) 2.23 (s, 3H); 1C NMR (125.7 MHz, CDCl$_3$) δ 168.8, 162.5 (d, $^1J_{C-F}$=247.3), 149.3, 147.1, 142.6, 142.4, 139.8, 131.3, 130.0, 125.1, 123.9, 121.2, 120.5, 120.1, 116.3 (d, $^2J_{C-F}$=22.0), 115 (d, $^2J_{C-F}$=20.7), 62.1, 24.6; ESI-HRMS [M+H]$^+$ calculated for C$_{16}$H$_{16}$FN$_2$O$_2$ 311.1190 found 311.1195.

7-Acetamido-4-(4'-fluorophenyl)-8-methoxyquinoline (13). The compound was prepared from 7-acetamido-4-bromo-8-methoxyquinoline and 4-fluorophenyl boronic acid using the general coupling procedure to give the title compound as an off white solid (45.5 mg, 88% yield). TLC (50% hexanes in acetone) $R_f$=0.32; Melting Point 159-161° C.; 1H NMR (500 MHz, CDCl$_3$) δ 8.91 (d, J=4.0 Hz, 1H), 8.61 (d, J=9.0 Hz, 1H), 8.13 (broad s, 1H), 7.62 (d, J=9.5 Hz, 1H), 7.46 (dd, J=5.5, 8.5 Hz, 2H), 7.26-7.20 (m, 3H), 4.23 (s, 3H), 2.30 (s, 3H); 1C NMR (100 MHz, CDCl$_3$) δ 168.8, 163.1 (d, $^1J_{C-F}$=246.9 Hz), 149.6, 147.8, 142.6, 134.0, 131.4 (d, $^3J_{C-F}$=7.8 Hz), 131.3 (d, $^3J_{C-F}$=8.2 Hz), 131.3 (d, $^2J_{C-F}$=16.0 Hz), 124.5, 121.6, 120.4, 115.8 (d, $^2J_{C-F}$=21.5 Hz), 62.4, 25.2; IR (neat) $v_{max}$ 3356.2, 2990.6, 2943.2, 2919.1, 2849.6, 1689.2, 1613.8, 1506.8, 1494.4, 1453.3, 1415.7, 1383.4, 1291.1; ESI-HRMS [M+H]$^+$ calculated for C$_{18}$H$_{16}$FN$_2$O$_2$ 311.1190 found 311.1195.

-Acetamido-4-(3'-trifluoromethyl)-8-methoxyquinoline (14). The compound was prepared from 7-acetamido-4-bromo-8-methoxyquinoline and 3-trifluomethyphenyl boronic acid using the general coupling procedure to give the title compound as an off white solid (76 mg, 99% yield). TLC (ethyl acetate) R; =0.15; Melting Point 130-131° C.; $^1$H NMR (500 MHz, CDCl$_3$) δ 8.95 (d, J=4.0 Hz, 1H), 8.64 (d, J=9.0 Hz, 1H), 8.15 (broad s, 1H), 7.76 (d, J=10.0 Hz, 2H), 7.66 (q, J=7.6 Hz, 2H), 7.55 (d, J=9.0 Hz, 1H), 7.27 (d, J=4.5 Hz, 1H), 4.24 (s, 3H), 230 (s, 3H); $^{13}$C NMR (125.7 MHz, CDCl$_3$) δ 168.8, 148.4 (d, $^1J_{C-F}$=303.7 Hz), 142.6 (d, $^4J_{C-F}$=18.1 Hz), 138.8, 132.9, 131.6, 131.3 (d, $^3J_{C-F}$=32.6 Hz), 129.2, 126.3, 125.5, 125.1, 122.9, 121.0 (d, $^2J_{C-F}$=70.7 Hz), 120.6 (d, $^1J_{C-F}$=31.4 Hz), 62.5, 25.2; IR (neat) $v_{max}$ 3328.3, 2981.1, 2939.3, 1668.1, 1616.3, 1509.6, 1442.9; ESI-HRMS [M+H]$^+$ calculated for C$_{19}$H$_{16}$F$_3$N$_2$O$_2$ 361.1158 found 361.1154.

7-Acetamido-4-(4'-trifluoromethylphenyl)-8-methoxyquinoline (15). The compound was prepared from 7-acetamido-4-bromo-8-methoxyquinoline and 4-trifluoromethylphenyl boronic acid using the general coupling procedure to give the title compound as an off white solid (58 mg, 95% yield). TLC (50% hexanes in acetone) $R_f$=0.20; Melting Point 159-160° C. $^1$H NMR (500 MHz, CDCl$_3$) δ 8.95 (d, J=4.5 Hz, 1H), δ 8.63 (d, J=9.5 Hz, 1H), 8.16 (broad s, 1H), 7.79 (d, J=8.0 Hz, 2H), 7.61 (d, J=8.0 Hz, 2H), 7.56 (d, J=9.0 Hz, 1H), 7.26 (d, J=4.5 Hz, 1H), 4.24 (s, 3H), 2.30 (s, 3H); 13C NMR (100 MHz, CDCl$_3$) δ 168.8, 148.4 (d, $^1J_{C-F}$=229.4 Hz), 142.6 (d, $^4J_{C-F}$=16.7 Hz), 142.1 (d, $^2J_{C-F}$=90.5 Hz), 130.8 (d, $^3J_{C-F}$=32.5 Hz), 129.9, 125.7 (q, $^1J_{C-F}$=3.7 Hz), 125.5, 124.0, 122.8, 121.3, 120.5 (d, $^3J_{C-F}$=35.0 Hz), 62.5, 25.1; IR (neat) $v_{max}$ 3597.9, 3418.8, 3291.1, 29460, 1701.5, 1686.0, 1612.3, 1497.6, 1456, 7, 1386.1; ESI-HRMS [M+H]$^+$ calculated for C$_{19}$H$_{16}$F$_3$N$_2$O$_2$ 361.1158 found 361.1160.

7-Acetamido-4-(3'-methoxyphenyl)-8-methoxyquinoline (16). The compound was prepared from 7-acetamido-4-bromo-8-methoxyquinoline and 3-methoxyphenyl boronic acid using the general coupling procedure to give the title compound as an off white solid (59.4 mg, 99% yield). TLC (ethyl acetate), R; =0.26; Melting Point 185-187° C.; $^1$H NMR (500 MHz, CDCl$_3$) δ 8.91 (d, J=4.0 Hz, 1H), 8.60 (d, J=9.5 Hz, 1H), 8.15 (broad s, 1H), 7.70 (d, J=9.5 Hz, 1H), 7.43 (t, J=7.7 Hz, 1H), 7.27 (s, 1H), 7.26-7.01 (m, 3H), 4.23 (s, 3H), 3.86 (s, 3H), 2.30 (s, 3H); $^{13}$C NMR (100 MHz, CDCl$_3$) δ 168.8, 159.7, 149.6, 148.7, 142.6, 142.5, 139.3, 131.3, 129.7, 124.5, 122.0, 120.3, 120.2, 115.2, 114.2, 62.4, 55.5, 25.2; IR (neat) $v_{max}$ 3322.6, 2920.2, 2849.2, 2836.7, 1687.3, 1612.2, 1579.1, 1500.1; ESI-HRMS [M+H]$^+$ calculated for C$_{19}$H$_{19}$N$_2$O$_3$ 323.1390 found 323.1393.

7-Acetamido-4-(2'-acetamidophenyl)-8-methoxyquinoline (17). To 40 mg (0.135 mmol) of 7-acetamido-4-bromo-8-methoxyquinoline in toluene/ethanol were added 45.24 mg (0.271 mmol) of 2-nitrophenyl boronic acid, 135.5 L (2 molar) potassium carbonate and 30.23 mg of tetrakis(triphenylphosphine) palladium (0) ligand. The mixture was heated at 85° C. for 16 hours. The reaction was allowed to cool to room temperature. The product was filtered over a pad of celite to recover the product. The celite was thoroughly washed with ethylacetate, concentrated and chromatographed on a silica gel using ethyl acetate to afford the product 56.9 mg. To 7-acetamido-4-(2'-nitrophenyl)-8-methoxyquinoline (40.0 mg (0.118 mmol) obtained was dissolved in 4.0 mL of ethanol, to which were added 94.0 mg of 10% palladium on carbon and 2.5 mL of cyclohexene, and the mixture was refluxed for 2.5 hours to generate the amine. The reaction was filtered hot through a pad of celite to recover the product. The filtrate was concentrated and dried in vacuo to give a red residue. Without purification, the red residue obtained was dissolved in 3 mL of acetic acid and 0.2 mL of acetic anhydride. The resulting orange became a light-yellow solution upon the addition of acetic anhydride, and the solution was stirred at room temperature under drying tube for 8 hours. The solvents were removed in vacuo to give a crude product. The crude product was purified by column chromatography using 50% ethyl acetate in acetone as the eluent on silica gel to give an off white solid 27.7 mg (67% yield). TLC (50% ethyl acetate in acetone) R; =0.2; Melting Point 232-234° C.; $^1$H NMR (500 MHz, DMSO-d6) δ 9.66 (s, 1H), δ 9.08 (s, 1H), 8.91 (d, 3=4.5 Hz, 1H), 8.17 (d, J=11.5 Hz, 1H), 7.66 (d, J=10.0 Hz, 1H), 7.49 (t, J=9.3 Hz, 1H), 7.35-7.29 (m, 3H), 7.17 (d, J=11.5 Hz, 1H), 4.09 (s, 3H), 2.17 (s, 3H), 1.67 (s, 3H); $^{13}$C NMR (100 MHz, CDCl$_3$) δ 169.1, 168.5, 149.2, 145.2, 142.5, 135.7, 131.5, 131.0, 130.7, 128.8, 126.3, 125.2, 124.2, 122.0, 121.3, 120.4, 61.7, 24.0, 23.0; IR (neat) $v_{max}$ 3249.8, 3218.0, 2925.5, 2360.6, 232978, 1671.5, 1612.2, 1523.4, 1503.6; ESI-HRMS [M+Na]$^+$ calculated for C$_{20}$H$_{19}$N$_3$O$_3$Na 372.1319 found 372.1337.

7-Acetamido-4-(4'-acetamidophenyl)-8-methoxyquinoline (18 The compound was prepared from 7-acetamido-4-bromo-8-methoxyquinoline and 3-methoxyphenyl boronic acid using the general coupling procedure to give the title compound as an off white solid 27.0 mg (65% yield). TLC (ethyl acetate) $R_f$=0.22; Melting Point 186-188° C.; $^1$H NMR (500 MHz, DMSO-d6) δ 10.15 (s, 1H), δ 9.66 (s, 1H), 8.87 (d, J=4.5 Hz, 1H), 8.27 (d, J=9.0 Hz, 1H), 7.76 (d, J=8.5 Hz, 2H), 7.60 (d, J=9.0 Hz, 1H), 7.47 (d, J=6.5 Hz, 2H), 7.34 (d, J=4.5 Hz, 1H), 4.07 (s. 3H), 2.18 (s, 3H), 2.09 (s, 3H); $^{13}$C NMR (125 MHz, CDCl$_3$) δ 169.2, 168.6, 149.3, 147.3, 144.3, 142.7, 139.7, 131.8, 131.1, 129.9, 123.8, 122.2, 120.3, 119.0, 61.7, 23.9; IR (neat) $v_{max}$ 3387.2, 3303.9, 3233.0, 3187.8, 3103.6, 3041.4, 1665.4, 1603.1, 1499.4; ESI-HRMS [M+Na]$^+$ calculated for $C_{20}H_{19}N_3O_3Na$ 372.1319 found 372.1323.

7-Acetamido-4-(3'-acetamidophenyl)-8-methoxyquinoline (19). The compound was prepared from 7-acetamido-4-bromo-8-methoxyquinoline and 3-acetamidophenyl boronic acid using the general coupling procedure to give the title compound as an off-white solid 26.0 mg (63% yield). TLC (ethyl acetate) $R_f$=0.22; Melting Point 228-230° C.; $^1$H NMR (500 MHz, DMSO-d6) δ 10.15 (s. 1H), δ 9.66 (s, 1H), 8.88 (d, J=4.0 Hz, 1H), 8.27 (d, J=9.0 Hz, 1H), 7.77 (d, J=8.0 Hz, 2H), 7.60 (d, J=9.5 Hz, 1H), 7.47 (d, J=8.5 Hz, 2H), 7.34 (d, J=4.0 Hz, 1H), 4.07 (s, 3H), 2.18 (s, 3H), 2.09 (s, 3H), 13C NMR (125 MHz, DMSO-d6) δ 169.3, 168.7, 149.4, 147.5, 142.7, 139.5, 137.8, 131.2, 129.2, 123.9, 122.5, 120.2, 119.8, 119.0, 61.8 24.0; IR (neat) $v_{max}$ 3302.9, 3228.4, 2928.3, 2851.4, 1693.4, 1673.1, 1585.2, 1504.7; ESI-HRMS [M+Na]$^+$ calculated for $C_{20}H_{19}N_3O_3Na$ 372.1319 found 372.1320.

7-Acetamido-4-(5'-fluoro-2'-hydroxyphenyl)-8-methoxyquinoline (20). The compound was prepared from 7-acetamido-4-bromo-8-methoxyquinoline and 5-fluoro-2-hydroxyphenyl boronic acid using the general coupling procedure to give the title compound as an off white solid (38 mg, 69% yield). TLC (ethyl acetate), $R_f$=0.20; Melting Point 150-152° C.; $^1$H NMR (500 MHz, DMSO-d6) δ 9.65 (broad s, 1H), 9.59 (s, 1H), 8.89 (d, J=4.5 Hz, 1H), 8.20 (d, J=9.0 Hz, 1H), 7.33 (d, J=4.0 Hz, 1H), 7.28 (d, J=9.0 Hz, 1H), 7.17 (td, J=3.5, 8.5 Hz, 1H), 7.00 (dd, J=5.0, 9.0 Hz, 1H), 7.17 (dd, J=3.0, 9.0 Hz, 1H), 4.09 (s, 3H), 2.18 (s, 3H); $^{13}$C NMR (125.7 MHz, DMSO-d6) δ 169.1, 155.2 (d, $^1J_{C-F}$=235.1 Hz), 150.9, 149.2, 144.5, 144.2, 130.9, 125.4, 1253, 1243, 122.1, 121.2, 120.8, 116.9 (d, $^1J_{C-F}$=23.3 Hz), 116.7 (d, $^3J_{C-F}$=8.0 Hz), 116.1 (d, $^2J_{C-F}$=22.5 Hz), 79.1, 61.7, 23.9; IR (neat) $v_{max}$ 3052.8, 2935.7, 2328.8, 1666.9, 1613.5, 1501.4; ESI-HRMS [M+H]$^+$ calculated for $C_{18}H_{16}FN_2O_3$ 327.1139 found 327.1143.

7-Acetamido-4-(2'-methoxy-5'-trifluoromethylphenyl)-8-methoxyquinoline (21). The compound was prepared from 7-acetamido-4-bromo-8-methoxyquinoline and 2-methoxy-5-trifluoromethylphenyl boronic acid using the general coupling, procedure to give the crude product which was purified through flash chromatography, using ethyl acetate as the solvent medium over silica gel to give the product as an off white solid (65.5 mg, 83% yield). TLC (ethyl acetate) R; =0.21; Melting Point 102-104° C.; $^1$H NMR (400 MHz, CDCl$_3$) δ 8.95 (d, J=4.4 Hz, 1H), 8.59 (d, J=9.5 Hz, 1H), 8.16 (broad s, 1H), 7.74 (dd, J=2.0, 8.8 Hz, 1H), 7.52 (d, J=2.0 Hz, 1H), 7.28-7.24 (m, 2H), 7.12 (d, J=8.8 Hz, 1H), 4.24 (s, 3H), 3.77 (s, 3H), 2.30 (s, 3H); $^{13}$C NMR (100 MHz, CDCl$_3$) δ 168.8, 159.3, 149.6, 144.6, 142.5, 142.2, 128.3 (q, $^4J_{C-F}$=3.5 Hz), 127.9 (q, $^2J_{C-F}$=71.4 Hz), 127.6 (q, $^4J_{C-F}$=3.7 Hz), 127.3, 125.6, 124.8, 124.3 (q, $^1J_{C-F}$=263.3 Hz), 123.5 (q, $^3J_{C-F}$=32.8 Hz), 123.2 (q, $^3J_{C-F}$=32.8 Hz), 122.9, 122.7, 121.8, 121.2, 120.2, 111.1, 62.5, 25; IR (neat) $v_{max}$ 3315.2, 2931.7, 2848.8, 1669.8, 1613.5, 1503.1, 1454.4; ESI-HRMS [M+H]$^+$ calculated for $C_{20}H_{16}FN_3O_2$ 391.1264 found 391.1270.

7-Acetamido-4-(5'-chloro-2'-methoxyphenyl)-8-methoxyquinoline (22). The compound was prepared from 7-acetamido-4-bromo-8-methoxyquinoline and 5-chloro-2-methoxyphenyl boronic acid using the general coupling procedure to give the title compound as an off white solid 120 mg (99% yield). TLC (30% hexane in ethyl acetate) $R_f$=0.21; Melting Point 198-200° C.; $^1$H NMR (400 MHz, DMSO-d6) δ 9.67 (broad s, 1H), 8.90 (d, J=4.4 Hz, 1H), 8.22 (d, J=9.2 Hz, 1H), 7.74 (dd, J=2.4, 8.8 Hz, 1H), 7.35-7.33 (m, 2H), 7.25 (d, J=8.8 Hz, 1H), 7.17 (d, J=9.2 Hz, 1H), 4.10 (s, 3H), 3.68 (s, 3H), 2.18 (s, 3H); $^{13}$C NMR (100 MHz, DMSO-d6) δ 169.1, 155.3, 149.3, 144.2, 143.8, 142.1, 131.1, 130.0, 129.7, 127.9, 124.3, 122.4, 121.1, 120.4, 113.4, 61.7, 55.9, 23.9; IR (neat) $v_{max}$ 3364.0, 29213, 2850.6, 168.5, 1608.5, 1494.1, 1451.1, 1411.2, 1373.0; ESI-HRMS [M+H]$^+$ calculated for $C_{19}H_{17}ClN_2O_3$ 356.0928 found 357.1005.

4-(Phenyl)-8-methoxy-7-pivalamidoquinoline (23). The compound was prepared from 4-bromo-8-methoxy-7-pivalamidoquinoline, and phenyl boronic acid using the general coupling procedure to give the pure title compound as an off white solid 53 mg (75%). TLC (30% hexane in ethyl acetate) $R_f$=0.41; Melting Point 139-140° C.; $^1$H NMR (500 MHz, CDCl$_3$) δ 8.92 (broad s, 1H), 8.61 (d, J=9.5 Hz, 1H), 8.48 (s, 1H), 7.67 (d, J=9.5 Hz, 1H), 7.53-747 (n, 5H), 7.26 (s, 1H), 4.20 (s, 3H), 1.39 (s, 9H); $^{13}$C NMR (125.7 MHz, CDCl$_3$) δ 177.1, 149.7, 148.9, 142.9, 142.5, 138.0, 131.7, 129.6, 128.7, 128.6, 122.0, 120.2, 62.1, 40.3, 27.7: IR (neat) $v_{max}$ 3429.1, 3030.7, 2943.4, 2862.0, 1685.3, 1611.3, 1499.7, 1449.4; ESI-HRMS [M+H]$^+$ calculated for $C_{21}H_{23}N_2O_2$ 335.1754 found 335.1759.

4-(5'-Fluoro-2-methoxyphenyl)-8-methoxy-7-pivalamidoquinoline (24). The compound was prepared from 4-bromo-8-methoxy-7-pivalamidoquinoline and 5-fluoro-methoxyphenyl boronic acid using the general coupling procedure to give the pure title compound as an off white solid 57 mg (63% yield). TLC (30% hexanes in ethylacetate), $R_f$=0.36; Melting Point 149-151° C.; $^1$H NMR (500 MHz, CDCl$_3$) δ 8.92 (d, J=4.5 Hz, 1H), 8.59 (d, J=9.5 Hz, 1H) 8.45 (broad s, 1H), 7.33 (d, J=9.5 Hz, 1H), 7.22 (d, J=4.0 Hz, 1H), 7.14 (td, J=3.0, 8.5 Hz, 1H), 6.99-6.96 (m, 2H), 4.20 (s, 3H), 3.66 (s, 3H), 1.38 (s, 9H); $^{13}$C NMR (125.7 MHz, CDCl$_3$) δ 177.1, 156.9 (d, $^1J_{C-F}$=240.0 Hz), 153.0, 149.6, 144.9, 142.7, 142.1, 131.6, 128.0 (d, $^1J_{C-F}$=7.5 Hz), 124.7, 124.2, 122.1, 121.0, 118.0 (d, $^2J_{C-F}$=23.8 Hz), 117.0 ((d, $^1J_{C-F}$=243.8 Hz), 116.1 (d, $^2J_{C-F}$=22.3 Hz), 112.3 (d, $3J_{C-F}$=8.1), 62.2, 56.2, 27.7; IR (neat) $v_{max}$ 3426.2, 2956.6, 2924.5, 2856.9, 1674.8, 1612.1, 1497.5, 1455.3; ESI-HRMS [M+H]$^+$ calculated for $C_{22}H_{24}FN_2O$ 383.1765 found 383.1769.

4-(5'-Fluoro-2'-methoxyphenyl)-8-methoxyquinoline-7-morpholineacetamide (25). Analog 25 was prepared from 4-bromo-8-methoxyquinoline-7-morpholineacetamide and 5-fluoro-2-methoxyphenylboronic acid using the general coupling procedure to give the crude product which was purified using 20% dichloromethane in ethyl acetate to give the pure title compound as an off white solid 71.4 mg (91%). TLC (20% dichloromethane in ethyl acetate) $R_f$=0.24; Melting Point 175-177° C.; $^1$H NMR (400 MHz, CDCl$_3$) δ 10.15 (broad s, 1H), 8.92 (d, J=4.4 Hz, 1H), 8.62 (d, J=9.2 Hz, 1H), 7.34 (d, J=9.2 Hz, 1H), 7.22 (d, J=4.4 Hz, 1H), 7.13 (dt, J=3.2 Hz, 8.6 Hz, 1H), 6.99-6.95 (m, 2H), 4.24 (s, 3H), 3.85 (broad t, J=4.4 Hz, 4H), 3.67 (s, 3H), 3.22 (s, 3H), 2.69 (broad t, J=4.4 Hz, 4H); $^{13}$C NMR (100 MHz, CDCl$_3$) δ 168.5, 156.9 (d, ° $J_{C-F}$=232.4 Hz), 153.0, 149.7, 144.9, 142.8, 142.4, 130.9, 128.0 (d, $^3J_{C-F}$=7.5 Hz), 124.9, 122.2, 121.1, 119.7, 118.0 (d, $^2J_{C-F}$ 23.6 Hz), 116.0 (d, $^2J_{C-F}$=22.5

Hz), 112.3 (d, $^1J_{C-F}$=8.2 Hz), 67.4, 62.8, 62.3, 56.2, 53.9; IR (neat) $v_{max}$ 3302.4, 2953.7, 2926.2, 2862.2, 2816.6, 1685.4, 1613.3, 1500.4, 1454.7, 1414.9; ESI-HRMS [M+H]$^+$ calculated for $C_{23}H_{24}FN_3O_4$ 425.1751 found 426.1832.

4-(5'-Fluoro-2-methoxyphenyl)-8-methoxyquinoline-7-morpholinepropionamide (26). Analog 26 was prepared from 4-bromo-8-methoxyquinoline-7-morpholinepropionamide and 5-fluoro-2-methoxyphenylboronic acid using the general coupling procedure to give the crude product which was purified using 40% hexanes in acetone, to give the pure title compound as an off white solid 60.2 mg (93% yield). TLC (40% hexanes in acetone) $R_f$=0.17; Melting Point 166-168° C.; $^1$H NMR (400 MHz, CDCl$_3$) δ 10.90 (broad s, 1H), 8.92 (d, J=3.2 Hz, 1H), 8.57 (d, J=9.2 Hz, 1H), 7.32 (d, J=9.2 Hz, 1H), 7.22 (d, J=2.8 Hz. 1H), 7.13 (t, J=8.4 Hz, 1H), 6.98 (d, J=6.0 Hz, 1H), 4.16 (s, 3H), 3.88 (s, 4H), 3.66 (s, 3H), 2.77 (t, J=5.2 Hz, 2H), 2.64 (s, 6H); $^{13}$C NMR (100 MHz, CDCl$_3$) δ 171.2, 156.8 (d, $^1J_{C-F}$=238.5 Hz), 153.0, 149.6, 144.8, 143.3, 142.5, 131.8, 128.1 (d, 3$J_{C-F}$=7.6 Hz), 124.8, 121.9, 121.1, 121.0, 118.0 (d, $^2J_{C-F}$=23.6 Hz), 116.0 (d, $^2J_{C-F}$=22.5 Hz), 112.2 (d, $^3J_{C-F}$=8.2 Hz), 66.7, 62.1, 56.2, 54.6, 53.3, 33.2; IR (neat) $v_m$ax 3042.0, 2921.5, 2850.5, 2815.2, 1678.0, 1610.0, 1582.8, 1500.3; ESI-HRMS [M+H]$^+$ calculated for $C_{24}H_2FN_3O_4$ 440.1980 found 440.1985.

4-(2'-Nitrophenyl)-8-methoxy-7-morpholinepropionamidoquinoline (27A). This analog was prepared from 4-bromo-8-methoxyquinoline-7-morpholinepropionamide and 2-nitrophenyboronic acid using the general coupling procedure to give the title compound as a yellow solid 104.6 mg (92%) TLC (40% hexanes in acetone) R; =0.19; Melting Point 178-180° C.; NMR (400 MHz, CDCl$_3$) δ 10.99 (broad s, 1H), (8.77 (d, J=4.4 Hz, 1H), 8.67 (d, J=9.6 Hz, 1H), 8.36-8.34 (m, 2H), 7.82 (d, J=7.6 Hz, 1H), 7.71 (t, J=8.2 Hz, 1H), 7.50 (d, J=9.2 Hz, 1H), 7.28 (d, J=4.4 Hz, 1H), 4.184 (s, 3H), 3.89 (t, J=4.6, 4H), 2.79-2.77 (m, 2H), 2.67-2.64 (s, 6H); $^{13}$C NMR (100 MHz, CDCl$_3$) δ 171.2, 149.4, 148.8, 145.0, 143.6, 142.4, 133.2 132.9, 132.3, 129.8, 124.8, 124.2, 121.9, 120.5, 119.4, 66.72, 62.2, 54.5, 53.3, 33.1; IR (neat) $v_{max}$ 2923, 2852.5, 2817.7, 2362.3, 2334.5 1677.9, 1609.9, 1578.3, 1504.9, 1454.1; ESI-HRMS [M+H]$^+$ calculated for $C_{23}H_{25}N_4O_5$ 437.1819 found 437.1825.

4-(2'-Acetamidophenyl)-8-methoxyquinoline-7-morpholinepropionamide (27). To 38.4 mg (0.088 mmol) of 27 Å was dissolved in 3.52 mL of ethanol, were added 69 mg of 10% palladium on carbon and 1.76 mL of cyclohexene and refluxed for 2.5 hours to generate the amine. The solution was filtered through a pad of celite to recover the product. The filtrate was concentrated and dried in vacuo to give a yellow residue. Without purification, the yellow residue obtained was dissolved in 1.5 mL of acetic acid and 1.5 mL of acetic anhydride. The resulting orange solution was stirred at room temperature under drying tube for 8 hours. The solvents were removed in vacuo to give a crude product. The crude product was purified by column chromatography using 10% of chloroform in acetone as the eluent on silica gel to give an off white solid 20 mg (20% yield) TLC (10% methanol in acetone) $R_f$=0.32; $^1$H NMR (400 MHz, CDCl$_3$) δ 10.9 (broad s, 1H), 8.89 (d, J=3.6 Hz, 1H), 8.60 (d, J=9.2 Hz, 1H), 8.29 (d, J=8.0 Hz, 1H), 7.51 (t, J=7.6 Hz, 1H), 7.32-725 (m, 4H), 7.02 (s, 1H), 4.15 (s, 3H), 3.86 (s, 4H), 2.78 (d, J=5.2 Hz, 2H) 1.89 (s, 3H); 13C NMR (100 MHz, CDCl$_3$) δ 171.3, 168.5, 149.7, 144.9, 143.3, 142.7, 135.3, 132.5, 130.4, 129.7, 128.2, 124.7, 124.5, 122.9, 122.0, 121.4, 121.2, 66.7, 62.1, 54.6, 53.4, 33.1, 29.8; IR (neat) $v_{max}$ 2920.8, 2852.5, 2358.6 1678.6, 1611.7, 1505.8, 1452.5, 1413.4; ESI-HRMS [M+H]$^+$ calculated for $C_{25}H_{29}N_4O_4$ 449.2183, found 449.2188.

7-Acetamido-4-(phenyl))-8-hydroxyquinoline (28). To a solution containing 250 mg (0.855 mmol) of the 7-acetamido-4-(phenyl)-8-methoxyquinoline starting material in 2.0 mL dry dichloromethane was added 8.561 mL of 1 M BBr$_3$ in DCM on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 237 mg (99% yield) of the product. TLC (ethyl acetate) $R_f$=0.32; Melting Point 177-179° C.; $^1$H NMR (500 MHz, DMSO-d6) δ 9.58 (broad s, 1H), 8.87 (d, J=4.0 Hz, 1H), 8.09 (d, J=8.5 Hz, 1H), 7.95-7.53 (m, 5H), 7.40 (d, J=4.0 Hz, 1H), 7.26 (d, J=9.0 Hz, 1H), 2.15 (s, 3H); $^{13}$C NMR (125.7 MHz, DMSO-d6) δ 168.7, 152.9, 147.9, 147.5, 142.9, 138.8, 137.5, 129.3, 128.7, 128.5, 123.5, 123.2, 120.7, 114.2, 23.6; IR (neat) $v_{max}$ 3427.9, 3278.6, 1702.9, 1624.8, 1503.0, 1453.9, 1403.1, 1296.1.

7-Acetamido-4-(fluorophenyl)-8-hydroxyquinoline (29). To a solution containing 244.4 mg (0.787 mmol) of the 7-acetamido-4-(3'-fluorophenyl)-8-methoxyquinoline starting material in 2.0 mL dry dichloromethane was added 7.87 mL of 1M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a light yellow solid 230 mg (98% yield). TLC (ethyl acetate) $R_f$=0.25; Melting Point 151-153° C.; $^1$H NMR (500 MHz, DMSO-d6) δ 10.21 (broad s, 1H), 9.59 (broad s, 11H), 8.88 (d, J=3.1 Hz, 1H), 8.11 (d, J=9.0 Hz, 1H), 7.61 (q, J=7.5 Hz, H), 7.44-7.36 (m, 4H) 7.24 (d, J=9.0 Hz, 1H), 2.15 (s, 3H); $^{13}$C NMR (125.7 MHz, DMSO-d6) δ 168.8, 162.1 (d, $^1J_{C-F}$=244.6 Hz), 147.9, 146.0, 142.8, 139.8 (d, $^3J_{C-F}$=7.5 Hz), 138.8, 130.7 (d, 2$J_{C-F}$=8.4 Hz), 125.6, 123.3, 122.9, 120.8, 116.2 (d, $^2J_{C-F}$=22.1 Hz), 115.4 (d, $^2J_{C-F}$=20.8 Hz), 114.0, 23.6; IR (neat) $v_{max}$ 3253.7, 3026.6, 1657.2, 1537.4, 1506.5; ESI-HRMS [M+H]$^+$ calculated for $C_{17}H_{14}FN_2O_2$ 297 1034 found 297.1043.

7~Acetamido-4-(4'-fluorophenyl))-8-hydroxyquinoline (30). To a solution containing 29.0 mg (0.093 mmol) of the 7-acetamido-4-(4'-fluorophenyl)-8-methoxyquinoline starting material in 0.5 mL dry dichloromethane was added 0.934 mL of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 27.0 mg (98% yield) of the product. TLC (ethyl acetate) $R_f$=0.25; Melting Point 161-163° C.; $^1$H NMR (500 MHz, DMSO-d6) δ 9.59 (broad s, 1H), 8.87 (d, J=4.0 Hz, 1H), 8.10 (d, J=9.0 Hz, 1H), 7.59 (dd, J=5.5, 8.0 Hz, 2H), 7.42-7.38 (m, 3H) 7.23 (d, J=9.0 Hz, 1H), 2.15 (s, 3H); $^{13}$C NMR (125.7 MHz, DMSO-d6) δ 168.9, 1623 (d, $^1J_{C-F}$=245.7 Hz), 148.0, 146.4, 142.9, 138.9, 133.8, 131.5

(d, $J_{C-F}$=8.17 Hz), 123.7, 123.3, 120.9, 115.7 (d, $^1J_{C-F}$=21.7 Hz), 114.2, 23.7; IR (neat) $v_{max}$ 3315.4, 3071.9, 2918.1, 2851.2, 1683.1, 1658.5, 1622.9, 1536.8, 1461.8; ESI-HRMS [M+H]$^+$ calculated for $C_{17}H_{14}FN_2O_2$ 297.1034 found 297.1040.

7-Acetamido-4-(3'-trifluoromethylphenyl))-8-hydroxyquinoline (31). To a solution containing 50.0 mg (0.138 mmol) of the 7-acetamido-4-(3'-trifluoromethylphenyl)-8-methoxyquinoline starting material in 1.0 mL dry dichloromethane was added 1.4 mL of 1M BBr$_3$ in dichloromethane at −78° C. on ice-salt bath and stirred at that temperature for 1 hour. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (25 mL×3), concentrated and dried in vacuo to afford an orange solid 40 mg (83% yield) of the product. TLC (ethyl acetate) $R_f$=0.22; Melting Point 133-135° C.; $^1$H NMR (400 MHz, DMSO-d6) δ 9.77 (broad s, 1H), 8.94 (d, J=4.4 Hz, 1H), 8.09 (d, J=9.2 Hz, 1H), 7.94-7.08 (m, 4H), 7.78 (d, J=7.5 Hz, 2H), 7.56 (d, J=4.0 Hz, 1H), 7.22 (d, J=9.2 Hz, 1H), 2.17 (s, 3H); $^{13}$C NMR (100 MHz, DMSO-d6) δ 169.2, 157.8, 147.4, 147.0, 1422, 1382, 137.7, 137.5, 133.5, 132.9, 129.9, 129.7, 129.4, 125.7, 125.5, 125.4, 124.6, 124.2, 124.1, 123.3, 122.8, 121.2, 114.3, 23.6; IR (neat) $v_{max}$ 2921.0, 2851.0, 1559.3, 1626.4, 1531.6, 1508.2, 1405.1; ESI-HRMS [M+H]$^+$ calculated for $C_{18}H_{14}F_3N_2O_2$ 347.1002 found 347.1010.

7-Acetamido-4-(4'-trifluoromethylphenyl))-8-hydroxyquinoline (32). To a solution containing 26.0 mg (0.0721 mmol) of the 7-acetamido-4-(4'-trifluoromethylphenyl)-8-methoxyquinoline starting material in 0.5 mL dry dichloromethane was added 0.720 mL of 1M BBr$_3$ in dichloromethane on ice-salt bath and stirred at that temperature for 15 minutes. The solution became orange upon the addition of BBr$_a$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 23.0 mg (92% yield) of the product. TLC (ethyl acetate) $R_f$=0.26; Melting Point 178-180° C.; $^1$H NMR (500 MHz, DMSO-d6) δ 9.68 (broad s, 1H), 8.93 (d, J=4.0 Hz, 1H), 8.09 (d, J=9.0 Hz, 1H), 7.94 (d, J=8.0 Hz, 2H), 7.78 (d, J=7.5 Hz, 2H), 7.49 (d, J=4.0 Hz, 1H) 7.22 (d, J=9.5 Hz, 1H), 2.16 (s. 3H); IR (neat) $v_{max}$ 3743.3, 3405.2, 2918.7, 2366.4, 2320.9, 1694.9, 1620.8, 1519.5, 1499.5, 1411.8; ESI-HRMS [M+H]$^+$ calculated for $C_{18}H_{14}F_3N_2O_2$ 347.1002 found 347.1005.

7-Acetamido-4-(3'-hydroxyphenyl))-8-hydroxyquinoline (33). To a solution containing 29.0 mg (0.089 mmol) of the 7-acetamido-4-(3'-methoxyphenyl)-8-methoxyquinoline starting material in 1.0 mL dry dichloromethane was added 1.8 mL of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a syrupy product 21.3 mg (80% yield) of the product. TLC (ethyl acetate) $R_f$=0.13; $^1$H NMR (500 MHz, DMSO-d6) δ 9.57 (broad s, 1H), 8.30 (d, J=4.5 Hz, 1H), 8.08 (d, J=9.0 Hz, 1H), 7.35 (m, 2H), 7.26 (d, J=9.0 Hz, 1H), 7.35 (m, 3H), 2.14 (s, 3H); 13C NMR (100 MHz, DMSO-d6) δ 168.7, 157.6, 147.8, 147.6, 143.3, 139.0, 138.8, 129.8, 123.3, 123.2, 120.4, 119.9, 116.1, 115.5, 113.9, 79.1, 23.7: IR (neat) $v_{max}$ 3202.2, 2919.1, 2850.2, 1659.0, 1625.7, 15821, 1534.0, 1505.81457.91404.0; ESI-HRMS [M+H]$^+$ calculated for $C_{17}H_{18}FN_2O_3$ 295.1077 found 295.1082.

7-Acetamido-4-(2'-acetamidophenyl)-8-hydroxyquinoline (34). To a solution containing 21.5 mg (0.0615 mmol) of the 7-acetamido-4-(2'-acetamidophenyl)-8-methoxyquinoline starting material in 0.5 mL dry dichloromethane was added 0.615 mL (10 equivalents) of 1 M BBr$_3$ in dichloromethane on ice-salt bath and stirred at that temperature for 15 minutes. The solution became orange upon the addition of BBr$_j$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 19.2 mg (93% yield) of the product TLC (50% acetone in ethyl acetate) $R_f$=0.24; Melting Point 214-216° C.; $^1$H NMR (500 MHz, DMSO-d6) δ 9.55 (broad s, 1H), 9.03 (broad s, 1H), 8.87 (d, J=4.0 Hz, 1H), 7.98 (d, J=9.0 Hz, 1H), 7.68 (d, J=7.5 Hz, 1H), 7.49 (t, J=6.5 Hz, 1H), 7.35-7.32 (m, 3H), 6.89 (d, J=9.0 Hz, 1H), 2.14 (s, 3H), 1.67 (s, 3H); $^{13}$C NMR (125.7 MHz, DMSO-d6) δ 168.7, 168.4, 147.8, 145.0, 142.7, 138.8, 135.7, 131.5, 130.6, 128.7, 126.1, 1250.1, 123.7, 123.1, 122.9, 121.5, 114.4, 23.6, 22.9; IR (neat) $v_{max}$ 32228.3, 2925.6, 2853.5, 2359.3, 2330.6, 1658.8, 15006.3, 1442.4, 1366.1, 1294.9, 1025.8; ESI-HRMS [M+Na]$^+$ calculated for $C_{19}H_{17}N_3NaO_3$ 358.1162 found 358.1156.

7-Acetamido-4-(4'-acetamidophenyl))-8-hydroxyquinoline (35). To a solution containing 26.4 mg (0.075 mmol) of the 7-acetamido-4-(4'-acetamidophenyl)-8-methoxyquinoline starting material in 0.5 mL dry DCM was added 0.76 mL (10 equivalent) of 1 M BBr$_3$ in DCM on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 15.0 mg (60% yield) of the product. TLC (50% acetone in ethyl acetate); $R_f$=0.22; $^1$H NMR (500 MHz, DMSO-d6) δ 10.1 (broad s, 1H), 9.56 (broad s, 1H), 8.83 (d, J=4.5 Hz, 1H), 8.09 (d, J=9.0 Hz, 1H), 7.77 (d, J=8.5 Hz, 2H), 7.49 (d, J=8.0 Hz, 2H), 7.36 (d, J=4.5 Hz, 1H), 7.29 (d, J=9.0 Hz, 1H), 2.14 (s, 3H), 2.10 (s, 3H); $^{13}$C NMR (125.7 MHz, DMSO-d6) δ 168.7, 168.5, 147.9, 147.1, 142.8, 139.7, 138.9, 131.9, 129.8, 123.3, 123.2, 123.1, 120.6, 118.9, 114.2, 24.1, 23.6: IR (neat) $v_{max}$ 3429.8, 3308.0, 2924.6, 1629.5, 1596.3, 1520.1, 1456.8; ESI-HRMS [M+H]$^+$ calculated for $C_{19}H_{18}N_3O_3$ 336.1343 found 336.1347.

7-Acetamido-4-(3'-acetamidophenyl)-8-hydroxyquinoline (36). To a solution containing 20.0 mg (0.0572 mmol) of the 7-acetamido-4-(3-acetamidophenyl)-8-methoxyquinoline starting material in 0.5 mL dry dichloromethane was added 0.615 mL (10 equivalents) of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 10 mg (% yield) of the product. TLC (20% methanol in ethyl acetate) $R_f$=0.21; Melting Point 156-158° C.; $^1$H NMR (500 MHz, DMSO-d6) δ 10.44 (broad s, 1H), 9.65 (broad s, 1H), 8.83 (d, J=5.0 Hz, 1H), 7.85 (s, 1H), 7.76 (d, J=10 Hz, 1H), 7.47 (t, J=10 Hz, 1H), 7.35 (d, J=5.5 Hz, 1H), 7.27-7.17 (m, 2H), 2.15 (s, 3H), 2.08 (s, 3H); IR (neat) $v_{max}$ 3233.4, 3057.9, 2920.7, 2850.9, 1665.0, 1543.6, 1428.4; ESI-HRMS [M+Na]$^+$ calculated for $C_{19}H_{17}N_3NaO_3$ 358.1162 found 358.1149.

7-Acetamido-4-(2'-hydroxy-5'-trifluoromethyl-phenyl))-8-hydroxyquinoline (37). To a solution containing 51 mg (0.132 mmol) of the 7-acetamido-4-(-2-methoxy-5'-trifluoromethyl phenyl)-8-methoxyquinoline starting material in 1.5 mL dry dichloromethane was added 3.0 mL of 1 M BBr$_3$ in dichloromethane at −78° C. and stirred at that temperature for 1 hour. The light-yellow solution was allowed to warm to room temperature and stirred at that temperature for 8 hours. The reaction was quenched by the gradual addition of ice-cold water, and the pH was adjusted with saturated NaHCO$_3$. The product was extracted with chloroform (20 mL×3), concentrated and dried in vacuo to afford an oil that solidify upon standing 20 mg (42% yield) of the product. TLC (Ethyl acetate) $R_f$=0.19; $^1$H NMR (400 MHz, DMSO-d6) δ 10.59 (broad s, 1H), 9.67 (broad s, 1H), 8.89 (d, J=4.4 Hz, 1H), 7.98 (d, J=8.8 Hz, 1H), 7.71 (dd, J=2.4, 8.8 Hz, 1H), 7.20 (d, J=8.4 Hz, 1H), 6.96 (d, J=8.8 Hz, 1H), 2.08 (s, 3H); ESI-HRMS [M+H]$^+$ calculated for $C_{18}H_{14}F_3N_2O_3$ 363.0951 found 363.0946.

7-Acetamido-4-(5'-chloro-2'-hydroxyphenyl)-8-hydroxyquinoline (38). To a solution containing 53 mg (0.149 mmol) of the 7-acetamido-4-(5'-chloro-2'-methoxyphenyl)-8-methoxyquinoline starting material in 1.5 mL dry dichloromethane was added 3.42 mL of 1 M BBr$_3$ in dichloromethane at −78° C. and stirred at that temperature for 1 hour. The light-yellow solution was allowed to warm to room temperature and stirred at that temperature for 8 hours. The reaction was quenched by the gradual addition of ice-cold water, and the pH was adjusted with saturated NaHCO$_3$. The product was extracted with chloroform (30 mL×3), concentrated and dried in vacuo to afford a light-yellow solid 43.6 mg (89% yield) of the product. TLC (ethyl acetate) $R_f$=0.11; Melting Point 234-236; $^1$H NMR (400 MHz, DMSO-d6) δ 9.90 (broad s, 1H), 9.56 (broad s, 1H), 8.86 (d, J=4.4 Hz, 1H), 7.99 (d, J=9.2 Hz, 1H), 7.39-7.36 (m, 2H), 7.24 (d, J=2.8 Hz, 1H), 7.03 (d, J=8.8 Hz, 1H), 6.97 (d, J=9.2 Hz, 1H), 2.14 (s, 3H); $^{13}$C NMR (100 MHz, DMSO-d6) δ 168.7, 153.6, 147.8, 144.1, 142.8, 138.6, 130.0, 129.4, 126.3, 123.8, 123.4, 123.0, 122.5, 121.6, 117.4, 114.9, 23.6; IR (neat) $v_{max}$ 3343.6, 3123.0, 22920.3, 2851.4, 1675.5, 1625.7, 1500.7 1468.2, 1410.3; ESI-HRMS [M+H]$^+$ calculated for $C_{17}H_{14}N_2O_3$ 329.0687 found 329.0687.

4-(Phenyl)-8-hydroxy-7-pivalamido-quinoline (39). To a solution containing 25.0 mg (0.074 mmol) of the 4-(phenyl)-7-pivalamido-8-methoxyquinoline starting material in 0.5 mL dry dichloromethane was added 0.75 mL of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 22.9 mg (96% yield) of the product. TLC (ethyl acetate) $R_f$=0.52; Melting Point 134-136° C.; $^1$H NMR (500 MHz, CD$_3$OD) δ 8.80 (broad s, 1H), 8.00 (d, J=8.5 Hz, 1H), 7.53-7.51 (m, 5H), 7.35 (d, J=9.0 Hz, 2H), 2.26 (s, 3H); $^{13}$C NMR (125 MHz, CD$_3$OD) δ 179.9, 150.5, 129.0, 144.4, 139.1, 130.5, 129.7, 125.7, 124.2, 122.2, 116.5, 40.4, 27.9; IR (neat) $v_{max}$ 3428.8, 3053.2, 2956.6, 2919.6, 2866.1, 1673.0, 1625.2, 1502.8, 1446.5, 1402.2; ESI-HRMS [M+H]$^+$ calculated for $C_{20}H_{21}N_2O_2$ 321.1598 found 321.1602.

4-(5'-Fluoro-2'-hydroxyphenyl)-8-hydroxy-7-pivalamido-quinoline (40). To a solution containing 47.0 mg (0.1228 mmol) of the 4-(5'-fluoro-2-hydroxyphenyl)-7-pivalamido-8-methoxyquinoline starting material in 1.0 mL dry dichloromethane was added 2.45 mL of 1M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 43.4 mg (99% yield) of the product. TLC (Ethyl acetate) $R_f$=0.52; Melting Point 161-163° C.; $^1$H NMR (500 MHz, CD$_3$OD) δ 8.82 (broad s, 1H), 7.91 (d, J=8.0 Hz, 1H), 8.24 (d, J=9.2 Hz, 1H), 7.36 (s, 1H), 7.14 (d, J=7.0 Hz, 1H), 6.97 (s, 2H), 1.37 (s, 9H); $^{13}$C NMR (125.7 MHz, CD$_3$OD) δ 180.0, 157.5 (d, $^1J_{C-F}$=237.4 Hz), 152.0, 149.2, 146.6, 140.4, 127.1, 126.3, 123.9 (d, $^2J_{C-F}$=24.6 Hz), 123.1, 118.2, 117.9, 117.1 (d, $^2J_{C-F}$=22.3 Hz), 40.7, 27.9; IR (neat) $v_{max}$ 3393.1, 3196.5, 2957.3, 2919.6, 2854.6, 1642.3, 1579.2, 1452.9; ESI-HRMS [M+H]$^+$ calculated for $C_{20}H_{20}N_2O_3$ 355.1452 found 355.1456.

4-(5'-Fluoro-2'-hydroxyphenyl)-8-hydroxyquinoline-7-morpholineacetamide (41). To a solution containing 33.5 mg (0.079 mmol) of compound 24 in 1.0 mL dry dichloromethane was added 1.9 mL of 1M BBr$_3$ in dichloromethane at −78° C. and stirred at that temperature for 20 minutes. The solution became orange upon the addition of BBr$_3$ and was allowed to warm to room temperature and stirred at that temperature overnight. The reaction was quenched by the gradual addition of ice-cold water, and the pH was adjusted with saturated NaHCO$_3$. The product was extracted with chloroform (20 mL×3), concentrated and dried in vacuo to afford a yellow solid a crude product which was chromatographed on reverse phase silica gel using gradient mobile phase of water (100-0%) and methanol (0-100%) to give 14 mg (45% yield) of the product. TLC (50% hexane in acetone) $R_f$=0.21; Melting Point 235-237° C.; $^1$H NMR (400 MHz, DMSO-d$_6$) δ 9.98 (broad s, 1H), 9.57 (broad s, 1H), 9.02 (d, J=4.4 Hz, 1H), 7.91 (d, J=9.2 Hz, 1H), 7.57 (d, J=8.8 Hz, 1H), 7.52 (d, J=4.4 Hz, 1H), 7.45 (broad s, 1H), 7.33 (broad s, 1H), 7.23-7.10 (m, 3H), 3.70 (s, 4H), 3.38 (s, 6H); $^{13}$C NMR (100 MHz, DMSO-d$_6$) δ 155.2 (d, $^1J_{C-F}$=233.5 Hz), 151.1, 150.5, 145.6 (d, $^2J_{C-F}$=26.6 Hz), 140.3, 135.4, 128.8, 125.2 (d, $^3J_{C-F}$ 7.7 Hz), 124.9, 123.4, 122.4, 119.0, 117.0 (d, $^1J_{C-F}$=5.9 Hz), 116.8 (d, $^3J_{C-F}$=9.4 Hz), 116.3 (d, $J_{C-F}$=22.2 Hz), 99.5, 65.3, 52.4, 51.6, 28.9; IR (neat) $v_{max}$ 3367.1, 3241.6, 3079.7, 2936.5, 2848.3, 16353, 1559.0, 1484.7, 1452.3, 1401.3; ESI-HRMS [M+H]$^+$ calculated for $C_{21}H_{21}FN_3O_4$ 398.1511 found 398.1523.

4-(5'-Fluoro-2'-hydroxyphenyl)-8-hydroxyquinoline-7-morpholinepropionamide (42). To a solution containing 33 mg (0.075 mmol) of the 4-(5-fluoro-2-methoxyphenyl)-8-methoxyquinoline-7-morpholinepropionamide starting material in 0.5 mL dry dichloromethane was added 1.50 mL of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 22.0 mg (95% yield) of the product. TLC (20% methanol in ethyl acetate) R$_f$=0.18: Melting Point 247-248° C.; $^1$H NMR (500 MHz, DMSO-d$_6$) δ 10.57 (broad s, 1H), 9.57 (broad s, 1H), 8.85 (d, J=4.0 Hz, 1H), 8.22 (d, J=9.0 Hz, 1H), 7.34 (d, J=4.5 Hz, 1H), 7.17 (dt, J=3.0, 7.5 Hz, 1H), 7.06 (dd, J=3.0, 9.0 Hz, 1H), 7.02-6.99 (m, 2H), 3.69 (t, J=3.75 Hz, 4H), 2.66-2.58 (m, 4H), 2.50 (s, 6H); $^{13}$C NMR (100 MHz, DMSO-d$_6$) δ 168.1, 155.2 (d, $^1J_{C-F}$=233 Hz), 150.9, 147.8, 144.5, 143.1, 138.4, 125.3 (d, J$_{C-F}$=7.8 Hz), 124.1, 123.2, 122.4, 121.8, 116.9 (d, $^2J_{C-F}$=32.5 Hz), 116.8, 116.1 (d, $^2J_{C-F}$=22.6 Hz), 115.0, 63.3, 52.2, 51.3, 29.9; DR (neat) v$_{max}$ 3403.2, 3296.6, 2925.5, 2852.5, 1673.7, 1610.2, 1498.0, 1451.8; ESI-HRMS [M+H]$^+$ calculated for C$_{20}$H$_{17}$N$_2$O$_3$ 333.1234 found 333.1235; ESI-HRMS [M+H]$^+$ calculated for C$_{22}$H$_{23}$FN$_3$O$_4$ 412.1667 found 412.1676.

4-(2'-Acetamidophenyl)-8-hydroxyquinoline-7-morpholinepropionamide (43). To a solution containing 21.8 mg (0.048 mmol) of the 4-(2-acetamido)-8-methoxyquinoline-7-morpholinepropionamide starting material and 0.5 ml dry dichloromethane was added 0.5 mL of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 17.1 mg (81% yield) of the product. TLC (10% acetone ethyl acetate) R$_f$=0.15; $^1$H NMR (500 MHz, DMSO-d$_6$) δ 10.60 (broad s, 1H), 9.03 (broad s, 1H), 8.87 (d, J=4.0 Hz, 1H), 8.26 (d, J=9.0 Hz, 1H), 7.67 (d, J=7.5 Hz, 1H), 7.49 (t, J=7.5 Hz, 1H), 7.35-7.30 (m, 3H), 6.89 (d, J=9.5 Hz, 1H), 4.10 (s, 4H), 2.64 (d, J=5.0 Hz, 2H), 2.58 (d, (d, J=5.0 Hz, 2H), 2.50 (s, 6H), 1.66 (s, 3H); ESI-HRMS [M+H]$^+$ calculated for C$_{20}$H$_{17}$N$_2$O$_3$ 333.1234 found 333.1235.

7-Acetamido-4-(2'-benzofuranyl)-8-methoxyquinoline (44). The compound was prepared from 7-acetamido-4-bromo-8-methoxyquinoline and 2-benzofuranylboronic acid using the general coupling procedure to give the title compound as an off white solid (56.2 mg, 85% yield). TLC (30% hexanes in ethyl acetate), R$_f$=0.25; Melting Point 139-141° C.; $^1$H NMR (500 MHz, CDCl$_3$) δ 8.96 (d, J=6.0 Hz, 1H), 8.76 (d, J=9.0 Hz, 1H), 8.31 (d, J=10 Hz, 1H), 8.16 (broad s, 1H), 7.72-7.69 (m, 2H), 7.62 (d, J=8.5 Hz, 1H), 7.40 (t, J=7.8 Hz, 1H), 7.33-7.30 (m, 2H), 4.23 (s, 3H), 2.32 (s, 3H); $^{13}$C NMR (100 MHz, CDCl$_3$) δ 168.8, 155.3, 152.6, 149.6, 143.0, 142.7, 136.1, 131.6, 128.6, 125.7, 123.5, 122.5, 121.7, 121.4, 120.9, 118.8, 111.7, 108.9, 62.5, 25.2; IR (neat) v$_{max}$ 3403.2, 3296.6, 2925.5, 2852.5, 1673.7, 1610.2, 1498.0, 1451.8: ESI-HRMS [M+H]$^+$ calculated for C$_{20}$H$_{16}$N$_2$O$_3$ 333.1234 found 333.1235.

7-Acetamido-4-(benzo[b]thiophen-2-yl)-8-m-ethoxyquinoline (45). The compound was prepared from 7-acetamido-4-bromo-8-methoxyquinoline 150 mg (0.5082 mmol) and benzo[b]thiophen-2-yl boronic acid (180.92 mg, 1.0164 mmol), palladium 11 acetate (11.40 mg, 0.0508 mmol), cesium carbonate (496.7 mg, 1.524 mmol), 1,2-bis(diphenylphosphino)ethane (20.24 mg, 0.0508 mmol), dioxane/water (9:1, 4 mL) and the mixture was heated at 85° C. for 8 hours. The reaction was filtered over a pad of celite, concentrated in vacuo to give a crude product which purified using silica gel and 30% hexane in ethyl acetate to give the title compound as an off white solid (166.1 mg, 94% yield).

TLC (30% hexanes in ethylacetate), R$_f$=0.10; Melting Point 201-203° C.; $^1$H NMR (400 MHz, CDCl$_3$) δ 8.93 (d, J=4.4 Hz, 1H), 8.69 (d, J=9.2 Hz, 1H), 8.16 (broad s, 1H), 8.10 (d, J=9.2 Hz, 1H) 7.92-7.87 (m, 2H), 7.57 (s, 1H), 7.46-7.40 (m, 3H), 4.23 (s, 3H), 2.32 (s, 3H); $^{13}$C NMR (100 MHz, DMSO-d$_6$) δ 169.2, 149.3, 144.2, 142.7, 139.9, 139.6, 131.7, 126.0, 124.4, 123.1, 122.8, 122.4, 121.0, 120.0, 108.9, 61.8, 24.0; IR (neat) v$_{max}$ 3369.7, 2920.6, 2851.4, 2851.4, 1698.3, 1610.9, 1491.7, 1434.4; ESI-HRMS [M+H]$^+$ calculated for C$_{20}$H$_{18}$N$_2$O$_2$S 349.1005 found 349.101.

7-Acetamido-4-(2-furanyl)-8-methoxyquinoline (46). The compound was prepared from 7-acetamido-4-bromo-8-methoxyquinoline and 2-furanylboronic acid using the general coupling procedure to give the title compound as an off white solid (47.2 mg, 99% yield). TLC (ethylacetate), R$_f$=0.28; Melting Point 111-113° C. $^1$H NMR (500 MHz, CDCl$_3$) δ 8.90 (d, J=4.5 Hz, 1H), 871 (d, J=9.0 Hz, 1H), 8.25 (d, J=9.5 Hz, 1H), 8.14 (broad 1H) 7.69 (s, 1H), 7.56 (d, J=4.5 Hz, 1H), 6.98 (d, J=3.0 Hz, 1H), 6.64 (t, J=2.0 Hz, 1H), 4.19 (s, 3H), 2.31 (s, 3H); $^{13}$C NMR (125.7 MHz, CDCl$_3$) δ 171.4, 153.5, 152.1, 146.9, 146.7, 145.4, 138.8, 134.1, 124.6, 124.1, 123.1, 120.2, 120.1, 115.2, 114.7, 65.0, 27.7; IR (neat) v$_{max}$ 3331.2, 3217.7, 3074.4, 2923.2, 2852.8, 2361.4, 1694.2, 1650.8, 1607.6, 1492.1; ESI-HRMS [M+H]$^+$ calculated for C$_{16}$H$_{15}$N$_2$O$_3$ 283.1077 found 283.1034.

7-Acetamido-4-(3-furanyl)-8-methoxyquinoline (47). The compound was prepared from 7-acetamido-4-bromo-8-methoxyquinoline and 3-furanylboronic acid using the general coupling procedure to give the title compound as an off white solid (52.9 mg, quantitative yield). TLC 50% hexane in acetone), R$_f$=0.21; Melting Point 130-132° C. $^1$H NMR (400 MHz, CDCl$_3$) δ 8.85 (d, J=4.4 Hz, 1H), 8.64 (d, J=9.2 Hz, 1H), 8.15 (broad s, 1H), 7.89 (d, J=9.2 Hz, 1H), 7.74 (s, 1H), 7.59 (t, J=1.6 Hz, 1H), 7.27 (d, J=4.4 Hz, 1H), 6.71 (d, J=1.2 Hz, 1H), 4.19 (s, 3H), 2.29 (s, 3H); $^{13}$C NMR (100 MHz, CDCl$_3$) δ 168.8, 149.6, 143.7, 142.7, 142.5, 141.4, 139.8, 131.4, 124.3, 122.8, 121.3, 120.4, 119.9, 116.6, 62.4, 25.1; IR (neat) v$_{max}$ 3276.2, 3125.6, 2926.7, 2855.6, 1754.7, 1654.3, 1609.6, 1500.0, 1454.7; ESI-HRMS [M+H]$^+$ calculated for C$_{16}$H$_{15}$N$_2$O$_3$ 283.1077 found 283.1083.

7-Acetamido-4-(thien-2-yl)-8-methoxyquinoline (48). The compound was prepared from 7-acetamido-4-bromo-8-methoxyquinoline and 2-thiopheneboronic acid using the general coupling procedure to give the title compound as an off-white solid (59.0 mg, quantitative yield). TLC (50% hexane in acetone R$_f$=0.32: Melting Point 128-130° C.; $^1$H NMR (400 MHz, CDCl$_3$) δ 8.85 (d, J=4.4 Hz, 1H), 8.64 (d, J=8.8 Hz, 1H), 8.19 (broad s, 1H), 8.01 (d, J=9.6 Hz, 1H), 8.30 (d, J=9.2 Hz, 1H), 7.48 (d, J=4.8 Hz, 1H), 7.34 (d, J=4.0 Hz, 1H), 7.18 (t, J=4.4 Hz, 1H), 4.18 (s, 3H), 2.28 (s, 3H); IR (neat) v$_{max}$ 3339.2, 3060.0, 2920.6, 2850.5, 1692.5, 1668.9, 1613.8, 1579.6, 1500.7, 1455.9; ESI-HRMS [M+H]$^+$ calculated for C$_{16}$H$_{15}$N$_2$O$_2$S 299.0849 found 299.0855.

7-Acetamido-4-(thien-3-yl)-8-methoxyquinoline (49). The compound was prepared from 7-acetamido-4-bromo-8-methoxyquinoline and 3-thiopheneboronic acid using the general coupling procedure to give the title compound as an off white solid (48.8 mg, % yield). TLC (ethyl acetate) Melting Point 130-132° C.; H NMR (400 MHz, CDCl$_3$) δ 8.88 (d, J=4.4 Hz, 1H), 8.62 (d, J=9.2 Hz, 1H) 8.13 (broad s, 1H), 7.83 (d, J=9.2 Hz, 1H), 7.50-7.49 (m, 2H), 7.32-7.30 (m, 2H), 4.21 (s, 3H), 2.3 (s, 3H); $^{13}$C NMR (100 MHz, CDCl$_3$) δ 168.5, 149.4, 143.25, 142.4, 138.2, 131.1, 128.6, 126.1, 124.9, 124.3, 121.4, 119.9, 62.1, 24.9; IR (neat) v$_{max}$ 3349.6, 3310.6, 3098.7, 3068.6, 2991.3, 2967.0, 2935.9, 2850.8, 1692.7, 1667.5, 1612.8 1514.0, 1501.4; ESI-HRMS [M+H]$^+$ calculated for $C_{16}H_{15}N_2O_2S$ 299.0849 found 299.0855.

7-Acetamido-4-(5-pyrindinyl)-8-methoxyquinoline (50). The compound was prepared from 7-acetamido-4-bromo-8-methoxyquinoline and pyrimidine-5-boronic acid using the general coupling procedure to give the title compound as an off white solid (72.3 mg, 81% yield). TLC (ethyl acetate), $R_f$=0.11; Melting Point 202-204° C.; $^1$H NMR (400 MHz, CDCl$_3$) δ 9.37 (s, 1H), 8.99 (d, J=4.4 Hz, 1H), 8.91 (s, 2H), 8.17 (s, 1H), 7.51 (d, J=9.2 Hz, 1H), 7.28 (d, J=4.0 Hz, 1H), 4.26 (s, 3H), 2.31 (s, 3H); C NMR (100 MHz, CDCl$_3$) δ 168.9, 158.8, 156.9, 154.9, 142.8, 142.5, 141.3, 132.0, 123.8, 121.3, 1207, 120.3, 62.6, 25.2; IR (neat) $v_{max}$ 3328.4, 3054.5, 2923.5, 2851.8, 1691.7, 1611.2, 1497.5, 1436.8; ESI-HRMS [M+H]$^+$ calculated for $C_{16}H_{15}N_4O_2$ 295.1190 found 295.1195.

4-(2'-benzofuranyl)-8-methoxyquinoline-7-morpholineacetamide (51). Analog 48 was prepared from 4-bromo-8-methoxyquinoline-7-morpholineacetamide and 2-benzofuranyl boronic acid using the general coupling procedure to give the title compound as an off white solid 109 mg (99%). TLC (Ethyl acetate) $R_f$=0.15; Melting Point 154-156° C.; $^1$H NMR (400 MHz, CDCl$_3$) δ 10.21 (broad s, 1H), 8.97 (d, J=4.4 Hz, 1H), 8.81 (d, J=9.2 Hz, 1H), 8.34 (d, J=9.6 Hz, 1H), 7.73-7.69 (m, 2H), 7.62 (d, J=1.4, 7.2 Hz, 1H), 7.40 (dt, J=4.4 Hz, 1H), 7.34-7.30 (m, 2H), 4.25 (s, 3H), 3.86 (broad t, J=4.6 Hz, 4H), 3.25 (s, 2H), 2.71 (broad t, J=4.4 Hz, 4H); ° 3C NMR (100 MHz, CDCl$_3$) δ 168.7, 153.4, 1527, 149.7, 143.2, 143.0, 136.2, 131.2, 128.6, 125.8, 123.6, 122.6, 121.8, 121.6, 120.5, 118.8, 111.7, 108.9, 67.4, 62.8, 62.4, 54.0; IR (neat) $v_{max}$ 3305.0, 2961.4, 2924.7, 2860.1, 28093, 1691.6, 161005, 1507.9, 1448.61415.8; ESI-HRMS [M+H]$^+$ calculated for $C_{24}H_{24}N_3O_4$ 418.1761 found 418.1763.

4-(2'-benzofuranyl)-8-methoxyquinoline-7-morpholinepropionamide (52). This analog was prepared from 4-bromo-8-methoxyquinoline-7-morpholinepropionamide and 2-benzofuranyl boronic acid using the general coupling procedure to give the pure title compound as an off white solid 84 mg (96%). TLC (ethyl acetate) $R_f$=0.17; Melting Point 105-107° C.; $^1$H NMR (400 MHz, CDCl$_3$) δ 10.97 (broad s, 1H), 8.97 (d, J=4.4 Hz, 1H), 8.78 (d, J=9.6 Hz, 1H), 8.32 (d, J=9.6 Hz, 1H), 7.72 (d, J=4.4 Hz, 1H), 7.70 (d, J=7.2 Hz, 1H), 7.62 (d, J=8.8 Hz, 1H), 7.40 (dt, J=1.4, 8.0 Hz, 1H), 7.33-7.30 (m, 2H), 4.17 (s, 3H), 3.91 (broad t, J=4.4 Hz, 4H), 2.80 (broad t, J=5.6 Hz, 4H), 2.69-2.63 (m, 6H); 13C NMR (100 MHz, CDCl$_3$) δ 171.4, 155.4, 152.7, 149.6, 143.6, 143.3, 136.1, 132.2, 128.6, 125.8, 123.6, 122.6, 122.0, 121.8, 121.4, 118.8, 111.7, 108.9, 66.8, 62.2, 54.6, 53.4, 33.2; IR (neat) $v_{max}$ 2922.7, 2852.6, 2816.3, 1676.4, 1608.9, 1501.0, 1451.9; ESI-HRMS [M+H]$^+$ calculated for $C_{25}H_{26}N_3O_4$ 432.1918 found 432.1929.

7-Acetamido-4-(2'-benzofuranyl))-8-hydroxyquinoline (53). To a solution containing 39.0 mg (0.117 mmol) of the 7-acetamido-4-(2-benzofuranyl)-8-methoxyquinoline starting material in 0.5 mL dry dichloromethane was added 1.17 mL (10 equivalents) of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 34.8 mg (94% yield) of the product. TLC (Ethyl acetate) $R_f$=0.23; Melting Point 222-224° C.; $^1$H NMR (500 MHz, DMSO-d6) δ 9.69 (broad s, 1H), 8.94 (d, J=4.5 Hz, 1H), 8.26 (d, J=9.5 Hz, 1H), 8.05 (d, J=9.5 Hz, 1H), 7.94 (d, J=4.5 Hz, 1H), 7.81-7.76 (m, 3H), 7.46 (t, J=8.5 Hz, 1H), 7.36 (t, J=7.5 Hz, 1H), 2.18 (s, 3H); C NMR (100 MHz, DMSO-d6) δ 168.5, 154.5, 152.4, 147.1, 140.0, 134.3, 128.3, 125.7, 124.1, 123.5, 121.8, 121.2, 118.7, 111.4, 108.8, 23.8; IR (neat) $v_{max}$ 3306.1, 1656.4, 1633.4, 1582.5, 1540.5, 1511.5, 1465.4, 1406.9; ESI-HRMS [M+H]$^+$ calculated for $C_{19}H_{15}N_2O_3$ 319.1077 found 319.1080.

7-Acetamido-4-(benzo[b]thiopen-2-yl))-8-hydroxyquinoline (54). To a solution containing 33.0 mg (0.0947 mmol) of the 7-Acetamido-4-(benzo[b]thiophen-2-yl)-8-methoxyquinoline starting material in 0.5 mL dry dichloromethane was added 0.95 mL (10 equivalents) of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 31.0 mg (98% yield) of the product. TLC (ethyl acetate) $R_f$=0.25; Melting Point 170-172° C.; $^1$H NMR (400 MHz, DMSO-d6) δ 9.63 (broad s, 1H), 8.90 (d, J=4.4 Hz, 1H), 8.21 (d, J=9.2 Hz, 1H), 8.09 (d, J=8.0 Hz, 1H), 8.00 (d, J=8.4 Hz, 1H), 7.89 (s, 1H), 7.76 (d, J=9.2 Hz, 1H), 7.63 (d, J=4.0 Hz, 1H) 7.50-7.45 (m, 2H), 2.16 (s, 3H) $^{13}$C NMR (100 MHz, DMSO-d6) δ 168.8, 147.9, 142.8, 139.8, 139.7, 139.0, 138.2, 125.9, 125.3, 124.9, 124.4, 124.0, 123.7, 122.5, 122.4, 121.3, 114.0, 23.7; IR (neat) $v_{max}$ 3319.3, 3053.1, 2919.82851.8, 1681.8, 1658.6, 1623.2, 1529.9, 1500.1, 1460.5; ESI-HRMS [M+H]$^+$ calculated for $C_{19}H_{15}N_2O_2S$ 335.0849 found 335.0849.

7-Acetamido-4-(2-furanyl))-8-hydroxyquinoline (55). To a solution containing 32 mg (0,107 mmol) of the 7-acetamido-4-(2-furanyl)-8-methoxyquinoline starting material in 1.0 mL dry dichloromethane was added 1.0 mL of 1 M BBr$_3$ in dichloromethane at −78° C. and stirred at that temperature for 1-hour. The solution became orange upon the addition of BBr$_3$ and was allowed to warm to room temperature and stirred at that temperature overnight. The reaction was quenched by the gradual addition of ice-cold water, and the pH was adjusted with saturated NaHCO$_3$ to pH=8. The product was extracted with chloroform (20 mL×3), concentrated and dried in vacuo to afford a yellow solid 30.3 mg (99% yield) of the product; TLC (ethyl acetate) $R_f$=0.15; Melting Point 185-187° C.; $^1$H NMR (400 MHz, DMSO-D6) δ 10.13 (broad s, 1H), 9.58 (broad s, 1H), 8.85 (d, J=4.8 Hz, 1H), 8.21 (d, J=9.2 Hz, 1H), 8.03 (s, 1H), 7.94 (d, J=9.2 Hz, 1H), 7.73 (d, J=3.2 Hz, 1H), 679 (d, J=1.2 Hz, 1H), 2.16 (s, 3H); $^{13}$C NMR (100 MHz, DMSO-D6) δ 168.8, 150.2, 147.9, 145.0, 144.7, 139.3, 134.6, 123.8, 120.4, 117.5, 114.2, 113.0, 112.5, 23.7; IR (neat) $v_{max}$ 3291.2, 2918.9, 2850.6, 1651.8, 1511.5, 1466.1, 1402.5; ESI-HRMS [M+H]$^+$ calculated for $C_{15}H_{13}N_2O_3$ 269.0921 found 269.0925.

7-Acetamido-4-(3-furanyl))-8-hydroxyquinoline (56). To a solution containing 38.8 mg (0.137 mmol) of the 7-acetamido-4-(3-furanyl)-8-methoxyquinoline starting material in 0.5 mL dry dichloromethane was added 1.37 mL of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 22.0 mg (60% yield) of the product. TLC (ethyl acetate) $R_f$=0.22; Melting Point 148-150° C.; $^1$H NMR (400 MHz, DMSO-D6) δ 9.57 (broad s, 1H), 8.82 (d, J=4.4 Hz, 1H), 8.26 (a, 1H), 8.16 (d, J=9.2 Hz, 1H), 7.92 (s, 1H), 7.60 (d, J=9.2 Hz, 1H), 749 (d, J=4.4 Hz, 1H) 6.99 (d, J=1.2 Hz, 1H), 2.15 (5, 3H); $^{13}$C NMR (100 MHz, DMSO-D6) δ 168.8, 148.4, 147.9, 144.2, 142.2, 138.9, 138.4, 123.4, 123.3, 122.8, 120.0, 111.4, 23.7; IR (neat) $v_{max}$ 3285.5, 2921.3, 2851.9, 1652.0, 1629.0, 1508.81463.4, 1404.9; ESI-HRMS [M+H]$^+$ calculated for $C_{15}H_{13}N_2O$ 269.0921 found 269.0927.

7-Acetamido-4-(thien-2-yl))-8-hydroxyquinoline (57). To a solution containing 32 mg (0.107 mmol) of the 7-Acetamido-4-(thien-2-yl)-8-methoxyquinoline starting material in 1.0 mL dry dichloromethane was added 1.0 mL of 1 M BBr$_3$ in dichloromethane at −78° C. and stirred at that temperature for 1 hour. The solution became orange upon the addition of BBr$_3$ and was allowed to warm to room temperature and stirred at that temperature overnight. The reaction was quenched by the gradual addition of ice-cold water, and the pH was adjusted with saturated NaHCO$_3$. The product was extracted with chloroform (20 mL×3), concentrated and dried in vacuo to afford a yellow solid 29 mg (95% yield) of the product. TLC (10% methanol in ethyl acetate) $R_f$=0.21; Melting Point 118-120° C.; $^1$H NMR (400 MHz, DMSO-d6) δ 9.60 (broad s, 1H), 8.84 (d, J=4.4 Hz, 1H), 8.19 (d, J=9.2 Hz, 1H), 7.85 (dd, J=12, 5.2 Hz, 1H), 770 (d, J=9.2 Hz, 1H), 7.57 (dd, J=1.2, 3.6 Hz, 1H), 7.53 (d, J=4.4 Hz, 1H), 7.32-7.302 (m, 1H), 2.16 (s, 3H); $^{13}$C NMR (100 MHz, DMSO-d6) δ 168.9, 147.8, 1428, 139.7, 139.1, 138.1, 129.1, 128.5, 128.3, 123.5, 122.5, 120.7, 113.9, 23.7; IR (neat) $v_{max}$ 3228.2, 29189.2850, 1666.6, 16224.2, 1525.0, 1498.0, 1457.3, 1400.3; ESI-HRMS [M+H]$^+$ calculated for $C_{15}H_{13}N_2O_2S$ 285.0692 found 285.0686.

7-Acetamido-4-(thien-3-yl)-8-hydroxyquinoline (58). To a solution containing 25.0 mg (0.0837 mmol) of the 7-Acetamido-4-(thien-3-yl)-8-methoxyquinoline starting material in 0.5 mL dry dichloromethane was added 0.837 mL of 1 M BBr$_3$ dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$. The product was extracted with chloroform (10 mL×3), concentrated and dried in vacuo to afford a yellow solid 23.0 mg (96% yield) of the product. TLC (ethyl acetate) $R_f$=0.25; Melting Point 152-153° C.; $^1$H NMR (400 MHz, DMSO-d6) δ 9.58 (broad s, 1H), 8.84 (d, J=4.4 Hz, 1H), 8.13 (d, J=9.2 Hz, 1H), 7.91 (d, J=1.6 Hz, 1H), 7.80-7.78 (m, 1H), 7.49-7.44 (m, 3H), 2.15 (s, 3H); $^{13}$C NMR (100 MHz, DMSO-d6) δ 168.8, 147.9, 142.7, 142.2, 138.9, 137.8, 128.8, 127.1, 126.0, 123.5, 123.2, 123.1, 120.5, 114.2, 23.7; IR (neat) v, 3297.4, 3108.5, 2958.2, 2920.1, 1665.6, 1622.6, 1525.7, 1497.9, 1460.7, 1411.8; ESI-HRMS [M+H]$^+$ calculated for $C_{15}H_{13}N_2O_2S$ 285.0692 found 285.0697.

7-Acetamido-4-(5-pyrimidinyl))-8-hydroxyquinoline (59). To a solution containing 26.2 mg (0.089 mmol) of the 7-acetamido-4-(5-pyrimidinyl)-8-hydroxyquinoline starting material in 0.5 mL dry dichloromethane was added 0.90 mL of 1 M BBr$_3$ in dichloromethane on ice-salt bath and stirred at that temperature for 15 minutes. The solution became orange upon the addition of BBr$_3$ and was allowed to warm to room temperature and stirred at that temperature for 8 hours. The reaction was quenched by the gradual addition of ice-cold water, and the pH was adjusted with saturated NaHCO$_3$.

The product was extracted with chloroform (10 mL×3), concentrated and dried in vacuo to afford a yellow solid 23.0 mg (92% yield) of the product. TLC (ethyl acetate) R; =0.13; Melting Point 211-213° C.; $^1$H NMR (400 MHz, DMSO-d6) δ 9.62 (broad s, 1H), 9.36 (s, 1H), 9.04 (s, 2H), 8.94 (d, J=4.4 Hz, 1H), 8.16 (d, J=9.2 Hz, 1H), 7.56 (d, J=4.0 Hz, 1H), 7.21 (d, J=9.2 Hz, 1H), 2.15 (s, 3H); $^{13}$C NMR (100 MHz, DMSO-d6) δ 168.8, 158.2, 156.7, 155.1, 147.9, 142.8, 140.6, 138.7, 131.4, 124.1, 123.8, 122.9, 121.4, 113.6, 23.7; IR (neat) $v_{max}$ 3518.2, 31971, 3048.3, 1695.6, 1624.6, 1507.8, 1459.8, 1425.2; ESI-HRMS [M+H]$^+$ calculated for $C_{15}H_{13}N_4O_2$ 281, 1033 found 281.1036.

4-(2-benzofuranyl)-8-hydroxyquinoline-7-morpholineacetamide (60). To 50 mg (0.1197 mmol) of the methoxy analog 48 dissolved in. 1.0 mL of dry dichloromethane under N$_2$?, was added 1.7 mL of 1.0 Molar BBr$_3$ in dichloromethane at −78° C. The orange suspension was stirred at −78° C. for 30 minutes and the reaction was allowed to warm to room temperature and stirred at that temperature overnight. The reaction was quenched by the addition of ice-cold water and the product was poured over ice and basified with saturated sodium hydrogen carbonate. The product was extracted with dichloromethane (25 mL×3). The organic layers were combined and concentrated in vacuo to give a crude product, which was chromatographed on reverse phase C-18 silica gel using gradient of water (100 to 0%) and methanol (0-100%) to give a pure product. TLC (50% hexane in acetone) $R_f$=0.21; Melting Point 240-242° C.; $^1$H NMR (400 MHz, DMSO-d6) δ 10.90 (broad s, 1H), 9.03 (s, 1H), 8.31-8.26 (m, 2H), 813 (d, J=7.2 Hz, 1H), 8.00 (s, 1H), 7.84 (d, J=7.6 Hz, 1H), 7.79 (d, J=8.4 Hz, 1H), 7.50 (t, J=7.6 Hz, 1H), 7.40 (t, J=6.8 Hz, 1H), 4.38 (s, 2H), 3.95-3.91 (m, 4H), 356-3.50 (m, 2H), 3.37 (s, 2H); $^{13}$C NMR (100 MHz, DMSO-d6) δ 163.4, 154.9, 128.0, 126.7, 125.0, 123.9, 122.3, 115.5, 111.7, 63.0, 56.9, 51.9, 48.5; IR (neat) $v_{max}$ 3384.8, 3337.9, 3214.8, 2978.5, 2921.8, 2853.8, 1704.9, 16283, 1591.8, 1547.1, 1520.5, 1453.4, 1418.2; ESI-HRMS [M+H]$^+$ calculated for $C_{23}H_{24}N_3O_4$ 404.1605 found 404.1613.

4-(2-benzofuranyl)-8-hydroxyquinoline-7-morpholine-propionamide (61). To 33.4 mg (0.077 mmol) of the methoxy analog 48 dissolved in. 1.0 mL of dry dichloromethane under N$_2$, was added 0.8 mL of 1.0 Molar BBr$_3$ in dichloromethane at 0° C. The orange suspension was stirred at 0° C. for 30 minutes and the reaction was allowed to warm to room temperature and stirred at that temperature overnight. The reaction was quenched by the addition of ice-cold water and the product was poured over ice and basified with saturated sodium hydrogen carbonate. The product was extracted with DCM (25 mL×3). The organic layers were combined and concentrated in vacuo to give 30 ng (93% yield) of a yellow solid. TLC (30% hexane in acetone) $R_f$=0.22; Melting Point 222-224° C. $^1$H NMR (400 MHz, DMSO-d6) δ 10.73 (broad s, 1H)), 8.94 (d, J=4.4 Hz, 1H), 8.56 (d, J=9.2 Hz, 1H), 8.05 (d, J=9.2 Hz, 1H), 7.89 (d, J=4.4 Hz, 1H), 7.82-7.76 (m, 4H), 7.45 (t, J=7.8 Hz, 1H), 7.36 (t, J=7.6 Hz, 1H), 3.72 (s, 4H), 3.32 (s, 4H), 2.68-2.62 (m, 3H); $^{13}$C NMR (100 MHz, DMSO-d6) δ 154.6, 152.2, 148.0, 139.0, 134.4, 128.2, 125.9, 123.6, 122.6, 118.7, 114.4, 111.5, 109.1, 65.9, 57.5, 53.9, 52.8; IR (neat) $v_m$a, 3296.1, 29213, 2852.1, 2816.6, 2768.2, 1653.2, 1582.8, 1542.8, 1510.5, 1462.4, 1403.3; ESI-HRMS [M+H]$^+$ calculated for $C_{24}H_{24}N_3O_4$ 418.1761 found.

Example 9

Synthesis of Amine Analogs

Synthesis of series 1 amine analogs. The synthetic methodology for generating the precursors of compounds X1-X3 (below) was recently reported [Abraham, A. D., et al. (2019) "Drug Design Targeting T-Cell Factor-Driven Epithelial-Mesenchymal Transition as a Therapeutic Strategy for Colorectal Cancer," J Med Chem, 2019. 62(22): p. 10182-10203]. This method employing various aromatic amines through nucleophilic aromatic substitution reaction ($S_NAr$) in refluxing ethanol generated analogs X4-X14 with excellent yields [Suresh, T., R. N. Kumar and P. S. Mohan, A facile approach to dibenzo [bf][1,6]naphthyridines using Vilsmeier conditions. Heterocyclic Communications, 2003. 9(1): p. 83-88]. However, several attempts to remove the methoxy group on these analogs using BBr$_3$ were unsuccessful (Scheme X, all compound numbers in the scheme should be preceded by X):

Scheme X

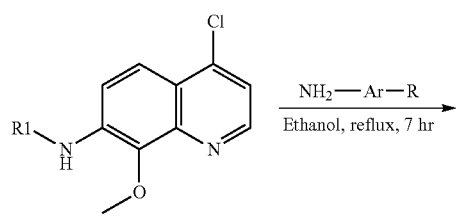

1 R1 = Acetyl
2 R1 = Morpholine acetyl
3 R1 = Morpholine propionyl

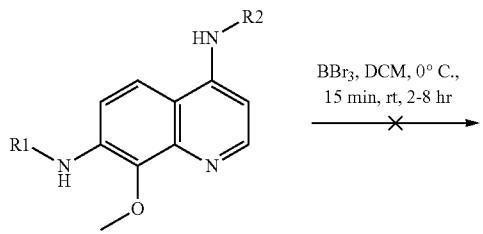

4  R1 = Acetyl, R2 = Phenyl
5  R1 = Acetyl, R2 = Benzoic Acid
6  R1 = Acetyl, R2 = 5'Indole
7  R1 = Acetyl, R2 = 4'-Indole
8  R1 = Acetyl, R2 = 5'-Indole, 2'-CH$_3$
9  R1 = Acetyl, R2 = 4'-F-Phenyl
10 R1 = Acetyl, R2 = 3'-F-Phenyl
11 R1 = Acetyl, R2 = 4'-hydroxyphenyl
12 R1 = Acetyl, R2 = 3'-hydroxyphenyl
13 R1 = Acetyl, R2 = 4'-CF$_3$-Phenyl
14 R1 = Acetyl, R2 = 3'-CF$_3$-Phenyl

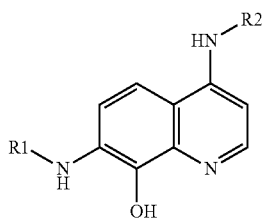

To generate the phenolic analogs X18-X30 (below), the order of the synthesis was changed by first generating the phenolic intermediates X15-X17 (below) in excellent yields via demethylation using BBr$_3$, followed by $S_NAr$, rather than progressing from $S_NAr$ to demethylation (Scheme X1, all compound numbers in the scheme should be preceded by X) [Ife, R. J., et al. "Reversible inhibitors of the gastric (H+/K+)-ATPase. 5. Substituted 2,4-diaminoquinazolines and thienopyrimidines," J Med Chem, 1995. 38(14): p. 2763-73; Leach, C. A., et al. "Reversible inhibitors of the gastric (H+/K+)-ATPase. 4. Identification of an inhibitor with an intermediate duration of action," J Med Chem, 1995. 38(14): p. 2748-62.]. The $S_NAr$ with X15-X17 was carried out using various aryl amines from simple aniline to "amino indole" derivatives in refluxing ethanol to obtain desired analogs X18-X30 (below) with 40-80% yields. The $S_NAr$ with these aryl amines proceeded smoothly, except for analogs X7 (above) and X21 (below), where 4 equivalents of 4-aminoindole was used, and the reaction was refluxed for up to 24-48 hours [Lakhdar, S., et al. "Nucleophilic reactivities of indoles". Journal of Organic Chemistry, 2006. 71(24): p. 9088-9095.].

Scheme XI. Synthesis of phenolic analogs

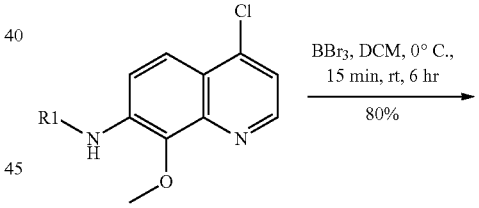

1 R1 = Acetyl
2 R1 = Morpholine acetyl
3 R1 = Morpholine propionyl

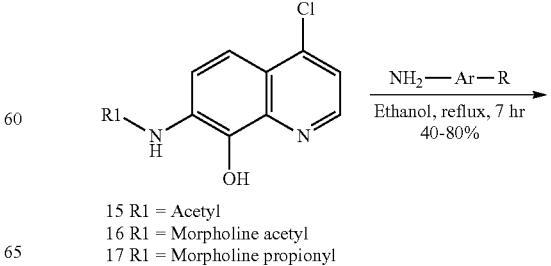

15 R1 = Acetyl
16 R1 = Morpholine acetyl
17 R1 = Morpholine propionyl

-continued

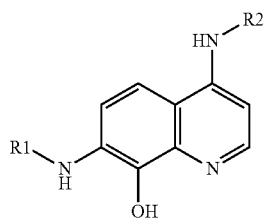

18 R1 = Acetyl, R2 = Phenyl
19 R1 = Acetyl, R2 = Benzoic Acid
20 R1 = Acetyl, R2 = 5'Indole
21 R1 = Acetyl, R2 = 4'-Indole
22 R1 = Acetyl, R2 = 5'-Indole, 2'-CH$_3$
23 R1 = Acetyl, R2 = 4'-F-Phenyl
24 R1 = Acetyl, R2 = 3'-F-Phenyl
25 R1 = Acetyl, R2 = 4'-hydroxyphenyl
26 R1 = Acetyl, R2 = 3'-hydroxyphenyl
27 R1 = Acetyl, R2 = 4'-CF$_3$-Phenyl
28 R1 = Acetyl, R2 = 3'-CF$_3$-Phenyl
29 R1 = Acetyl, R2 = 2'-F-4'-HdroxyPhenyl
30 R1 = Acetyl, R2 = 2'-F-5'-HdroxyPhenyl CADD studies indicated that all of the "alkyl amine" analogs displayed better interactions with the N-terminal domain of Topolla, and indicated that these analogs would be potent against TOP2A-dependent TCF transcription activities and EMT. Attempts were made to synthesize analogs X33-X38 (below) by coupling the alkyl amines to phenolic intermediates X15-X17 in refluxing ethanol, but no desired products were obtained, since these amines are not aryl amines and would not react by S$_N$Ar conditions. The synthesis of analogs was attempted by carrying out Buchwald-Hartwig amination method using the alkyl amines of choice with X15-X17 in the presence of 2,2'-bis(diphenylphosphino)-1,1'-binapthyl (BINAP), Cs$_2$CO$_3$, Pd(OAc)$_2$, and 1,4-dioxane (Scheme XIII, all compound numbers in the scheme should be preceded by X), but again no desired product was obtained [Daumar, P., et al., "Synthesis and evaluation of (18)F-labeled ATP competitive inhibitors of topoisomerase II as probes for imaging topoisomerase II expression," Eur J Med Chem, 2014. 86: p. 769-8.]. Hence, the coupled amine products with phenolic intermediates X15-X17, could not be obtained either by direct amination or with the aid of a ligand.

Scheme XIII. Exemplary failed attempt to synthesize

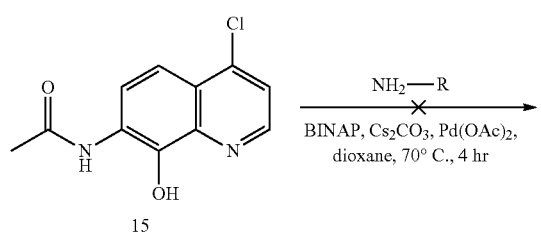

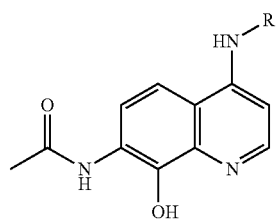

37 R2 = Cyclobutyl
38 R2 = Cyclopentyl
39 R2 = Cyclohexyl
40 R2 = Cycloheptyl

Interestingly, Buchwald Hartwig amination was then attempted with X1-X3 using the same conditions described above and the reaction proceeded smoothly to completion within 2 hours, which afforded the syntheses of X31-X36 with 76-99% yield (Scheme XIV, where all compound numbers should be preceded by X). It was initially assumed that demethylation of X31-X36 with BBr$_3$ would not work as observed and described above. Nevertheless, the demethylation process was attempted in the presence of 1 Molar BBr$_3$/DCM, and surprisingly compound X37-X42 were obtained in 71-99% yield.

Scheme XIV. Synthesis of series 4 alkyl amine analogs.

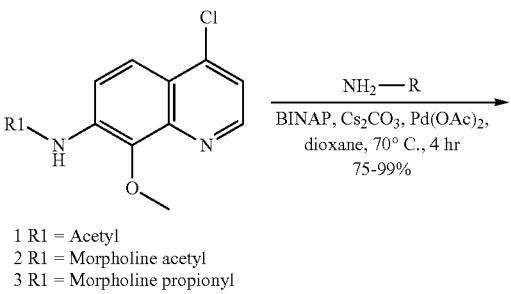

1 R1 = Acetyl
2 R1 = Morpholine acetyl
3 R1 = Morpholine propionyl

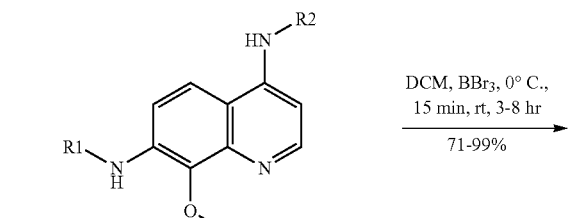

31 R1 = Acetyl, R2 = Cyclobutyl
32 R1 = Acetyl, R2 = Cyclopentyl
33 R1 = Acetyl, R2 = Cyclohexyl
34 R1 = Acetyl, R2 = Cycloheptyl
35 R1 = Morpholine acetyl, R2 = Cyclohexyl
36 R1 = Morpholine propionyl, R2 = Cyclohexyl -continued

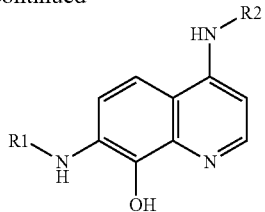

37 R1 = Acetyl, R2 = Cyclobutyl
38 R1 = Acetyl, R2 = Cyclopentyl
39 R1 = Acetyl, R2 = Cyclohexyl
40 R1 = Acetyl, R2 = Cycloheptyl
41 R1 = Morpholine acetyl, R2 = Cyclohexyl
42 R1 = Morpholine propionyl, R2 = Cyclohexyl Experimental Methods and Materials General Experimental Section. All commercial chemicals were used as supplied unless otherwise stated. All solvents used were dried and distilled using standard procedures. All reactions were performed under an inert atmosphere of ultrapure nitrogen with oven-dried glassware unless otherwise noted. All organic extracts were dried over sodium sulfate. Thin layer chromatography (TLC) was performed using Aluminum backed plates coated with 60 Å Silica gel F254 (Sorbent Technologies, Norcross, GA, USA). Plates were visualized using a UV lamp ($\lambda$max=254 nm). Column chromatography was carried out using 230-400 mesh 60 Å silica gel. Proton ($\delta$H) and carbon ($\delta$C) nuclear magnetic resonances were recorded on a Bruker Avance III 400 ($^1$H 400 MHz, $^{13}$C 100 MHz), Varian 500 MHz spectrometer (500 MHz proton, 125.7 MHz carbon). All chemical shifts are recorded in parts per million (ppm), referenced to residual solvent frequencies ($^1$H NMR: Me4Si=0, CDCl$_3$=7.26, D$_2$O=4.79, CD$_3$OD=4.87 or 3.31, DMSO-d6=2.50, Acetone-d6=2.05 and $^{13}$C NMR: CDCl$_3$=77.16; CD$_3$OD=49.0. DMSO-d6=39.5, Acetone-d6=29.9 Coupling constants (J) values are expressed in hertz (Hz). The following splitting abbreviations were used: s=singlet, d=doublet, t=triplet, q=quartet, p=pentet, m=multiplet, br=broad, dd=doublet of doublets, dt=doublet of triplets, td=triplet of doublets. High-resolution mass spectra (HRMS) were recorded on a Bruker Q-TOF-2 Micromass spectrometer equipped with lock spray, using ESI with methanol as the carrier solvent. Accurate mass measurements were performed using leucine enkephalin as a lock mass and the data were processed using MassLynx 4.1. Exact m/z values are reported in Daltons. HRMS were also recorded using Q Exactive mass spectrometer (Thermo Fisher Scientific, San Jose, CA, USA) operated independently in positive or negative ion mode, scanning in full MS mode (2 $\mu$scans) from 150 to 1500 m/z at 140,000 resolution, with 4 kV spray voltage, 45 sheath gas, 15 auxiliary gas. Acquired data were then converted from raw to mzXML file format using Mass Matrix (Cleveland, OH, USA). Metabolites assignments, isotopologue distributions, and correction for expected natural abundances of deuterium, $^{13}$C, and $^{15}$N isotopes were performed using MAVEN (Princeton, NJ, USA). Melting points (m.p.) were determined using a Stuart melting point apparatus (SMP20 and SMP40) and the values are uncorrected. Infrared (IR) spectra were recorded on a Thermo Nicolet vatar 360 FT-IR fitted with a Smart Orbit diamond ATR sampler (oils and solids were examined neat), and Bruker ALPHA platinum ATR. Absorption maxima ($v_{max}$) are recorded in wavenumbers (cm-1). Compounds with relevant biological activity were assessed by NMR and HPLC with purity ≥95% as determined by Shimadzu prominence HPLC system equipped with a photodiode array detector (PDA) and a Hypersil Gold™ C18 selectivity LC column (5 $\mu$m, 1750 Å, 250 mm×4.6 mm) with a flow rate of 1.0 mL/min. Compounds were eluted with a gradient of water methanol or acetone over 25-40 min.

TOP2A ATPase Assay. The mode of inhibition of TOP2A analogs were tested with a DNA relaxation assay and the inorganic phosphate (pi) generated was measured with malachite green phosphate reagent (Abcam, MA) in black polystyrene 384-well assay plates (Thermo Fisher Scientific, MA). ATP-dependent DNA relaxation assays in 15 $\mu$L contained 2 U hTopoII$\alpha$ (Topogen, CO), 85 $\mu$g/mL (10 nM) supercoiled plasmid (a gift from AstraZeneca), and various concentrations of ATP (between 0 and 1800 nM) and analog 3 and 7 (between 0 and 20 $\mu$M) in 50 mM Tris-HCl (pH 7.5), 150 mM KCl, 5% (v/v) glycerol, 10 mM MgCl$_2$, 1 mM dithiothreitol, 0.002% (w/v) Brij-35, and 200 nM bovine serum albumin (BSA). A duplicate plate was prepared in the same way except for the omission of the enzyme. Reactions were conducted at 37° C. for 1 h. An addition of 70 $\mu$L of ddH$_2$O and 15 $\mu$L of phosphate reagent were added to each well and the plates were incubated in dark at room temp for 30 min before OD$_{600}$ was read with a BioTek plate reader.

TOP2A decatenation assay. Human TOP2A, kDNA, and assay buffers were obtained from TopoGEN (Buena Vista, CO). The synthesized compounds were screened for their TOP2A inhibitory activity by the intensity of DNA decatenation bands on a DNA gel when compared to the vehicle. Compounds were initially incubated with TOP2A (3 U/reaction) for 20 min at a 30 $\mu$M and 1.2% DMSO concentration in a 37° C. incubator without CO$_2$. The decatenation reaction was initiated immediately after by adding 2 mM ATP and 35 ng/reaction of kDNA, then incubated for 1 h in a 37° C. water bath. The samples were loaded into a 0.8% agarose gel in 1× Tris-Borate-EDTA (TBE) at a 0.2 $\mu$g/mL ethidium bromide concentration and allowed to run in an electrophoretic chamber for 1 h at 100V. Compounds with the highest inhibitory activity were selected for 2-fold serial dilution dose-response assays (58.6 nM-30 $\mu$M). The dose-response assays followed the same protocol with the exception of 4 U/reaction of TOP2A, 3D cell culture of tumor organoids. Cell lines were cultured as tumor organoid using phenol red free RPMI-1640 containing 5% FBS. Tumor organoid were generated by seeding 5,000 cells/well (or as indicated) into un-coated 96-well U-bottom Ultra Low Attachment Microplates (PerkinElmer, MA) followed by centrifugation for 15 min at 1000 rpm to promote cells aggregation. A final concentration of 2% Matrigel was then added and tumor organoid were formed for 72 h under incubation (5% CO$_2$, 37° C., humidity) before treatment, and maintained under standard cell culture conditions during treatment time courses.

3D Tumor organoid TOPflash reporter assay. Stable engineered cells containing pCDH-TOPflash-luc-EF1-puro [Zhou, Q., et al. "Topoisomerase II$\alpha$ mediates TCF-dependent epithelial-mesenchymal transition in colon cancer," Oncogene, 2016. 35(38): p. 4990-9.] were used to generate tumor organoids arrayed in 96-well plates and treated for 72 h with TOP2A inhibitors. One-Glo™ luciferase reagent and CellTiter-Glo™ 3D cell viability reagent (Promega, WI) were used to determine the TCF reporter activity in viable cells. Briefly, reagents were added to the spheroids at 1:1 ratio (v:v) and the plates were placed on an orbital shaker (300 rpm) for 10 min at room temperature before the luminescence was read with Envision plate reader (PerkinElmer, MA). TCF reporter activity was normalized to organoid viability and inhibitors treated conditions were normalized to DMSO treated controls.

pCDH-EcadherinPromoter-mCherry-EF1-Puro (EcadPro-RFP) plasmid cloning. The CMV promoter in pCDH-CMV-MCS-EF1-puro plasmid was digested out and replaced with E-cadherin promoter using ClaI and XbaI restriction enzymes. The mCherry cassette was then inserted using EcoRI and NotI downstream of Ecadherin promoter. pEcad/luc-zeo was a generous gift from Dr. Jennifer Richer, PhD (University of Colorado), and the mCherry cassette was a generous gift from Dr. Jerome Schaack, PhD (University of Colorado). VimPro-GFP and EcadPro-RFP reporter assays. Stable VimPro-GFP or EcadPro-RFP SW620 reporter cells were generated using pCDH-VimPro-GFP-EF1-puro virus or pCDH-EcadPro-mCherry-EF1-puro virus as previously reported. [Zhou, Q et al "Topoisomerase IIα mediates TCF-dependent epithelial-mesenchymal transition in colon cancer," Oncogene, 2016. 35(38): p. 4990-9.] Transduced cells were selected with puromycin at 2 µg/mL. The stable fluorescent labeled reporter cells were then used to generate tumor organoids as described. Tumor organoids were then treated with TOP2A inhibitors at 10 µM for an additional 72 h. Following treatment, tumor organoids were stained with 16 µM of Hoechst 33342 for 1 h, which functions as a nuclear stain for imaging segmentation. Images were taken with a 5× air objective. Z stacks were set at 20 µm apart for a total of 7 layers. Imaging analysis was performed using an Opera Phenix high content screening (HCS) system and Harmony high-content imaging and analysis software interface (PerkinElmer, MA). Nuclei were identified with Hoechst 33342 stain within each layer, and cells were found with either GFP or mCherry channel. The intensities of each fluorescence channel within the cells were calculated and thresholds were set based on the background intensities. Percentages of GFP or mCherry positive cells were calculated and normalized to the DMSO treated group.

Tumor organoid cytotoxicity. SW620 tumor organoids were grown as previously outlined. CellTox™ Green-Express Cytotoxicity Assay (Promega, WI) solution was prepared per manufacturer's protocol. Briefly, organoids were treated for 72 h with CellTox™ Green Express (0.5×) reagent and various doses of TOP2A inhibitors over a range of 0-to-40 µM. Organoids were then imaged using the Opera Phenix HCS system (PerkinElmer, MA). CellTox™ Green Express was excited at 488 nm and emission was detected at 500-550 nm. Mean intensity of the whole well was utilized for calculating cytotoxicity with Lysis Buffer (Promega, WI, 0.025×) as the 0% viability control and 0.4% DMSO as the 100% viability control. Intensity values were normalized to these controls using GraphPad Prism 7.0 (GraphPad, CA).

CADD Molecular Modeling Method. Computer aided drug design were performed using the Discovery Studio (Dassault Systemés Biovia). The crystal structure of Topolla (PDB:1ZXM, 1.87 Å) was obtained from the protein data bank and prepared using the CHARM force field in the Discovery Studio. Water molecules were removed, and the residues were corrected for physiological pH. Binding sites were identified as stated in the discovery studio protocol and were defined as whole residues within a 10 Å. Neo and other analogs were prepared using discovery studio and preferred to not generate isomers of the analogs prepared. The receptor and the analogs were minimized based on Discovery Studio algorithm using a root-mean-square gradient tolerance of 3. The CDOCKER and Libdock protocol were used for the docking studies of neo and other analogs in the ATP binding site. The CDOKER approach was set to generate 10 poses of each analog, while the Libdock was set to generate 100 poses of each analog. Top ranked poses were analyzed for binding interactions.

Statistical analysis. Biological data were subjected to one-way ANOVA or using the Student's t-test analysis with Prism v7.0 (GraphPad Software Inc, La Jolla, CA, USA). All experiments were replicated on separate days two or three times as indicated (n=3 for each replicate) unless otherwise described.

Chemical Syntheses

7-Acetamido-4-chloro-8-methoxyquinoline (X1). To 300 mg (1.257 mmol) of 4-chloro-8-methoxy-7-nitroquinoline were added 489 mg (7 equivalents) of iron powder, 18 mL water/ethanol (2:8), 134 mg (2 equivalents) ammonium chloride. The mixture was refluxed for 1.5 h and allowed to cool to room temperature. The mixture was filtered over a pad of celite and washed with Methanol. The filtrate was diluted with water, and the pH was adjusted with $NaHCO_3$ to pH=8. The product was extracted with ethyl acetate, dried over sodium sulfate and concentrated in vacuo to generate the aniline intermediate. Without purification, the aniline was dissolved in 5 mL acetic acid and 2 mL acetic anhydride under drying tube for 8 h. The solvents were removed by concentrating the product in vacuo to generate the crude product, which was purified by flash chromatography using silica gel as the solid phase, and 20% dichloromethane in ethyl acetate to afford 301 mg (96% yield) TLC (Ethyl acetate) R; =0.17; Melting Point 114-116° C.; $^1H$ NMR (400 MHz, $CDCl_3$) δ 8.76 (d, J=7.2 Hz, 1H), 8.73 (d, J=4.0 Hz, 1H), 8.13 (broad s, 1H), 7.96 (d, J=7.6 Hz, 1H), 7.40 (d, J=4.0, 1H), 4.18 (s, 3H), 2.29 (s, 3H); $^{13}C$ NMR (100 MHz, $CDCl_3$) δ 168.7, 149.3, 142.8, 142.2, 132.2, 123.9, 121.0, 120.1, 119.8, 62.5, 25.1; IR (neat) $v_{max}$ 3337.0, 3195.8, 2954.9, 2924.2, 28527, 2361.4, 1694.8, 1610.3, 1507.8, 1442.8; ESI-HRMS $[M+Na]^+$ calculated for $C_{12}H_{11}ClN_2O_2Na$ 273.0401 found 273.0403.

4-Chloro-8-methoxy-7-(2-(morpholin-4-yl)acetamido) quinoline (X2). To 150 mg (0.628 mmol) of 4-chloro-8-methoxy-7-nitroquinoline were added 246 mg (7 equivalents) of iron powder, 9 ml water/ethanol (2:8), 67.2 mg (2 equivalents) ammonium chloride. The mixture was refluxed for 1.5 hours and allowed to cool to room temperature. The mixture was filtered over a pad of celite and washed with methanol. The filtrate was diluted with water, and the pH was adjusted with $NaHCO_3$ to pH=8. The product was extracted with ethyl acetate, dried over sodium sulfate and concentrated in vacuo to generate the aniline intermediate. Without purification the aniline was dissolved in 3 ml of dry DCM, to which were added 2 molar equivalents of morpholine acetic acid (193.7 mg), 220 µL TEA (2.5 equivalents, 159.37 mg), 450 µL (418.08 mg, 1.2 equivalents) of T3P. The resulting solution was stirred for 24 hours under nitrogen. The reaction was quenched by the addition of water, and the pH was adjusted with saturated $NaHCO_3$ until pH=8. The product was isolated using 30 ml of DCM×3, and dried over sodium sulfate. The solvents were removed by concentrating the product in vacuo to generate the crude product, which was purified by flash chromatography using silica gel as the solid phase, and 50% hexane in acetone to afford 200.6 mg (92% yield). TLC (50% hexane in acetone)

4-Chloro-8-methoxy-7-(3-(morpholin-4-yl)propanamido) quinoline (X3). To 150 mg (0.628 mmol) of 4-chloro-8-methoxy-7-nitroquinoline were added 246 mg (7 equivalents) of iron powder, 9 ml water/ethanol (2:8), 67.2 mg (2 equivalents) ammonium chloride. The mixture was refluxed for 1.5 hours and allowed to cool to room temperature. The mixture was filtered over a pad of celite and washed with Methanol. The filtrate was diluted with water, and the pH was adjusted with $NaHCO_3$ to pH=8. The product was extracted with ethyl acetate, dried over sodium sulfate and concentrated in vacuo to generate the aniline intermediate. Without purification the aniline was dissolved in 3 ml of dry DCM, to which were added 2 molar equivalents of morpholine propionic acid hydrochloride (246.5 mg), 220 μL TEA (2.5 equivalents, 159.37 mg), 450 μL (418.08 mg, 1.2 equivalents) of T3P. The resulting solution was stirred for 24 hours under nitrogen. The reaction was quenched by the addition of water, and the pH was adjusted with saturated $NaHCO_3$ until pH=8. The product was isolated using 30 ml of DCM×3, and dried over sodium sulfate. The solvents were removed by concentrating the product in vacuo to generate the crude product, which was purified by flash chromatography using silica gel as the solid phase, and 50% hexane in acetone to afford 200.6 mg (91% yield) of syrupy product. TLC (50% hexane in acetone) $R_f$=0.22; $^1$H NMR (500 MHz, $CDCl_3$) δ 10.96 (s, 1H), 8.79 (d, J=11.5 Hz, 1H), 8.75 (d, J=5.5 Hz, 2H), 7.96 (d, J=12.0 Hz, 1H), 7.40 (d, J=5.0 Hz, 1H), 4.12 (s, 3H), 3.87 (s, 4H), 2.77 (t, J=6.8 Hz, 2H), 2.65 (t, J=7.5 Hz, 6H); 13C NMR (125 MHz, $CDCl_3$) δ 171.4, 149.5, 143.3, 143.2, 142.9, 133.0, 124.1, 122.2, 120.2, 119.9, 66.7, 62.2, 54.5, 53.3, 33.2; IR (neat) $v_{max}$ 3170.0, 2924.9, 2855.5, 2822.1, 1686.9, 1611.9, 1513.7, 1457.5, 1418.5, 1402.6; ESI-HRMS [M+H]$^+$ calculated for $C_{17}H_{21}ClN_3O_3$ 350.1266, found 350.1260.

General method for nucleophilic aromatic substitution reaction ($SN_{Ar}$) X4-X14 To 50 mg (0.199 mmol) of 7-acetamido-4-chloro-8-methoxyquinoline was dissolved in 7 mL of ethanol to which was added 2 equivalents (0.398 mmol) of amine at room temperature and the resulting yellow solution was refluxed for 8 h. The yellow solution was washed with water followed by extraction with chloroform (30 mL)×3. The Chloroform extracts were combined, dried over sodium sulfate and filtered off to give a yellow filtrate. The filtrate was concentrated and dried under high vacuum to give a crude yellowish orange product which was chromatographed on silica gel using 5-10% methanol in ethyl acetate to afford pure product.

7-Acetamido-4-((phenyl)amino)-8-methoxyquinoline (X4). The compound was prepared from 50 mg (0.199 mmol) of 7-acetamido-4-chloro-8-methoxyquinoline and 37 mg (36.0 6 μL, 0.398 mmol) of aniline using the general method for $SN_{Ar}$ to afford 54 mg (88% yield). TLC (20% methanol in ethyl acetate) $R_f$=0.25; Melting Point 214-215° C.; $^1$H NMR (400 MHz, Acetone-$d_6$) δ 8.97 (broad s, 1H), 3.58 (d, J=9.2 Hz, 1H), 8.48 (d, J=5.2 Hz, 1H), 8.26 (broad s, 1H), 8.01 (d, J=9.2 Hz, 1H) 7.44-7.39 (multiplet, 4H), 7.19-7.17 (multiplet, 1H) 6.95 (d, J=5.2 Hz, 1H), 4.14 (s, 3H), 2.24 (s, 3H); $^{13}$C NMR (125.7 MHz, DMSO) δ 169.1, 149.9, 14'7.9, 144.0.143.4.1405, 131.3.129.3, 123.7, 122.4, 119.5, 117.3, 116.8, 100.8, 61.5, 24.0; IR (neat) $v_{max}$ 2924.5, 2854.6, 1676.1, 1615.9, 1582.9, 1532.4; ESI-HRMS [M+H]$^+$ calculated for $C_{18}H_{18}N_3O_2$ 308.1394 found 308.1411.

7-Acetamido-4-((3-benzoic)amino)-8-methoxyquinoline (X5) The compound was prepared from 50 mg (0.199 mmol) of 7-acetamido-4-chloro-8-methoxyquinoline and 54.58 mg (2 equivalents, 0.398 mmol) of 3-amino benzoic acid at room temperature, and the 110 resulting solution was refluxed for 8 hours. The yellow solution was cooled to room temperature, concentrated and dried in vacuo to give a crude yellowish orange product, which was recrystallized with chloroform to afford an off-white solid of about 50 mg (72% yield). TLC (50% methanol in ethyl acetate) $R_f$=0.17; Melting Point 236-238° C.; $^1$H NMR (500 MHz, DMSO-d6) δ; 10.89 (br s, 1H), 10.14 (br s, 1H), 8.44 (s, 2H), 3.40 (d, J=7.0 Hz, 1H), 7.99-7.97 (m, 2H), 7.76-7.70 (m, 2H), 6.82 (d, J=6.5 Hz, 1H), 3.89 (s, 3H), 2.25 (s, 3H); $^{13}$C NMR (125.7 MHz, DMSO-d6) δ 169.7, 166.5, 154.6, 143.2, 138.3, 137.5, 135.2, 133.4, 132.5, 130.3, 129.5, 128.0, 125.8, 121.9, 113.9, 114.1, 99.8, 61.6, 24.0; IR (neat) $v_{max}$ 3118.0, 3068.2, 2961.5, 1711.1, 1662.6, 1618.3, 1586.2, 1510.0, 1454.0; ESI-HRMS [M+H]$^+$ calculated for $C_{19}H_{15}N_3O_4$ 352.1292 found 352.1297.

7-Acetamido-4-((5-indole)amino)-8-methoxyquinoline (X6). The compound was prepared from 50 mg (0.199 mmol) of 7-acetamido-4-chloro-8-methoxyquinoline and 52.6 mg (2 equivalents, 0.398 mmol) of 5-amino indole using the general method for $SN_{Ar}$ to afford 58 mg (84% yield). TLC (30% methanol in ethyl acetate) $R_f$=0.25; Melting Point 170-172° C.; $^1$H NMR (500 MHz, DMSO-d6) δ 11.1 (broad s, 1H), 9.53 (broad s, 1H), 8.85 (broad s, 1H), 8.30 (d, J=5.5 Hz, 1H), 8.21 (d, J=9.0 Hz, 1H), 8.12 (d, J=9.5 Hz, 1H), 7.47 (d, J=9.0 Hz, 2H), 7.39 (t, J=2.5 Hz, 1H), 7.07 (dd, J=2.0, 8.5 Hz, 1H), 6.51 (d, J=5.5 Hz, 1H), 6.45 (s, 1H), 4.02 (s, 3H), 2.20 (s, 3H); $^{13}$C NMR (125.7 MHz, DMSO-d6) δ 169.1, 1501, 149.8, 143.9, 143.3, 133.8, 131.3, 131.1, 128.2, 126.2, 119.3, 118.9, 116.7, 116.2, 112.1, 101.1, 99.4, 61.3, 24.0; IR (neat) $v_{max}$ 3165.2, 2924.5, 2852.7, 2363.4, 2334.3, 1674.2, 1617.9, 1590.7, 1503.3; ESI-HRMS [M+H]$^+$ calculated for $C_{20}H_{19}N_4O_2$ 347.1503 found 347.1493.

7-Acetamido-4-((4-indole)amino)-8-methoxyquinoline (X7). The compound was prepared from 50 mg (0.199 mmol) of 7-acetamido-4-chloro-8-methoxyquinoline and 105.2 mg (4 equivalents, 0.796 mmol) of 4-amino indole using the general method for $SN_{Ar}$ to afford 60 mg (87% yield). TLC (30% methanol in ethyl acetate) $R_f$=0.32: Melting Point 200-202° C.; $^1$H NMR (400 MHz, DMSO-d6) δ 11.4 (broad s, 1H), 9.98 (broad s, 1H), 9.83 (broad s, 1H), 8.37 (d, J=9.2 Hz, 1H), 8.30 (d, J=8.0 Hz, 2H), 7.42 (d, J=8.0 Hz, 1H), 7.37 (t, J=2.6 Hz, 1H), 7.20 (t, J=8.0 Hz, 1H), 7.02 (d, J=7.6 Hz, 1H), 6.35 (d, J=6.0 Hz, 1H), 6.21 (s, 1H), 3.96 (s, 3H), 2.22 (s, 3H); $^{13}$C NMR (125.7 MHz, DMSO-d6) δ 170.1, 137.6, 133.2, 130.1, 126.0, 123.7, 121.9, 121.1, 118.4, 115.9, 110.8, 101.2, 99.8, 61.8, 24.2; IR (neat) $v_{max}$ 3211.8, 2920.6, 2852.7, 2367.3, 2340.1, 1676.1, 1617.9, 1582.9; ESI-HRMS [M+H]$^+$ calculated for $C_{20}H_{19}N_4O_2$ 347.1503 found 347.1508.

7-Acetamido-4-(((2-methyl)-5-indole)amino)-8-methoxyquinoline (X8). The compound was prepared from 50 mg (0.199 mmol) of 7-acetamido-4-chloro-8-methoxyquinoline and 58.2 mg (2 equivalents, 0.398 mmol) of 5-amino-2-methyl using the general method for $SN_{Ar}$ to afford 60 mg (84% yield). TLC (30% methanol in ethyl acetate) $R_f$=0.22; Melting Point 236-237° C.; $^1$H NMR (400 MHz, DMSO-d6) δ 11.01 (broad s, 1H), 9.57 (broad s, 1H), 8.95 (broad s, 1H), 8.28 (d, J=5.2 Hz, 1H), 8.20 (d, J=9.2 Hz, 1H), 8.13 (d, J=9.2 Hz, 1H), 7.34 (d, J=7.6 Hz, 2H), 6.96 (d, J=5.6 Hz, 1H), 6.35 (d, J=6.0 Hz, 1H), 6.13 (s, 1H), 4.00 (s, 3H), 2.39 (s, 3H) 2.19 (s, 3H); $^{13}$C NMR (125.7 MHz, DMSO-d6) δ 169.3, 150.8, 149.1, 143.5, 142.3, 136.8, 134.2, 131.5, 130.7, 129.3, 119.3, 118.2, 116.9, 116.5, 115.4, 111.2, 99.4, 61.4, 24.1, 13.5; IR (neat) $v_{max}$ 2910.9, 2842.9, 1678.1, 1614.0, 1582.9, 1536.3; ESI-HRMS [M+H]$^+$ calculated for $C_{20}H_{21}N_4O_2$ 361.1659 found 361.1664.

7-Acetamido-4-((4-fluorophenyl)amino)-8-methoxyquinoline (X9). The compound was prepared from 35.8 mg (0.143 mmol) of 7-acetamido-4-chloro-8-methoxyquinoline and 15.87 mg (1 equivalent, 0.142 mmol) of 4-fluoroaniline using the general method for SN$_{Ar}$ to afford 42.5 mg (91% yield). TLC (30% methanol in ethyl acetate) R$_f$=0.52; $^1$H NMR (500 MHz, DMSO-d6) δ 9.56 (s, 1H), 8.93 (s, 1H), 8.41 (d, J=5.0 Hz, 1H), 8.24 (d, J=9.0 Hz, 1H), 8.06 (d, J=9.5 Hz, 1H), 7.38 (dd, J=3.5 Hz, J=5.0 Hz, 1H), 7.26 (t, J=8.75 Hz, 1H), 6.71 (d, J=5.5 Hz, 1H), 4.02 (s, 3H), 2.20 (s, 3H); $^{13}$C NMR (125.7 MHz, DMSO) δ 169.1, 158.7 (d, $^1J_{C-F}$=240.7 Hz), 149.8, 148.4, 143.8, 143.2, 136.6, 131.3, 125.0 (d, J$_{C-F}$=8.1 Hz), 119.4, 117.0, 116.7, 116.0 (d, $^2J_{C-F}$=22.3 Hz), 100.2, 61.4, 24.0; ESI-HRMS [M+Na]$^+$ calculated for C$_{18}$H$_{18}$N$_3$O$_3$Na 348.1119 found 348.1129.

7-Acetamido-4-((3-fluorophenyl)amino)-8-methoxyquinoline (X10). The compound was prepared from 62 mg (0.2473 mmol) of 7-acetamido-4-chloro-8-methoxyquinoline and 35.72 mg (2 equivalents, 47.54 μL, 0.4946 mmol) of 3-fluoroaniline using the general method for SN$_{Ar}$ to afford 57 mg (71% yield). TLC (10% methanol in ethyl acetate) R$_f$=0.23; $^1$H NMR (500 MHz, DMSO-d6) δ 9.57 (s, 1H), 9.03 (s, 1H), 8.50 (d, J=5.5 Hz, 1H), 8.27 (d, J=9.0 Hz, 1H), 8.02 (d, J=9.5 Hz, 1H), 7.41 (q, J=7.6 Hz, 1H), 7.20 (d, J=8.0 Hz, 1H), 7.16 (d, J=11.0 Hz, 1H), 7.03 (d, J=5.0 Hz; 1H), 6.90 (t, J=8.5 Hz, 1H), 4.03 (s, 3H), 2.20 (s, 3H); $^{13}$C NMR (125.7 MHz, DMSO-d6) δ 169.1, 155.2 (d, $^1J_{C-F}$=235.2 Hz), 154.3, 150.9, 149.2, 144.5, 144.2, 130.9, 125.4 (d, $^1J_{CF}$=7.6 Hz), 124.3, 122.2, 121.2, 120.8, 116.9 (d, $^2J_{C-F}$=23.4 Hz), 116.7 (d, $^3J_{C-F}$=8.0 Hz), 116.1 (d, J$_{C-F}$=22.5 Hz), 79.1, 61.7, 23.9; IR (neat) v$_{max}$ 3285.1, 321, 2928.0, 2893.2, 1680.5, 1612.9, 1576.3, 1526.9; ESI-HRMS [M+H]$^+$ calculated for C$_{18}$H$_{17}$FN$_3$O$_2$ 326.1299 found 326.1304.

7-Acetamido-4-((4-hydroxyphenyl)amino)-8-methoxyquinoline (X11). The compound was prepared from 33.5 mg (0.133 mmol) of 7-acetamido-4-chloro-8-methoxyquinoline and 14.75 mg (1 equivalent, 0.133 mmol) of 4-amino-phenol using the general method for S$_N$Ar to afford 42 mg (98% yield). TLC (20% methanol in ethyl acetate) R$_f$=0.21; MP 249° C.; $^1$H NMR (500 MHz, DMSO-d6) δ 9.52 (s, 1H), 9.44 (broad s, 1H), 8.70 (s, 1H), 8.32 (d, J=5.0 Hz, 1H), 8.12 (d, J=9.0 Hz, 1H), 8.05 (d, J=9.5 Hz, 1H), 7.14 (d, J=8.5 Hz, 1H), 6.84 (d, J=8.5 Hz, 1H), 6.49 (d, J=5.0 Hz, 1H) 4.01 (s, 3H), 2.19 (s, 3H); $^{13}$C NMR (125.7 MHz) δ 169.0, 154.8, 149.8, 149.6, 143.1, 131.1, 130.9, 126.1, 119.0, 116.6, 115.9, 99.4, 61.4, 24.0; IR (neat) v$_{max}$ 3304.8, 2957.8, 2929.2, 2362.1, 2331.5, 1676.9, 1653.1, 1617.1, 1577.9, 1540.5; ESI-HRMS [M+H]$^+$ calculated for C$_{18}$H$_{18}$N$_3$O$_3$ 324.1343 found 324.1358.

7-Acetamido-4-((3-hydroxyphenyl)amino)-8-methoxyquinoline (X12). The compound was prepared from 33.0 mg (0.131 mmol) of 7-acetamido-4-chloro-8-methoxyquinoline and 14.30 mg (1 equivalent, 0.131 mmol) of 3-amino-phenol using the general method for SN$_A$, to afford 40.2 mg (95% yield). TLC (30% methanol in ethyl acetate) R$_f$=0.44; $^1$H NMR (500 MHz, DMSO-d6) δ 9.59 (s, 1H), 9.52 (s, 1H), 8.93 (broad s, 1H), 8.52 (broad s, 1H), 8.32 (d, J=5.0 Hz, 1H), 8.21 (d, J=8.5 Hz, 1H), 8.11 (d, J=9.5 Hz, 1H), 7.22 (d, J=8.0 Hz, 1H), 7.14 (t, J=8.0 Hz, 1H), 7.00 (d, J=8.0 Hz, 1H), 6.89 (t, J=7.5 Hz, 1H), 6.20 (d, J=5.5 Hz, 1H), 4.02 (s, 3H), 4.01 (s, 3H) 2.20 (s, 3H); 13C NMR (125.7 MHz, DMSO) δ 169.1, 158.2, 149.4, 148.2, 141.4, 131.6, 129.9, 119.5, 117.0, 113.1, 111.1, 109.3, 61.1, 24.0; ESI-HRMS [M+H]$^+$ calculated for C$_{18}$H$_{18}$N$_3$O$_3$ 324.1343 found 324.1342.

7-Acetamido-4-((4-trifluoromethylphenyl)amino)-8-methoxyquinoline (X13). The compound was prepared from 64 mg (0.2553 mmol) of 7-acetamido-4-chloro-8-methoxyquinoline and 82.27 mg (2 equivalents, 0.5106 mmol) of 4-trifluoromethylaniline using the general method for SN$_{Ar}$ to afford 77 mg (81% yield). TLC (10% methanol in ethyl acetate) R$_f$=0.32; Melting Point 237-239° C.; $^1$H NMR (500 MHz, DMSO-d6) δ 9.59 (s, 1H), 9.23 (s, 1H), 8.56 (d, J=5.0 Hz, 1H), 8.28 (d, J=9.0 Hz, 1H), 8.01 (d, J=9.5 Hz, 1H), 7.70 (d, J=8.5 Hz, 2H), 7.50 (d, J=8.5 Hz, 2H), 7.16 (d, J=5.5 Hz, 1H), 4.04 (s, 3H), 2.20 (s, 3H); $^{13}$C NMR (100 MHz, DMSO-d6) δ 169.1, 149.9, 146.2, 145.2, 143.7 (d, $^2J_{C-F}$=50.4 Hz), 131.5, 128.6, 126.5 (q, $^4J_{C-F}$=3.8 Hz and 11.1 Hz), 124.5 (d, J$_{C-F}$=269.4 Hz), 122.7, (d, $^2J_{C-F}$=90 Hz), 122.1 (d, 3J$_{C-F}$=31.9 Hz), 120.1, 119.9, 118.2, 117.1, 103.5, 61.5, 24.0; IR (neat) v$_{max}$ 3404.8, 3349.3, 2927.6, 2901, 1676.3, 1616.7, 1584.5, 1532.8; ESI-HRMS [M+H]$^+$ calculated for C$_{19}$H$_{17}$F$_3$N$_3$O$_2$ 376.1267, found 376.1274.

7-Acetamido-4-((3-trifluoromethylphenyl)amino)-8-methoxyquinoline (14). The compound was prepared from 63 mg (0.2513 mmol) and 80.98 mg (2 equivalents, 0.5026 mmol) of 3-trifluoromethylaniline using the general method for SN$_{Ar}$ to afford 90 mg (95% yield). TLC (10% methanol in ethyl acetate) R$_f$=0.32: $^1$H NMR (500 MHz, DMSO-d6) δ 9.58 (s, 1H), 918 (s, 1H), 8.52 (d, J=5.0 Hz, 1H), 8.27 (d, J=9.0 Hz, 1H), 803 (d, J=9.0 Hz, 1H), 7.68-7.59 (m, 3H), 7.41 (d, J=7.5 Hz, 1H), 7.01 (d, J=5.5 Hz, 1H), 4.03 (s, 3H), 2.20 (s, 3H); $^{13}$C NMR (125.7 MHz, DMSO-d6) δ 169.2, 162.7 (d, $^1J_{C-F}$=242.6 Hz), 150.0, 146.9, 144.0, 143.5, 142.9 (d, $^4J_{C-F}$=10.4 Hz), 131.4, 130.9 (d, $^4J_{C-F}$=9.7 Hz), 119.8, 117.7, 117.0 (d, $^4J_{C-F}$=32.8 Hz), 109.5 (d, $^1J_{C-F}$=21.1 Hz), 107.9 (d, $^3J_{C-F}$=24.1 Hz), 102.1, 61.5, 24.0; IR (neat) v$_{max}$ 3411.3, 3349.30, 3292.5, 3011.7, 2943.7, 2855.9, 1674.8, 1615.9, 1588.8, 1577.4, 1540.3.

7-Acetamido-4-chloro-8-hydroxyquinoline (X15). To 600 mg (2.393 mmol) of 7-Acetamido-4-bromo-8-methoxyquinoline in 5 mL of dry dichloromethane was added 2.5 equivalents of 1M BBr$_3$ in dichloromethane (5.983 mmol) at 0° C. for 10 minutes. The reaction was allowed to stir at that temperature for additional 20 minutes, during this period the reaction became orange suspension. The reaction was then warmed to room temperature and stirred at that temperature overnight. The reaction was quenched by the addition of ice-cold water and basified using saturated aqueous sodium bicarbonate, and extract with of chloroform (50 ml, ×3). The organic layers were combined and concentrated in vacuo to give a crude product, which was recrystallized with ethanol to give 490 mg (87% yield) as a light-yellow solid. TLC (Ethylacetate) R$_f$=0.32; Melting Point 186-188° C.; $^1$H NMR (400 MHz, DMSO-d6) δ 10.46 (broad s, 1H), δ 9.62 (broad s, 1H), 8.76 (d, J=4.8 Hz, 1H), 8.30 (d, J=9.2 Hz, 1H), 7.69 (d, J=4.4 Hz, 1H), 7.60 (d, J=9.2 Hz, 1H), 2.16 (s, 3H); $^{13}$C NMR (100 MHz, DMSO-d6) δ 168.8, 148.0, 142.6, 141.0, 139.1, 124.6, 124.2, 122.6, 120.5, 112.4, 23.6; IR (neat) v$_{max}$ 3289.8, 2359.1, 2924.2, 2328.8, 1654.3, 1626.6, 1522.2, 1501.8; ESI-HRMS [M+H]$^+$ calculated for C$_{11}$H$_{10}$ClN$_2$O$_2$ 237.0425 found 237.0430.

4-Chloro-8-hydroxy-7-(3-(morpholin-4-yl)propanamido) quinoline (X16). To 682 mg (1.949 mmol) of 4-chloro-8-methoxyquinoline-7-morpholinepropionamide in 4 ml of dry dichloromethane was added 2.5 equivalents of 1M BBr$_3$ in dichloromethane (9.752 ml) at 0° C. for 10 minutes. The reaction was allowed to stir at that temperature for additional 20 minutes, during this period the reaction became dark orange suspension. The reaction was then warmed to room temperature and stirred at that temperature overnight. The reaction was quenched by the addition of ice-cold water and basified using saturated aqueous sodium bicarbonate, and extract with of chloroform (50 ml, ×3). The organic layers were combined and concentrated in vacuo to give a crude product, which was recrystallized with ethanol to give 400 mg (61% yield). TLC (Ethylacetate). $^1$H NMR (500 MHz, DMSO-d6) δ 10.75 (broad s, 1H), 10.58 (broad s, 1H), 8.76 (d, J=4.5 Hz, 1H), 8.59 (d, J=9.5 Hz, 1H), 7.67 (d, J=4.5 Hz, 1H), 7.61 (d, J=9.5 Hz, 1H), 3.70 (s, 4H), 2.64 (s, 4H), 2.50 (s, 4H); $^{13}$C NMR (100 MHz, DMSO-d6) δ 170.7, 148.2, 141.6, 141.1, 138.9, 125.5, 122.7, 122.2, 120.3, 112.7, 65.8, 53.8, 52.8, 32.7; IR (neat) $v_{max}$ 3100.7, 2966.3, 2927.0, 2862.9, 2810.5, 2771.0, 1654.1, 1616.8, 1536.8, 1497.0; ESI-HRMS [M+H]$^+$ calculated for $C_{16}H_{19}ClN_3O_3$ 336.1109 found 336.1114.

General method for nucleophilic aromatic substitution reaction (SN$_{Ar}$) for analogs X18-X30 To 40 mg (0.199 mmol) of 7-acetamido-4-chloro-8-methoxyquinoline was dissolved in 7 mL of ethanol to which was added 2 equivalents (0.398 mmol) of amine at room temperature and the resulting yellow solution was refluxed for 8 h. The yellow solution was washed with water followed by extraction with chloroform (30 mL)×3. The chloroform extracts were combined, dried over sodium sulfate and filtered off to give a yellow filtrate. The filtrate was concentrated and dried under high vacuum to give a crude yellowish orange product which was which was recrystallized in ethanol to give the titled compound 7-Acetamido-8-hydroxy 4-((phenyl)amino)quinoline (X18). The compound was prepared from 40 mg (0.169 mmol) of 7-acetamido-4-chloro-8-hydroxyquinoline and 39.35 mg (38.58 µL, 0.422 mmol) of aniline using the general method of SN$_{Ar}$ to give alight yellow solid, 30.6 mg (62% yield). TLC (20% methanol in ethyl acetate) Melting Point 262-264° C.; $^1$H NMR (400 MHz, DMSO-d$_6$) δ 11.00 (broad s, 1H), 10.85 (broad s, 1H), 8.29 (d, J=7.2 Hz, 1H), 8.24 (d, J=9.2 Hz, 1H), 7.95 (d, J=9.2 Hz, 1H), 7.56 (t, J=7.8 Hz, 2H), 7.47 (d, J=7.6 Hz, 2H), 7.42 (t, J=7.2 Hz, 1H), 6.73 (d, J=7.2 Hz, 1H), 2.26 (s, 3H); $^{13}$C NMR (100 MHz, DMSO-d6) δ 170.9, 154.5, 142.3, 137.2, 131.2, 129.9, 128.1, 127.4, 125.5, 122.0, 114.8, 114.0, 99.6, 23.45; IR (neat) $v_{max}$ 3379.1, 3203.9, 2997.0, 2253.2, 1651.1, 1585.7, 1535.0; ESI-HRMS [M+H]$^+$ calculated for $C_{17}H_{16}N_3O_2$ 294.1237 found 294.1244.

7-Acetamido-8-hydroxy-4-(3-benzoic)amino)quinoline X(19). The compound was prepared from 40 ng (0.169 mmol) of 7-acetamido-4-chloro-8-hydroxyquinoline and 34.7 mg, 0.253 mmol of 3-aminobenzoic acid using the general method of SN$_{Ar}$ to give alight yellow solid, 46.8 mg (82% yield). TLC (20% methanol in ethyl acetate) Melting Point 322-324° C.; $^1$H NMR (400 MHz, DMSO-d$_6$) δ 10.94 (broad s, 1H), 10.89 (broad s, 1H), 8.33 (d, J=7.2 Hz, 1H), 8.23 (d, J=9.2 Hz, 1H), 7.99-7.94 (m, 3H), 7.76 (d, J=8.0 Hz, 1H), 7.69 (t, J=7.8 Hz, 1H), 6.82 (d, J=6.8 Hz, 1H), 2.26 (s, 3H); $^{13}$C NMR (125.7 MHz, DMSO-d6) δ 170.8, 166.5, 154.3, 142.6, 137.7, 137.3, 132.5, 131.3, 130.3, 129.5, 128.1, 127.8, 125.9, 122.2, 115.0, 114.0, 99.7, 23.4; IR (neat) $v_{max}$ 3262.5, 3108.1, 3030.7, 2363.5, 2323.1, 1686.0, 1627.4, 1575.2, 1524.6, 1305.3: ESI-HRMS [M+H]$^+$ calculated for $C_{18}H_{18}N_3O_4$ 338.1135 found 338.1143.

7-Acetamido-8-hydroxy-4-((5-indole)amino)quinoline (X20). The compound was prepared from 35.4 mg (0.1495 mmol) of 7-acetamido-4-chloro-8-hydroxyquinoline and 19.7 mg (0.1495 mmol) of 5-aminoindole using the general method of SN$_{Ar}$ to afford 45.2 mg (91% yield) of pure product. TLC (20% methanol in ethyl acetate) as a light yellow solid $R_f$=0.16; Melting Point 266-268° C.; $^1$H NMR (400 MHz, DMSO-d6) δ 11.41 (broad s, 1H), 10.71 (broad s, 1H), 10.55 (broad s, 1H), 8.21 (d, J=6.8 Hz, 1H), 8.14 (d, J=9.2 Hz, 1H), 7.94 (d, J=9.2 Hz, 1H), 7.58 (m, 2H) 7.46 (s, 1H), 7.11 (dd, J=2.0, 8.8 Hz, 1H) 6.57 (d, J=6.8 Hz, 1H). 6.50 (d, J=2.8 Hz, 1H), 2.24 (s, 3H); $^{13}$C NMR (100 MHz, DMSO-d6) δ 170.5, 154.7, 142.6, 138.2, 134.8, 132.1, 128.8, 126.9, 121.5, 119.2, 117.2, 114.6, 113.0, 112.6, 101.5, 99.3, 23.5; IR (neat) $v_{max}$ 3368.5, 3331.0, 3240.4, 2918.3, 2376.9, 1665.1, 1551.7, 1446.6; ESI-HRMS [M+H]$^+$ calculated for $C_{19}H_{17}N_4O_2$ 333.1346 found 333.1350.

7-Acetamido-8-hydroxy-4-((4-indole)amino)quinoline (X21). The compound was prepared from 40.3 mg (0.170 mmol) of 7-acetamido-4-chloro-8-hydroxyquinoline and 45.0 mg (0.214 mmol, 2 equivalents) of 4-aminoindole using the general method of SN$_{Ar}$ to afford 49 mg (86% yield) of pure product as a light-yellow solid, TLC (20% methanol in ethyl acetate) $R_f$=0.13; Melting Point 311-313° C.; $^1$H NMR (400 MHz, DMSO-d6) δ 11.57 (broad s, 1H), 11.10 (broad s, 1H), 11.03 (broad s, 1H), 8.33 (d, J=9.2 Hz, 1H), 8.22 (d, J=6.8 Hz, 1H), 7.99 (d, J=9.2 Hz, 1H), 7.52 (t, J=8.0 Hz, 1H), 7.42 (s, 1H), 7.24 (1, J=7.6 Hz, 1H) 7.09 (d, J=7.2 Hz, 1H), 6.35 (d, J=6.8 Hz, 1H), 6.23 (s, 1H), 2.27 (s, 3H); $^{13}$C NMR (100 MHz, DMSO-d6) δ 170.8, 154.7, 141.8, 137.4, 137.1, 131.0, 128.3, 128.1, 126.3, 123.6, 121.9, 121.5, 116.4, 114.5, 114.1, 111.6, 100.2, 99.1, 23.4; IR (neat) $v_{max}$ 3198.2, 3005.4, 23.66.8, 1654.2, 1597.3, 1537.7, 1454.8; ESI-HRMS [M+H]$^+$ calculated for $C_{19}H_{17}N_4O_2$ 333.1346 found 333.1348.

7-Acetamido-8-hydroxy-4-(((2-methyl)-5-indole)amino)quinoline (X22). The compound was prepared from 40.4 mg (0.171 mmol) of 7-acetamido-4-chloro-8-hydroxyquinoline and 29.95 mg (0,205 mmol, 1.2 equivalents) of 5-amino-2-methylindole using the general method of SN$_{Ar}$ to afford 41.3 mg (70% yield) of pure product. TLC (20% methanol in ethyl acetate) $R_f$=0.17; Melting Point 268-270° C.; $^1$H NMR (400 MHz, DMSO-d6) δ 11.2 (broad s, 1H). 10.9 (broad s, 1H), 10.7 (broad s, 1H), 8.20 (t, J=5.4 Hz, 2H), 7.92 (d, J=9.2 Hz, 1H), 7.43 (d, J=8.8 Hz, 2H), 7.01 (dd, J=2.4, 8.4 Hz, 1H), 6.55 (d, J=7.2 Hz, 1H) 6.20 (s, 1H), 2.41 (s, 3H), 2.26 (s, 3H); $^{13}$C NMR (100 MHz, DMSO-d6) δ 170.7, 155.3, 141.9, 137.5, 137.3, 135.1, 131.2, 129.2, 128.2, 127.9, 121.7, 118.0, 116.2, 114.4, 113.6, 111.6, 99.5, 99.3, 23.4, 13.4; IR (neat) $v_{max}$ 3272.6, 3188.9, 3075.9, 3010.9, 2965.7, 2925.6, 1654.5, 1626.9, 1606.1, 1580.5, 1478.0, 1449.6, 13697, 1294.6, 1214.0; ESI-HRMS [M+H]$^+$ calculated for $C_{20}H_{19}N_4O_2$ 347.1503 found 347.1508.

7-Acetamido-8-hydroxy-4-((4-fluorophenyl)amino)quinoline (X23). The compound was prepared from 40 mg (0.169 mmol) of 7-acetamido-4-chloro-8-hydroxyquinoline and 18.87 mg (16.32 µL, 0.169 mmol) of 3-hydroxyaniline using the general method of SN$_{Ar}$ to afford 23 mg (44% yield) of pure light-yellow solid. TLC (10% methanol in ethyl acetate) $R_f$=0.2; Melting Point 274-276° C.; $^1$H NMR (400 MHz, DMSO-d6) δ 11.96 (broad s, 1H), 10.81 (broad s, 1H), 8.29 (d, J=6.8 Hz, 1H), 8.21 (d, J=9.2 Hz, 1H), 7.93 (d, J=9.2 Hz, 1H), 7.42 (dd, J=5.0, 9.0 Hz, 2H), 7.40 (t, J=8.8 Hz, 2H), 6.67 (d, J=7.2 Hz, 1H), 2.26 (s, 3H); $^{13}$C NMR (125.7 MHz, DMSO-d6) δ 171.4, 160.9 (d, $^1J_{C-F}$=244.6 Hz), 154.8, 142.5, 137.7, 133.6, 131.4, 128.0 (d, $^3J_{C-F}$=8.5 Hz), 122.4, 116.7 (d, $^2J_{C-F}$=22.7 Hz), 115.0, 114.0, 99.8, 23.5; IR (neat) $v_{max}$ 3609.4, 3359.0, 3187.2, 3049.5, 2963.8, 2926.8, 2887.8, 2825.9, 1612.3, 1588.0, 1561.0, 1534.9, 1508.4; ESI-HRMS [M+H]$^+$ calculated for $C_{17}H_{15}FN_3O_2$ 312.1143 found 312.1150.

7-Acetamido-8-hydroxy-4-((3-fluorophenyl)amino)quinoline (X24). The compound was prepared from 40.2 mg (0.169 mmol) of 7-acetamido-4-chloro-8-hydroxyquinoline and 18.87 mg (16.32 µL, 0.169 mmol) of 3-hydroxyaniline using the general method of SN$_A$, to afford 33.1 mg (63% yield) of pure product as a yellow solid. TLC (10% methanol in ethyl acetate) $R_f$=0.15; Melting Point 270-272° C.; $^1$H NMR (400 MHz, DMSO-d6) δ 10.98 (broad s, 1H), 10.91 (broad s, 1H), 8.34 (d, J=5.2 Hz, 1H), 8.24 (d, J=7.6 Hz, 1H), 7.96 (d, J=7.6 Hz, 1H), 7.60 (q, J=6.4 Hz, 1H), 7.41 (d, J=8.0 Hz, 1H), 7.35 (d, J=6.4 Hz, 1H), 7.25 (t, J=6.0 Hz, 1H), 6.88 (d, J=5.6 Hz, 1H), 2.26 (s, 3H); $^{13}$C NMR (125.7 MHz, DMSO-d6) δ 170.8, 162.5 (d, $^1J_{C-F}$=245.1 Hz), 154.2, 142.5, 139.1 (d, $^3J_{C-F}$=10.3 Hz), 137.2, 131.5 (d, $^3J_{C-F}$=9.3 Hz), 131.2, 128.2, 122.2, 121.3, 114.9, 114.0, 113.9, 112.4 (d, $^2J_{C-F}$=23.5 Hz), 23.4; IR (neat) $v_{max}$ 3358.9, 2967.3, 2357.1, 2330.4, 1606.2, 1586.8, 1540.4, 1457.3; ESI-HRMS [M+H]$^+$ calculated for $C_{17}H_{15}FN_3O_2$ 312.1143 found 312.1149.

7-Acetamido-8-hydroxy-4-((4-hydroxyphenyl)amino) quinoline (X26). The compound was prepared from 40 mg (0.169 mmol) of 7-acetamido-4-chloro-8-hydroxyquinoline and 36.89 mg (0.338 mmol) of 3-hydroxyaniline using the general method of $SN_{Ar}$ to afford 31 mg (60% yield) of pure product yellow solid. TLC (10% methanol in ethyl acetate) $R_f$=0.21; Melting Point 279-281° C.; $^1$H NMR (500 MHz, DMSO-d6) δ 9.50 (broad s, 1H), 8.96 (broad s, 1H), 8.37 (s, 1H), 8.02 (d, J=8.0 Hz, 1H), 7.73 (d, J=8.5 Hz, 1H), 7.20 (s, 1H), 6.90 (s, 1H), 6.80 (d, J=9.0 Hz, 2H), 6.58 (d, J=5.5 Hz, 1H), 2.15 (s, 3H); IR (neat) $v_{max}$ 3367.0, 3329.6, 3248.2, 2915.5, 2357.4, 2330.9, 1664.4, 1541.9, 1489.6, 1448.0; ESI-HRMS [M+H]$^+$ calculated for $C_{17}H_{16}N_3O_3$ 310.1186 found 310.1194.

7-Acetamido-8-hydroxy-4-((4-trifluoromethylphenyl) amino)quinoline (X27). The compound was prepared from 40.2 mg (0.1698 mmol) of 7-acetamido-4-chloro-8-hydroxyquinoline and 32.8 mg (0.2038 mmol, 1.2 equivalents) of 4-trifluoromethylaniline using the general method of $SN_A$ to afford 47 mg (77% yield) of pure light-yellow solid. TLC (20% methanol in ethyl acetate) $R_f$=0.21; Melting Point 277-279° C.; $^1$H NMR (400 MHz, DMSO-d6) δ 10.96 (broad s, 1H), 10.89 (broad s, 1H), 8.36 (d, J=7.2 Hz, 1H), 8.23 (d, J=9.2 Hz, 1H), 7.92 (d, J=8.4 Hz, 3H), 7.73 (d, J=8.4 Hz, 2H), 6.98 (d, J=6.8 Hz, 1H), 2.26 (s, 3H); $^{13}$C NMR (125.7 MHz, DMSO-d6) δ 170.9, 153.8, 142.8, 141.5, 137.4, 131.5, 128.1, 126.9, 126.6, 125.2, 123.0, 122.4, 115.4, 114.2, 100.5, 23.4; IR (neat) $v_{max}$ 3229.8, 2995.6, 2364.3, 2324.6, 1686.0, 1588.2, 1524.3, 1456.1, 1328.9; ESI-HRMS [M+H]$^+$ calculated for $C_{18}H_{15}F_3N_3O_2$ 362.1111 found 362.1113.

7-Acetamido-8-hydroxy-4-((3-trifluoromethylphenyl) amino)quinoline (28). The compound was prepared from 40.6 mg (0.171 mmol) of 7-acetamido-4-chloro-8-hydroxyquinoline and 33.1 mg (0.206 mmol, 1.2 equivalents) of 3-trifluoromethylaniline using the general method of $SN_{Ar}$ to afford 44 mg (71% yield) of pure light-yellow solid. TLC (20% methanol in ethyl acetate) $R_f$=0.2; Melting Point 278-280° C.; $^1$H NMR (500 MHz, DMSO-d6) δ 10.96 (broad s, 2H), 8.36 (d, J=7.0 Hz, 1H), 8.26 (d, J=9.0 Hz, 1H), 7.98 (d, J=9.0 Hz, 1H), 7.87 (s, 1H), 7.84-7.74 (m, 3H), 6.85 (d, J=7.0 Hz, 1H), 2.26 (s, 3H); $^{13}$C NMR (125.7 MHz, DMSO-d6) δ 1780.8, 154.1, 142.8, 138.5, 137.3, 131.4, 131.1, 130.5 (d, $^2J_{C-F}$=32.1 Hz), 129.1, 128.1, 123.7 (d, $^1J_{C-F}$=272.8 Hz), 123.5, 122.2, 121.9, 115.1, 114.0, 100.0, 23.4; IR (neat) $v_{max}$ 3649.5, 3336.8, 3191.8, 2972.2, 2905.1, 2827.7, 2361.5, 2330.7, 1649.3, 1607.0, 1588.0, 1561.3, 1535.2, 1490.1; ESI-HRMS [M+H]$^+$ calculated for $C_{18}H_{15}F_3N_3O_2$ 362.1111 found 362.1113.

7-Acetamido-8-hydroxy-4-((2-fluoro-4-hydroxyphenyl) amino)quinoline (X29). The compound was prepared from 41.1 mg (0.174 mmol) of 7-acetamido-4-chloro-8-hydroxyquinoline and 28.7 mg (0.225 mmol. 1.3 equivalents) of 2-fluoro-4-hydroxylaniline using the general method of $SN_{Ar}$ to afford 34 mg (60% yield) as a yellow solid. TLC (20% methanol in ethyl acetate) $R_f$=0.28; Melting Point 213-2150c $^1$H NMR (500 MHz, DMSO-d6) δ 11.00 (broad s, 1H), 10.56 (broad s, 1H), 8.29 (d, J=6.5 Hz, 1H), 8.18 (d, J=9.0 Hz, 1H), 7.94 (d, J=9.5 Hz, 1H), 7.33 (t, J=9.0 Hz, 1H), 6.87 (d, J=12.0 Hz, 2H), 6.81 (d, J=9.0 Hz, 1H) 6.39 (d, J=7.0 Hz, 1H), 2.26 (s, 3H); $^{13}$C NMR (125.7 MHz, DMSO-d6) δ 170.8, 158.9 (d, $^3J_{C-F}$=11.06 Hz), 157.6 (d, $^1J_{C-F}$=247.5 Hz), 155.6, 142.3, 137.2, 130.9, 129.7, 128.2, 122.2, 115.1 (d, $^3J_{C-F}$=12.4 Hz), 114.3, 113.8, 112.6, 103.8 (d, $^2J_{C-F}$=21.8 Hz), 99.7, 23.4; IR (neat) $v_{max}$ 2919.9, 2850.7, 2360.7, 2342.1, 1692.9, 1619.5, 1524.5, 1461.0, 1291.6, 1140.5, 1008.4, 915.7, 791.1; ESI-HRMS [M+H]$^+$ calculated for $C_{17}H_{15}FN_3O_3$ 328.1019 found 328.1095.

7-Acetamido-8-hydroxy-4-((2-fluoro-5-hydroxyphenyl) amino)quinoline (X30). The compound was prepared from 41.5 mg (0.175 mmol) of 7-acetamido-4-chloro-8-hydroxyquinoline and 28.97 mg (0.228 mmol, 1.3 equivalents) of 2-fluoro-5-hydroxylaniline using the general method of $SN_{Ar}$ to afford 41.2 mg (71% yield) as yellow solid. TLC (20% methanol in ethyl acetate) $R_f$=0.21; $^1$H NMR (500 MHz, DMSO-d6) δ 9.59 (broad s, 1H), 8.99 (broad s, 1H), 8.36 (d, J=5.5 Hz, 1H), 8.01 (d, J=9.0 Hz, 1H), 7.76 (d, J=9.5 Hz, 1H), 7.17 (t, J=9.8 Hz, 1H), 6.81-6.79 (m, 1H), 6.71-6.68 (m, 1H) 6.39-6.38 (m, 1H), 2.15 (s, 3H); $^{13}$C NMR (125.7 MHz, DMSO-d6) δ 169.4, 154.2, 150.6, 149.9 (d, $^1J_{C-F}$=237.9 Hz), 146.1, 141.2, 136.2, 126.6 (d, $^3J_{C-F}$=13.2 Hz), 125.7 (d, $J_{C-F}$=237.4 Hz), 121.3, 116.9 (d, $^2J_{C-F}$=21.2 Hz), 115.6, 114.0, 113.6, 111.4, 100.8, 23.6: IR (neat) $v_{max}$ 3060.5, 1503.4, 1451.0, 1374.5, 1307.7, 1219.0; ESI-HRMS [M+H]$^+$ calculated for $C_{17}H_{15}FN_3O_3$ 328.1019 found 328.1096.

General Method for Buchwald-Hartwig Amination

To 1 molar equivalent of 7-Acetamido-4-chloro-8-methoxyquinoline, were added, 1.4 molar equivalents of cycloalkyamines, 0.1 molar equivalents of palladium 11 acetate, 0.2 molar equivalents of BINAP, 5 molar equivalents of $Cs_2CO_3$, and 3 mL of 1,4-dioxane. The mixture was heated at 90° under $N_2$ for 5 h. The reaction was cooled to room temperature and filtered over a pad of celite and washed with ethyl acetate and DCM. The filtrate was concentrated in vacuo to remove the solvent to give a crude coupling product. The crude product was chromatographed on silica gel, using 10% methanol in ethyl acetate to afford pure product as an off white solid.

7-Acetamido-4-((cyclobutyl)amino)-8-methoxyquinoline (31). The compound was prepared from 52 mg (0.207 mmol) of 7-acetamido-4-chloro-8-methoxyquinoline and 14.89 mg (17.87 μL (0.290 mmol, 1.4 molar equivalents) of cyclobutylamine using the general method of Buchwald-Hartwig amination to afford 42.5 mg (72% yield) as an off white solid. TLC (20% methanol in ethyl acetate) $R_f$=0.23; Melting Point 178-180° C.; $^1$H NMR (500 MHz, DMSO-d6) δ 9.47 (s, 1H), 8.34 (d, J=3.5 Hz, 1H), 8.11 (d, J=8.0 Hz, 1H), 7.95 (d, J=9.0 Hz, 1H), 7.19 (s, 1H), 6.28 (d, J=4.0 Hz, 1H), 4.05-4.02 (m, 1H) 3.98 (s, 3H), 2.41 (d, J=6.0 Hz, 2H), 2.16 (s, 3H), 2.08 (t, J=9.2 Hz, 2H), 1.808-1.75 (m, 2H); $^{13}$C NMR (125.7 MHz, DMSO-d6) δ 169.0, 149.8, 149.0, 142.6, 141.6, 130.9, 118.6, 116.7, 116.3, 98.4, 61.3, 47.7, 29.5, 24.0, 14.9; IR (neat) $v_{max}$ 3285.9, 2933.7, 1671.2, 1615.5, 1581.1, 1536.9, 1514.3, 1414.3, 1380.0, 1298.6, 1209.6, 11453, 1051.5; ESI-HRMS [M+H]$^+$ calculated for $C_{16}H_{20}N_3O_2$ 286.1550 found 286.1557.

7-Acetamido-4-((cyclopentyl)amino)-8-methoxyquinoline (X32) The compound was prepared from 52 mg (0.207 mmol) of 7-acetamido-4-chloro-8-methoxyquinoline and 24.7 mg (28.6 μL (0.290 mmol, 1.4 molar equivalents) of cyclopentylamine using the general method of Buchwald-Hartwig amination to afford 71.4 mg (87% yield) as an off white solid. TLC (20% methanol in ethyl acetate) $R_f$=0.23;

Melting Point 138-140° C.; $^1$H NMR (500 MHz, DMSO-d6) δ 9.53 (s, 1H), 8.35 (d, J=4.5 Hz, 1H), 8.10 (d, J=8.0 Hz, 1H), 8.03 (d, J=9.0 Hz, 1H), 7.02 (s, 1H), 6.45 (d, J=4.5 Hz, 1H), 3.97 (s, 4H), 3.62 (s, 1H). 2.16 (s, 3H), 2.03 (s, 2H), 1.73-1.58 (m, 6H); $^{13}$C NMR (125.7 MHz, DMSO-d6) δ 169.0, 150.3, 148.9, 143.3, 141.6, 131.2, 118.7, 117.0, 116.1, 98.5, 61.3, 53.8, 31.88, 23.9; IR (neat) $v_{max}$ 3292.8, 2949.3, 2867.4, 1670.0, 1615.4, 1539.4, 1490.2, 1459.6, 14143, 1381.1, 1297.7; ESI-HRMS [M+Na]$^+$ calculated for $C_{17}H_{22}N_3O_2$ 300.1707 found 300.1717.

7-Acetamido-4-((cyclohexyl)amino)-8-methoxyquinoline (X33). The compound was prepared from 35.0 mg (0.139 mmol) of 7-acetamido-4-chloro-8-methoxyquinoline and 19.38 mg (22.4 µL (0.195 mmol, 1.4 molar equivalents) of cyclohexylamine using the general method of Buchwald-Hartwig amination to afford 43 mg (98% yield) as an off white solid. TLC (10% methanol in ethyl acetate) $R_f$=0.19; Melting Point 200-202° C.; $^1$H NMR (500 MHz, DMSO-d6) δ 9.51 (s, 1H), 8.33 (d, J=5.5 Hz, 1H), 8.10 (d, J=9.5 Hz, 1H), 7.96 (d, J=9.5 Hz, 1H), 6.75 (d, J=7.0 Hz, 1H), 6.43 (d, J=5.5 Hz, 1H), 3.97 (s, 3H), 3.45 (s, 1H), 2.16 (s, 3H), 1.98 (d, J=8.5 Hz, 2H), 1.76 (d, J=6.5 Hz, 2H), 1.65 (d, J=13.0 Hz, 1H), 1.39-1.34 (m, 4H), 1.18-1.15 (m, 1H); $^{13}$C NMR (125.7 MHz, DMSO-d6) δ 169.0, 149.8, 149.2, 143.8, 142.9, 142.8, 1309, 118.4, 116.8, 116.4, 97.9, 61.3, 31.9, 25.4, 24.9, 24.1; IR (neat) $v_{max}$ 3314.8, 2922.5, 2850.0, 1676.5, 1614.8, 1522.2, 1459.8, 1413.5, 1329.7; ESI-HRMS [M+Na]$^+$ calculated for $C_{18}H_{24}N_3O_2$ 314.1863 found 314.1868.

7-Acetamido-4-((cycloheptyl)amino)-8-methoxyquinoline (X34). The compound was prepared from 51.0 mg (0.203 mmol) of 7-acetamido-4-chloro-8-methoxyquinoline and 32.24 mg (36.26 µL (0.284 mmol, 1.4 molar equivalents) of cycloheptylamine using the general method of Buchwald-Hartwig amination to afford 64.1 mg (96% yield) as an off white solid. TLC (20% methanol in ethyl acetate) $R_f$=0.32; Melting Point 192-194° C.; $^1$H NMR (500 MHz, DMSO-d6) δ 9.45 (s, 1H), 8.34 (d, J=5.0 Hz, 1H), 8.08 (d, J=9.5 Hz, 1H), 7.96 (d, J=9.0 Hz, 1H), 6.68 (d, J=7.5 Hz, 1H), 6.31 (d, J=4.5 Hz, 1H), 3.98 (s, 3H), 3.62 (s, 1H), 2.16 (s, 3H), 1.94 (t, J=6.5 Hz, 2H), 1.86 (s, 1H), 1.69 (t, J=6.5 Hz, 3H), 1.64-1.61 (m, 2H), 1.57-1.49 (m, 4H); $^{13}$C NMR (125.7 MHz, DMSO-d6) δ 168.9, 149.9, 148.8, 143.9, 142.9, 130.8, 118.3, 116.6, 88.1, 61.2, 52.8, 33.4, 28.9, 24.0; IR (neat) $v_{max}$ 3362.2, 2921.0, 2854.5, 1677.4, 1614.8, 1580.9, 1540.2; ESI-HRMS [M+H]$^+$ calculated for $C_{19}H_{26}N_3O_2$ 328.2020 found 328.2027.

4-((cyclohexyl)amino)-8-methoxy-7-((2-morpholin-4-yl)acetamido)quinoline (X35). The compound was prepared from 50.0 mg (0.149 mmol) of compound 2 and 20.67 mg (23.9 µL, 0.208 mmol, 1.4 molar equivalents) of cyclohexylamine using the general method of Buchwald-Hartwig amination to afford 43.6 mg (74% yield) as an off white solid. $^1$H NMR (400 MHz, CD$_3$OD) δ 8.54 (d, J=2.4 Hz, 1H), 8.31 (d, J=6.4 Hz, 1H), 8.13 (d, J=9.6 Hz, 1H), 6.74 (d, J=6.4 Hz, 1H), 4.00 (s, 3H), 3.82 (s, 4H), 3.72 (s, 1H), 2.70 (s, 4H), 2.10 (s, 2H), 1.97 (s, 1H), 1.90 (s, 2H), 1.76 (d, J=12.4 Hz, 1H), 1.56-1.45 (m, 4H), 1.32-1.25 (m, 2H); $^{13}$C NMR (100 MHz, DMSO-d6) δ 168.2, 149.6, 142.0, 130.5, 117.6, 116.1, 115.7, 97.8, 66.5, 61.9, 61.4, 53.2, 51.1, 31.9, 25.4, 24.8 ESI-HRMS [M+H]$^+$ calculated for $C_{22}H_{31}N_4O_3$ 399.2391 found 399.2395.

4-((cyclohexyl)amino)-8-methoxy-7-((3-morpholin-4-yl)propanamido)quinoline (X36). The compound was prepared from 50.0 mg (0.143 mmol) of compound 3 and 21.26 mg (24.6 µL, 0.214 mmol, 1.5 molar equivalents) of cyclohexylamine using the general method of Buchwald-Hartwig amination to afford 48.6 mg (83% yield) as an off white solid. $^1$H NMR (400 MHz, 400 MHz, CD$_3$OD) δ 8.47 (d, J=9.6 Hz, 1H), 8.28 (d, J=6.8 Hz, 1H), 8.18 (d, J=9.6 Hz, 1H), 6.86 (d, J=7.2 Hz, 1H), 3.80 (t, J=4.6 Hz, 4H), 2.83 (t, J=6.2 Hz, 2H), 2.75 (t, J=6.2 Hz, 2H), 2.64 (broad s, 4H), 2.11 (d, J=8.8 Hz, 2H), 1.94 (s, 1H), 1.93 (d, J=9.6 Hz, 2H), 1.77 (d, J=13.2 Hz, 1H), 1.61-1.46 (n, 4H); $^{13}$C NMR (100 MHz, CD$_3$OD) δ 173.8, 156.0, 143.6, 140.2, 136.1, 135.2, 122.1, 119.7, 115.6, 99.3, 67.7, 62.3, 55.2, 54.5, 54.4, 34.0, 33.0, 26.4, 26. ESI-HRMS [M+H]$^+$ calculated for $C_{23}H_{33}N_4O_3$ 413.2547 found 413.2557.

General Method of demethylation of cycloalkylamine quinolines X37-X42

To a solution containing 1 molar of cycloalkylaminequinolines starting material in 1.0 mL dry DCM was added 1 molar BBr$_3$ (6 equivalents) in DCM on ice-salt bath and stirred at that temperature for 15 minutes. The resulting orange solution was allowed to warm to room temperature and stirred at that temperature for 8 hr. The reaction was quenched by the gradual addition of ice-cold water, and the pH was adjusted with saturated NaHCO$_3$. The product was extracted with chloroform (10 mL×3), concentrated and dried in vacuo to afford a yellow solid that was purified using reverse phase silica gel and 50-0% water in methanol to afford pure product.

7-Acetamido-8-hydroxy-4-((cyclobutyl)amino)quinoline (37). The compound was prepared from 43 mg (0.153 mmol) of 7-acetamido-4-((cyclobutyl)amino)-8-methoxyquinoline and 0.6 mL (4 equivalents) of 1 M BBr$_3$ in DCM using the general method of demethylation to afford a yellow solid 29 mg (71% yield) of the product. TLC (20% methanol in ethyl acetate) $R_f$=0.16; Melting Point 209-211° C.; $^1$H NMR (400 MHz, CDCl$_3$) δ 8.93 (d, J=4.4 Hz, 1H), 8.58 (d, J=9.2 Hz, 1H), 8.14 (broad s, 1H), 7.34 (d, J=9.2 Hz, 1H), 7.24 (d, J=4.4 Hz, 1H), 7.18-7.13 (m, 1H), 7.00-6.97 (m, 2H), 4.23 (s, 3H), 3.68 (s, 3H), 2.29 (s, 3H), IR (neat) $v_{max}$ 3318.6, 2932.0, 2896.4, 2848.1, 2775.0, 1660.8, 1605.1, 1544.2, 1507.0, 14663, 1425.6; ESI-HRMS [M+H]$^+$ calculated for $C_{15}H_{16}N_3O_2$ 272.1394 found 272.1399.

7-Acetamido-8-hydroxy-4-((cyclopentyl)amino)quinoline (X38). The compound was prepared from 38.1 mg (0.127 mmol) of 7-acetamido-4-((cyclopentyl)amino)-8-methoxyquinoline 0.51 mL (4 equivalents) of 1M BBr$_3$ in DCM using the general method of demethylation to afford a yellow solid 31.6 mg (87% yield) of the product. TLC (20% methanol in ethyl acetate), $R_f$=0.15, Melting Point 209-211° C.; $^1$H NMR (400 MHz, DMSO-d6) δ 9.30 (broad s, 1H), 8.23 (d, J=5.2 Hz, 1H), 7.98 (d, J=9.2 Hz, 1H), 7.40 (d, J=9.2 Hz, 1H), 6.84 (d, J=6.0 Hz, 1H), 6.41 (d, J=5.2 Hz, 1H), 4.00-3.93 (m, 1H), 2.10 (s, 3H), 2.04-2.01 (m, 2H), 1.74-1.58 (m, 6H); $^{13}$C NMR (100 MHz, DMSO-d6) δ 168, 150.5, 146.4, 123.6, 119.0, 115.5, 98.1, 53.7, 31.9, 23.9; IR (neat) $v_{max}$ 3326.7, 2921.7, 2855.5, 1661.4, 1601.7, 1563.7, 1500.0, 1465.4; ESI-HRMS [M+H]$^+$ calculated for $C_{16}H_{20}N_3O_2$ 286.1550 found 286.1554.

7-Acetamido-8-hydroxy-4-((cyclohexyl)amino)quinoline (X39). The compound was prepared from 40 mg (0.1276 mmol) of 7-acetamido-4-((cyclohexyl)amino)-8-methoxyquinoline and 1.3 ml (10 equivalents) of 1 M BBr$_3$ in DCM using the general method of demethylation to afford a yellow solid 37.6 mg (98% yield) of the product. TLC (20% methanol in ethyl acetate) $R_f$=0.16; Melting Point 238-240° C.; $^1$H NMR (500 MHz, DMSO-d6) δ 09.51 (broad s, 1H), 8.23 (d, J=3.5 Hz, 1H), 7.93 (d, J=8.5 Hz, 1H), 7.55 (d, J=9.0 Hz, 1H), 7.16 (s, 1H), 6.52 (s, 1H), 3.54 (broads, 1H), 2.12

(s, 3H), 1.96 (s, 2H), 1.77 (s, 2H), 1.65 (d, J=12.0 Hz, 1H), 1.39 (s, 4H), 1.22 (s, 1H); $^{13}$C NMR (125.7 MHz, DMSO-d6) δ 168.6, 150.8, 145.5, 143.3, 136.0, 124.1, 119.7, 115.0, 108.7, 97.6, 51.3, 31.8, 25.3, 24.7, 23.7; IR (neat) $v_{max}$ 3328.9, 2919.1, 2851.3, 1660.7, 1608.4, 1563.7, 1506.3, 1473.8, 1371.3, 1313.3, 1212.9, 1103.0; ESI-HRMS [M+H]$^+$ calculated for $C_{17}H_{22}N_3O_2$ 300.1707 found 300.1710.

7-Acetamido-8-hydroxy-4-((cycloheptyl)amino)quinoline (X40). The compound was prepared from 61.6 mg (0.188 mmol) of 7-acetamido-4-((cycloheptyl)amino)-8-methoxyquinoline and 752 μL (4 equivalents) of 1 M BBr$_3$ in DCM using the general method of demethylation to afford a yellow solid 52.2 mg (89% yield) of the product. TLC (ethyl acetate) $R_f$=0.12; Melting Point 189-191° C.; $^1$H NMR (400 MHz, DMSO-d6) δ 9.27 (broad s, 1H), 8.21 (d, J=5.2 Hz, 1H), 7.98 (d, J=9.2 Hz, 1H), 7.35 (d, J=8.8 Hz, 1H), 6.74 (d, J=6.8 Hz, 1H), 6.31 (d, J=5.6 Hz, 1H), 3.68-3.64 (m, 1H), 2.10 (s, 3H), 1.98-1.92 (s, 2H), 1.71-1.50 (m 11H), $^{13}$C NMR (100 MHz, DMSO-d6) δ 167.9, 149.6, 146.2, 123.8, 118.9, 115.6, 97.6, 53.0, 33.5, 27.9, 24.0; IR (neat) $v_{max}$ 3844.4, 3743.5, 3678.6, 3648.9, 3620.1, 2918.9, 2851.3, 2363.1, 1655.8, 1548.4, 1512.0, 1462.5, 1426.6; ESI-HRMS [M+H]$^+$ calculated for $C_{18}H_{24}N_3O_2$ 314.1863 found 314.1867.

4-((cyclohexyl)amino)-8-hydroxy-7-((2-morpholin-4-yl)acetamido)quinoline (X41). The compound was prepared from 27 mg (0.067 mmol) of analog 35 and 677 μL (10 equivalents) of 1 M BBr$_3$ in DCM using the general method of demethylation to afford a yellow solid 20 mg (77% yield) of the product. $^1$H NMR (400 MHz, DMSO-d6) δ 9.84 (broad s, 1H), 8.20 (d, J=8.8 Hz, 1H), 8.12 (d, J=5.6 Hz, 1H), 7.34 (d, J=8.8 Hz, 1H), 7.12 (d. J=7.2 Hz, 1H), 6.43 (d, J=6.0 Hz, 1H), 3.61 (s, 3H), 3.50-3.49 (m, 2H), 3.10 (s, 2H), 2.44 (s, 5H), 1.90-187 (m, 2H), 1.73-1.71 (m, 2H), 1.61-158 (in, 1H) 1.35, (broad s, 5H), $^{13}$C NMR (100 MHz, DMSO-d6) δ 167.6, 151.5, 144.1, 124.9, 117.4, 114.8, 97.0, 66.4, 62.0, 53.2, 51.5, 31.8, 25.3, 24. ESI-HRMS [M+H]$^+$ calculated for $C_{21}H_{29}N_4O_3$ 385.2234 found 385.2236.

4-((cyclohexyl)amino)-8-hydroxy-7-((3-morpholin-4-yl)propanamido)quinoline (X42). The compound was prepared from 20 mg (0.048 mmol) of analog 36 and 485 μL (10 equivalents) of 1 M BBr$_3$ in DCM using the general method of demethylation to afford a yellow solid 16 mg (83% yield) of the product. $^1$H NMR (400 MHz, Methanol-d4) 8.23 (d, J=8.8 Hz, 1H), 8.13 (d, J=6.8 Hz, 1H), 7.34 (d, J=9.2 Hz, 1H), 6.67 (d, J=6.8 Hz, 1H), 3.79 (t, J=4.4 Hz, 3H), 3.74 (broad s, 1H), 3.49-3.45 (m, 1H), 2.79 (t, J=6.4 Hz, 2H), 2.68 (t, J=6.4 Hz, 2H), 2.58 (s, 3H), 2.08 (broad s, 2H), 2.01-1.98 (m, 1H), 1.89-187 (m, 3H), 1.77-1.734 (m. 1H), 1.57-1.44 (m, 4H). $^{13}$C NMR (100 MHz, DMSO-d6) δ 163.7, 146.7, 138.8, 131.1, 123.7, 120.3, 112.1, 106.4, 96.4, 88.2, 58.2, 46.1, 45.0, 44.6, 25.1, 23.6, ESI-HRMS [M+H]$^+$ calculated for $C_{22}H_{31}N_4O_3$ 399.2391 found 399.2390 nd 418.1770.

Example 9

Synthesis of Amine Analogs

Synthesis of series 1 amine analogs. The synthetic methodology for generating the precursors of compounds X1-X3 (below) was recently reported [Abraham, A. D., et al. (2019) "Drug Design Targeting T-Cell Factor-Driven Epithelial-Mesenchymal Transition as a Therapeutic Strategy for Colorectal Cancer," J Med Chem, 2019. 62(22): p. 10182-10203]. This method employing various aromatic amines through nucleophilic aromatic substitution reaction (S$_N$Ar) in refluxing ethanol generated analogs X4-X14 with excellent yields [Suresh, T., R. N. Kumar and P. S. Mohan, A facile approach to dibenzo [bf][1,6]naphthyridines using Vilsmeier conditions. Heterocyclic Communications, 2003. 9(1): p. 83-88]. However, several attempts to remove the methoxy group on these analogs using BBr$_3$ were unsuccessful (Scheme X, all compound numbers in the scheme should be preceded by X):

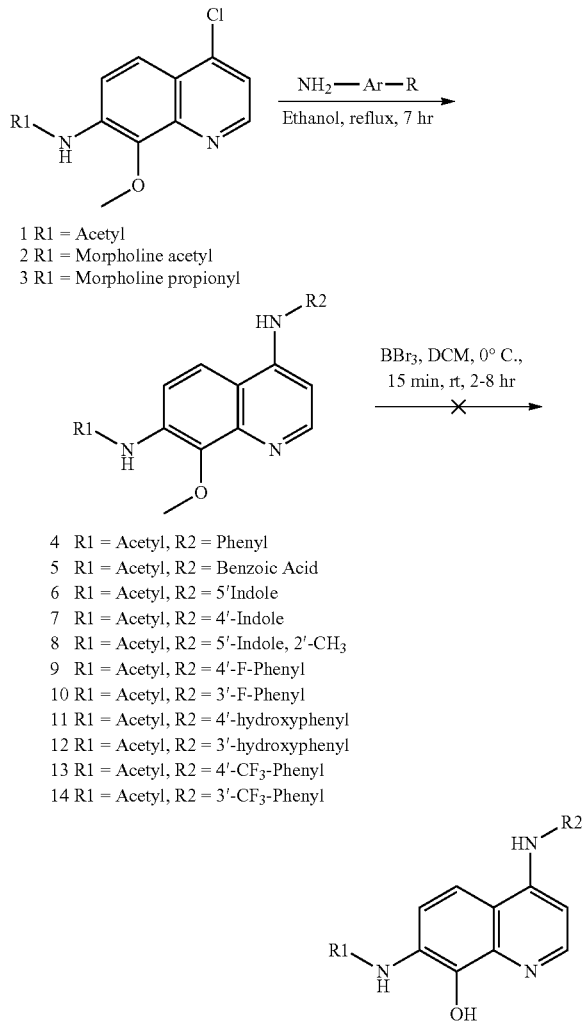

Scheme X

1 R1 = Acetyl
2 R1 = Morpholine acetyl
3 R1 = Morpholine propionyl

4  R1 = Acetyl, R2 = Phenyl
5  R1 = Acetyl, R2 = Benzoic Acid
6  R1 = Acetyl, R2 = 5'Indole
7  R1 = Acetyl, R2 = 4'-Indole
8  R1 = Acetyl, R2 = 5'-Indole, 2'-CH$_3$
9  R1 = Acetyl, R2 = 4'-F-Phenyl
10 R1 = Acetyl, R2 = 3'-F-Phenyl
11 R1 = Acetyl, R2 = 4'-hydroxyphenyl
12 R1 = Acetyl, R2 = 3'-hydroxyphenyl
13 R1 = Acetyl, R2 = 4'-CF$_3$-Phenyl
14 R1 = Acetyl, R2 = 3'-CF$_3$-Phenyl To generate the phenolic analogs X18-X30 (below), the order of the synthesis was changed by first generating the phenolic intermediates X15-X17 (below) in excellent yields via demethylation using BBr$_3$, followed by S$_N$Ar, rather than progressing from S$_N$Ar to demethylation (Scheme X1, all compound numbers in the scheme should be preceded by X) [Ife, R. J., et al. "Reversible inhibitors of the gastric (H+/K+)-ATPase. 5. Substituted 2,4-diaminoquinazolines and thienopyrimidines," J Med Chem, 1995. 38(14): p. 2763-73; Leach, C. A., et al. "Reversible inhibitors of the gastric (H+/K+)-ATPase. 4. Identification of an inhibitor with an intermediate duration of action," J Med Chem, 1995. 38(14): p. 2748-62.]. The S$_N$Ar with X15-X17 was carried out using various aryl amines from simple aniline to "amino indole"

derivatives in refluxing ethanol to obtain desired analogs X18-X30 (below) with 40-80% yields. The S$_N$Ar with these aryl amines proceeded smoothly, except for analogs X7 (above) and X21 (below), where 4 equivalents of 4-aminoindole was used, and the reaction was refluxed for up to 24-48 hours [Lakhdar, S., et al, "Nucleophilic reactivities of indoles". Journal of Organic Chemistry, 2006. 71(24): p. 9088-9095.].

nylphosphino)-1,1'-binapthyl (BINAP), Cs$_2$CO$_3$, Pd(OAc)$_2$, and 1,4-dioxane (Scheme X111, all compound numbers in the scheme should be preceded by X), but again no desired product was obtained [Daumar, P., et al., "Synthesis and evaluation of (18)F-labeled ATP competitive inhibitors of topoisomerase II as probes for imaging topoisomerase II expression," Eur J Med Chem, 2014. 86: p. 769-8.]. Hence, the coupled amine products with phenolic intermediates X15-X17, could not be obtained either by direct amination or with the aid of a ligand.

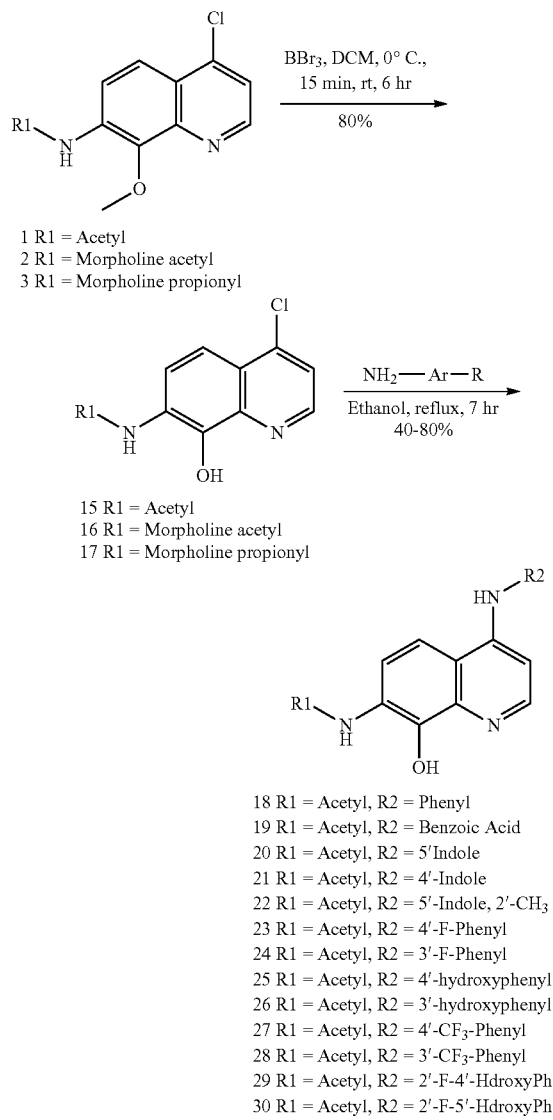

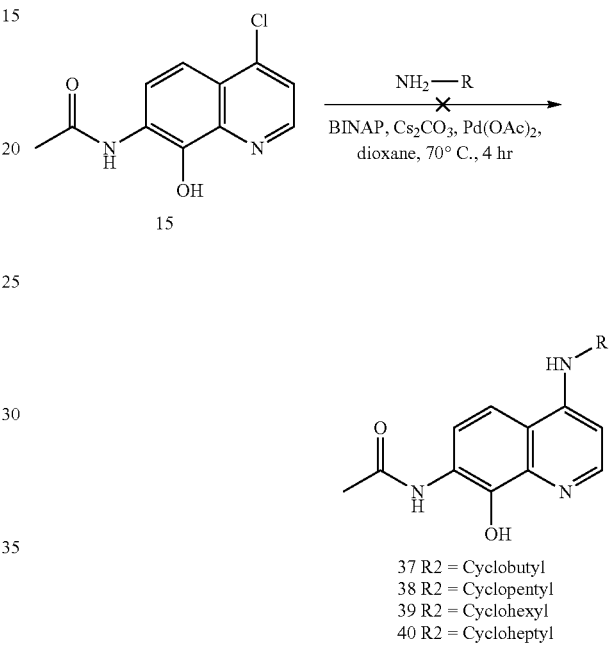

CADD studies indicated that all of the "alkyl amine" analogs displayed better interactions with the N-terminal domain of Topolla, and indicated that these analogs would be potent against TOP2A-dependent TCF transcription activities and EMT. Attempts were made to synthesize analogs X33-X38 (below) by coupling the alkyl amines to phenolic intermediates X15-X17 in refluxing ethanol, but no desired products were obtained, since these amines are not aryl amines and would not react by S$_N$Ar conditions. The synthesis of analogs was attempted by carrying out Buchwald-Hartwig amination method using the alkyl amines of choice with X15-X17 in the presence of 2,2'-bis(diphe- Interestingly, Buchwald Hartwig amination was then attempted with X1-X3 using the same conditions described above and the reaction proceeded smoothly to completion within 2 hours, which afforded the syntheses of X31-X36 with 76-99% yield (Scheme XIV, where all compound numbers should be preceded by X). It was initially assumed that demethylation of X31-X36 with BBr$_3$ would not work as observed and described above. Nevertheless, the demethylation process was attempted in the presence of 1 Molar BBr$_3$/DCM, and surprisingly compound X37-X42 were obtained in 71-99% yield.

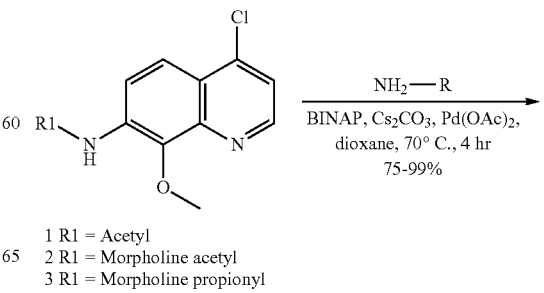

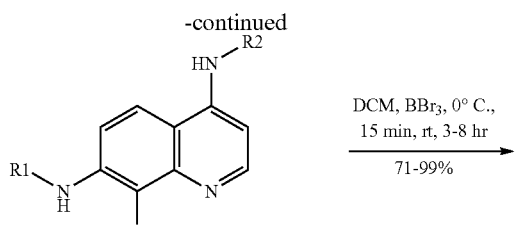

DCM, BBr₃, 0° C.,
15 min, rt, 3-8 hr
71-99%

31 R1 = Acetyl, R2 = Cyclobutyl
32 R1 = Acetyl, R2 = Cyclopentyl
33 R1 = Acetyl, R2 = Cyclohexyl
34 R1 = Acetyl, R2 = Cycloheptyl
35 R1 = Morpholine acetyl, R2 = Cyclohexyl
36 R1 = Morpholine propionyl, R2 = Cyclohexyl

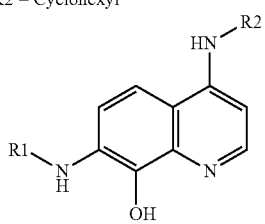

37 R1 = Acetyl, R2 = Cyclobutyl
38 R1 = Acetyl, R2 = Cyclopentyl
39 R1 = Acetyl, R2 = Cyclohexyl
40 R1 = Acetyl, R2 = Cycloheptyl
41 R1 = Morpholine acetyl, R2 = Cyclohexyl
42 R1 = Morpholine propionyl, R2 = Cyclohexyl Experimental Methods and Materials General Experimental Section. All commercial chemicals were used as supplied unless otherwise stated. All solvents used were dried and distilled using standard procedures. All reactions were performed under an inert atmosphere of ultrapure nitrogen with oven-dried glassware unless otherwise noted. All organic extracts were dried over sodium sulfate. Thin layer chromatography (TLC) was performed using Aluminum backed plates coated with 60 Å Silica gel F254 (Sorbent Technologies, Norcross, GA, USA). Plates were visualized using a UV lamp ($\lambda$max=254 nm). Column chromatography was carried out using 230-400 mesh 60 Å silica gel. Proton ($\delta$H) and carbon ($\delta$C) nuclear magnetic resonances were recorded on a Bruker Avance III 400 ($^1$H 400 MHz, $^{13}$C 100 MHz), Varian 500 MHz spectrometer (500 MHz proton, 125.7 MHz carbon). All chemical shifts are recorded in parts per million (ppm), referenced to residual solvent frequencies ($^1$H NMR: Me4Si=0, CDCl₃=7.26, D₂O=4.79, CD₃OD=4.87 or 3.31, DMSO-d6=2.50, Acetone-d6=2.05 and $^{13}$C NMR: CDCl₃=77.16; CD₃OD=49.0, DMSO-d6=39.5, Acetone-d6=29.9 Coupling constants (J) values are expressed in hertz (Hz). The following splitting abbreviations were used: s=singlet, d=doublet, t=triplet, q=quartet, p=pentet, m=multiplet, br=broad, dd=doublet of doublets, dt=doublet of triplets, td=triplet of doublets. High-resolution mass spectra (HRMS) were recorded on a Bruker Q-TOF-2 Micromass spectrometer equipped with lock spray, using ESI with methanol as the carrier solvent. Accurate mass measurements were performed using leucine enkephalin as a lock mass and the data were processed using MassLynx 4.1. Exact m/z values are reported in Daltons. HRMS were also recorded using Q Exactive mass spectrometer (Thermo Fisher Scientific, San Jose, CA, USA) operated independently in positive or negative ion mode, scanning in full MS mode (2 µscans) from 150 to 1500 m/z at 140,000 resolution, with 4 kV spray voltage, 45 sheath gas, 15 auxiliary gas. Acquired data were then converted from raw to mzXML file format using Mass Matrix (Cleveland, OH, USA). Metabolites assignments, isotopologue distributions, and correction for expected natural abundances of deuterium, $^{13}$C, and $^{15}$N isotopes were performed using MAVEN (Princeton, NJ, USA). Melting points (m.p.) were determined using a Stuart melting point apparatus (SMP20 and SMP40) and the values are uncorrected. Infrared (IR) spectra were recorded on a Thermo Nicolet vatar 360 FT-IR fitted with a Smart Orbit diamond ATR sampler (oils and solids were examined neat), and BrukerALPHA platinum ATR. Absorption maxima ($v_{max}$) are recorded in wavenumbers (cm-1). Compounds with relevant biological activity were assessed by NMR and HPLC with purity ≥95% as determined by Shimadzu prominence HPLC system equipped with a photodiode array detector (PDA) and a Hypersil Gold™ C18 selectivity LC column (5 µm, 1750 Å, 250 mm×4.6 mm) with a flow rate of 1.0 mL/min. Compounds were eluted with a gradient of water methanol or acetone over 25-40 min.

TOP2A ATPase Assay. The mode of inhibition of TOP2A analogs were tested with a DNA relaxation assay and the inorganic phosphate (pi) generated was measured with malachite green phosphate reagent (Abcam, MA) in black polystyrene 384-well assay plates (Thermo Fisher Scientific, MA). ATP-dependent DNA relaxation assays in 15 µL contained 2 U hTopoIIa (Topogen, CO), 85 µg/mL (10 nM) supercoiled plasmid (a gift from AstraZeneca), and various concentrations of ATP (between 0 and 1800 nM) and analog 3 and 7 (between 0 and 20 µM) in 50 mM Tris-HCl (pH 7.5), 150 mM KCl, 5% (v/v) glycerol, 10 mM MgCl₂, 1 mM dithiothreitol, 0.002% (w/v) Brij-35, and 200 nM bovine serum albumin (BSA). A duplicate plate was prepared in the same way except for the omission of the enzyme. Reactions were conducted at 37° C. for 1 h. An addition of 70 µL of ddH₂O and 15 µL of phosphate reagent were added to each well and the plates were incubated in dark at room temp for 30 min before OD₆₀₀ was read with a BioTek plate reader.

TOP2A decatenation assay. Human TOP2A, kDNA, and assay buffers were obtained from TopoGEN (Buena Vista, CO). The synthesized compounds were screened for their TOP2A inhibitory activity by the intensity of DNA decatenation bands on a DNA gel when compared to the vehicle. Compounds were initially incubated with TOP2A (3 U/reaction) for 20 min at a 30 µM and 1.2% DMSO concentration in a 37° C. incubator without CO₂. The decatenation reaction was initiated immediately after by adding 2 mM ATP and 35 ng/reaction of kDNA, then incubated for 1 h in a 37° C. water bath. The samples were loaded into a 0.8% agarose gel in 1× Tris-Borate-EDTA (TBE) at a 0.2 µg/mL ethidium bromide concentration and allowed to run in an electrophoretic chamber for 1 h at 100V. Compounds with the highest inhibitory activity were selected for 2-fold serial dilution dose-response assays (53.6 nM-30 µM). The dose-response assays followed the same protocol with the exception of 4 U/reaction of TOP2A.

3D cell culture of tumor organoids. Cell lines were cultured as tumor organoid using phenol red free RPMI-1640 containing 5% FBS. Tumor organoid were generated by seeding 5,000 cells/well (or as indicated) into un-coated 96-well U-bottom Ultra Low Attachment Microplates (PerkinElmer, MA) followed by centrifugation for 15 min at 1000 rpm to promote cells aggregation. A final concentration of 2% Matrigel was then added and tumor organoid were formed for 72 h under incubation (5% CO₂, 37° C., humidity) before treatment, and maintained under standard cell culture conditions during treatment time courses.

3D Tumor organoid TOPflash reporter assay. Stable engineered cells containing pCDH-TOPflash-luc-EF1-puro [Zhou, Q., et al. "Topoisomerase IIα mediates TCF-dependent epithelial-mesenchymal transition in colon cancer," Oncogene, 2016. 35(38): p. 4990-9.] were used to generate tumor organoids arrayed in 96-well plates and treated for 72 h with TOP2A inhibitors. One-Glo™ luciferase reagent and CellTiter-Glo™ 3D cell viability reagent (Promega, WI) were used to determine the TCF reporter activity in viable cells. Briefly, reagents were added to the spheroids at 1:1 ratio (v:v) and the plates were placed on an orbital shaker (300 rpm) for 10 min at room temperature before the luminescence was read with Envision plate reader (PerkinElmer, MA). TCF reporter activity was normalized to organoid viability and inhibitors treated conditions were normalized to DMSO treated controls.

pCDH-EcadherinPromoter-mCherry-EF1-Puro (EcadPro-RFP) plasmid cloning. The CMV promoter in pCDH-CMV-MCS-EF1-puro plasmid was digested out and replaced with E-cadherin promoter using ClaI and XbaI restriction enzymes. The mCherry cassette was then inserted using EcoRI and NotI downstream of Ecadherin promoter. pEcad/luc-zeo was a generous gift from Dr. Jennifer Richer, PhD (University of Colorado), and the mCherry cassette was a generous gift from Dr. Jerome Schaack, PhD (University of Colorado). VimPro-GFP and EcadPro-RFP reporter assays. Stable VimPro-GFP or EcadPro-RFP SW620 reporter cells were generated using pCDH-VimPro-GFP-EF1-puro virus or pCDH-EcadPro-mCherry-EF1-puro virus as previously reported. [Zhou, Q et al "Topoisomerase IIα mediates TCF-dependent epithelial-mesenchymal transition in colon cancer," Oncogene, 2016. 35(38): p. 4990-9.] Transduced cells were selected with puromycin at 2 µg/mL. The stable fluorescent labeled reporter cells were then used to generate tumor organoids as described. Tumor organoids were then treated with TOP2A inhibitors at 10 µM for an additional 72 h. Following treatment, tumor organoids were stained with 16 µM of Hoechst 33342 for 1 h, which functions as a nuclear stain for imaging segmentation. Images were taken with a 5× air objective. Z stacks were set at 20 Lm apart for a total of 7 layers. Imaging analysis was performed using an Opera Phenix high content screening (HCS) system and Harmony high-content imaging and analysis software interface (PerkinElmer, MA). Nuclei were identified with Hoechst 33342 stain within each layer, and cells were found with either GFP or mCherry channel. The intensities of each fluorescence channel within the cells were calculated and thresholds were set based on the background intensities. Percentages of GFP or mCherry positive cells were calculated and normalized to the DMSO treated group.

Tumor organoid cytotoxicity. SW620 tumor organoids were grown as previously outlined. CellTox™-Green-Express Cytotoxicity Assay (Promega, WI) solution was prepared per manufacturer's protocol. Briefly, organoids were treated for 72 h with CellTox™ Green Express (0.5×) reagent and various doses of TOP2A inhibitors over a range of 0-to-40 µM. Organoids were then imaged using the Opera Phenix HCS system (PerkinElmer, MA). CellTox™ Green Express was excited at 488 nm and emission was detected at 500-550 nm. Mean intensity of the whole well was utilized for calculating cytotoxicity with Lysis Buffer (Promega, WI, 0.025×) as the 0% viability control and 0.4% DMSO as the 100% viability control. Intensity values were normalized to these controls using GraphPad Prism 7.0 (GraphPad. CA).

CADD Molecular Modeling Method. Computer aided drug design were performed using the Discovery Studio (Dassault Systemés Biovia). The crystal structure of TopoIIa (PDB:1ZXM, 1.87 Å) was obtained from the protein data bank and prepared using the CHARM force field in the Discovery Studio. Water molecules were removed, and the residues were corrected for physiological pH. Binding sites were identified as stated in the discovery studio protocol and were defined as whole residues within a 10 Å. Neo and other analogs were prepared using discovery studio and preferred to not generate isomers of the analogs prepared. The receptor and the analogs were minimized based on Discovery Studio algorithm using a root-mean-square gradient tolerance of 3. The CDOCKER and Libdock protocol were used for the docking studies of neo and other analogs in the ATP binding site. The CDOKER approach was set to generate 10 poses of each analog, while the Libdock was set to generate 100 poses of each analog. Top ranked poses were analyzed for binding interactions.

Statistical analysis. Biological data were subjected to one-way ANOVA or using the Student's t-test analysis with Prism v7.0 (GraphPad Software Inc, La Jolla, CA, USA). All experiments were replicated on separate days two or three times as indicated (n=3 for each replicate) unless otherwise described.

Results of Assays for XXX are presented in Table 3 (below)

TABLE 3

| Compound Identification | | TOP2A Enzyme Inhibition | | Modulation or Reversion of EMT Based on Biomarker Expression in SW620 Cells | |
|---|---|---|---|---|---|
| | | % TOP2A Decatenation inhibition | TOP2A Inhibition | Vimentin Down-regulation | E-cadherin Up-regulation |
| Name | Structure | (30 µM) | $IC_{50}$ (µM) | $EC_{50}$ (µM) | $EC_{50}$ (µM) |
| AA-29-216 | 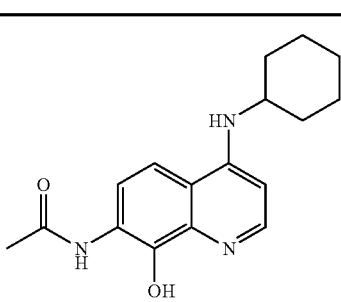 | 100 | 0.29 | 20.6 | 17.8 |

TABLE 3-continued

| Compound Identification | | TOP2A Enzyme Inhibition | | Modulation or Reversion of EMT Based on Biomarker Expression in SW620 Cells | |
| --- | --- | --- | --- | --- | --- |
| | | % TOP2A Decatenation inhibition | TOP2A Inhibition | Vimentin Down-regulation | E-cadherin Up-regulation |
| Name | Structure | (30 μM) | IC$_{50}$ (μM) | EC$_{50}$ (μM) | EC$_{50}$ (μM) |
| AA-34-130 | | 100 | 1.53 | 59 | 36.5 |
| AA-34-131 | | 92 | 2.16 | 23 | 21.3 |
| AA-34-132 | | 94 | 6.56 | 27.65 | 100.2 |
| AA-34-171 | | 62 | — | 17.52 | 48.22 |
| AA-34-180 | | 0 | — | 13.04 | 65.52 |

TABLE 3-continued

| Compound Identification | | TOP2A Enzyme Inhibition | | Modulation or Reversion of EMT Based on Biomarker Expression in SW620 Cells | |
|---|---|---|---|---|---|
| | | % TOP2A Decatenation inhibition | TOP2A Inhibition | Vimentin Down-regulation | E-cadherin Up-regulation |
| Name | Structure | (30 μM) | IC$_{50}$ (μM) | EC$_{50}$ (μM) | EC$_{50}$ (μM) |
| AA-29-136 | | 90 | — | 4.1 | 8.4 |
| AA-29-146 | | 100 | — | 7.4 | 9.7 |
| AA-29-148 | | 100 | — | 25.9 | 7.6 |
| AA-29-157 | | — | — | 29.87 | 179.7 |

TABLE 3-continued

| | | TOP2A Enzyme Inhibition | | Modulation or Reversion of EMT Based on Biomarker Expression in SW620 Cells | |
|---|---|---|---|---|---|
| Compound Identification | | % TOP2A Decatenation inhibition | TOP2A Inhibition | Vimentin Down-regulation | E-cadherin Up-regulation |
| Name | Structure | (30 µM) | IC$_{50}$ (µM) | EC$_{50}$ (µM) | EC$_{50}$ (µM) |
| AA-29-158 | (structure: 7-acetamido-8-hydroxy-4-((4-(trifluoromethyl)phenyl)amino)quinoline) | — | — | 1.363 | 65.14 |
| AA-29-145 | (structure: 7-acetamido-4-((4-fluorophenyl)amino)-8-hydroxyquinoline) | — | — | — | — |
| AA-29-147 | (structure: 7-acetamido-8-hydroxy-4-((1H-indol-4-yl)amino)quinoline) | — | — | 14.78 | 145.5 |
| AA-29-144 | (structure: 7-acetamido-8-hydroxy-4-((3-hydroxyphenyl)amino)quinoline) | — | — | — | — |

TABLE 3-continued

| Compound Identification | | TOP2A Enzyme Inhibition | | Modulation or Reversion of EMT Based on Biomarker Expression in SW620 Cells | |
| --- | --- | --- | --- | --- | --- |
| | | % TOP2A Decatenation inhibition | TOP2A Inhibition | Vimentin Down-regulation | E-cadherin Up-regulation |
| Name | Structure | (30 µM) | IC$_{50}$ (µM) | EC$_{50}$ (µM) | EC$_{50}$ (µM) |
| AA-29-139 | | — | — | — | — |
| AA-29-149 | | — | — | — | — |
| AA-29-155 | | — | — | 9.561 | 128.3 |
| AA-29-171 | | — | — | 26.58 | 138.6 |

TABLE 3-continued

| | | TOP2A Enzyme Inhibition | | Modulation or Reversion of EMT Based on Biomarker Expression in SW620 Cells | |
| | | % TOP2A | | | |
| Compound Identification | | Decatenation inhibition | TOP2A Inhibition | Vimentin Down-regulation | E-cadherin Up-regulation |
| Name | Structure | (30 μM) | IC$_{50}$ (μM) | EC$_{50}$ (μM) | EC$_{50}$ (μM) |
| AA-29-172 | 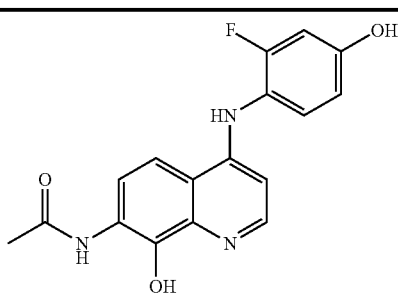 | — | — | 45.87 | 58.53 |

Chemical Syntheses

7-Acetamido-4-chloro-8-methoxyquinoline (X1). To 300 mg (1.257 mmol) of 4-chloro-8-methoxy-7-nitroquinoline were added 489 mg (7 equivalents) of iron powder, 18 mL water/ethanol (2:8), 134 mg (2 equivalents) ammonium chloride. The mixture was refluxed for 1.5 h and allowed to cool to room temperature. The mixture was filtered over a pad of celite and washed with Methanol. The filtrate was diluted with water, and the pH was adjusted with NaHCO$_3$ to pH=8. The product was extracted with ethyl acetate, dried over sodium sulfate and concentrated in vacuo to generate the aniline intermediate. Without purification, the aniline was dissolved in 5 mL acetic acid and 2 mL acetic anhydride under drying tube for 8 h. The solvents were removed by concentrating the product in vacuo to generate the crude product, which was purified by flash chromatography using silica gel as the solid phase, and 20% dichloromethane in ethyl acetate to afford 301 mg (96% yield) TLC (Ethyl acetate) R$_f$=0.17; Melting Point 114-116° C.; $^1$H NMR (400 MHz, CDCl$_3$) δ 8.76 (d, J=7.2 Hz, 1H), 8.73 (d, J=4.0 Hz, 1H), 8.13 (broad s, 1H), 7.96 (d, J=7.6 Hz, 1H), 7.40 (d, J=4.0, 1H), 4.18 (s, 3H), 2.29 (s, 3H); C NMR (100 MHz, CDCl$_3$) δ 168.7, 149.3, 142.8, 142.2, 132.2, 123.9, 121.0, 120.1, 119.8, 62.5, 25.1; IR (neat) ν$_{max}$ 3337.0, 3195.8, 2954.9, 2924.2, 2852.7, 2361.4, 1694.8, 1610.3, 1507.8, 1442.8; ESI-HRMS [M+Na]$^+$ calculated for C$_{12}$H$_{11}$ClN$_2$O$_2$Na 273.0401 found 273.0403.

4-Chloro-8-methoxy-7-(2-(morpholin-4-yl)acetamido)quinoline (X2). To 150 mg (0.628 mmol) of 4-chloro-8-methoxy-7-nitroquinoline were added 246 mg (7 equivalents) of iron powder, 9 ml water/ethanol (2:8), 67.2 mg (2 equivalents) ammonium chloride. The mixture was refluxed for 1.5 hours and allowed to cool to room temperature. The mixture was filtered over a pad of celite and washed with methanol. The filtrate was diluted with water, and the pH was adjusted with NaHCO$_3$ to pH=8. The product was extracted with ethyl acetate, dried over sodium sulfate and concentrated in vacuo to generate the aniline intermediate. Without purification the aniline was dissolved in 3 ml of dry DCM, to which were added 2 molar equivalents of morpholine acetic acid (193.7 mg), 220 μL TEA (2.5 equivalents, 159.37 mg), 450 μL (418.08 mg, 1.2 equivalents) of T3P. The resulting solution was stirred for 24 hours under nitrogen. The reaction was quenched by the addition of water, and the pH was adjusted with saturated NaHCO$_3$ until pH=8. The product was isolated using 30 ml of DCM×3, and dried over sodium sulfate. The solvents were removed by concentrating the product in vacuo to generate the crude product, which was purified by flash chromatography using silica gel as the solid phase, and 50% hexane in acetone to afford 200.6 mg (92% yield). TLC (50% hexane in acetone)

4-Chloro-8-methoxy-7-(3-(morpholin-4-yl)propanamido)quinoline (X3). To 150 mg (0.628 mmol) of 4-chloro-8-methoxy-7-nitroquinoline were added 246 mg (7 equivalents) of iron powder, 9 ml water/ethanol (2:8), 67.2 mg (2 equivalents) ammonium chloride. The mixture was refluxed for 1.5 hours and allowed to cool to room temperature. The mixture was filtered over a pad of celite and washed with Methanol. The filtrate was diluted with water, and the pH was adjusted with NaHCO$_3$ to pH=8. The product was extracted with ethyl acetate, dried over sodium sulfate and concentrated in vacuo to generate the aniline intermediate. Without purification the aniline was dissolved in 3 ml of dry DCM, to which were added 2 molar equivalents of morpholine propionic acid hydrochloride (246.5 mg), 220 μL TEA (2.5 equivalents, 159.37 mg), 450 μL (418.08 mg, 1.2 equivalents) of T3P. The resulting solution was stirred for 24 hours under nitrogen. The reaction was quenched by the addition of water, and the pH was adjusted with saturated NaHCO$_3$ until pH=8. The product was isolated using 30 ml of DCM×3, and dried over sodium sulfate. The solvents were removed by concentrating the product in vacuo to generate the crude product, which was purified by flash chromatography using silica gel as the solid phase, and 50% hexane in acetone to afford 200.6 mg (91% yield) of syrupy product. TLC (50% hexane in acetone) R$_f$=0.22; $^1$H NMR (500 MHz, CDCl$_3$) δ 1.96 (s. 1H), 8.79 (d, J=11.5 Hz, 1H), 8.75 (d, J=5.5 Hz, 2H), 7.96 (d, J=12.0 Hz, 1H), 7.40 (d, J=5.0 Hz, 1H), 4.12 (s, 3H), 3.87 (s, 4H), 2.77 (t, J=6.8 Hz, 2H), 2.65 (t, J=7.5 Hz, 6H); $^{13}$C NMR (125 MHz, CDCl$_3$) δ 171.4, 149.5, 143.3, 1432, 142.9, 133.0, 124.1, 122.2, 120.2, 119.9, 667, 62.2, 54.5, 53.3, 33.2; IR (neat) ν$_{max}$ 3170.0, 2924.9, 2855.5, 2822.1, 1686.9, 1611.9, 1513.7, 1457.5, 1418.5, 1402.6; ESI-HRMS [M+H]$^+$ calculated for C$_{17}$H$_{21}$ClN$_3$O$_3$ 350.1266, found 350.1260.

General Method for Nucleophilic Aromatic Substitution Reaction (SN$_{Ar}$) X4-X14

To 50 mg (0.199 mmol) of 7-acetamido-4-chloro-8-methoxyquinoline was dissolved in 7 mL of ethanol to which was added 2 equivalents (0.398 mmol) of amine at room temperature and the resulting yellow solution was refluxed for 8 h. The yellow solution was washed with water followed by extraction with chloroform (30 mL)×3. The Chloroform extracts were combined, dried over sodium sulfate and filtered off to give a yellow filtrate. The filtrate was concentrated and dried under high vacuum to give a crude yellowish orange product which was chromatographed on silica gel using 5-10% methanol in ethyl acetate to afford pure product.

7-Acetamido-4-((phenyl)amino)-8-methoxyquinoline (X4). The compound was prepared from 50 mg (0.199 mmol) of 7-acetamido-4-chloro-8-methoxyquinoline and 37 mg (36.0 6 µL, 0.398 mmol) of aniline using the general method for SN$_{Ar}$ to afford 54 mg (88% yield). TLC (20% methanol in ethyl acetate) R$_f$=0.25; Melting Point 214-215° C.; $^1$H NMR (400 MHz, Acetone-d$_6$) δ 8.97 (broad s, 1H), 8.58 (d, J=9.2 Hz, 1H), 8.48 (d, J=5.2 Hz, 1H), 8.26 (broad s, 1H), 8.01 (d, J=9.2 Hz, 1H) 7.44-7.39 (multiplet, 4-H), 7.19-7.17 (multiplet, 1H) 6.95 (d, J=5.2 Hz, 1H), 4.14 (s, 3H), 2.24 (s, 3H); $^{13}$C NMR (125.7 MHz, DMSO) δ 169.1, 149.9, 147.9, 144.0, 143.4, 140.5, 131.3, 129.3, 123.7, 122.4, 119.5, 117.3, 1168, 100.8, 61.5, 24.0; IR (neat) v$_{max}$ 2924.5, 2854.6, 1676.1, 1615.9, 1582.9, 1532.4; ESI-HRMS [M+H]$^+$ calculated for C$_{18}$H$_{18}$N$_3$O$_2$ 308.1394 found 308.1411.

7-Acetamido-4-((3-benzoic)amino)-8-methoxyquinoline (X5). The compound was prepared from 50 mg (0.199 mmol) of 7-acetamido-4-chloro-8-methoxyquinoline and 54.58 mg (2 equivalents, 0.398 mmol) of 3-amino benzoic acid at room temperature, and the resulting solution was refluxed for 8 hours. The yellow solution was cooled to room temperature, concentrated and dried in vacuo to give a crude yellowish orange product, which was recrystallized with chloroform to afford an off-white solid of about 50 mg (72% yield). TLC (50% methanol in ethyl acetate) R$_f$=0.17; Melting Point 236-238° C.; $^1$H NMR (500 MHz, DMSO-d6) δ; 10.89 (br s, 1H), 10.14 (br s, 1H), 8.44 (s, 2H), 8.40 (d, J=7.0 Hz, 1H), 7.99-7.97 (m, 2H), 7.76-7.70 (m, 2H), 6.82 (d, J=6.5 Hz, 1H), 3.89 (s, 3H), 2.25 (s, 3H); 1C NMR (125.7 MHz, DMSO-d6) δ 169.7, 166.5, 154.6, 143.2, 138.3, 137.5, 135.2, 133.4, 132.5, 130.3, 129.5, 128.0, 125.8, 121.9, 118.9, 114.1, 99.8, 61.6, 24.0; IR (neat) v$_{max}$ 3118.0, 3068.2, 2961.5, 1711.1, 1662.6, 1618.3, 1586.2, 1510.0, 1454.0; ESI-HRMS [M+H]$^+$ calculated for C$_{19}$H$_{18}$N$_3$O$_4$ 352.1292 found 352.1297.

7-Acetamido-4-((5-indole)amino)-8-methoxyquinoline (X6). The compound was prepared from 50 mg (0.199 mmol) of 7-acetamido-4-chloro-8-methoxyquinoline and 52.6 mg (2 equivalents, 0.398 mmol) of 5-amino indole using the general method for SN$_{Ar}$ to afford 58 mg (84% yield). TLC (30% methanol in ethyl acetate) R$_f$=0.25; Melting Point 170-172° C.; $^1$H NMR (500 MHz, DMSO-d6) δ 11.1 (broad s, 1H), 9.53 (broad s, 1H), 8.85 (broad s, 1H), 8.30 (d, J=5.5 Hz, 1H), 8.21 (d, J=9.0 Hz, 1H), 8.12 (d, J=9.5 Hz, 1H), 7.47 (d, J=9.0 Hz, 2H), 7.39 (t, J=2.5 Hz, 1H), 7.07 (dd, J=2.0, 8.5 Hz, 1H), 6.51 (d, J=5.5 Hz, 1H), 6.45 (s, 1H), 4.02 (s, 3H), 2.20 (s, 3H); $^{13}$C NMR (125.7 MHz, DMSO-d6) δ 169.1, 150.1, 149.8, 143.9, 143.3, 133.8, 131.3, 131.1, 128.2, 126.2, 119.3, 118.9, 116.7, 116.2, 112.1, 101.1, 99.4, 61.3, 24.0; IR (neat) v$_{max}$ 3165.2, 2924.5, 2852.7, 2363.4, 2334.3, 1674.2, 1617.9, 1590.7, 1503.3; ESI-HRMS [M+H]$^+$ calculated for C$_{20}$H$_{19}$N$_4$O$_2$ 347.1503 found 347.1493.

7-Acetamido-4-((4-indole)amino)-8-methoxyquinoline (X7) The compound was prepared from 50 mg (0.199 mmol) of 7-acetamido-4-chloro-8-methoxyquinoline and 105.2 mg (4 equivalents, 0.796 mmol) of 4-amino indole using the general method for SN$_{Ar}$ to afford 60 mg (87% yield). TLC (30% methanol in ethyl acetate) R; =0.32; Melting Point 200-202° C.; $^1$H NMR (400 MHz, DMSO-d6) δ 11.4 (broad s, 1H), 9.98 (broad s, 1H), 9.83 (broad s, 1H), 8.37 (d, J=9.2 Hz, 1H), 8.30 (d, J=8.0 Hz, 2H), 7.42 (d, J=8.0 Hz, 1H), 7.37 (t, J=2.6 Hz, 1H), 7.20 (t, J=8.0 Hz, 1H), 7.02 (d, J=7.6 Hz, 1H), 6.35 (d, J=6.0 Hz, 1H) 6.21 (s, 1H), 3.96 (s, 3H), 2.22 (s, 3H); $^{13}$C NMR (125.7 MHz, DMSO-d6) δ 170.1, 137.6, 133.2, 130.1, 126.0, 123.7, 121.9, 121.1, 118.4, 115.9, 110.8, 101.2, 99.8, 61.8, 24.2; IR (neat) v$_{max}$ 3211.8, 29206, 2852.7, 2367.3, 2340.1, 1676.1, 1617.9, 1582.9; ESI-HRMS [M+H]$^+$ calculated for C$_{20}$H$_{19}$N$_4$O$_2$ 347.1503 found 347.1508.

7-Acetamido-4-(((2-methyl)-5-indole)amino)-8-methoxyquinoline (X8). The compound was prepared from 50 mg (0.199 mmol) of 7-acetamido-4-chloro-8-methoxyquinoline and 58.2 mg (2 equivalents, 0.398 mmol) of 5-amino-2-methyl using the general method for SN$_A$, to afford 60 mg (84% yield). TLC (30% methanol in ethyl acetate) R$_f$=0.22; Melting Point 236-237° C.; $^1$H NMR (400 MHz, DMSO-d6) δ 11.01 (broad s, 1H), 9.57 (broad s, 1H), 8.95 (broad s, 1H), 8.28 (d, J=5.2 Hz, 1H), 8.20 (d, J=9.2 Hz, 1H), 8.13 (d, J=9.2 Hz, 1H), 7.34 (d, J=7.6 Hz, 2H), 6.96 (d, J=5.6 Hz, 1H), 6.35 (d, J=6.0 Hz, 1H), 6.13 (s, 1H), 4.00 (s, 3H), 2.39 (s, 3H) 2.19 (s, 3H); $^{13}$C NMR (125.7 MHz, DMSO-d6) δ 169.3, 150.8, 149.1, 143.5, 142.3, 136.8, 134.2, 131.5, 130.7, 129.3, 119.3, 118.2, 116.9, 116.5, 115.4, 111.2, 99.4, 61.4, 24.1, 13.5; IR (neat) v$_{max}$ 2910.9, 2842.9, 1678.1, 1614.0, 1582.9, 1536.3; ESI-HRMS [M+H]$^+$ calculated for C$_{21}$H$_{21}$N$_4$O$_2$ 361.1659 found 361.1664.

7-Acetamido-4-((4-fluorophenyl)amino)-8-methoxyquinoline (X9). The compound was prepared from 35.8 mg (0.143 mmol) of 7-acetamido-4-chloro-8-methoxyquinoline and 15.87 mg (1 equivalent, 0.142 mmol) of 4-fluoroaniline using the general method for S$_N$Ar to afford 42.5 mg (91% yield). TLC (30% methanol in ethyl acetate) R$_f$=0.52; $^1$H NMR (500 MHz, DMSO-d6) δ 9.56 (s, 1H), 8.93 (s, 1H), 8.41 (d, J=5.0 Hz, 1H), 8.24 (d, J=9.0 Hz, 1H), 8.06 (d, J=9.5 Hz, 1H), 7.38 (dd, J=3.5 Hz, J=5.0 Hz, 1H), 7.26 (t, J=8.75 Hz, 1H), 6.71 (d, J=5.5 Hz, 1H), 4.02 (s, 3H), 2.20 (s, 3H); $^{13}$C NMR (125.7 MHz, DMSO) δ 169.1, 158.7 (d, $^1$J$_{C-F}$=240.7 Hz), 149.8, 148.4, 143.8, 143.2, 136.6, 131.3, 125.0 (d, $^1$J$_{C-F}$=8.1 Hz), 119.4, 117.0, 116.7, 116.0 (d, $^2$J$_{C-F}$=22.3 Hz), 100.2, 61.4, 24.0; ESI-HRMS [M+Na]$^+$ calculated for C$_{16}$H$_{16}$N$_3$O$_3$Na 348.1119 found 348.1129.

7-Acetamido-4-((3-fluorophenyl)amino)-8-methoxyquinoline (X10). The compound was prepared from 62 mg (0.2473 mmol) of 7-acetamido-4-chloro-8-methoxyquinoline and 35.72 mg (2 equivalents, 47.54 µL, 0.4946 mmol) of 3-fluoroaniline using the general method for SN$_{Ar}$ to afford 57 mg (71% yield). TLC (10% methanol in ethyl acetate) R$_f$=0.23; $^1$H NMR (500 MHz, DMSO-d6) δ 9.57 (s, 1H), 9.03 (s, 1H), 8.50 (d, J=5.5 Hz, 1H), 8.27 (d, J=9.0 Hz, 1H), 8.02 (d, J=9.5 Hz, 1H), 7.41 (q, J=7.6 Hz, 1H), 7.20 (d, J=8.0 Hz, 1H), 7.16 (d, J=11.0 Hz, 1H), 7.03 (d, J=5.0 Hz, 1H), 6.90 (t, J=8.5 Hz, 1H), 4.03 (s, 3H), 2.20 (s, 3H); $^{13}$C NMR (125.7 MHz, DMSO-d6) δ 169.1, 155.2 (d, $^1$J$_{C-F}$=235.2 Hz), 154.3, 150.9, 149.2, 144.5, 144.2, 130.9, 125.4 (d, $^3J_{C-F}$=7.6 Hz), 124.3, 122.2, 121.2, 120.8, 116.9 (d, $^2J_{C-F}$=23.4 Hz), 116.7 (d, $^3J_{C-F}$=8.0 Hz), 116.1 (d, $^2J_{C-F}$=22.5 Hz), 79.1, 61.7, 23.9; IR (neat) $v_{max}$ 3285.1, 321, 2928.0, 2893.2, 1680.5, 1612.9, 1576.3, 1526.9; ESI-HRMS [M+H]$^+$ calculated for $C_{18}H_{17}FN_3O_2$ 326.1299 found 326.1304.

7-Acetamido-4-((4-hydroxyphenyl)amino)-8-methoxyquinoline (X11). The compound was prepared from 33.5 mg (0.133 mmol) of 7-acetamido-4-chloro-8-methoxyquinoline and 14.75 mg (1 equivalent, 0.133 mmol) of 4-amino-phenol using the general method for $SN_{Ar}$ to afford 42 mg (98% yield). TLC (20% methanol in ethyl acetate) R; =0.21; MP 249° C.; $^1$H NMR (500 MHz, DMSO-d6) δ 9.52 (s, 1H), 9.44 (broad s, 1H), 8.70 (s, 1H), 832 (d, J=5.0 Hz, 1H), 8.12 (d, J=9.0 Hz, 1H), 8.05 (d, J=9.5 Hz, 1H), 7.14 (d, J=8.5 Hz, 1H), 6.84 (d, J=8.5 Hz, 1H), 6.49 (d, J=5.0 Hz, 1H) 4.01 (s, 3H), 2.19 (s, 3H); $^{13}$C NMR (125.7 MHz) δ 169.0, 154.8, 149.8, 149.6, 143.1, 131.1, 130.9, 126.1, 119.0, 116.6, 115.9, 99.4, 61.4, 24.0; IR (neat) $v_{max}$ 3304.8, 2957.8, 2929.2, 2362.1, 2331.5, 1676.9, 1653.1, 1617.1, 1577.9, 1540.5; ESI-HRMS [M+H]$^+$ calculated for $C_{18}H_{18}N_3O_3$ 324.1343 found 324.1358.

7-Acetamido-4-((3-hydroxyphenyl)amino)-8-methoxyquinoline (X12). The compound was prepared from 33.0 mg (0.131 mmol) of 7-acetamido-4-chloro-8-methoxyquinoline and 14.30 mg (1 equivalent, 0.131 mmol) of 3-amino-phenol using the general method for $SN_{Ar}$ to afford 40.2 mg (95% yield). TLC (30% methanol in ethyl acetate) $R_f$=0.44; $^1$H NMR (500 MHz, DMSO-d6) δ 9.59 (s, 1H), 9.52 (s, 1H), 8.93 (broad s, 1H), 8.52 (broad s, 1H), 8.32 (d, J=5.0 Hz, 1H), 8.21 (d, J=8.5 Hz, 1H), 8.11 (d, J=9.5 Hz, 1H), 7.22 (d, J=8.0 Hz, 1H), 7.14 (t, J=8.0 Hz, 1H), 7.00 (d, J=8.0 Hz, 1H), 6.89 (t, J=7.5 Hz, 1H), 6.20 (d, J=5.5 Hz, 1H), 4.02 (s, 3H), 4.01 (s, 3H) 2.20 (s, 3H); $^{13}$C NMR (125.7 MHz, DMSO) δ 169.1, 158.2, 149.4, 148.2, 141.4, 131.6, 129.9, 119.5, 117.0, 113.1, 111.1, 109.3, 61.1, 24.0; ESI-HRMS [M+H]$^+$ calculated for $C_{19}H_{18}N_3O_3$ 324.1343 found 324.1342.

7-Acetamido-4-((4-trifluoromethylphenyl)amino)-8-methoxyquinoline (X13). The compound was prepared from 64 mg (0.2553 mmol) of 7-acetamido-4-chloro-8-methoxyquinoline and 82.27 mg (2 equivalents, 0.5106 mmol) of 4-trifluoromethylaniline using the general method for $SN_{Ar}$r to afford 77 mg (81% yield). TLC (10% methanol in ethyl acetate) R$_1$=0.32; Melting Point 237-239° C.; $^1$H NMR (500 MHz, DMSO-d6) δ 9.59 (s, 1H), 9.23 (s, 1H), 8.56 (d, J=5.0 Hz, 1H), 8.28 (d, J=9.0 Hz, 1H), 8.01 (d, J=9.5 Hz, 1H), 7.70 (d, J=8.5 Hz, 2H), 7.50 (d, J=8.5 Hz, 2H), 7.16 (d, J=5.5 Hz, 1H), 4.04 (s, 3H), 2.20 (s, 3H); $^{13}$C NMR (100 MHz, DMSO-d6); δ 169.1, 149.9, 146.2, 145.2, 143.7 (d, $^2J_{C-F}$=50.4 Hz), 131.5, 128.6, 126.5 (q, $^4J_{C-F}$=3.8 Hz and 11.1 Hz), 124.5 (d, $^1J_{C-F}$=269.4 Hz), 122.7, (d, $^2J_{C-F}$=90 Hz), 122.1 (d, $^3J_{C-F}$=31.9 Hz), 120.1, 119.9, 118.2, 117.1, 103.5, 61.5, 24.0; IR (neat) $v_{max}$ 3404.8, 3349.3, 2927.6, 2901, 1676.3, 1616.7, 1584.5, 1532.8; ESI-HRMS [M+H]$^+$ calculated for $C_{19}H_{17}F_3N_3O_2$ 376.1267, found 376.1274.

7-Acetamido-4-((3-trifluoromethylphenyl)amino)-8-methoxyquinoline (X14). The compound was prepared from 63 mg (0.2513 mmol) and 80.98 mg (2 equivalents, 0.5026 mmol) of 3-trifluoromethylaniline using the general method for $SN_{Ar}$ to afford 90 mg (95% yield). TLC (10% methanol in ethyl acetate) $R_f$=0.32; $^1$H NMR (500 MHz, DMSO-d6) δ 9.58 (s, 1H), 918 (s, 1H), 8.52 (d, J=5.0 Hz, 1H), 8.27 (d, J=9.0 Hz, 1H), 8.03 (d, J=9.0 Hz, 1H), 7.68-7.59 (m, 3H), 7.41 (d, J=7.5 Hz, 1H), 7.01 (d, J=5.5 Hz, 1H), 4.03 (s, 3H), 2.20 (s, 3H); $^{13}$C NMR (125.7 MHz, DMSO-d6) δ 169.2, 162.7 (d, $^1J_{C-F}$=242.6 Hz), 150.0, 146.9, 144.0, 143.5, 142.9 (d, $^1J_{C-F}$=10.4 Hz), 131.4, 130.9 (d, $^4J_{C-F}$=9.7 Hz), 119.8, 117.7, 117.0 (d, $^4J_{C-F}$=32.8 Hz), 109.5 (d, $^1J_{C-F}$=21.1 Hz), 107.9 (d, $J_{C-F}$=$^{24}$0.1 Hz), 102.1, 61.5, 24.0; IR (neat) $v_{max}$ 3411.3, 3349.30, 3292.5, 3011.7, 2943.7, 2855.9, 1674.8, 1615.9, 1588.8, 1577.4, 1540.3.

7-Acetamido-4-chloro-8-hydroxyquinoline (X15). To 600 mg (2.393 mmol) of 7-Acetamido-4-bromo-8-methoxyquinoline in 5 mL of dry dichloromethane was added 2.5 equivalents of 1M BBr$_3$ in dichloromethane (5.983 mmol) at 0° C. for 10 minutes. The reaction was allowed to stir at that temperature for additional 20 minutes, during this period the reaction became orange suspension. The reaction was then warmed to room temperature and stirred at that temperature overnight. The reaction was quenched by the addition of ice-cold water and basified using saturated aqueous sodium bicarbonate, and extract with of chloroform (50 ml, ×3). The organic layers were combined and concentrated in vacuo to give a crude product, which was recrystallized with ethanol to give 490 mg (87% yield) as a light-yellow solid. TLC (Ethylacetate) R$_f$=0.32; Melting Point 186-188° C.; 1H NMR (400 MHz, DMSO-d6) δ 10.46 (broad s, 1H), δ 9.62 (broad s, 1H), 8.76 (d, J=4.8 Hz, 1H), 8.30 (d, J=9.2 Hz, 1H), 7.69 (d, J=4.4 Hz, 1H), 7.60 (d, J=9.2 Hz, 1H), 2.16 (s, 3H); $^{13}$C NMR (100 MHz, DMSO-d6) δ 168.8, 1480, 142.6, 141.0, 139.1, 124.6, 124.2, 122.6, 120.5, 112.4, 23.6; IR (neat) $v_{max}$ 3289.8, 2359.1, 2924.2, 2328.8, 1654.3, 1626.6, 1522.2, 1501.8; ESI-HRMS [M+H]$^+$ calculated for $C_{11}H_{10}ClN_2O_2$ 237.0425 found 237.0430.

4-Chloro-8-hydroxy-7-(3-(morpholin-4-yl)propanamido) quinoline (X16). To 682 mg (1.949 mmol) of 4-chloro-8-methoxyquinoline-7-morpholinepropionamide in 4 ml of dry dichloromethane was added 2.5 equivalents of 1M BBr$_3$ in dichloromethane (9.752 ml) at 0° C. for 10 minutes. The reaction was allowed to stir at that temperature for additional 20 minutes, during this period the reaction became dark orange suspension. The reaction was then warmed to room temperature and stirred at that temperature overnight. The reaction was quenched by the addition of ice-cold water and basified using saturated aqueous sodium bicarbonate, and extract with of chloroform (50 ml, ×3). The organic layers were combined and concentrated in vacuo to give a crude product, which was recrystallized with ethanol to give 400 mg (61% yield). TLC (Ethylacetate). 1H NMR (500 MHz, DMSO-d6) δ 10.75 (broad s, 1H), 10.58 (broad s, 1H), 8.76 (d, J=4.5 Hz, 1H), 8.59 (d, J=9.5 Hz, 1H), 7.67 (d, J=4.5 Hz, 1H), 7.61 (d, J=9.5 Hz, 1H), 3.70 (s, 4H), 2.64 (s, 4H), 2.50 (s, 4H); $^{13}$C NMR (100 MHz, DMSO-d6) δ 170.7, 148.2, 141.6, 141.1, 138.9, 125.5, 122.7, 122.2, 120.3, 112.7, 65.8, 53.8, 52.8, 32.7; IR (neat) $v_{max}$ 3100.7, 2966.3, 2927.0, 2862.9, 2810.5, 2771.0, 1654.1, 1616.8, 1536.8, 1497.0; ESI-HRMS [M+H]$^+$ calculated for $C_{15}H_{19}ClN_3O_3$ 336.1109 found 336.1114.

General method for nucleophilic aromatic substitution reaction (SN$_{Ar}$) for analogs X18-X30. To 40 mg (0,199 mmol) of 7-acetamido-4-chloro-8-methoxyquinoline was dissolved in 7 mL of ethanol to which was added 2 equivalents (0.398 mmol) of amine at room temperature and the resulting yellow solution was refluxed for 8 h. The yellow solution was washed with water followed by extraction with chloroform (30 mL)×3. The chloroform extracts were combined, dried over sodium sulfate and filtered off to give a yellow filtrate. The filtrate was concentrated and dried under high vacuum to give a crude yellowish orange product which was which was recrystallized in ethanol to give the titled compound 7-Acetamido-8-hydroxy 4-((phenyl)amino) quinoline (X18). The compound was prepared from 40 mg (0.169 mmol) of 7-acetamido-4-chloro-8-hydroxyquinoline and 39.35 mg (38.58 μL, 0.422 mmol) of aniline using the general method of $SN_{Ar}$ to give a light yellow solid, 30.6 mg (62% yield). TLC (20% methanol in ethyl acetate) Melting Point 262-264° C.; $^1$H NMR (400 MHz, DMSO-d$_6$) δ 11.00 (broad s, 1H), 10.85 (broad s, 1H), 8.29 (d, J=7.2 Hz, 1H), 8.24 (d, J=9.2 Hz, 1H), 7.95 (d, J=9.2 Hz, 1H), 7.56 (t, J=7.8 Hz, 2H), 7.47 (d, J=7.6 Hz, 2H), 7.42 (t, J=7.2 Hz, 1H), 6.73 (d, J=7.2 Hz, 1H), 2.26 (s, 3H); $^{13}$C NMR (100 MHz, DMSO-d6) δ 170.9, 154.5, 142.3, 137.2, 131.2, 129.9, 128.1, 127.4, 125.5, 122.0, 114.8, 114.0, 99.6, 23.45; IR (neat) $v_{max}$ 3379.1, 3203.9, 2997.0, 2253.2, 1651.1, 1585.7, 1535.0; ESI-HRMS [M+H]$^+$ calculated for $C_{17}H_{16}N_3O_2$ 294.1237 found 294.1244.

7-Acetamido-8-hydroxy-4-((3-benzoic)amino)quinoline X(19). The compound was prepared from 40 mg (0.169 mmol) of 7-acetamido-4-chloro-8-hydroxyquinoline and 34.7 mg, 0.253 mmol of 3-aminobenzoic acid using the general method of $SN_{Ar}$ to give a light yellow solid, 46.8 mg (82% yield). TLC (20% methanol in ethyl acetate) Melting Point 322-324° C.; $^1$H NMR (400 MHz, DMSO-d$_6$) δ 10.94 (broad s, 1H), 10.89 (broad s, 1H), 8.33 (d, J=7.2 Hz, 1H), 8.23 (d, J=9.2 Hz, 1H), 7.99-7.94 (m, 3H), 7.76 (d, J=8.0 Hz, 1H), 7.69 (t, J=7.8 Hz, 1H), 6.82 (d, J=6.8 Hz, 1H), 2.26 (s, 3H); $^{13}$C NMR (125.7 MHz, DMSO-d6) δ 170.8, 166.5, 154.3, 142.6, 137.7, 137.3, 132.5, 131.3, 130.3, 129.5, 128.1, 127.8, 125.9, 122.2, 115.0, 114.0, 99.7, 23.4; IR (neat) $v_{max}$ 3262.5, 3108.1, 3030.7, 2363.5, 2323.1, 1686.0, 1627.4, 1575.2, 1524.6, 1305.3; ESI-HRMS [M+H]$^+$ calculated for $C_{18}H_{16}N_3O_4$ 338.1135 found 338.1143.

7-Acetamido-8-hydroxy-4-((5-indole)amino)quinoline (X20). The compound was prepared from 35.4 mg (0.1495 mmol) of 7-acetamido-4-chloro-8-hydroxyquinoline and 19.7 mg (0.1495 mmol) of 5-aminoindole using the general method of SNAr to afford 45.2 mg (91% yield) of pure product. TLC (20% methanol in ethyl acetate) as a light yellow solid R$_f$=0.16; Melting Point 266-268° C.; $^1$H NMR (400 MHz, DMSO-d6) δ 11.41 (broad s, 1H), 10.71 (broad s, 1H), 10.55 (broad s, 1H), 8.21 (d, J=6.8 Hz, 1H), 8.14 (d, J=9.2 Hz, 1H), 7.94 (d, J=9.2 Hz, 1H), 7.58 (m, 2H) 7.46 (s, 1H), 7.11 (dd, J=2.0, 8.8 Hz, 1H) 6.57 (d, J=6.8 Hz, 1H), 6.50 (d, J=2.8 Hz, 1H), 2.24 (s, 3H); $^{13}$C NMR (100 MHz, DMSO-d6) δ 170.5, 154.7, 142.6, 138.2, 134.8, 132.1, 128.8, 126.9, 121.5, 119.2, 117.2, 114.6, 113.0, 112.6, 101.5, 99.3, 23.5; IR (neat) $v_{max}$ 3368.5, 3331.0, 3240.4, 2918.3, 2376.9, 1665.1, 1551.7, 1446.6; ESI-HRMS [M+H]$^+$ calculated for $C_{19}H_{17}N_4O_2$ 333.1346 found 333.1350.

7-Acetamido-8-hydroxy-4-((4-indole)amino)quinoline (X21). The compound was prepared from 40.3 mg (0.170 mmol) of 7-acetamido-4-chloro-8-hydroxyquinoline and 45.0 mg (0.214 mmol, 2 equivalents) of 4-aminoindole using the general method of $SN_{Ar}$ to afford 49 mg (86% yield) of pure product as a light-yellow solid. TLC (20% methanol in ethyl acetate) R$_f$=0.13; Melting Point 311-313° C.; $^1$H NMR (400 MHz, DMSO-d6) δ 11.57 (broad s, 1H), 11.10 (broad s, 1H), 11.03 (broad s, 1H), 8.33 (d, J=9.2 Hz, 1H), 8.22 (d, J=6.8 Hz, 1H), 7.99 (d, J=9.2 Hz, 1H), 7.52 (t, J=8.0 Hz, 1H), 7.42 (s, 1H), 7.24 (t, J=7.6 Hz, 1H) 7.09 (d, J=7.2 Hz, 1H), 6.35 (d, J=6.8 Hz, 1H), 6.23 (s, 1H), 2.27 (s, 3H); $^{13}$C NMR (100 MHz, DMSO-d6) δ 170.8, 154.7, 141.8, 137.4, 137.1, 131.0, 128.3, 128.1, 126.3, 123.6, 121.9, 121.5, 116.4, 114.5, 114.1, 111.6, 100.2, 99.1, 23.4; IR (neat) $v_{max}$ 3198.2, 3005.4, 23.66.8, 1654.2, 1597.3, 1537.7, 1454.8; ESI-HRMS [M+H]$^+$ calculated for $C_{19}H_{17}N_4O_2$ 333.1346 found 333.1348.

7-Acetamido-8-hydroxy-4-((2-methyl)-5-indole)amino) quinoline (X22). The compound was prepared from 40.4 mg (0.171 mmol) of 7-acetamido-4-chloro-8-hydroxyquinoline and 29.95 mg (0.205 mmol, 1.2 equivalents) of 5-amino-2-methylindole using the general method of $SN_{Ar}$ to afford 41.3 mg (70% yield) of pure product. TLC (20% methanol in ethyl acetate) R$_f$=0.17; Melting Point 268-270° C.; $^1$H NMR (400 MHz, DMSO-d6) δ 11.2 (broad s, 1H), 10.9 (broad s, 1H), 10.7 (broad s, 1H), 8.20 (t, J=5.4 Hz, 2H), 7.92 (d, J=9.2 Hz, 1H), 7.43 (d, J=8.8 Hz, 2H), 7.01 (dd, J=2.4, 8.4 Hz, 1H), 6.55 (d, J=7.2 Hz, 1H) 6.20 (s, 1H), 2.41 (s, 3H), 2.26 (s, 3H); $^{13}$C NMR (100 MHz, DMSO-d6) δ 170.7, 155.3, 141.9, 137.5, 137.3, 135.1, 131.2, 129.2, 128.2, 127.9, 121.7, 118.0, 116.2, 114.4, 113.6, 111.6, 99.5, 99.3, 23.4, 13.4; IR (neat) $v_{max}$ 3272.6, 3188.9, 3075.9, 3010.9, 2965.7, 2925.6, 1654.5, 1626.9, 1606.1, 1580.5, 1478.0, 1449.6, 1369.7, 1294.6, 1214.0; ESI-HRMS [M+H]$^+$ calculated for $C_{20}H_{19}N_4O_2$ 347.1503 found 347.1508.

7-Acetamido-8-hydroxy-4-((4-fluorophenyl)amino)quinoline (X23). The compound was prepared from 40 mg (0.169 mmol) of 7-acetamido-4-chloro-8-hydroxyquinoline and 18.87 mg (16.32 μL, 0.169 mmol) of 3-hydroxyaniline using the general method of $SN_{Ar}$ to afford 23 mg (44% yield) of pure light-yellow solid. TLC (10% methanol in ethyl acetate) R$_f$=0.2; Melting Point 274-276° C.; $^1$H NMR (400 MHz, DMSO-d6) δ 11.96 (broad s, 1H), 10.81 (broad s, 1H), 8.29 (d, J=6.8 Hz, 1H), 8.21 (d, J=9.2 Hz, 1H), 7.93 (d, J=9.2 Hz, 1H), 7.42 (dd, J=5.0, 9.0 Hz, 2H), 7.40 (t, J=8.8 Hz, 2H), 6.67 (d, J=7.2 Hz, 1H), 2.26 (s, 3H); $^{13}$C NMR (125.7 MHz, DMSO-d6) δ 171.4, 160.9 (d, $^1J_{C-F}$=244.6 Hz), 154.8, 142.5, 137.7, 133.6, 131.4, 128.0 (d, $^3J_{C-F}$=8.5 Hz), 122.4, 116.7 (d, $^2J_{C-F}$=22.7 Hz), 115.0, 114.0, 99.8, 23.5; IR (neat) $v_{max}$ 3609.4, 3359.0, 3187.2, 3049.5, 2963.8, 2926.8, 2887.8, 2825.9, 1612.3, 1588.0, 1561.0, 1534.9, 1508.4; ESI-HRMS [M+H]$^+$ calculated for $C_{17}H_{15}FN_3O_2$ 312.1143 found 312.1150.

7-Acetamido-8-hydroxy-4-((3-fluorophenyl)amino)quinoline (X24). The compound was prepared from 40.2 mg (0.169 mmol) of 7-acetamido-4-chloro-8-hydroxyquinoline and 18.87 mg (16.32 μL, 0.169 mmol) of 3-hydroxyaniline using the general method of $SN_{Ar}$ to afford 33.1 mg (63% yield) of pure product as a yellow solid. TLC (10% methanol in ethyl acetate) R$_f$=0.15; Melting Point 270-272° C.; $^1$H NMR (400 MHz, DMSO-d6) δ 10.98 (broad s, 1H), 10.91 (broad s, 1H), 8.34 (d, J=5.2 Hz, 1H), 8.24 (d, J=7.6 Hz, 1H), 7.96 (d, J=7.6 Hz, 1H), 7.60 (q, J=6.4 Hz, 1H), 7.41 (d, J=8.0 Hz, 1H), 7.35 (d, J=6.4 Hz, 1H), 7.25 (t, J=6.0 Hz, 1H), 6.88 (d, J=5.6 Hz, 1H), 2.26 (s, 3H); $^{13}$C NMR (125.7 MHz, DMSO-d6) δ 170.8, 162.5 (d, $^1J_{C-F}$=245.1 Hz), 154.2, 142.5, 139.1 (d, $^1J_{C-F}$=10.3 Hz), 137.2, 131.5 (d, $^3J_{C-F}$=9.3 Hz), 131.2, 128.2, 122.2, 121.3, 114.9, 114.0, 113.9, 112.4 (d, $^2J_{C-F}$=23.5 Hz), 23.4; IR (neat) $v_{max}$ 3358.9, 2967.3, 2357.1, 2330.4, 1606.2, 1586.8, 1540.4, 1457.3; ESI-HRMS [M+H]$^+$ calculated for $C_{17}H_{15}FN_3O_2$ 312.1143 found 312.1149.

7-Acetamido-8-hydroxy-4-((4-hydroxyphenyl)amino) quinoline (X26). The compound was prepared from 40 mg (0.169 mmol) of 7-acetamido-4-chloro-8-hydroxyquinoline and 36.89 mg (0.338 mmol) of 3-hydroxyaniline using the general method of $SN_{Ar}$ to afford 31 mg (60% yield) of pure product yellow solid. TLC (10% methanol in ethyl acetate) R$_f$=0.21; Melting Point 279-281° C.; $^1$H NMR (500 MHz, DMSO-d6) δ 9.50 (broad s, 1H), 8.96 (broad s, 1H), 8.37 (s, 1H), 8.02 (d, J=8.0 Hz, 1H), 7.73 (d, J=8.5 Hz, 1H), 7.20 (s, 1H), 6.90 (s, 1H), 6.80 (d, J=9.0 Hz, 2H), 6.58 (d, J=5.5 Hz, 1H), 2.15 (s, 3H); IR (neat) $v_{max}$ 3367.0, 3329.6, 3248.2, 2915.5, 2357.4, 2330.9, 1664.4, 1541.9, 1489.6, 1448.0: ESI-HRMS [M+H]$^+$ calculated for $C_{17}H_{16}N_2O_3$ 310.1186 found 310.1194.

7-Acetamido-8-hydroxy-4-((4-trifluoromethylphenyl)amino)quinoline (X27). The compound was prepared from 40.2 mg (0.1698 mmol) of 7-acetamido-4-chloro-8-hydroxyquinoline and 32.8 mg (0.2038 mmol, 1.2 equivalents) of 4-trifluoromethylaniline using the general method of $SN_{Ar}$ to afford 47 mg (77% yield) of pure light-yellow solid. TLC (20% methanol in ethyl acetate) $R_f$=0.21; Melting Point 277-279° C.; $^1$H NMR (400 MHz, DMSO-d6) δ 10.96 (broad s, 1H), 10.89 (broad s, 1H), 8.36 (d, J=7.2 Hz, 1H), 8.23 (d, J=9.2 Hz, 1H), 7.92 (d, J=8.4 Hz, 3H), 7.73 (d, J=8.4 Hz, 2H), 6.98 (d, J=6.8 Hz, 1H), 2.26 (s, 3H); 13C NMR (125.7 MHz, DMSO-d6) δ 170.9, 153.8, 142.8, 141.5, 137.4, 131.5, 128.1, 126.9, 126.6, 125.2, 123.0, 122.4, 115.4, 114.2, 100.5, 23.4; IR (neat) $v_{max}$ 3229.8, 2995.6, 2364.3, 2324.6, 1686.0, 1588.2, 1524.3, 1456.1, 1328.9; ESI-HRMS [M+H]$^+$ calculated for $C_{18}H_{15}F_3N_3O_2$ 362.1111 found 362.1113.

7-Acetamido-8-hydroxy-4-((3-trifluoromethylphenyl)amino)quinoline (X28). The compound was prepared from 40.6 mg (0.171 mmol) of 7-acetamido-4-chloro-8-hydroxyquinoline and 33.1 mg (0.206 mmol, 1.2 equivalents) of 3-trifluoromethylaniline using the general method of $SN_{Ar}$ to afford 44 mg (71% yield) of pure light-yellow solid. TLC (20% methanol in ethyl acetate) $R_f$=0.2; Melting Point 278-280° C.; $^1$H NMR (500 MHz, DMSO-d6) δ 10.96 (broad s, 2H), 8.36 (d, J=7.0 Hz, 1H), 8.26 (d, J=9.0 Hz, 1H), 7.98 (d, J=9.0 Hz, 1H), 7.87 (s, 1H), 7.84-7.74 (m, 3H), 6.85 (d, J=7.0 Hz, 1H), 2.26 (s, 3H); $^{13}$C NMR (125.7 MHz, DMSO-d6) δ 1780.8, 154.1, 142.8, 138.5, 137.3, 131.4, 131.1, 130.5 (d, $^2J_{C-F}$=32.1 Hz), 129.1, 128.1, 123.7 (d, $J_{C-F}$=272-8 Hz), 123.5, 122.2, 121.9, 115.1, 114.0, 100.0, 23.4: IR (neat) $v_{max}$ 3649.5, 3336.8, 3191.8, 2972.2, 2905.1, 2827.7, 2361.5, 23307, 1649.3, 1607.0, 1588.0, 1561.3, 1535.2, 1490.1; ESI-HRMS [M+H]Y calculated for $C_{18}H_{15}F_3N_3O_2$ 362.1111 found 362.1113.

7-Acetamido-8-hydroxy-4-((2-fluoro-4-hydroxyphenyl)amino)quinoline (X29). The compound was prepared from 41.1 rag (0.174 mmol) of 7-acetamido-4-chloro-8-hydroxyquinoline and 28.7 mg (0.225 mmol, 1.3 equivalents) of 2-fluoro-4-hydroxylaniline using the general method of $SN_{Ar}$ to afford 34 mg (60% yield) as a yellow solid. TLC (20% methanol in ethyl acetate) $R_f$=0.28; Melting Point 213-215° C. $^1$H NMR (500 MHz, DMSO-d6) δ 11.00 (broad s, 1H), 10.56 (broad s, 1H), 8.29 (d, J=6.5 Hz, 1H), 8.18 (d, J=9.0 Hz, 1H), 7.94 (d, J=9.5 Hz, 1H), 733 (t, J=9.0 Hz, 1H), 6.87 (d, J=12.0 Hz, 2H), 6.81 (d, J=9.0 Hz, 1H) 6.39 (d, J=7.0 Hz, 1H), 2.26 (s, 3H); $^{13}$C NMR (125.7 MHz, DMSO-d6) δ 170.8, 158.9 (d, $^3J_{C-F}$=11.06 Hz), 157.6 (d, $^1J_{C-F}$=247.5 Hz), 155.6, 1423, 137.2, 130.9, 129.7, 128.2, 122.2, 115.1 (d, $^1J_{C-F}$=12.4 Hz), 114.3, 113.8, 112.6, 103.8 (d, $^2J_{C-F}$=21.8 Hz), 99.7, 23.4; IR (neat) $v_{max}$ 2919.9, 28507, 2360.7, 2342.1, 1692.9, 1619.5, 1524.5, 1461.0, 1291.6, 1140.5, 1008.4, 915.7, 791.1: ESI-HRMS [M+H]$^+$ calculated for $C_{17}H_{15}FN_3O_3$ 328.1019 found 328.1095.

7-Acetamido-8-hydroxy-4-((2-fluoro-5-hydroxyphenyl)amino)quinoline (X30). The compound was prepared from 41.5 mg (0.175 mmol) of 7-acetamido-4-chloro-8-hydroxyquinoline and 28.97 mg (0.228 mmol, 1.3 equivalents) of 2-fluoro-5-hydroxylaniline using the general method of $SN_{Ar}$ to afford 41.2 mg (71% yield) as yellow solid. TLC (20% methanol in ethyl acetate) $R_f$=0.21; $^1$H NMR (500 MHz, DMSO-d6) δ 9.59 (broad s, 1H), 8.99 (broad s, 1H), 8.36 (d, J=5.5 Hz, 1H), 8.01 (d, J=9.0 Hz, 1H), 7.76 (d, J=9.5 Hz, 1H), 7.17 (t, J=9.8 Hz, 1H), 6.81-6.79 (m, 1H), 6.71-6.68 (m, 1H) 6.39-6.38 (m, 1H), 2.15 (s, 3H); $^{13}$C NMR (125.7 MHz, DMSO-d6) δ 169.4, 154.2, 150.6, 149.9 (d, $^1J_{C-F}$=237.9 Hz), 146.1, 141.2, 136.2, 126.6 (d, $^3J_{C-F}$=13.2 Hz), 125.7 (d, $^1J_{C-F}$=237.4 Hz), 121.3, 116.9 (d, $^2J_{C-F}$=21.2 Hz), 115.6, 114.0, 113.6, 111.4, 100.8, 23.6: IR (neat) $v_{max}$ 3060.5, 1503.4, 1451.0, 1374.5, 1307.7, 1219.0; ESI-HRMS [M+H]$^+$ calculated for $C_{17}H_{15}FN_3O_3$ 328.1019 found 328.1096.

General Method for Buchwald-Hartwig Amination

To 1 molar equivalent of 7-Acetamido-4-chloro-8-methoxyquinoline, were added, 1.4 molar equivalents of cycloalkyamines, 0.1 molar equivalents of palladium 11 acetate, 0.2 molar equivalents of BINAP, 5 molar equivalents of $Cs_2CO_3$, and 3 mL of 1,4-dioxane. The mixture was heated at 90° C. under $N_2$ for 5 h. The reaction was cooled to room temperature and filtered over a pad of celite and washed with ethyl acetate and DCM. The filtrate was concentrated in vacuo to remove the solvent to give a crude coupling product. The crude product was chromatographed on silica gel, using 10% methanol in ethyl acetate to afford pure product as an off white solid.

7-Acetamido-4-((cyclobutyl)amino)-8-methoxyquinoline (X31). The compound was prepared from 52 mg (0.207 mmol) of 7-acetamido-4-chloro-8-methoxyquinoline and 14.89 mg (17.87 μL (0.290 mmol, 1.4 molar equivalents) of cyclobutylamine using the general method of Buchwald-Hartwig amination to afford 42.5 mg (72% yield) as an off white solid. TLC (20% methanol in ethyl acetate) $R_f$=0.23; Melting Point 178-180° C.; $^1$H NMR (500 MHz, DMSO-d6) δ 9.47 (s, 1H), 8.34 (d, J=3.5 Hz, 1H), 8.11 (d, J=8.0 Hz, 1H), 7.95 (d. J=9.0 Hz, 1H), 7.19 (s, 1H), 6.28 (d, J=4.0 Hz, 1H), 4.05-4.02 (m, 1H) 3.98 (s, 3H), 2.41 (d, J=6.0 Hz, 2H), 2.16 (s, 3H), 2.08 (t, J=9.2 Hz. 2H), 1.808-1.75 (m, 2H); $^{13}$C NMR (125.7 MHz, DMSO-d6) δ 169.0, 149.8, 149.0, 142.6, 141.6, 130.9, 118.6, 116.7, 116.3, 98.4, 61.3, 47.7, 29.5, 24.0, 14.9; IR (neat) $v_{max}$ 3285.9, 2933.7, 1671.2, 1615.5, 1581.1, 1536.9, 1514.3, 1414.3, 1380.0, 1298.6, 1209.6, 1145.3, 1051.5; ESI-HRMS [M+H]$^+$ calculated for $C_{16}H_{20}N_3O_2$ 286.1550 found 286.1557.

7-Acetamido-4-((cyclopentyl)amino)-8-methoxyquinoline (X32) The compound was prepared from 52 mg (0.207 mmol) of 7-acetamido-4-chloro-8-methoxyquinoline and 24.7 mg (28.6 μL (0.290 mmol, 1.4 molar equivalents) of cyclopentylamine using the general method of Buchwald-Hartwig amination to afford 71.4 mg (87% yield) as an off white solid. TLC (20% methanol in ethyl acetate) $R_f$=0.23; Melting Point 138-140° C.; ° H NMR (500 MHz, DMSO-d6) δ 9.53 (s, 1H), 8.35 (d, J=4.5 Hz, 1H), 8.10 (d, J=8.0 Hz, 1H), 8.03 (d, J=9.0 Hz, 1H), 7.02 (s, 1H), 6.45 (d, J=4.5 Hz, 1H), 3.97 (s, 4H), 3.62 (s, 1H), 2.16 (s, 3H), 2.03 (s, 2H), 1.73-1.58 (m, 6H); $^{13}$C NMR (125.7 MHz, DMSO-d6) δ 169.0, 150.3, 148.9, 143.3, 141.6, 131.2, 118.7, 117.0, 116.1, 98.5, 613, 53.8, 31.88, 23.9; IR (neat) $v_{max}$ 3292.8, 29493, 2867.4, 1670.0, 1615.4, 1539.4, 1490.2, 1459.6, 1414.3, 1381.1, 1297.7; ESI-HRMS [M+Na]$^+$ calculated for $C_{17}H_{22}N_3O_2$ 300.1707 found 300.1717.

7-Acetamido-4-((cyclohexyl)amino)-8-methoxyquinoline (X33). The compound was prepared from 35.0 mg (0.139 mmol) of 7-acetamido-4-chloro-8-methoxyquinoline and 19.38 mg (22.4 μL (0.195 mmol, 1.4 molar equivalents) of cyclohexylamine using the general method of Buchwald-Hartwig amination to afford 43 mg (98% yield) as an off white solid. TLC (10% methanol in ethyl acetate) $R_f$=0.19; Melting Point 200-202° C.; $^1$H NMR (500 MHz, DMSO-d6) δ 9.51 (s, 1H), 8.33 (d, J=5.5 Hz, 1H), 8.10 (d, J=9.5 Hz, 1H), 7.96 (d, J=9.5 Hz, 1H), 6.75 (d, J=7.0 Hz, 1H), 6.43 (d, J=5.5 Hz, 1H), 3.97 (s, 3H), 3.45 (s, 1H), 2.16 (s, 3H), 1.98 (d, J=8.5 Hz, 2H), 1.76 (d, J=6.5 Hz, 2H), 1.65 (d, J=13.0

Hz, 1H), 1.39-1.34 (m, 4H), 1.18-1.15 (m, 1H); $^{13}$C NMR (125.7 MHz, DMSO-d6) δ 169.0, 149.8, 149.2, 143.8, 142.9, 142.8, 130.9, 118.4, 116.8, 116.4, 97.9, 61.3, 31.9, 25.4, 24.9, 24.1; IR (neat) $v_{max}$ 3314.8, 2922.5, 2850.0, 1676.5, 1614.8, 1522.2, 1459.8, 1413.5, 1329.7: ESI-HRMS [M+Na]$^+$ calculated for $C_{18}H_{24}N_3O_2$ 314.1863 found 314.1868.

7-Acetamido-4-((cycloheptyl)amino)-8-methoxyquinoline (X34). The compound was prepared from 51.0 mg (0.203 mmol) of 7-acetamido-4-chloro-8-methoxyquinoline and 32.24 mg (36.26 μL (0.284 mmol, 1.4 molar equivalents) of cycloheptylamine using the general method of Buchwald-Hartwig amination to afford 64.1 mg (96% yield) as an off white solid. TLC (20% methanol in ethyl acetate) $R_f$=0.32; Melting Point 192-194° C.; $^1$H NMR (500 MHz, DMSO-d6) δ 9.45 (s, 1H), 8.34 (d, J=5.0 Hz, 1H), 8.08 (d, J=9.5 Hz, 1H), 7.96 (d, J=9.0 Hz, 1H), 6.68 (d, J=7.5 Hz, 1H), 6.31 (d, J=4.5 Hz, 1H), 3.98 (s, 3H), 3.62 (s, 1H), 2.16 (s, 3H), 1.94 (t, J=6.5 Hz, 2H), 1.86 (s, 1H), 1.69 (t, J=6.5 Hz, 3H), 1.64-1.61 (m, 2H), 1.57-1.49 (m, 4H); $^{13}$C NMR (125.7 MHz, DMSO-d6) δ 168.9, 149.9, 148.8, 143.9, 142.9, 130.8, 118.3, 116.6, 88.1, 61.2, 52.8, 33.4, 28.9, 24.0; IR (neat) $v_{max}$ 3362.2, 2921.0, 2854.5, 1677.4, 1614.8, 1580.9, 1540.2; ESI-HRMS [M+H]$^+$ calculated for $C_{19}H_{26}N_3O_2$ 328.2020 found 328.2027.

4-((cyclohexyl)amino)-8-methoxy-7-((2-morpholin-4-yl)acetamido)quinoline (X35). The compound was prepared from 50.0 mg (0.149 mmol) of compound 2 and 20.67 mg (23.9 μL, 0.208 mmol, 1.4 molar equivalents) of cyclohexylamine using the general method of Buchwald-Hartwig amination to afford 43.6 mg (74% yield) as an off white solid, $^1$H NMR (400 MHz, CD$_3$OD) δ 8.54 (d, J=2.4 Hz, 1H), 8.31 (d, J=6.4 Hz, 1H), 8.13 (d, J=9.6 Hz, 1H), 6.74 (d, J=6.4 Hz, 1H), 4.00 (s, 3H), 3.82 (s, 4H), 3.72 (s, 1H), 2.70 (s, 4H), 2.10 (s, 2H), 1.97 (s, 1H), 1.90 (s, 2H), 1.76 (d, J=12.4 Hz, 1H), 1.56-1.45 (m, 4H), 1.32-1.25 (m, 2H); $^{13}$C NMR (100 MHz, DMSO-d6) δ 168.2, 149.6, 142.0, 130.5, 117.6, 116.1, 115.7, 97.8, 66.5, 61.9, 61.4, 53.2, 51.1, 31.9, 25.4, 24.8 ESI-HRMS [M+H]$^+$ calculated for $C_{22}H_{31}N_4O_3$ 399.2391 found 399.2395.

4-((cyclohexyl)amino)-8-methoxy-7-((3-morpholin-4-yl)propanamido)quinoline (X36). The compound was prepared from 50.0 mg (0.143 mmol) of compound 3 and 21.26 mg (24.6 μL, 0.214 mmol, 1.5 molar equivalents) of cyclohexylamine using the general method of Buchwald-Hartwig amination to afford 48.6 mg (83% yield) as an off white solid. $^1$H NMR (400 MHz, 400 MHz, CD$_3$OD) δ 8.47 (d, J=9.6 Hz, 1H), 8.28 (d, J=6.8 Hz, 1H), 8.18 (d, J=9.6 Hz, 1H), 6.86 (d, J=7.2 Hz, 1H), 3.80 (t, J=4.6 Hz, 4H), 2.83 (t, J=6.2 Hz, 2H), 2.75 (t, J=6.2 Hz, 2H), 2.64 (broad s, 4H), 2.11 (d, J=8.8 Hz, 2H), 1.94 (s, 1H), 1.93 (d, J=9.6 Hz, 2H), 1.77 (d, J=13.2 Hz, 1H), 1.61-1.46 (m, 4H); $^{13}$C NMR (100 MHz, CD$_3$OD) δ 173.8, 156.0, 143.6, 140.2, 136.1; 135.2, 122.1, 119.7, 115.6, 99.3, 67.7, 62.3, 55.2, 54.5, 54.4, 34.0, 33.0, 26.4, 26. ESI-HRMS [M+H]$^+$ calculated for $C_{23}H_{33}N_4O_3$ 413.2547 found 413.2557.

General method of demethylation of cycloalkylamine quinolines X37-X42 To a solution containing 1 molar of cycloalkylaminequinolines starting material in 1.0 mL dry DCM was added 1 molar BBr$_3$ (6 equivalents) in DCM on ice-salt bath and stirred at that temperature for 15 minutes. The resulting orange solution was allowed to warm to room temperature and stirred at that temperature for 8 hr. The reaction was quenched by the gradual addition of ice-cold water, and the pH was adjusted with saturated NaHCO$_3$. The product was extracted with chloroform (10 mL×3), concentrated and dried in vacuo to afford a yellow solid that was purified using reverse phase silica gel and 50-0% water in methanol to afford pure product.

7-Acetamido-8-hydroxy-4-((cyclobutyl)amino)quinoline (X37). The compound was prepared from 43 mg (0.153 mmol) of 7-acetamido-4-((cyclobutyl)amino)-8-methoxyquinoline and 0.6 mL (4 equivalents) of 1 M BBr$_3$ in DCM using the general method of demethylation to afford a yellow solid 29 mg (71% yield) of the product. TLC (20% methanol in ethyl acetate) $R_f$=0.16; Melting Point 209-211° C.; $^1$H NMR (400 MHz, CDCl$_3$) δ 8.93 (d, J=4.4 Hz, 1H), 8.58 (d, J=9.2 Hz, 1H), 8.14 (broad s, 1H), 7.34 (d, J=9.2 Hz, 1H), 7.24 (d, J=4.4 Hz, 1H), 7.18-7.13 (m, 1H), 7.00-6.97 (m, 2H), 4.23 (s, 3H), 3.68 (s, 3H), 2.29 (s, 3H), IR (neat) $v_{max}$ 3318.6, 2932.0, 2896.4, 2848.1, 2775.0, 1660.8, 1605.1, 1544.2, 1507.0, 1466.3, 1425.6; ESI-HRMS [M+H]$^+$ calculated for $C_{15}H_{18}N_3O_2$ 272.1394 found 272.1399.

7-Acetamido-8-hydroxy-4-((cyclopentyl)amino)quinoline (X38). The compound was prepared from 38.1 mg (0.127 mmol) of 7-acetamido-4-((cyclopentyl)amino)-8-methoxyquinoline 0.51 mL (4 equivalents) of 1M BBr$_3$ in DCM using the general method of demethylation to afford a yellow solid 31.6 mg (87% yield) of the product. TLC (20% methanol in ethyl acetate), $R_f$=0.15, Melting Point 209-211° C.; $^1$H NMR (400 MHz, DMSO-d6) δ 9.30 (broad s, 1H), 8.23 (d, J=5.2 Hz, 1H), 7.98 (d, J=9.2 Hz, 1H), 7.40 (d, J=9.2 Hz, 1H), 6.84 (d, J=6.0 Hz, 1H), 6.41 (d, J=5.2 Hz, 1H), 4.00-3.93 (m, 1H), 2.10 (s, 3H), 2.04-2.01 (m, 2H), 1.74-1.58 (m, 6H); $^{13}$C NMR (100 MHz, DMSO-d6) δ 168, 150.5, 146.4, 123.6, 119.0, 115.5, 98.1, 53.7, 31.9, 23.9; IR (neat) $v_{max}$ 3326.7, 2921.7, 2855.5, 1661.4, 1601.7, 1563.7, 1500.0, 1465.4; ESI-HRMS [M+H]$^+$ calculated for $C_{16}H_{20}N_3O_2$ 286.1550 found 286.1554.

7-Acetamido-8-hydroxy-4-((cyclohexyl)amino)quinoline (X39). The compound was prepared from 40 mg (0.1276 mmol) of 7-acetamido-4-((cyclohexyl)amino)-8-methoxyquinoline and 1.3 ml (10 equivalents) of 1 M BBr$_3$ in DCM using the general method of demethylation to afford a yellow solid 37.6 mg (98% yield) of the product. TLC (20% methanol in ethyl acetate) $R_f$=0.16; Melting Point 238-240° C.; $^1$H NMR (500 MHz, DMSO-d6) δ 9.51 (broad s, 1H), 8.23 (d, J=3.5 Hz, 1H), 7.93 (d, J=8.5 Hz, 1H), 7.55 (d, J=9.0 Hz, 1H), 7.16 (s, 1H), 6.52 (s, 1H), 3.54 (broads, 1H), 2.12 (s, 3H), 1.96 (s, 2H), 1.77 (s, 2H), 1.65 (d, J=12.0 Hz, 1H), 1.39 (s, 4H), 1.22 (s, 1H); $^{13}$C NMR (125.7 MHz, DMSO-d6) δ 168.6, 150.8, 145.5, 143.3, 136.0, 124.1, 119.7, 115.0, 108.7, 97.6, 51.3, 31.8, 25.3, 24.7, 23.7; IR (neat) $v_{max}$ 3328.9, 2919.1, 2851.3, 1660.7, 1608.4, 1563.7, 1506.3, 1473.8, 1371.3, 1313.3, 1212.9, 1103.0; ESI-HRMS [M+H]$^+$ calculated for $C_{17}H_{22}N_3O_2$ 300.1707 found 300.1710.

7-Acetamido-8-hydroxy-4-((cycloheptyl)amino)quinoline (X40). The compound was prepared from 61.6 mg (0.188 mmol) of 7-acetamido-4-((cycloheptyl)amino)-8-methoxyquinoline and 752 μL (4 equivalents) of 1 M BBr$_3$ in DCM using the general method of demethylation to afford a yellow solid 52.2 mg (89% yield) of the product. TLC (ethyl acetate) $R_f$=0.12; Melting Point 189-191° C.; $^1$H NMR (400 MHz, DMSO-d6) δ 9.27 (broad s, 1H), 8.21 (d, J=5.2 Hz, 1H), 7.98 (d, J=9.2 Hz, 1H), 7.35 (d, J=8.8 Hz, 1H), 6.74 (d, J=6.8 Hz, 1H), 6.31 (d, J=5.6 Hz, 1H), 3.68-3.64 (m, 1H), 2.10 (s, 3H), 1.98-1.92 (s, 2H), 1.71-1.50 (m 11H), $^{13}$C NMR (100 MHz, DMSO-d6) δ 167.9, 149.6, 146.2, 123.8, 118.9, 115.6, 97.6, 53.0, 33.5, 27.9, 24.0; IR (neat) $v_{max}$ 3844.4, 3743.5, 3678.6, 3648.9, 3620.1, 2918.9, 28513, 2363.1, 1655.8, 1548.4, 1512.0, 1462.5, 1426.6; ESI-HRMS [M+H]f calculated for $C_{18}H_{24}N_3O_2$ 314.1863 found 314.1867.

4-((cyclohexyl)amino)-8-hydroxy-7-((2-morpholin-4-yl)acetamido)quinoline (X41). The compound was prepared from 27 mg (0.067 mmol) of analog 35 and 677 μL (10 equivalents) of 1 M BBr$_3$ in DCM using the general method of demethylation to afford a yellow solid 20 mg (77% yield) of the product. $^1$H NMR (400 MHz, DMSO-d6) δ 9.84 (broad s, 1H), 8.20 (d, J=8.8 Hz, 1H), 8.12 (d, J=5.6 Hz, 1H), 7.34 (d, J=8.8 Hz, 1H), 7.12 (d, J=7.2 Hz, 1H), 6.43 (d, J=6.0 Hz, 1H), 3.61 (s, 3H), 3.50-3.49 (m, 2H), 3.10 (s, 2H), 2.44 (s, 5H), 1.90-187 (m, 2H), 1.73-1.71 (m, 2H), 1.61-158 (n, 1H) 1.35, (broad s, 5H), $^{13}$C NMR (100 MHz, DMSO-d6) δ 167.6, 151.5, 144.1, 124.9, 117.4, 114.8, 97.0, 66.4, 62.0, 53.2, 51.5, 31.8, 25.3, 24. ESI-HRMS [M+H]$^+$ calculated for C$_{21}$H$_{20}$N$_4$O$_3$ 385.2234 found 385.2236.

4-((cyclohexyl)amino)-8-hydroxy-7-((3-morpholin-4-yl)propanamido)quinoline (X42). The compound was prepared from 20 mg (0.048 mmol) of analog 36 and 485 μL. (10 equivalents) of 1 M BBr$_3$ in DCM using the general method of demethylation to afford a yellow solid 16 mg (83% yield) of the product. $^1$H NMR (400 MHz, Methanol-d4) 8.23 (d, J=8.8 Hz, 1H), 8.13 (d, J=6.8 Hz, 1H), 7.34 (d, J=9.2 Hz, 1H), 6.67 (d, J=6.8 Hz, 1H), 3.79 (t, J=4.4 Hz, 3H), 3.74 (broad s, 1H), 3.49-3.45 (m, 1H), 2.79 (t, J=6.4 Hz, 2H), 2.68 (t, J=6.4 Hz, 2H), 2.58 (s, 3H), 2.08 (broad s, 2H), 2.01-1.98 (m, 1H), 1.89-187 (m, 3H), 1.77-1.734 (m. 1H), 1.57-1.44 (m, 4H). $^{13}$C NMR (100 MHz, DMSO-d6) δ 163.7, 146.7, 138.8, 131.1, 123.7, 120.3, 112.1, 106.4, 96.4, 88.2, 58.2, 46.1, 45.0, 44.6, 25.1, 23.6, ESI-HRMS [M+H]$^+$ calculated for C$_{22}$H$_{31}$N$_4$O$_3$ 399.2391 found 399.2390.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

What is claimed is:

1. A compound of formula:

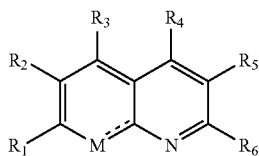

or a pharmaceutically acceptable salt, or solvate, thereof, wherein:
R$^1$ is —NR$^7$CO—R$^8$ or —CO—NR$^7$—R$^8$, wherein R$^7$ is H or C1-C3 alkyl optionally substituted with one or more halogen, hydroxyl, or C1-C3 alkoxy and R$^8$ is H, or alkyl, or cycloalkyl both optionally substituted with one or more halogen, hydroxyl, C1-C3 alkyl, C1-C3 alkoxy, or heterocyclic optionally substituted with one or more oxo (=O), halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic;

R$^2$, R$^3$ and R$^5$ are independently H, halogen, C1-C3 alkyl or OR$^9$, wherein R$^9$ is H or C1-C3 alkyl, where the C1-C3 alkyls are optionally substituted with one or more halogen, hydroxyl, C1-C3 alkoxy or C1-C3 hydroxyalkyl;

R$^4$ is aryl or heteroaryl, which are optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic; and R$^6$ is H, —COOR$^{11}$, or —CONR$^{12}$R$^{13}$, wherein R$^{11}$, R$^{12}$, and R$^{13}$ are independently alkyl or cycloalkyl each optionally substituted with one or more halogen, hydroxyl, C1-C3 alkyl, C1-C3 alkoxy, or heterocyclic which in turn is optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic, or aryl or heterocyclic optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.

2. The compound, or pharmaceutically acceptable salt, or solvate thereof, of claim 1, wherein R$^1$ is —NR$^7$CO—R$^8$.

3. The compound, or pharmaceutically acceptable salt, or solvate thereof, of claim 1, wherein R$^1$ is or —CO—NR$^7$—R$^8$.

4. The compound, or pharmaceutically acceptable salt, or solvate thereof, of claim 1, wherein R$^1$ is —NR$^7$CO—R$^8$, and wherein R$^8$ is alkyl, or cycloalkyl each of which is optionally substituted with a heterocyclic group which in turn is optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.

5. The compound, or pharmaceutically acceptable salt, or solvate thereof, of claim 1, wherein R$^1$ is —NHCO—CH$_3$.

6. The compound, or pharmaceutically acceptable salt, or solvate thereof, of claim 1, wherein R$^8$ is alkyl, or cycloalkyl each of which is optionally substituted with a heterocyclic group which is in turn optionally substituted with one or more halogen, hydroxyl, C1-C6 alkyl, C3-C6 cycloalkyl, C1-C6 acyl, C1-C3 haloalkyl, C1-C3 alkoxy, C1-C3 hydroxyalkyl, or heterocyclic.

7. The compound, or pharmaceutically acceptable salt, or solvate thereof, of claim 1, wherein R$^2$, R$^3$ and R$^5$ are independently, H, halogen, or C1-C3 alkyl.

8. The compound, or pharmaceutically acceptable salt, or solvate thereof, of claim 1, wherein R$^6$ is H.

9. The compound, or pharmaceutically acceptable salt, or solvate thereof, of claim 1, wherein R$^4$ is a phenyl group substituted with at least one fluorine or is an optionally-substituted heteroaryl group.

10. A compound of chemical structure:

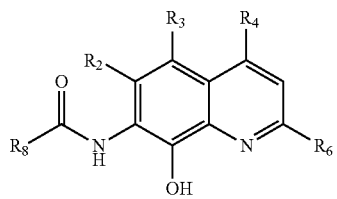

or a pharmaceutically acceptable salt, or solvate, thereof, wherein:
R$^2$ is H or OCH$_3$;
R$^3$ is H or OCH$_3$;
R$^4$ is phenyl optionally substituted with one or more of halogen, hydroxyl, C1-C6 acyl, or optionally-substituted heterocyclylalkyl; or
R$^4$ is benzofuranyl, furyl or thienyl each of which is optionally substituted with one or more of halogen, hydroxyl, C1-C3 alkyl or halomethyl;
R$^6$ is H, or COOH; and
R$^8$ is H, optionally-substituted C1-C6 alkyl, or optionally-substituted heterocyclylalky.

11. The compound of claim 1 or a pharmaceutically acceptable salt, or solvate thereof, of chemical structure selected from the group consisting of:

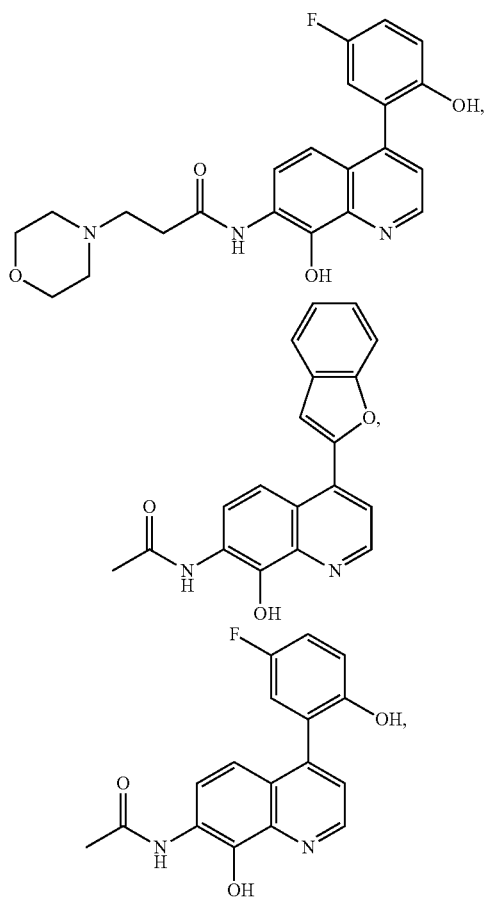

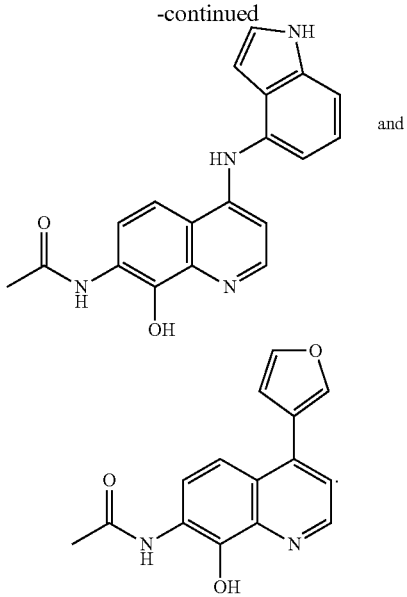

12. A pharmaceutical composition comprising at least one topoisomerase IIα (TOP2A) inhibitor compound, pharmaceutically acceptable salt, or solvate thereof, of claim 1 at least one pharmaceutically acceptable additive.

13. A pharmaceutical kit containing a pharmaceutical composition of claim 12, prescribing information for the composition, and a container.

14. A method for inhibiting TOP2A activity in a subject, including administering to the subject a therapeutically effective amount of a TOP2A inhibitor compound, pharmaceutically acceptable salt or solvate thereof of claim 1.

15. A method of treating, or ameliorating cancer, or preventing metastasis of a cancer in a subject, comprising administering a therapeutically-effective amount of a compound, pharmaceutically acceptable salt or solvate thereof of claim 1 inhibits TOP2A to a subject in need thereof.

16. The method of claim 15, wherein the cancer is colorectal cancer, breast cancer, sarcomas, testicular cancer, lung cancer, lymphoma, leukemia, neuroblastoma, or ovarian cancer.

17. The compound, or pharmaceutically acceptable salt, or solvate thereof, of claim 1, wherein each of R$^2$, R$^3$, R$^5$ and R$^6$ is H.

18. The compound, or pharmaceutically acceptable salt, or solvate thereof, of claim 10, wherein R$^2$ and R$^3$ are H.

19. The compound, or pharmaceutically acceptable salt, or solvate thereof, of claim 1, wherein:
R$^4$ is a phenyl group which is optionally substituted with one or more fluorine, hydroxyl, C1-C6 alkyl, C3-C6 cycloalkyl, C1-C6 acyl, C1-C3 haloalkyl, C1-C3 alkoxy, or C1-C3 hydroxyalkyl, and which is substituted with at least one fluorine; or
R$^4$ is benzofuranyl, furyl or thienyl each of which is optionally substituted with one or more of halogen, hydroxyl, C1-C3 alkyl or halomethyl.

* * * * *